United States Patent
Jensen et al.

(10) Patent No.: US 12,258,397 B2
(45) Date of Patent: Mar. 25, 2025

(54) PRODUCTION OF ENGINEERED T-CELLS BY SLEEPING BEAUTY TRANSPOSON COUPLED WITH METHOTREXATE SELECTION

(71) Applicants: Seattle Children's Hospital, Seattle, WA (US); University of Washington, Seattle, WA (US)

(72) Inventors: Michael C. Jensen, Bainbridge Island, WA (US); Suzie Pun, Seattle, WA (US); Nataly Kacherovsky, Seattle, WA (US)

(73) Assignees: Seattle Children's Hospital, Seattle, WA (US); University of Washington, Seattle, WA (US)

( * ) Notice: Subject to any disclaimer, the term of this patent is extended or adjusted under 35 U.S.C. 154(b) by 746 days.

(21) Appl. No.: 17/096,138

(22) Filed: Nov. 12, 2020

(65) Prior Publication Data

US 2021/0139583 A1     May 13, 2021

Related U.S. Application Data

(62) Division of application No. 15/302,449, filed as application No. PCT/US2015/024868 on Apr. 8, 2015, now abandoned.

(60) Provisional application No. 62/090,845, filed on Dec. 11, 2014, provisional application No. 62/089,730, filed on Dec. 9, 2014, provisional application No. 62/088,363, filed on Dec. 5, 2014, provisional application No. 62/058,973, filed on Oct. 2, 2014, provisional application No. 61/986,479, filed on Apr. 30, 2014, provisional application No. 61/977,751, filed on Apr. 10, 2014.

(51) Int. Cl.
| | |
|---|---|
| C07K 16/28 | (2006.01) |
| A61K 35/12 | (2015.01) |
| A61K 35/28 | (2015.01) |
| A61K 38/17 | (2006.01) |
| A61K 39/00 | (2006.01) |
| A61K 39/395 | (2006.01) |
| C07K 14/705 | (2006.01) |
| C07K 14/71 | (2006.01) |
| C07K 14/715 | (2006.01) |
| C07K 14/725 | (2006.01) |
| C07K 16/32 | (2006.01) |
| C12N 5/0783 | (2010.01) |
| C12N 9/12 | (2006.01) |
| C12N 15/85 | (2006.01) |

(52) U.S. Cl.
CPC ......... *C07K 16/2803* (2013.01); *A61K 35/28* (2013.01); *A61K 38/1774* (2013.01); *A61K 38/179* (2013.01); *A61K 38/1793* (2013.01); *A61K 39/3955* (2013.01); *A61K 39/4611* (2023.05); *A61K 39/4631* (2023.05); *A61K 39/464412* (2023.05); *C07K 14/7051* (2013.01); *C07K 14/70517* (2013.01); *C07K 14/70521* (2013.01); *C07K 14/70578* (2013.01); *C07K 14/71* (2013.01); *C07K 14/7151* (2013.01); *C07K 16/2818* (2013.01); *C07K 16/32* (2013.01); *C12N 5/0636* (2013.01); *C12N 5/0638* (2013.01); *C12N 9/12* (2013.01); *C12N 15/85* (2013.01); *C12Y 207/10001* (2013.01); *A61K 2035/124* (2013.01); *A61K 2039/505* (2013.01); *A61K 2039/572* (2013.01); *C07K 2317/14* (2013.01); *C07K 2317/524* (2013.01); *C07K 2317/526* (2013.01); *C07K 2317/53* (2013.01); *C07K 2317/622* (2013.01); *C07K 2317/73* (2013.01); *C07K 2319/02* (2013.01); *C07K 2319/03* (2013.01); *C07K 2319/33* (2013.01); *C12N 2510/00* (2013.01); *C12N 2800/90* (2013.01)

(58) Field of Classification Search
CPC .. C07K 16/2803; A61K 35/17; C12N 5/0636; C12N 15/86
USPC ....................................................... 435/320.1
See application file for complete search history.

(56) References Cited

U.S. PATENT DOCUMENTS

| | | | |
|---|---|---|---|
| 5,783,186 | A | 7/1998 | Arakawa et al. |
| 6,040,177 | A | 3/2000 | Riddell et al. |
| 6,133,027 | A | 10/2000 | Yee et al. |
| 7,070,995 | B2 | 7/2006 | Jensen |

(Continued)

FOREIGN PATENT DOCUMENTS

| | | |
|---|---|---|
| CN | 1809277 | 7/2006 |
| DE | 10 2011118018 | 4/2013 |

(Continued)

OTHER PUBLICATIONS

Jonnalagadda et al., "Efficient Selection of Genetically Modified Human T Cells Using Methotrexate-Resistant Human Dihydrofolate Reductase". Gene Ther. Aug. 2013 ;20(8):853-860. (Year: 2013).*

(Continued)

*Primary Examiner* — Allison M Fox
*Assistant Examiner* — Hanan Isam Abuzeineh
(74) *Attorney, Agent, or Firm* — Knobbe, Martens, Olson & Bear LLP

(57) ABSTRACT

Aspects of the invention described herein include methods of treating, inhibiting, ameliorating and/or eliminating a virus or cancer cells in a subject utilizing genetically engineered human T-cells having receptors for a molecule presented by the virus or the cancer cells, wherein the genetically engineered T cells are isolated utilizing a two-stage MTX selection that employs increasing concentrations of MTX.

17 Claims, 59 Drawing Sheets

Specification includes a Sequence Listing.

(56) References Cited

U.S. PATENT DOCUMENTS

| | | | |
|---|---|---|---|
| 7,446,179 B2 | 11/2008 | Jensen et al. | |
| 7,709,253 B2 | 5/2010 | Gambhir et al. | |
| 7,910,101 B2 | 3/2011 | Cunningham et al. | |
| 8,802,374 B2 | 8/2014 | Jensen | |
| 8,822,647 B2 | 9/2014 | Jensen | |
| 8,916,381 B1 | 12/2014 | June et al. | |
| 8,975,071 B1 | 3/2015 | June et al. | |
| 9,328,156 B2 | 5/2016 | June et al. | |
| 9,447,194 B2 | 9/2016 | Jensen | |
| 9,481,728 B2 | 11/2016 | June et al. | |
| 9,499,629 B2 | 11/2016 | June et al. | |
| 9,518,123 B2 | 12/2016 | June et al. | |
| 9,540,445 B2 | 1/2017 | June et al. | |
| 9,629,877 B2* | 4/2017 | Cooper | C07K 14/5443 |
| 9,701,758 B2 | 7/2017 | Cooper et al. | |
| 9,856,322 B2 | 1/2018 | Campana et al. | |
| 10,125,193 B2 | 11/2018 | Cooper et al. | |
| 10,172,885 B2 | 1/2019 | Pule | |
| 10,221,245 B2 | 3/2019 | Brogdon et al. | |
| 10,266,592 B2 | 4/2019 | Jensen et al. | |
| 10,287,350 B2 | 5/2019 | Kochenderfer | |
| 10,358,474 B2 | 7/2019 | Baeuerle et al. | |
| 10,457,730 B2 | 10/2019 | Pule et al. | |
| 10,533,055 B2 | 1/2020 | Chen et al. | |
| 10,604,740 B2 | 3/2020 | Li et al. | |
| 10,611,837 B2 | 4/2020 | Jensen et al. | |
| 10,626,187 B2 | 4/2020 | Wiltzius et al. | |
| 10,639,329 B2 | 5/2020 | Dropulic et al. | |
| 10,738,279 B2 | 8/2020 | Lee | |
| 10,780,118 B2 | 9/2020 | Jensen | |
| 10,800,833 B2 | 10/2020 | Jantz et al. | |
| 10,828,352 B2 | 11/2020 | Berger et al. | |
| 10,844,120 B2 | 11/2020 | Wiltzius et al. | |
| 10,865,242 B2 | 12/2020 | Jensen | |
| 10,869,888 B2 | 12/2020 | Xiao et al. | |
| 10,927,184 B2 | 2/2021 | Brogdon et al. | |
| 11,034,763 B2 | 6/2021 | Wu et al. | |
| 11,104,732 B2 | 8/2021 | Cao et al. | |
| 2002/0111474 A1 | 8/2002 | Capon et al. | |
| 2003/0143559 A1 | 7/2003 | Bracken et al. | |
| 2003/0148982 A1 | 8/2003 | Brenner et al. | |
| 2003/0215427 A1 | 11/2003 | Jensen | |
| 2004/0037816 A1 | 2/2004 | Boyd | |
| 2005/0060762 A1* | 3/2005 | Bleck | C07K 16/1282 435/456 |
| 2005/0129671 A1 | 6/2005 | Cooper et al. | |
| 2006/0160090 A1 | 7/2006 | Anzures et al. | |
| 2006/0160104 A1* | 7/2006 | Johnson | G16B 20/00 435/6.14 |
| 2006/0246548 A1 | 11/2006 | Jensen | |
| 2007/0020237 A1 | 1/2007 | Yoon | |
| 2007/0087346 A1 | 4/2007 | Ciliberto et al. | |
| 2007/0166318 A1 | 7/2007 | Macina et al. | |
| 2008/0044413 A1 | 2/2008 | Hammond | |
| 2008/0096813 A1 | 4/2008 | Frankel et al. | |
| 2009/0098142 A1 | 4/2009 | Kasalan et al. | |
| 2009/0098604 A1 | 4/2009 | Gallo et al. | |
| 2010/0226901 A1 | 9/2010 | Smolke | |
| 2011/0287020 A1 | 11/2011 | Gruber et al. | |
| 2012/0046645 A1 | 2/2012 | Cal | |
| 2012/0148552 A1 | 6/2012 | Jensen et al. | |
| 2012/0297493 A1 | 11/2012 | Cooper et al. | |
| 2012/0301447 A1 | 11/2012 | Jensen | |
| 2013/0011394 A1 | 1/2013 | Knoetgen | |
| 2013/0071414 A1 | 3/2013 | Dotti et al. | |
| 2013/0143559 A1 | 6/2013 | Nishida et al. | |
| 2013/0280220 A1 | 10/2013 | Ahmed et al. | |
| 2013/0287748 A1 | 10/2013 | June et al. | |
| 2014/0056868 A1 | 2/2014 | Zechiedrich et al. | |
| 2014/0099309 A1 | 4/2014 | Power | |
| 2014/0112956 A1 | 4/2014 | Karlsson-Parra et al. | |
| 2014/0120622 A1 | 5/2014 | Gregory | |
| 2014/0271635 A1 | 9/2014 | Brogdon et al. | |
| 2014/0314795 A1 | 10/2014 | Riddell et al. | |
| 2015/0038684 A1 | 2/2015 | Jensen | |
| 2015/0038694 A1 | 2/2015 | Nicotra | |
| 2015/0120622 A1 | 4/2015 | Kobatake | |
| 2015/0299656 A1 | 10/2015 | Gattinoni et al. | |
| 2015/0329640 A1 | 11/2015 | Finer | |
| 2016/0017048 A1 | 1/2016 | Dotti et al. | |
| 2017/0015746 A1 | 1/2017 | Jensen | |
| 2017/0029774 A1 | 2/2017 | Jensen et al. | |
| 2017/0209543 A9 | 7/2017 | Jensen | |
| 2017/0224733 A1 | 8/2017 | Badie et al. | |
| 2018/0028567 A1 | 2/2018 | Li et al. | |
| 2019/0248891 A1 | 8/2019 | Jensen et al. | |
| 2020/0181624 A1 | 6/2020 | Jensen et al. | |
| 2020/0215108 A1 | 7/2020 | Jensen et al. | |
| 2021/0002364 A1 | 1/2021 | Jensen et al. | |
| 2021/0085719 A1 | 3/2021 | Jensen et al. | |
| 2021/0371517 A1 | 12/2021 | Jensen | |
| 2022/0064292 A1 | 3/2022 | Jensen | |
| 2022/0372140 A1 | 11/2022 | Jensen | |
| 2022/0380461 A1 | 12/2022 | Jensen | |
| 2022/0411805 A1 | 12/2022 | Jensen | |
| 2023/0130938 A1 | 4/2023 | Jensen | |

FOREIGN PATENT DOCUMENTS

| | | |
|---|---|---|
| JP | 2006-518753 | 8/2006 |
| RU | 2003 129 528 A | 4/2005 |
| WO | WO 92/08796 | 5/1992 |
| WO | WO 94/00143 | 1/1994 |
| WO | WO 98/18923 | 5/1998 |
| WO | WO 00/23573 | 4/2000 |
| WO | WO 01/098506 | 12/2001 |
| WO | WO 02/33101 | 4/2002 |
| WO | WO 02/072605 | 9/2002 |
| WO | WO 02/097099 | 12/2002 |
| WO | WO 03/025228 | 3/2003 |
| WO | WO 03/087338 | 10/2003 |
| WO | WO 04/029284 | 4/2004 |
| WO | WO 05/017102 | 2/2005 |
| WO | WO 05/040212 | 5/2005 |
| WO | WO 05/108617 | 11/2005 |
| WO | WO 07/073499 | 6/2007 |
| WO | WO 07/137267 | 11/2007 |
| WO | WO 08/012237 | 1/2008 |
| WO | WO 09/013359 | 1/2009 |
| WO | WO 09/091826 | 7/2009 |
| WO | WO 10/036986 | 4/2010 |
| WO | WO 10/141543 | 12/2010 |
| WO | WO 11/041093 | 4/2011 |
| WO | WO 11/056894 | 5/2011 |
| WO | WO 12/031744 | 3/2012 |
| WO | WO 12/079000 | 6/2012 |
| WO | WO 12/099973 | 7/2012 |
| WO | WO 12/129514 | 9/2012 |
| WO | WO 12/140130 | 10/2012 |
| WO | WO 12/167192 | 12/2012 |
| WO | WO 13/059593 | 4/2013 |
| WO | WO 13/074916 | 5/2013 |
| WO | WO 13/123061 | 8/2013 |
| WO | WO 13/126733 | 8/2013 |
| WO | WO 13/154760 | 10/2013 |
| WO | WO 13/177533 | 11/2013 |
| WO | WO 13/178635 | 12/2013 |
| WO | WO 14/031687 | 2/2014 |
| WO | WO 14/039044 | 3/2014 |
| WO | WO 14/055657 | 4/2014 |
| WO | WO 14/055668 | 4/2014 |
| WO | WO 14/139672 | 9/2014 |
| WO | WO 14/153270 | 9/2014 |
| WO | WO 15/066551 | 5/2015 |
| WO | WO 15/075468 | 5/2015 |
| WO | WO 15/092024 | 6/2015 |
| WO | WO 15/105522 | 7/2015 |
| WO | WO 15/142675 | 9/2015 |

(56) References Cited

FOREIGN PATENT DOCUMENTS

| WO | WO 15/157399 | 10/2015 |
|---|---|---|
| WO | WO 15/157432 | 10/2015 |

OTHER PUBLICATIONS

Kacherovsky et al., "Combination of Sleeping Beauty transposition and chemically induced dimerization selection for robust production of engineered cells". Nucleic Acids Res. Jun. 2012 ;40(11):e85 (Year: 2012).*
Nakazawa et al., May 2009, 231. Expression of multiple transgenes in human T cells from PiggyBac transposons, Molecular Therapy, 17(Suppl 1):S91.
Ahmed et al., "Regression of experimental medulloblastoma following transfer of HER2-specific T cells," Cancer Res. (Jun. 15, 2007) 67(12):5957-64.
Ahmed, Nabil, "CMV-specific Cytotoxic T Lymphocytes Expressing CAR Targeting HER2 in Patients With GBM (HERT-GBM)," ClinicalTrials.gov Identifier: NCT01109095 (Apr. 22, 2010) pp. 1-8.
Ahmed, Nabil, "Her2 Chimeric Antigen Receptor Expressing T Cells in Advanced Sarcoma," ClinicalTrials.gov Identifier: NCT00902044 (May 14, 2009) pp. 1-11.
Altschul et al., "Local Alignment Statistics, [27] Multiple Alignment and Phylogenetic Trees," Methods in Enzymology (1996) 266:460-480.
Bejcek et al. "Development and Characterization of Three Recombinant Single Chain Antibody Fragments (scFvs) Directed against the CD19 Antigen," Cancer Res (1995) 55:2346-2351.
Brentjens et al: "CD19-targeted T cells rapidly induce molecular remissions in adults with chemotherapy-refractory acute lymphoblastic leukemia", Science Translational Medicine, 5(177), Mar. 20, 2013.
Budde et al., "Combining a CD20 Chimeric Antigen Receptor and an Inducible Caspase 9 Suicide Switch to Improve the Efficacy and Safety of T Cell Adoptive Immunotherapy for Lymphoma", PLoS One (2013) 8(12): e82742. https://doi.org/10.1371/journal.pone.0082742.
Cartellieri et al., "A Novel Ex Vivo Isolation and Expansion Procedure for Chimeric Antigen Receptor Engrafted Human T Cells," PLoS One (Apr. 3, 2014) vol. 9, No. 4, e93745, pp. 1-12.
Cha et al., "IL-7 + IL-15 are superior to IL-2 for the ex vivo expansion of 4T1 mammary carcinoma-specific T cells with greater efficacy against tumors in vivo," Breast Cancer Research and Treatment, Springer, NY, US (Oct. 14, 2009) vol. 122, No. 2, pp. 359-369.
Chen et al., "Ex vivo expansion of dendritic-cell-activated antigen-specific CD4+ T cells with anti-CD3/CD28, interleukin 7, and interleukin-15: Potential for adoptive T-cell immunotherapy," Clinical Immunology (2006) vol. 119, pp. 21-31.
Chen et al., "Minicircle DNA vectors devoid of bacterial DNA result in persistent and high-level transgene expression in vivo", Mol Ther. (2003) 8(3), 495-500.
Chen et al: "Fusion Protein Linkers: Property, Design and Functionality", Adv Drug Deliv Rev., Oct. 15, 2013; 65(10), pp. 1357-1369.
Cho et al., "Structure of the extracellular region of HER2 alone and in complex with the Herceptin Fab", Nature (Feb. 13, 2003) 421(6924):756-760.
Converse et al: "Counterselection and Co-Delivery of Transposon and Transposase Functions for Sleeping Beauty-Mediated Transposition in Cultured Mammalian Cells", Bioscience Reports, Kluwer Academic Publishers-Plenum Publishers, NE (Dec. 1, 2004) vol. 24, No. 6, pp. 577-594.
Crewe et al., "Metabolism of Tamoxifen by recombinant human cytochrome P-450 enzymes: Formation of the 4-hydroxy, 4'-hydroxy and N-desmethyl metabolites and isomerization of trans-4-hydroxytamoxifen,"Drug Metab Dispos (2002) 30(8): 869-874,.
Database Geneseq [Online] May 5, 2005 (May 5, 2005 ), "Human splice variant protein expressed in ovary cells DEX0487 002.orf.

4.", XP002771301, retrieved from EBI accession No. GSP:ADY30515. Database accession No. ADY30515 ; & WO 2005/017102 A2 (Diadexus Inc [US]; Macina Roberto A [US]; Turner Leah R [US]; Sun Yong) Feb. 24, 2005 (Feb. 24, 2005).
Database UniProt [Online] Oct. 3, 2012 (Oct. 3, 2012), "SubName: Full=Receptor tyrosine-protein kinase erbB-2 {ECO: 00003131Ensembl:ENSP00000464252}; Flags: Fragment;", XP002771300, retrieved from EBI accession No. UNIPROT:J3QRJ7 Database accession No. J3QRJ7.
Dotti, Gianpietro, et al. "Design and development of therapies using chimeric antigen recepto-expressing T cells." Immunological reviews 257.1 (2014): 107-126.
Ercikan-Abali et al., "Active Site-Directed Double Mutants of Dihydrofolate Reductase," Cancer Res., (1996) vol. 56, No. 18, pp. 4142-4145.
Gallinari et al., "A Functionally Orthogonal Estrogen Receptor-Based Transcription Switch Specifically Induced by a Nonsteroid Synthetic Ligand." Chemistry and Biology (Aug. 1, 2005) vol. 12, No. 8, pp. 883-893.
Gargett et al., "Different cytokine and stimulation conditions influence the expansion and immune phenotype of third-generation chimeric antigen receptor T cells specific for tumor antigen GD2," Cytotherapy (2015) 17.4: 487-495.
Garrett et al., "Novel engineered trastuzumab conformational epitopes demonstrate in vitro and in vivo antitumor properties against HER-2/neu," The Journal of Immunology (Jun. 1, 2007) 178:7120-7131.
Giry-Laterriere et al. "Polyswitch lentivectors: 'all-in-one' lentiviral vectors for drug-inducible gene expression, live selection, and recombination cloning, *Human Gene Therapy*", Oct. 2011, 22:1255-1267.
Godiska et al., "Linear plasmid vector for cloning of repetitive or unstable sequences in *Excherichia coli*," (Dec. 29, 2009) Nuc Acids Res, vol. 38, No. 6, e88, pp. 1-9.
Gottschalk, Stephen, "Her2 and TGFBeta CTLs in Treatment of Her2 Positive Malignancy (HERCREEM)", ClinicalTrials.gov Identifier: NCT00889954 (Apr. 29, 2009) pp. 1-9.
Grada et al., "TanCAR: A Novel Bispecific Chimeric Antigen Receptor for Cancer Immunotherapy", Mol Ther Nucleic Acids, (Jul. 9, 2013) 2:e105. doi: 10.1038/mtna.2013.32.
Han Weidong, "Treatment of Chemotherapy Refractory Human Epidermal growth Factor Receptor-2(HER-2) Positive Advanced Solid Tumors (CART-HER-2)", (Sep. 5, 2013) ClinicalTrials.gov Identifier: NCT01935843, pp. 1-7.
Holtkamp et al., "Modification of antigen-encoding RNA increases stability, translational efficacy, and T-cell stimulatory capacity of dendritic cells," Blood (Oct. 28, 2014), 2006/108:509-4017.
Hong et al., "Diverse solid tumors expressing a restricted epitope of L1-CAM can be targeted by chimeric antigen receptor redirected T lymphocytes," J Immunotherapy (2014) vol. 37, No. 2, pp. 93-104.
Hudecek et al. Receptor affinity and extracellular domain modifications affect tumor recognition by ROR1-specific chimeric antigen receptor T-cells. Clin Cancer Res. Jun. 15, 2013; 19(12): 3153-3164.
Hudecek et al., Nov. 16, 2012, The Non-Signaling Extracellular Spacer Domain of CD19-Specific Chimeric Antigen Receptors Is Decisive for in Vivo Anti-Tumor Activity, Blood, 120(21):951, 3 pp.
Huls et al., "First Clinical Trials Employing Sleeping Beauty Gene Transfer System and Artificial Antigen Presenting Cells to Generate and Infuse T Cells Expressing CD19-Specific Chimeric Antigen Receptor," Blood (2013) 122:166-166.
Jensen et al., "Designing chimeric antigen receptors to effectively and safely target tumors," Curr Opin Immunol. (Apr. 2015) 33:9-15.
Johansen et al., "Evaluation of Tet-on system to avoid transgene down-regulation in ex vivo gene transfer to the CNS," Gene Therapy (2002) 9:1291-1301.
Johnston et al. "Regulated expression of erythropoietin from an AAV vector safely improves the anemia of beta-thalassemia in a mouse model," Mol Ther. Apr. 1, 2003, 7(4):493-497.
Jonnalagadda et al., "Efficient selection of genetically modified human T cells using methotrexate-resistant human dihydrofolate reductase," Gene Therapy, vol. 20, No. 8, Jan. 10, 2013, pp. 853-860.

(56) References Cited

OTHER PUBLICATIONS

Kacherovsky et al., "Combination of Sleeping Beauty transposition and chemically induced dimerization selection for robust production of engineered cells," Nucleic Acids Research (2012) 49(11):e85.
Kacherovsky et al., "Multiplexed 1-16 gene transfer to a human T-cell line by combining Sleeping Beauty transposon system with methotrexate selection", Biotechnology and Bioengineering (Jul. 23, 2015) vol. 112, No. 7, pp. 1429-1436.
Kay et al, "A robust system for production of minicircle DNA vectors",12, Nov. 21, 2010, pp. 1287-1289.
Klebanoff et al., "IL-15 enhances the in vivo antitumor activity of tumor-reactive CD8+ T Cells," PNAS (Feb. 17, 2004) vol. 101, No. 7, pp. 1969-1974.
Kowolik et al., "CD28 costimulation provided through a CD19-specific chimeric antigen receptor enhances in vivo persistence and antitumor efficacy of adoptively transferred T cells," Cancer Res. (2006) 66(22):10995-11004.
Kunkele et al., "Functional Tuning of CARs Reveals Signaling Threshold above which CD8+ CTL Antitumor Potency is Attenuated Due to Cell Fas-FasL-Dependent AICD," Cancer Immunol Res. (Jan. 9, 2015) vol. 3, No. 4, pp. 368-379.
Lemaigre et al., "Transcriptional control of genes that regulate glycolysis and gluconeogenesis in adult liver," Biochem. J. (1994) 303:1-14.
Leung et al., "Luminescent detection of DNA-binding proteins," Nuc Acids Res (2012) 40(3): 941-955.
Likar et al., "Using a mutated variant human deoxycytidine-kinase as a reporter gene for assessing adoptive T-cell therapy," Questions hematology, oncology and immunopathology in pediatrics (2012) vol. 11, No. 2, pp. 23-31. (Russian Language).
Littlewood et al., "A modified oestrogen receptor ligand-binding domain as an improved switch for the regulation of heterologous proteins," Nucleic Acids Res (May 25, 1995) 23(10):1686-1690.
Litvinova et al., "The influence of immunoregulatory cytokines IL-2, IL-7, and IL-15 upon activation, proliferation, and apoptosis of immune memory T-cells in vitro," Cell and Tissue Biology (Dec. 11, 2013) vol. 7, No. 6, pp. 539-544.
Loeken, Mary R., "Effects of mutation of the CREB binding site of the somatostatin promoter on cyclic AMP responsiveness in CV-1 cells", *Gene Expr.* (1993) 3(3):253-264.
Lupton et al., "Dominant positive and negative selection using a hygromycin phosphotransferase-thymidine kinase fusion gene," Mol Cell Biol. (Jun. 1991) 11(6):3374-3378.
Maher, "Immunotherapy of Malignant Disease Using Chimeric Antigen Receptor Engrafted T Cells", *ISRN Oncology*, vol. 2012, pp. 1-23, Nov. 14, 2012.
Mátés et al., "Molecular evolution of a novel hyperactive Sleeping Beauty transposase enables robust stable gene transfer in vertebrates," Nature Genetics (Jun. 2009) vol. 41, No. 6, pp. 753-761.
McGehee et al., "Differentiation-specific element: a cis-acting developmental switch required for the sustained transcriptional expression of the angiotensinogen gene during hormonal-induced differentiation of 3T3-L1 fibroblasts to adipocytes," Mol. Endocrinol. (Apr. 1993) 7(4):551-560.
Morgan et al., "Case report of a serious adverse event following the administration of T cells transduced with a chimeric antigen receptor recognizing ERBB2," Mol Ther. (Apr. 2010) 18(4):843-51. doi: 10.1038/mt.2010.24. Epub Feb. 23, 2010.
O'Reilly et al., "Identification of an activating transcription factor (ATF) binding site in the human transforming growth factor-beta 2 promoter," J. Biol. Chem. (Oct. 5, 1992) 267:19938-19943.
Papapetrou et al. "Harnessing endogenous miR-181a to segregate transgenic antigen receptor expression in developing versus post-thymic T cells in murine hematopoietic chimeras", The Journal of clinical investigation. Jan. 5, 2009:119(1):157-68.
Park et al., "Adoptive Transfer of Chimeric Antigen Receptor Re-Directed Cytolytic T Lymphocyte Clones in Patients with Neuroblastoma," Mol. Ther. (Apr. 2007) vol. 15, No. 4; pp. 825-833.

Pezutto et al., May 1, 1987, CD19 monoclonal antibody HD37 inhibits anti-immunoglobulin-induced B cell activation and proliferation, The Journal of Immunology, 138(9):2793-2799.
Pollock et al. "Delivery of a stringent dimerizer-regulated gene expression system in a single retroviral vector," Proc Natl Acad Sci. USA Nov. 21, 2000, 97(24):13221-1326.
Promega, "pSP64 Poly(A) Vector Sequence and Map," Technical Bulletin No. 052, Revised May 2000, pp. 1-8.
Riddell et al. "Adoptive therapy with chimeric antigen receptor modified T cells of defined subset composition." Cancer journal (Sudbury, Mass. ) 20.2 (2014): 141-144.
Riddell et al., "Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington," Human Gene Therapy (1992) 3(3):319-338.
Roscilli et al., "Long-term and tight control of gene expression in mouse skeletal muscle by a new hybrid human transcription factor," Molecular Therapy (Nov. 2002) 1;6(5):653-63.
Sadelain et al., "The basic principles of chimeric antigen receptor (CAR) design," Cancer discovery (2013) 3 (4): 388-98. DOI: 10.1158/2159-8290.CD-12-0548.
Schmittgen et al. "Analyzing real-time PCR data by the comparative C(T) method", *Nat Protoc.* 2008;3(6):1101-8.
Sharma et al., "Efficient Sleeping Beauty DNA Transposition from DNA Minicircles," Mol Ther Nuc Acids (2013) 2:e74, 1-10.
Terakura et al., "Generation of CD19-chimeric antigen receptor modified CD8+ T cells derived from virus-specific central memory T cells," Gene Therapy (Oct. 26, 2011) 119(1), pp. 72-82.
Treisman, R. "The SRE: a growth factor responsive transcriptional regulator. (PMID:2133110)", *Seminars in Cancer Biology*, Feb. 1, 1990, 1(1):47-58.
Vigna et al., "Robust and Efficient Regulation of Transgene Expression in Vivo by Improved Tetracycline-Dependent Lentiviral Vectors," Mol. Therapy (2002) 5(3):252-261.
Vogt et al., "Doxycycline-regulated gene expression in the opportunisticfumigatus," BMC Microbiol. (2005) 5(1):11 pages.
Wang et al., "Phenotypic and Functional Attributes of Lentivirus Modified CD19-specific Human CD8+ Central Memory Tcells Manufactured at Clinical Scale," J Immunotherapy (2012) vol. 35, pp. 689-701.
Wang et. al., "A transgene-encoded cell surface polypeptide for selection, in vivo tracking, and ablation of engineered cells", Blood, vol. 118, No. 5, Aug. 4, 2011 (Aug. 4, 2011), pp. 1255-1263.
Weill et al., "Translational control by changes in poly(A) tail length: recycling mRNAs," Nature Structural & Molecular Biology (Jun. 2012) vol. 19, No. 6, pp. 577-585.
Xu et al., "Closely related T-memory stem cells correlate with in vivo expansion of CAR.CD19-T cells and are preserved by IL-7 and IL-15," Blood (Jun. 12, 2014) vol. 123, No. 24, pp. 3750-3759.
Yant et al. "Mutational Analysis of the N-Terminal DNA-Binding Domain of Sleeping Beauty Transposase: Critical Residues for DNA Binding and Hyperactivity in Mammalian Cells," Mol. Cell. Biol. (2004) 24(20):9239-9247.
Ye et al., "Characterization of a silencer regulatory element in the human interferon-gamma promoter," J. Biol. Chem., (Oct. 14, 1994) 269:25728-25734.
Zambon et al., "Increased Expression of the Pro-Apoptotic Protein BIM: A Mechanism for cAMP/PKA-Induced Apoptosis of Immature T Cells," J. Biol. Chem. (2011) 286(38):33260-33267.
Extended European Search Report dated Jul. 17, 2017 in the European Patent Application No. 15776501.7, filed on Oct. 20, 2016.
First Examination Report issued Mar. 1, 2017, received in New Zealand application 725081 filed Oct. 12, 2016.
International Search Report mailed Jul. 10, 2015, received in PCT/US2015/24868 filed Apr. 8, 2015.
Aalberse et al., "IgG4 breaking the rules," Immunology (2002) 105:9-19.
Aertgeerts et al., "Structural analysis of the mechanism of inhibition and allosteric activation of the kinase domain of HER2 protein," Journal of Biological Chemistry (2011) vol. 286, No. 21, p. 18756-18765, Весь ТЕКСТ, с. 18759-18765.

(56) References Cited

OTHER PUBLICATIONS

Berglund et al., "The epitope space of the human proteome," Protein Science (2008) 17:606-613.
Burns et al., 2010, A high molecular weight melanoma-associated antigen-specific chimeric antigen receptor redirects lymphocytes to target human melanomas, Cancer Research, 70(8):3027-3033.
Chen et al., 2013, Fusion protein linkers: property, design and functionality, Advanced Drug Delivery Reviews, 65(10):1357-1369.
Chen et al., Jan. 2007, Generation of a transgenic mouse model with chondrocyte-specific and tamoxifen-inducible expression of cre recombinase, Genesis, 45:44-50.
Chen et al., Sep. 15, 2005, NF-κ-B RelA phosphorylation regulates RelA acetylation, Molecular and Cellular Biology, 25(18):7966-7975.
Circosta et al., "T Cell Receptor (TCR) Gene Transfer with Lentiviral Vectors Allows Efficient Redirection of Tumor Specificity in Naïve and Memory T Cells Without Prior Stimulation of Endogenous TCR," Human Gene Therapy (Nov. 18, 2009) vol. 20, No. 12, pp. 1576-1588.
Courtney et al., 2018, TCR signaling: mechanisms of initiation and propagation, Trends in Biochemical Sciences, 43(2):108-123.
Dolezal et al., 2000, ScFv multimers of the anti-neuraminidase antibody NC10: shortening of the linker in single-chain Fv fragment assembled in VL to VH orientation drives the formation of dimers, trimers, tetramers and higher molecular mass multimers, Protein Engineering, 13(8):565-574.
Edwards et al., 2003, The remarkable flexibility of the human antibody repertoire; isolation of over one thousand different antibodies to a single protein, BLyS, J. Mol. Biol., 334:103-118.
Frankel et al., "Characterization of diphtheria fusion proteins targeted to the human interleukin-3 receptor," Protein engineering (2000) vol. 13, No. 8, p. 575-581.
Gagnon et al., "IL-6, in Synergy with IL-7 or IL-15, Stimulates TCR-Independent Proliferation and Functional Differentiation of CD8+ T Lymphocytes," The Journal of Immunology (2008) 180:7958-7968.
Ghatar et al., "Epitope Mapping of Human HER2 Specific Mouse Monoclonal Antibodies Using Recombinant Extracellular Subdomains," Asian Pacific Journal of Cancer Prevention (2017) 18(11):3103-3110.
Guedan et al., 2018, Enhancing CAR T cell persistence through ICOS and 4-1BB costimulation, JCI Insight, 3(1):11-13.
Guha et al., 2017, Frontline science: functionally impaired geriatric CAR-T cells rescued by increased α5β1 integrin expression, Journal of Leukocyte Biology, 102(2):201-208.
Hege et al., 2017, Safety, tumor trafficking and immunogenicity of chimeric antigen receptor (CAR)-T cells specific for TAG-72 in colorectal cancer, Journal for Immunotherapy of Cancer, 5(1):1-14.
Hudecek et al., Sep. 11, 2014, "The Nonsignaling Extracellular Spacer Domain of Chimeric Antigen Receptors Is Decisive for In Vivo Antitumor Activity", Cancer Immunology Research, 3(2):125-135.
Jensen et al: "Design and implementation of adoptive therapy with chimeric antigen receptor-modified T cells", Immunological Reviews., Special Issue, Dec. 13, 2013 vol. 257, No. 1; 127-144.
Kanamori et al., A human-tissue type whose host is a human cell expression of plasminogen activator, Tissue Culture Research, 8(2):31-39, 1990.
Kochenderfer et al., Accession No. ADM64594.1, FMC63-28Z receptor protein, Jun. 11, 2012, Genbank.
Lin et al., 2009, Optimization and validation of a robust human T-cell culture method for monitoring phenotypic and polyfunctional antigen-specific CD4 and CD8 T-cell responses, Cytotherapy, 11(7):912-922.
Liu et al., "IL-21 synergizes with IL-7 to augment expansion and anti-tumor function of cytotoxic T cells," International Immunology (2007) vol. 19, No. 10, pp. 1213-1221.
Lloyd et al., 2009, Modelling the human immune response: performance of a $10^{11}$ human antibody repertoire against a broad panel of therapeutically relevant antigens, Protein Engineering, Design & Selection 22(3):159-168.
Long et al., 2015, 4-1BB costimulation ameliorates T cell exhaustion induced by tonic signaling of chimeric antigen receptors, Nature Medicine, 21(6):581-590.
Maeda et al., 1997, Engineering of functional chimeric protein G—Vargula Luciferase, Analytical Biochemistry, 249(2):147-152.
Maus et al., 2013, T cells expressing chimeric antigen receptors can cause anaphylaxis in humans, Cancer Immunology Research, 1(1):26-31.
McKinlay et al., "Blood monocytes, myeloid dendritic cells and the cytokines interleukin (IL)-7 and IL-15 maintain human CD4+ T memory cells with mixed helper/regulatory function," Immunology (2006) vol. 120, pp. 392-403.
Muftuoglu et al., "CD161 Expression Identifies a Distinct Subset of Drug-Effluxing Viral-Specific Memory CD4+ T Cells That Preferentially Survive Cytotoxic Chemotherapy," Blood (2012) 122(21):2024.
Pakula et al., "Genetic analysis of protein stability and function," Annual review of genetics (1989) vol. 23, No. 1, p. 289-310, c.305-306.
Pelloquin et al., Dec. 1986, Human B lymphocytes immortalization by Epstein-Barr virus in the presence of cyclosporin A, In Vitro Cell Dev Biol, 22(12):689-694.
Richman et al., 2018, High-affinity GD2-specific CAR T cells induce fatal encephalitis in a preclinical neuroblastoma model, Cancer Immunology Research, 6(1):36-46.
Robinsons et al., Jan. 1991, Metabolites, pharmacodynamics, and pharmacokinetics of tamoxifen in rats and mice compared to the breast cancer patient, Drug Metab Dispos, 19(1):36-43.
Sadelain et al., 2009, The promise and potential pitfalls of chimeric antigen receptors, Current Opinion in Immunology, 21:215-223.
Schamel et al., 2019, The TCR is an allosterically regulated macromolecular machinery changing its conformation while working, Immunological Reviews, 291(1):8-25.
Sengupta et al., "Interleukin-13 Receptor Alpha 2-Targeted Glioblastoma Immunotherapy," BioMed Research International, (Aug. 27, 2014) vol. 2014, Article ID: 952128, pp. 1-8.
Surh et al., "Homeostasis of memory T cells," Immunological Reviews (2006) vol. 211, pp. 154-163.
Teplyakov et al., 2014, Antibody modeling assessment II. Structures and models, Proteins: Structure, Function, and Bioinformatics, 82(8):1563-1582.
Turtle et al., 2016, CD19 CAR-T cells of defined CD4+: CD8+ composition in adult B cell ALL patients, The Journal of Clinical Investigation, 126(6):2123-2138.
Wilke et al., Apr. 27, 2012, Dual targeting of ErbB2 and MUC1 in breast cancer using chimeric antigen receptors engineered to provide complementary signaling, Journal of Clinical Immunology, 32(5):1059-1070.
Yang et al., Feb. 16, 2010, Functional interplay between acetylation and methylation of the RelA subunit of NF-κ-B, Molecular and Cellular Biology, 30(9):2170-2180.
Zeng et al., "Synergy of IL-21 and IL-15 in regulating CD8+ T cell expansion and function," JEM (Jan. 3, 2005) vol. 201, No. 1, pp. 139-148.
Zheng, Changyu et al., "All Human EF1 Promoters Are Not Equal: Markedly Affect Gene Expression in Constructs from Different Sources," International Journal of Medical Sciences (2014) 11(5):404-408.
Hu et al., 2004, Insufficient p65 phosphorylation at S536 specifically contributes to the lack of NF-κB activation and transformation in resistant JB6 cells, Carcinogenesis, 25(10):1991-2003.
Majowicz et al., 2012, Murine CD4+ CD25-cells activated in vitro with PMA/ionomycin and anti-CD3 acquire regulatory function and ameliorate experimental colitis in vivo, BMC Gastroenterology, 12:1-9.
Badri et al., 2016, Optimization of radiation dosing schedules for proneural glioblastoma, J Math Bio, 72(5):1301-1336.
Baylot et al., 2017, TCTP Has a Crucial Role in the Different Stages of Prostate Cancer Malignant Progression, Results Probl Cell Differ, 64:255-261.

(56) References Cited

OTHER PUBLICATIONS

Dolgikh et al., 2013, Heterologous expression of the extracellular domain of the HER2 receptor in bacteria, Scientific notes of St. Petersburg State Medical University named after. I. P. Pavlova, 20(4):70-73.

Jost et al., 2013, Structural basis for eliciting a cytotoxic effect in HER2-overexpressing cancer cells via binding to the extracellular domain of HER2, Structure, 21(11):1979-1991.

Kim et al, 2007, Efficiency of the Elongation Factor-1alpha Promoter in Mammalian Embryonic Stem Cells Using Lentiviral Gene Delivery Systems, Stem Cells and Development, 16:537-545.

Olsen et al., Feb. 2013, Pitfalls in determining the cytokine profile of human T cells, Journal of Immunological Methods, 390:106-112.

Pan et al., 2022, CAR race to cancer immunotherapy: from CAR T, CAR NK to CAR macrophage therapy, J Exp Clin Cancer Res, 41(1):119.

Sentman, Aug. 1, 0213, Challenges of creating effective chimeric antigen receptors for cancer therapy, Immunotherapy 5(8):783-785.

\* cited by examiner

Amaxa electroporation 1-2 hours after thawing PBMC

- SB100X:
  - DNA (5 or 10ug)
- Transposons (10ug)
  - GFP

EXP-14-CV4715_Transact and SB100X

- mcGFP:SB - both ratios similar
- >90% GFP positive after 1 week
- Minimal difference in MFI for 50 versus 100 nM MTX EXP-14-CV4715_Transact and SB100X 2014-12-15_SBFP_d14

LHOROW-EXP-14-CV4717_248481-SB100X RNA and multiplex electroporation

20141414_58FPd14_50_L_040.fcs
Live cells
7212

- DNA-lower concentration lower efficiency but better growth.
- RNA-higher concentration higher efficiency and MFI, similar growth.
- DNA higher initial efficiency than RNA, higher MFI.
- → try higher RNA concentrations? SB100X toxicity?

- DNA-lower concentration lower efficiency but better growth.
- RNA-higher concentration higher efficiency and MFI, similar growth.
- DNA higher initial efficiency than RNA, higher MFI.
- → try higher RNA concentrations? SB100X toxicity?

20141414_SBCARd14_50_C_026.fcs
Live cells
4138

20141414_SBCARd14_50_H_027.fcs
Live cells
1921

20141414_SBCARd14_0_I_025.fcs
Live cells
8455

20141414_SBCARd14_50_M_030.fcs
Live cells
2572

LHOROW-EXP-14-CV4717_248481-SB100X RNA and multiplex electroporation

- DNA-lower concentration better growth.
- RNA-higher concentration better expression,
  lower concentration better growth initially--- too few + cells/well
- DNA better than RNA
- → try higher RNA concentrations? SB100X toxicity?

MTX enrichment for positive cells. For multiple copies? NO-higher MTX?

SEQUENCE LISTING

<160> NUMBER OF SEQ ID NOS: 7

<210> SEQ ID NO 1
<211> LENGTH: 352
<212> TYPE: DNA
<213> ORGANISM: Artificial Sequence
<220> FEATURE:
<223> OTHER INFORMATION: Synthetic DNA transposon of copied inverted
      repeat in description from Tanichthys albonubes

<400> SEQUENCE: 1
cagttgaagt cggaagttta catacactta agttggagtc attaaaactc gtttttcaac      60
tactccacaa atttcttgtt aacaaacaat agttttggca agtcagttag gacatctact     120
ttgtgcatga cacaagtcat ttttccaaca attgtttaca gacagattat ttcacttata     180
attcactgta tcacaattcc agtgggtcag aagtttacat acactaagtt gactgtgcct     240
ttaaacagct tggaaaattc cagaaaatga tgtcatggct ttagaagctt ctgatagact     300
aattgacatc atttgagtca attggaggtg tacctgtgga tgtatttcaa gg             352

<210> SEQ ID NO 2
<211> LENGTH: 564
<212> TYPE: DNA
<213> ORGANISM: Artificial Sequence
<220> FEATURE:
<223> OTHER INFORMATION: Human protein with dihydrofolate reductase
      double mutation

<400> SEQUENCE: 2
atggttggtt cgctaaactg catcgtcgct gtgtcccaga acatgggcat cggcaagaac      60
ggggacttcc cctggccacc gctcaggaat gaatccagat atttccagag aatgaccaca     120
acctcttcag tagaaggtaa acagaatctg gtgattatgg gtaagaagac ctggttctcc     180
attcctgaga agaatcgacc tttaaagggt agaattaatt tagttctcag cagagaactc     240
aaggaacctc cacaaggagc tcattttctt tccagaagtc tagatgatgc cttaaaactt     300
actgaacaac cagaattagc aaataaagta gacatggtct ggatagttgg tggcagttct     360
gtttataagg aagccatgaa tcacccaggc catcttaaac tatttgtgac aaggatcatg     420
caagactttg aaagtgacac gttttttcca gaaattgatt tggagaaata taaacttctg     480
ccagaatacc caggtgttct ctctgatgtc caggaggaga aaggcattaa gtacaaattt     540
gaagtatatg agaagaatga ttaa                                             564

<210> SEQ ID NO 3

-continued

```
<211> LENGTH: 187
<212> TYPE: PRT
<213> ORGANISM: Artificial Sequence
<220> FEATURE:
<223> OTHER INFORMATION: Human protein with dihydrofolate reductase
      double mutation

<400> SEQUENCE: 3
```

Met Val Gly Ser Leu Asn Cys Ile Val Ala Val Ser Gln Asn Met Gly
1               5                   10                  15

Ile Gly Lys Asn Gly Asp Phe Pro Trp Pro Leu Arg Asn Glu Ser
            20                  25                  30

Arg Tyr Phe Gln Arg Met Thr Thr Thr Ser Ser Val Glu Gly Lys Gln
            35                  40                  45

Asn Leu Val Ile Met Gly Lys Lys Thr Trp Phe Ser Ile Pro Glu Lys
50                  55                  60

Asn Arg Pro Leu Lys Gly Arg Ile Asn Leu Val Leu Ser Arg Glu Leu
65                  70                  75                  80

Lys Glu Pro Pro Gln Gly Ala His Phe Leu Ser Arg Ser Leu Asp Asp
                85                  90                  95

Ala Leu Lys Leu Thr Glu Gln Pro Glu Leu Ala Asn Lys Val Asp Met
            100                 105                 110

Val Trp Ile Val Gly Gly Ser Ser Val Tyr Lys Glu Ala Met Asn His
        115                 120                 125

Pro Gly His Leu Lys Leu Phe Val Thr Arg Ile Met Gln Asp Phe Glu
    130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Asp Val Gln Glu Glu Lys Gly Ile
                165                 170                 175

Lys Tyr Lys Phe Glu Val Tyr Glu Lys Asn Asp
            180                 185

```
<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
acaagatcat ccgcagcaac                                             20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ttgaagtgca tgtggctgtc                                             20

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
```

```
acaactttgg tatcgtggaa gg                                              22

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
gccatcacgc cacagtttc                                                  19
```

PRODUCTION OF ENGINEERED T-CELLS BY SLEEPING BEAUTY TRANSPOSON COUPLED WITH METHOTREXATE SELECTION

CROSS-REFERENCE TO RELATED APPLICATIONS

This application is a division of U.S. application Ser. No. 15/302,449, filed Oct. 6, 2016 which is a U.S. National Phase Application of PCT Int. App. No. PCT/US2015/024868 filed on Apr. 8, 2015 which claims the benefit of priority to U.S. Prov. App. No. 62/058,973, filed Oct. 2, 2014, U.S. Prov. App. No. 61/977,751, filed Apr. 10, 2014, U.S. Prov. App. No. 61/986,479, filed Apr. 30, 2014, U.S. Prov. App. No. 62/089,730 filed Dec. 9, 2014, U.S. Prov. App. No. 62/090,845, filed Dec. 11, 2014, and U.S. Prov. App. No. 62/088,363, filed Dec. 5, 2014 which are each expressly incorporated by reference in its entirety.

REFERENCE TO SEQUENCE LISTING

The present application is being filed along with a Sequence Listing in electronic format. The Sequence Listing is provided as a file entitled SCRI077D1SEQ.TXT, created Nov. 11, 2020, which is approximately 4 Kb in size. The information in the electronic format of the Sequence Listing is incorporated herein by reference in its entirety.

FIELD OF THE INVENTION

Aspects of the invention described herein include methods of treating, inhibiting, ameliorating and/or eliminating a virus or cancer cells in a subject utilizing genetically engineered human T-cells having receptors for a molecule presented by the virus or the cancer cells.

BACKGROUND OF THE INVENTION

Engineered human T-cells are a promising therapeutic route for cancer immunotherapy and viral therapy. T-cells expressing chimeric antigen receptors combined with additional genes to enhance T-cell proliferation, survival, or tumor homing can further improve efficacy but require multiple stable gene transfer events. Accordingly, methods are needed to increase production efficiency for multiplexed engineered cells. Efficient, stable transduction of T-cells can be achieved using a Sleeping Beauty transposon system in minicircles that are introduced by nucleofection. Rapid selection of transduced cells with methotrexate (MTX) for cells expressing a mutant dihydrofolate reductase (DHFRdm) resistant to metabolic inhibition can also be achieved.

SUMMARY OF THE INVENTION

Described herein are approaches for the preferential amplification of T cells expressing multiple transgenes, preferably encoding receptors or chimeric receptors specific for a molecule presented by a virus or a cancer cell. In some alternatives, selection pressure on transformed T cells is applied in a two-stage MTX selection utilizing increasing concentrations of MTX.

In one alternative, a gene delivery polynucleotide for stable insertion of a nucleic acid into an oligonucleotide is provided, wherein the nucleic acid for insertion is flanked by inverted terminal repeat gene sequences in the gene delivery polynucleotide and wherein the gene delivery polynucleotide is selectable is provided, wherein the gene delivery polynucleotide comprises a first sequence, wherein the first sequence comprises a first inverted terminal repeat gene sequence, a second sequence, wherein the second sequence comprises a second inverted terminal repeat gene sequence, a third sequence, wherein the third sequence comprises a promoter region sequence, a fourth sequence, wherein the fourth sequence comprises at least one gene encodes a protein or encodes a sequence for mRNA transcription, and wherein the fourth sequence is optimized, a fifth sequence, wherein the fifth sequence comprises at least one selectable marker cassette encoding a double mutant of dihydrofolate reductase, wherein the double mutant of dihydrofolate reductase has a 15,000 fold or about 15,000 fold reduced affinity for methotrexate, wherein the methotrexate can be used to select for cells transduced with the gene delivery polynucleotide to enhance the ratio of cells expressing the at least one gene and wherein the fifth sequence is optimized, a sixth sequence, wherein the sixth sequence comprises a first attachment site (attP) and a seventh sequence, wherein the seventh sequence comprises a second attachment site (attB) wherein each of the first sequence, second sequence, third sequence, fourth sequence, fifth sequence, sixth sequence, and seventh sequence have a 5' terminus and a 3 terminus, and wherein the 3' terminus of the first sequence comprising the first inverted terminal repeat gene sequence is adjacent to the 5' terminus of the third sequence, the 3' terminus of the third sequence is adjacent to the 5' terminus of the fourth sequence, the 3' terminus of the fourth sequence is adjacent to the 5' terminus of the fifth sequence and the 3' terminus of the fifth sequence is adjacent to the 5' terminus of the second sequence comprising a second inverted terminal repeat. In some alternatives, the gene encoding the double mutant of human dihydrofolate reductase comprises the DNA sequence:

(SEQ ID NO: 2)
ATGGTTGGTTCGCTAAACTGCATCGTCGCTGTGTCCCAGAACATGGGCAT

CGGCAAGAACGGGGACTTCCCCTGGCCACCGCTCAGGAATGAATCCAGAT

ATTTCCAGAGAATGACCACAACCTCTTCAGTAGAAGGTAAACAGAATCTG

GTGATTATGGGTAAGAAGACCTGGTTCTCCATTCCTGAGAAGAATCGACC

TTTAAAGGGTAGAATTAATTTAGTTCTCAGCAGAGAACTCAAGGAACCTC

CACAAGGAGCTCATTTTCTTTCCAGAAGTCTAGATGATGCCTTAAAACTT

ACTGAACAACCAGAATTAGCAAATAAAGTAGACATGGTCTGGATAGTTGG

TGGCAGTTCTGTTTATAAGGAAGCCATGAATCACCCAGGCCATCTTAAAC

TATTTGTGACAAGGATCATGCAAGACTTTGAAAGTGACACGTTTTTTCCA

GAAATTGATTTGGAGAAATATAAACTTCTGCCAGAATACCCAGGTGTTCT

CTCTGATGTCCAGGAGGAGAAAGGCATTAAGTACAAATTTGAAGTATATG

AGAAGAATGATTAA.

In some alternatives, the double mutant of human dihydrofolate reductase comprises the protein sequence:

(SEQ ID NO: 3)
MVGSLNCIVA VSQNMGIGKN GDFPWPPLRN ESRYFQRMTT

TSSVEGKQNL VIMGKKTWFS IPEKNRPLKG RINLVLSREL

-continued

```
KEPPQGAHFL SRSLDDDALKL TEQPELANKV DMVWIVGGSS

VYKEAMNHPG HLKLFVTRIM QDFESDTFFP EIDLEKYKLL

PEYPGVLSDV QEEKGIKYKF EVYEKND.
```

In some alternatives, the gene delivery polynucleotide is circular. In some alternatives, the gene delivery polynucleotide is at least 1 kB to 5 kB. In some alternatives, the gene delivery polynucleotide is a minicircle. In some alternatives, the promoter region comprises an EF1 promoter sequence. In some alternatives, the fourth sequence comprises one, two, three, four, or five genes that encode proteins. In some alternatives, the fourth sequence is codon optimized to reduce the total GC/AT ratio of the fourth sequence. In some alternatives, the fourth sequence is optimized by codon optimization for expression in humans. In some alternatives, the fourth sequence is a consensus sequence generated from a plurality of nucleic acids that encode a plurality of related proteins. In some alternatives, the fourth sequence is a consensus sequence generated from a plurality of nucleic acids that encode a plurality of related proteins, such as a plurality of antibody binding domains, which are specific for the same epitope. In some alternatives, the plurality of related proteins comprise a plurality of antibody binding domains, wherein the plurality of antibody binding domains are specific for the same epitope. In some alternatives, the fifth sequence is codon optimized for expression in humans and/or to reduce the total GC/AT ratio of the fifth sequence. In preferred alternatives, the fifth sequence is optimized by codon optimization for expression in humans. In some alternatives, the protein is a protein for therapy. In some alternatives, the codon optimization and/or a consensus sequence is generated by comparing the variability of sequence and/or nucleobases utilized in a plurality of related sequences. In some alternatives, the protein comprises an antibody or a portion thereof, which may be humanized. In some alternatives, the double mutant of dihydrofolate reductase comprises amino acid mutations of L22F and F31S. In some alternatives, the T cells are precursor T cells. In some alternatives, the precursor T cells are hematopoietic stem cells.

In some alternatives, a method of generating engineered multiplexed T-cells for adoptive T-cell immunotherapy is provided, wherein the method comprises providing a gene delivery polynucleotide, introducing the gene delivery polynucleotide into a T-cell, providing a vector encoding a Sleeping Beauty transposase, introducing the vector encoding the Sleeping Beauty transposase into the T-cell, selecting the cells comprising the gene delivery polynucleotide wherein selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range and isolating the T-cells expressing a phenotype under selective pressure. In some alternatives, the gene delivery polynucleotide comprises a first sequence, wherein the first sequence comprises a first inverted terminal repeat gene sequence, a second sequence, wherein the second sequence comprises a second inverted terminal repeat gene sequence, a third sequence, wherein the third sequence comprises a promoter region sequence, a fourth sequence, wherein the fourth sequence comprises at least one gene encoding a protein, and wherein the fourth sequence is optimized, a fifth sequence, wherein the fifth sequence comprises at least one selectable marker cassette encoding a double mutant of dihydrofolate reductase, wherein the double mutant of dihydrofolate reductase has a 15,000 fold or about 15,000 fold reduced affinity for methotrexate, wherein the methotrexate can be used as a selection mechanism to selectively amplify cells transduced with the gene delivery polynucleotide and wherein the fifth sequence is optimized, a sixth sequence, wherein the sixth sequence comprises a first attachment site (attP) and a seventh sequence, wherein the seventh sequence comprises a second attachment site (attB) wherein each of the first sequence, second sequence, third sequence, fourth sequence, fifth sequence, sixth sequence, and seventh sequence have a 5' terminus and a 3 ' terminus, and wherein the 3' terminus of the first sequence comprising the first inverted terminal repeat gene sequence is adjacent to the 5' terminus of the third sequence, the 3' terminus of the third sequence is adjacent to the 5' terminus of the fourth sequence, the 3' terminus of the fourth sequence is adjacent to the 5' terminus of the fifth sequence and the 3' terminus of the fifth sequence is adjacent to the 5' terminus of the second sequence comprising a second inverted terminal repeat. In some alternatives, the gene encoding the double mutant of human dihydrofolate reductase comprises the DNA sequence:

```
                                      (SEQ ID NO: 2)
ATGGTTGGTTCGCTAAACTGCATCGTCGCTGTGTCCCAGAACATGGGCAT

CGGCAAGAACGGGGACTTCCCCTGGCCACCGCTCAGGAATGAATCCAGAT

ATTTCCAGAGAATGACCACAACCTCTTCAGTAGAAGGTAAACAGAATCTG

GTGATTATGGGTAAGAAGACCTGGTTCTCCATTCCTGAGAAGAATCGACC

TTTAAAGGGTAGAATTAATTTAGTTCTCAGCAGAGAACTCAAGGAACCTC

CACAAGGAGCTCATTTTCTTTCCAGAAGTCTAGATGATGCCTTAAAACTT

ACTGAACAACCAGAATTAGCAAATAAAGTAGACATGGTCTGGATAGTTGG

TGGCAGTTCTGTTTATAAGGAAGCCATGAATCACCCAGGCCATCTTAAAC

TATTTGTGACAAGGATCATGCAAGACTTTGAAAGTGACACGTTTTTTCCA

GAAATTGATTTGGAGAAATATAAACTTCTGCCAGAATACCCAGGTGTTCT

CTCTGATGTCCAGGAGGAGAAAGGCATTAAGTACAAATTTGAAGTATATG

AGAAGAATGATTAA.
```

In some alternatives, the double mutant of human dihydrofolate reductase comprises the protein sequence:

```
                                      (SEQ ID NO: 3)
MVGSLNCIVA VSQNMGIGKN GDFPWPPLRN ESRYFQRMTT

TSSVEGKQNL VIMGKKTWFS IPEKNRPLKG RINLVLSREL

KEPPQGAHFL SRSLDDALKL TEQPELANKV DMVWIVGGSS

VYKEAMNHPG HLKLFVTRIM QDFESDTFFP EIDLEKYKLL

PEYPGVLSDV QEEKGIKYKF EVYEKND.
```

In some alternatives, the gene delivery polynucleotide is circular. In some alternatives, the gene delivery polynucleotide is at least 1 kB to 5 kB. In some alternatives, the gene delivery polynucleotide is a minicircle. In some alternatives, the promoter region comprises an EF1 promoter sequence. In some alternatives, the fourth sequence comprises one, two, three, four, or five genes that encode proteins. In some alternatives, the fourth sequence is codon optimized to reduce the total GC/AT ratio of the fourth sequence. In some alternatives, the fourth sequence is optimized by codon optimization for expression in humans. In some alternatives, the fourth sequence is a consensus sequence generated from a plurality of nucleic acids that encode a plurality of related proteins. In some alternatives, the fourth sequence is a consensus sequence generated from a plurality of nucleic acids that encode a plurality of related proteins, such as a plurality of antibody binding domains, which are specific for the same epitope. In some alternatives, the plurality of related proteins comprise a plurality of antibody binding domains, wherein the plurality of antibody binding domains are specific for the same epitope. In some alternatives, the fifth sequence is codon optimized to reduce the total GC/AT ratio of the fifth sequence. In some alternatives, the fifth sequence is optimized by codon optimization for expression in humans. In some alternatives, the protein is a protein for therapy. In some alternatives, the codon optimization and/or consensus sequence is generated by comparing the variability of sequence and/or nucleobases utilized in a plurality of related sequences. In some alternatives, the protein comprises an antibody or a portion thereof, which may be humanized. In some alternatives, the double mutant of dihydrofolate reductase comprises amino acid mutations of L22F and F31S. In some alternatives, the double mutant of dihydrofolate reductase comprises amino acid mutations of L22F and F31S. In some alternatives, the introducing is performed by electroporation. In some alternatives, the selecting is performed by increasing selective pressure through the selective marker cassette. In some alternatives, the selection reagent comprises an agent for selection. In some alternatives, the agent for selection is methotrexate. In some alternatives, the first concentration range is at least 50 nM-100 nM and the second concentration range is at least 75 to 150 nM. In some alternatives, the first concentration is 50 nM, 60 nM, 70 nM, 80 nM, 90 nM, or 100 nM or any concentration that is between a range of concentrations defined by any two of the aforementioned concentrations, and the second concentration range is 75 nM, 80 nM, 90 nM, 100 nM, 110 nM, 120 nM, 130 nM, 140 nM, or 150 nM or any concentration that is between a range of concentrations defined by any two of the aforementioned concentrations. In some alternatives, the first concentration range is at least 75 nM-150 nM and the second concentration range is at least 112.5 nM to 225 nM. In some alternatives, the first concentration is 75 nM, 85 nM, 95 nM, 105 nM, 115 nM, 125 nM, 135 nM, 145 nM, or 150 nM or any concentration that is between a range of concentrations defined by any two of the aforementioned concentrations, and the second concentration range is 112 nM, 122 nM, 132 nM, 142 nM, 152 nM, 162 nM, 172 nM, 182 nM, 192 nM, 202 nM, 212 nM, or 225 nM or any concentration that is between a range of concentrations defined by any two of the aforementioned concentrations. In some alternatives, the first concentration range is at least 300 nM-675 nM and the first concentration range is at least 450 nM to 1012 nM. In some alternatives, the first concentration is 300 nM, 350 nM, 400 nM, 450 nM, 500 nM, 550 nM, 600 nM, 650 nM, or 675 nM or any concentration that is between a range of concentrations defined by any two of the aforementioned concentrations, and the second concentration range is 450 nM, 500 nM, 550 nM, 600 nM, 650 nM, 700 nM, 750 nM, 800 nM, 850 nM, 900 nM, 1000 nM, or 1012 nM or any concentration that is between a range of concentrations defined by any two of the aforementioned concentrations. In some alternatives, the first round of selection comprises exposing the T-cells to the selection agent for 2, 3, 4, 5, 6 or 7 days before the second round of selection. In some alternatives, the second round of selection comprises exposing the T-cells to the selection agent for at least 2, 3, 4, 5, 6, 7, 8, 9, 10, 11, 12, 13, or 14 days or any time that is between a range of times defined by any two of the aforementioned time points before isolation. In some alternatives, the T cells are precursor T cells. In some alternatives, the precursor T cells are hematopoietic stem cells.

In some alternatives, a method of increasing protein production in a T-cell is provided, wherein the method comprises providing a polynucleotide of, introducing the polynucleotide into a cell, providing a vector encoding a Sleeping Beauty transposase, introducing the vector encoding the Sleeping Beauty transposase into the T-cell, selecting the cells comprising the gene delivery polynucleotide wherein selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range and isolating the cells expressing a phenotype under selective pressure. In some alternatives, the gene delivery polynucleotide comprises a first sequence, wherein the first sequence comprises a first inverted terminal repeat gene sequence, a second sequence, wherein the second sequence comprises a second inverted terminal repeat gene sequence, a third sequence, wherein the third sequence comprises a promoter region sequence, a fourth sequence, wherein the fourth sequence comprises at least one gene encoding a protein, and wherein the fourth sequence is optimized, a fifth sequence, wherein the fifth sequence comprises at least one selectable marker cassette encoding a double mutant of dihydrofolate reductase, wherein the double mutant of dihydrofolate reductase has a 15,000 fold or about 15,000 fold reduced affinity for methotrexate, wherein the methotrexate can be used as a selection mechanism to selectively amplify cells transduced with the gene delivery polynucleotide and wherein the fifth sequence is optimized, a sixth sequence, wherein the sixth sequence comprises a first attachment site (attP) and a seventh sequence, wherein the seventh sequence comprises a second attachment site (attB) wherein each of the first sequence, second sequence, third sequence, fourth sequence, fifth sequence, sixth sequence, and seventh sequence have a 5' terminus and a 3 terminus, and wherein the 3' terminus of the first sequence comprising the first inverted terminal repeat gene sequence is adjacent to the 5' terminus of the third sequence, the 3' terminus of the third sequence is adjacent to the 5' terminus of the fourth sequence, the 3' terminus of the fourth sequence is adjacent to the 5' terminus of the fifth sequence and the 3' terminus of the fifth sequence is adjacent to the 5' terminus of the second sequence comprising a second inverted terminal repeat. In some alternatives, the gene encoding the double mutant of human dihydrofolate reductase comprises the DNA sequence:

(SEQ ID NO: 2)
ATGGTTGGTTCGCTAAACTGCATCGTCGCTGTGTCCCAGAACATGGGCAT

CGGCAAGAACGGGGACTTCCCCTGGCCACCGCTCAGGAATGAATCCAGAT

-continued

```
ATTTCCAGAGAATGACCACAACCTCTTCAGTAGAAGGTAAACAGAATCTG

GTGATTATGGGTAAGAAGACCTGGTTCTCCATTCCTGAGAAGAATCGACC

TTTAAAGGGTAGAATTAATTTAGTTCTCAGCAGAGAACTCAAGGAACCTC

CACAAGGAGCTCATTTTCTTTCCAGAAGTCTAGATGATGCCTTAAAACTT

ACTGAACAACCAGAATTAGCAAATAAAGTAGACATGGTCTGGATAGTTGG

TGGCAGTTCTGTTTATAAGGAAGCCATGAATCACCCAGGCCATCTTAAAC

TATTTGTGACAAGGATCATGCAAGACTTTGAAAGTGACACGTTTTTTCCA

GAAATTGATTTGGAGAAATATAAACTTCTGCCAGAATACCCAGGTGTTCT

CTCTGATGTCCAGGAGGAGAAAGGCATTAAGTACAAATTTGAAGTATATG

AGAAGAATGATTAA.
```

In some alternatives, the double mutant of human dihydrofolate reductase comprises the protein sequence:

```
                                          (SEQ ID NO: 3)
MVGSLNCIVA VSQNMGIGKN GDFPWPPLRN ESRYFQRMTT

TSSVEGKQNL VIMGKKTWFS IPEKNRPLKG RINLVLSREL

KEPPQGAHFL SRSLDDALKL TEQPELANKV DMVWIVGGSS

VYKEAMNHPG HLKLFVTRIM QDFESDTFFP EIDLEKYKLL

PEYPGVLSDV QEEKGIKYKF EVYEKND.
```

In some alternatives, the gene delivery polynucleotide is circular. In some alternatives, the gene delivery polynucleotide is at least 1 kB to 5 kB. In some alternatives, the gene delivery polynucleotide is a minicircle. In some alternatives, the promoter region comprises an EF1 promoter sequence. In some alternatives, the fourth sequence comprises one, two, three, four, or five genes that encode proteins. In some alternatives, the fourth sequence is codon optimized to reduce the total GC/AT ratio of the fourth sequence. In some alternatives, the fourth sequence is optimized by codon optimization for expression in humans. In some alternatives, the fourth sequence is a consensus sequence generated from a plurality of nucleic acids that encode a plurality of related proteins. In some alternatives, the fourth sequence is a consensus sequence generated from a plurality of nucleic acids that encode a plurality of related proteins, such as a plurality of antibody binding domains, which are specific for the same epitope. In some alternatives, the plurality of related proteins comprise a plurality of antibody binding domains, wherein the plurality of antibody binding domains are specific for the same epitope. In some alternatives, the fifth sequence is codon optimized to reduce the total GC/AT ratio of the fifth sequence. In some alternatives, the fifth sequence is optimized by codon optimization for expression in humans. In some alternatives, the protein is a protein for therapy. In some alternatives, the codon optimization and/or consensus sequence is generated by comparing the variability of sequence and/or nucleobases utilized in a plurality of related sequences. In some alternatives, the protein comprises an antibody or a portion thereof, which may be humanized. In some alternatives, the double mutant of dihydrofolate reductase comprises amino acid mutations of L22F and F31S. In some alternatives, the double mutant of dihydrofolate reductase comprises amino acid mutations of L22F and F31S. In some alternatives, the introducing is performed by electroporation. In some alternatives, the selecting is performed by increasing selective pressure through the selective marker cassette. In some alternatives, the selection reagent comprises an agent for selection. In some alternatives, the agent for selection is methotrexate. In some alternatives, the first concentration range is at least 50 nM-100 nM and the second concentration range is at least 75 to 150 nM. In some alternatives, the first concentration is 50 nM, 60 nM, 70 nM, 80 nM, 90 nM, or 100 nM or any concentration that is between a range of concentrations defined by any two of the aforementioned concentrations, and the second concentration range is 75 nM, 80 nM, 90 nM, 100 nM, 110 nM, 120 nM, 130 nM, 140 nM, or 150 nM or any concentration that is between a range of concentrations defined by any two of the aforementioned concentrations. In some alternatives, the first concentration range is at least 75 nM-150 nM and the second concentration range is at least 112.5 nM to 225 nM. In some alternatives, the first concentration is 75 nM, 85 nM, 95 nM, 105 nM, 115 nM, 125 nM, 135 nM, 145 nM, 150 nM or any concentration that is between a range of concentrations defined by any two of the aforementioned concentrations, and the second concentration range is 112 nM, 122 nM, 132 nM, 142 nM, 152 nM, 162 nM, 172 nM, 182 nM, 192 nM, 202 nM, 212 nM, or 225 nM or any concentration that is between a range of concentrations defined by any two of the aforementioned concentrations. In some alternatives, the first concentration range is at least 300 nM-675 nM and the first concentration range is at least 450 nM to 1012 nM. In some alternatives, the first concentration is 300 nM, 350 nM, 400 nM, 450 nM, 500 nM, 550 nM, 600 nM, 650 nM, or 675 nM or any concentration that is between a range of concentrations defined by any two of the aforementioned concentrations, and the second concentration range is 450 nM, 500 nM, 550 nM, 600 nM, 650 nM, 700 nM, 750 nM, 800 nM, 850 nM, 900 nM, 1000 nM, or 1012 nM or any concentration that is between a range of concentrations defined by any two of the aforementioned concentrations. In some alternatives, the first round of selection comprises exposing the T-cells to the selection agent for 2, 3, 4, 5, 6 or 7 days before the second round of selection. In some alternatives, the second round of selection comprises exposing the T-cells to the selection agent for at least 2, 3, 4, 5, 6, 7, 8, 9, 10, 11, 12, 13, or 14 days or any time that is between a range of times defined by any two of the aforementioned time points before isolation. In some alternatives, the T cells are precursor T cells. In some alternatives, the precursor T cells are hematopoietic stem cells.

In some alternatives, an engineered multiplexed T-cell for adoptive T-cell immunotherapy generated by any one of the methods of is provided. In some alternatives, the engineered multiplexed T-cells for adoptive T-cell immunotherapy is generated by a method, wherein the method comprises providing a gene delivery polynucleotide, introducing the gene delivery polynucleotide into a T-cell, providing a vector encoding a Sleeping Beauty transposase, introducing the vector encoding the Sleeping Beauty transposase into the T-cell, selecting the cells comprising the gene delivery polynucleotide wherein selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range and isolating the T-cells expressing a phenotype under selective pressure. In some alternatives, the gene delivery polynucleotide comprises a first sequence, wherein the first sequence comprises a first inverted terminal repeat gene sequence, a second sequence, wherein the second sequence comprises a second inverted terminal repeat gene sequence, a third sequence, wherein the third sequence comprises a promoter region sequence, a fourth sequence, wherein the fourth sequence comprises at least one gene encoding a protein, and wherein the fourth sequence is optimized, a fifth sequence, wherein the fifth sequence comprises at least one selectable marker cassette encoding a double mutant of dihydrofolate reductase, wherein the double mutant of dihydrofolate reductase has a 15,000 fold or about 15,000 fold reduced affinity for methotrexate, wherein the methotrexate can be used as a selection mechanism to selectively amplify cells transduced with the gene delivery polynucleotide and wherein the fifth sequence is optimized, a sixth sequence, wherein the sixth sequence comprises a first attachment site (attP) and a seventh sequence, wherein the seventh sequence comprises a second attachment site (attB) wherein each of the first sequence, second sequence, third sequence, fourth sequence, fifth sequence, sixth sequence, and seventh sequence have a 5' terminus and a 3 terminus, and wherein the 3' terminus of the first sequence comprising the first inverted terminal repeat gene sequence is adjacent to the 5' terminus of the third sequence, the 3' terminus of the third sequence is adjacent to the 5' terminus of the fourth sequence, the 3' terminus of the fourth sequence is adjacent to the 5' terminus of the fifth sequence and the 3' terminus of the fifth sequence is adjacent to the 5' terminus of the second sequence comprising a second inverted terminal repeat. In some alternatives, the gene encoding the double mutant of human dihydrofolate reductase comprises the DNA sequence:

```
                                              (SEQ ID NO: 2)
ATGGTTGGTTCGCTAAACTGCATCGTCGCTGTGTCCCAGAACATGGGCAT

CGGCAAGAACGGGGACTTCCCCTGGCCACCGCTCAGGAATGAATCCAGAT

ATTTCCAGAGAATGACCACAACCTCTTCAGTAGAAGGTAAACAGAATCTG

GTGATTATGGGTAAGAAGACCTGGTTCTCCATTCCTGAGAAGAATCGACC

TTTAAAGGGTAGAATTAATTTAGTTCTCAGCAGAGAACTCAAGGAACCTC

CACAAGGAGCTCATTTTCTTTCCAGAAGTCTAGATGATGCCTTAAAACTT

ACTGAACAACCAGAATTAGCAAATAAAGTAGACATGGTCTGGATAGTTGG

TGGCAGTTCTGTTTATAAGGAAGCCATGAATCACCCAGGCCATCTTAAAC

TATTTGTGACAAGGATCATGCAAGACTTTGAAAGTGACACGTTTTTTCCA

GAAATTGATTTGGAGAAATATAAACTTCTGCCAGAATACCCAGGTGTTCT

CTCTGATGTCCAGGAGGAGAAAGGCATTAAGTACAAATTTGAAGTATATG

AGAAGAATGATTAA.
```

In some alternatives, the double mutant of human dihydrofolate reductase comprises the protein sequence:

```
                                              (SEQ ID NO: 3)
MVGSLNCIVA VSQNMGIGKN GDFPWPPLRN ESRYFQRMTT

TSSVEGKQNL VIMGKKTWFS IPEKNRPLKG RINLVLSREL

KEPPQGAHFL SRSLDDALKL TEQPELANKV DMVWIVGGSS

VYKEAMNHPG HLKLFVTRIM QDFESDTFFP EIDLEKYKLL

PEYPGVLSDV QEEKGIKYKF EVYEKND.
```

In some alternatives, the gene delivery polynucleotide is circular. In some alternatives, the gene delivery polynucleotide is at least 1 kB to 5 kB. In some alternatives, the gene delivery polynucleotide is a minicircle. In some alternatives, the promoter region comprises an EF1 promoter sequence. In some alternatives, the fourth sequence comprises one, two, three, four, or five genes that encode proteins. In some alternatives, the fourth sequence is codon optimized to reduce the total GC/AT ratio of the fourth sequence. In some alternatives, the fourth sequence is optimized by codon optimization for expression in humans. In some alternatives, the fourth sequence is a consensus sequence generated from a plurality of nucleic acids that encode a plurality of related proteins. In some alternatives, the fourth sequence is a consensus sequence generated from a plurality of nucleic acids that encode a plurality of related proteins, such as a plurality of antibody binding domains, which are specific for the same epitope. In some alternatives, the plurality of related proteins comprise a plurality of antibody binding domains, wherein the plurality of antibody binding domains are specific for the same epitope. In some alternatives, the fifth sequence is codon optimized to reduce the total GC/AT ratio of the fifth sequence. In some alternatives, the fifth sequence is optimized by codon optimization for expression in humans. In some alternatives, the protein is a protein for therapy. In some alternatives, the codon optimization and/or consensus sequence is generated by comparing the variability of sequence and/or nucleobases utilized in a plurality of related sequences. In some alternatives, the protein comprises an antibody or a portion thereof, which may be humanized. In some alternatives, the double mutant of dihydrofolate reductase comprises amino acid mutations of L22F and F31S. In some alternatives, the double mutant of dihydrofolate reductase comprises amino acid mutations of L22F and F31S. In some alternatives, the introducing is performed by electroporation. In some alternatives, the selecting is performed by increasing selective pressure through the selective marker cassette. In some alternatives, the selection reagent comprises an agent for selection. In some alternatives, the agent for selection is methotrexate. In some alternatives, the first concentration range is at least 50 nM-100 nM and the second concentration range is at least 75 to 150 nM. In some alternatives, the first concentration is 50 nM, 60 nM, 70 nM, 80 nM, 90 nM, or 100 nM or any concentration that is between a range of concentrations defined by any two of the aforementioned concentrations, and the second concentration range is 75 nM, 80 nM, 90 nM, 100 nM, 110 nM, 120 nM, 130 nM, 140 nM, or 150 nM or any concentration that is between a range of concentrations defined by any two of the aforementioned concentrations. In some alternatives, the first concentration range is at least 75 nM-150 nM and the second concentration range is at least 112.5 nM to 225 nM. In some alternatives, the first concentration is 75 nM, 85 nM, 95 nM, 105 nM, 115 nM, 125 nM, 135 nM, 145 nM, or 150 nM or any concentration that is between a range of concentrations defined by any two of the aforementioned concentrations, and the second concentration range is 112 nM, 122 nM, 132 nM, 142 nM, 152 nM, 162 nM, 172 nM, 182 nM, 192 nM, 202 nM, 212 nM, or 225 nM or any concentration that is between a range of concentrations defined by any two of the aforementioned concentrations. In some alternatives, the first concentration range is at least 300 nM-675 nM and the first concentration range is at least 450 nM to 1012 nM. In some alternatives, the first concentration is 300 nM, 350 nM, 400 nM, 450 nM, 500 nM, 550 nM, 600 nM, 650 nM, or 675 nM or any concentration that is between a range of concentrations defined by any two of the aforementioned concentrations, and the second concentration range is 450 nM, 500 nM, 550 nM, 600 nM, 650 nM, 700 nM, 750 nM, 800 nM, 850 nM, 900 nM, 1000 nM, or 1012 nM or any concentration that is between a range of concentrations defined by any two of the aforementioned concentrations. In some alternatives, the first round of selection comprises exposing the T-cells to the selection agent for 2, 3, 4, 5, 6 or 7 days before the second round of selection. In some alternatives, the second round of selection comprises exposing the T-cells to the selection agent for at least 2, 3, 4, 5, 6, 7, 8, 9, 10, 11, 12, 13, or 14 days or any time that is between a range of times defined by any two of the aforementioned time points before isolation. In some alternatives, the gene delivery polynucleotide comprises a first sequence, wherein the first sequence comprises a first inverted terminal repeat gene sequence, a second sequence, wherein the second sequence comprises a second inverted terminal repeat gene sequence, a third sequence, wherein the third sequence comprises a promoter region sequence, a fourth sequence, wherein the fourth sequence comprises at least one gene encoding a protein, and wherein the fourth sequence is optimized, a fifth sequence, wherein the fifth sequence comprises at least one selectable marker cassette encoding a double mutant of dihydrofolate reductase, wherein the double mutant of dihydrofolate reductase has a 15,000 fold or about 15,000 fold reduced affinity for methotrexate, wherein the methotrexate can be used as a selection mechanism to selectively amplify cells transduced with the gene delivery polynucleotide and wherein the fifth sequence is optimized, a sixth sequence, wherein the sixth sequence comprises a first attachment site (attP) and a seventh sequence, wherein the seventh sequence comprises a second attachment site (attB) wherein each of the first sequence, second sequence, third sequence, fourth sequence, fifth sequence, sixth sequence, and seventh sequence have a 5' terminus and a 3 ' terminus, and wherein the 3' terminus of the first sequence comprising the first inverted terminal repeat gene sequence is adjacent to the 5' terminus of the third sequence, the 3' terminus of the third sequence is adjacent to the 5' terminus of the fourth sequence, the 3' terminus of the fourth sequence is adjacent to the 5' terminus of the fifth sequence and the 3' terminus of the fifth sequence is adjacent to the 5' terminus of the second sequence comprising a second inverted terminal repeat. In some alternatives, the gene encoding the double mutant of human dihydrofolate reductase comprises the DNA sequence:

```
                                      (SEQ ID NO: 2)
ATGGTTGGTTCGCTAAACTGCATCGTCGCTGTGTCCCAGAACATGGGCAT

CGGCAAGAACGGGGACTTCCCCTGGCCACCGCTCAGGAATGAATCCAGAT

ATTTCCAGAGAATGACCACAACCTCTTCAGTAGAAGGTAAACAGAATCTG

GTGATTATGGGTAAGAAGACCTGGTTCTCCATTCCTGAGAAGAATCGACC

TTTAAAGGGTAGAATTAATTTAGTTCTCAGCAGAGAACTCAAGGAACCTC

CACAAGGAGCTCATTTTCTTTCCAGAAGTCTAGATGATGCCTTAAAACTT

ACTGAACAACCAGAATTAGCAAATAAAGTAGACATGGTCTGGATAGTTGG

TGGCAGTTCTGTTTATAAGGAAGCCATGAATCACCCAGGCCATCTTAAAC

TATTTGTGACAAGGATCATGCAAGACTTTGAAAGTGACACGTTTTTTCCA

GAAATTGATTTGGAGAAATATAAACTTCTGCCAGAATACCCAGGTGTTCT

CTCTGATGTCCAGGAGGAGAAAGGCATTAAGTACAAATTTGAAGTATATG

AGAAGAATGATTAA.
```

In some alternatives, the double mutant of human dihydrofolate reductase comprises the protein sequence:

```
                                      (SEQ ID NO: 3)
MVGSLNCIVA VSQNMGIGKN GDFPWPPLRN ESRYFQRMTT

TSSVEGKQNL VIMGKKTWFS IPEKNRPLKG RINLVLSREL

KEPPQGAHFL SRSLDDALKL TEQPELANKV DMVWIVGGSS

VYKEAMNHPG HLKLFVTRIM QDFESDTFFP EIDLEKYKLL

PEYPGVLSDV QEEKGIKYKF EVYEKND.
```

In some alternatives, the gene delivery polynucleotide is circular. In some alternatives, the gene delivery polynucleotide is at least 1 kB to 5 kB. In some alternatives, the gene delivery polynucleotide is a minicircle. In some alternatives, the promoter region comprises an EF1 promoter sequence. In some alternatives, the fourth sequence comprises one, two, three, four, or five genes that encode proteins. In some alternatives, the fourth sequence is codon optimized to reduce the total GC/AT ratio of the fourth sequence. In some alternatives, the fourth sequence is optimized by codon optimization for expression in humans. In some alternatives, the fourth sequence is a consensus sequence generated from a plurality of nucleic acids that encode a plurality of related proteins. In some alternatives, the fourth sequence is a consensus sequence generated from a plurality of nucleic acids that encode a plurality of related proteins, such as a plurality of antibody binding domains, which are specific for the same epitope. In some alternatives, the plurality of related proteins comprise a plurality of antibody binding domains, wherein the plurality of antibody binding domains are specific for the same epitope. In some alternatives, the fifth sequence is codon optimized to reduce the total GC/AT ratio of the fifth sequence. In some alternatives, the fifth sequence is optimized by codon optimization for expression in humans. In some alternatives, the protein is a protein for therapy. In some alternatives, the codon optimization and/or consensus sequence is generated by comparing the variability of sequence and/or nucleobases utilized in a plurality of related sequences. In some alternatives, the protein comprises an antibody or a portion thereof, which may be humanized. In some alternatives, the double mutant of dihydrofolate reductase comprises amino acid mutations of L22F and F31S. In some alternatives, the introducing is performed by electroporation. In some alternatives, the selecting is performed by increasing selective pressure through the selective marker cassette. In some alternatives, the selection reagent comprises an agent for selection. In some alternatives, the agent for selection is methotrexate. In some alternatives, the first concentration range is at least 50 nM-100 nM and the second concentration range is at least 75 to 150 nM. In some alternatives, the first concentration is 50 nM, 60 nM, 70 nM, 80 nM, 90 nM, or 100 nM or any concentration that is between a range of concentrations defined by any two of the aforementioned concentrations, and the second concentration range is 75 nM, 80 nM, 90 nM, 100 nM, 110 nM, 120 nM, 130 nM, 140 nM, or 150 nM or any concentration that is between a range of concentrations defined by any two of the aforementioned concentrations. In some alternatives, the first concentration range is at least 75 nM-150 nM and the second concentration range is at least 112.5 nM to 225 nM. In some alternatives, the first concentration is 75 nM, 85 nM, 95 nM, 105 nM, 115 nM, 125 nM, 135 nM, 145 nM, or 150 nM or any concentration that is between a range of concentrations defined by any two of the aforementioned concentrations, and the second concentration range is 112 nM, 122 nM, 132 nM, 142 nM, 152 nM, 162 nM, 172 nM, 182 nM, 192 nM, 202 nM, 212 nM, or 225 nM or any concentration that is between a range of concentrations defined by any two of the aforementioned concentrations. In some alternatives, the first concentration range is at least 300 nM-675 nM and the first concentration range is at least 450 nM to 1012 nM. In some alternatives, the first concentration is 300 nM, 350 nM, 400 nM, 450 nM, 500 nM, 550 nM, 600 nM, 650 nM, or 675 nM or any concentration that is between a range of concentrations defined by any two of the aforementioned concentrations, and the second concentration range is 450 nM, 500 nM, 550 nM, 600 nM, 650 nM, 700 nM, 750 nM, 800 nM, 850 nM, 900 nM, 1000 nM, or 1012 nM or any concentration that is between a range of concentrations defined by any two of the aforementioned concentrations. In some alternatives, the first round of selection comprises exposing the T-cells to the selection agent for 2, 3, 4, 5, 6 or 7 days before the second round of selection. In some alternatives, the second round of selection comprises exposing the T-cells to the selection agent for at least 2, 3, 4, 5, 6, 7, 8, 9, 10, 11, 12, 13, or 14 days or any time that is between a range of times defined by any two of the aforementioned time points before isolation. In some alternatives, the T cells are precursor T cells. In some alternatives, the precursor T cells are hematopoietic stem cells.

In some alternatives, a method of treating, inhibiting, or ameliorating cancer or a disease in a subject is provided, wherein the method comprises administering to the subject the modified or engineered multiplexed T-cell generated as described below. In some alternatives, the engineered multiplexed T-cells for adoptive T-cell immunotherapy is generated by a method, wherein the method comprises providing a gene delivery polynucleotide, introducing the gene delivery polynucleotide into a T-cell, providing a vector encoding a Sleeping Beauty transposase, introducing the vector encoding the Sleeping Beauty transposase into the T-cell, selecting the cells comprising the gene delivery polynucleotide wherein selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range and isolating the T-cells expressing a phenotype under selective pressure. In some alternatives, the gene delivery polynucleotide comprises a first sequence, wherein the first sequence comprises a first inverted terminal repeat gene sequence, a second sequence, wherein the second sequence comprises a second inverted terminal repeat gene sequence, a third sequence, wherein the third sequence comprises a promoter region sequence, a fourth sequence, wherein the fourth sequence comprises at least one gene encoding a protein, and wherein the fourth sequence is optimized, a fifth sequence, wherein the fifth sequence comprises at least one selectable marker cassette encoding a double mutant of dihydrofolate reductase, wherein the double mutant of dihydrofolate reductase has a 15,000 fold or about 15,000 fold reduced affinity for methotrexate, wherein the methotrexate can be used as a selection mechanism to selectively amplify cells transduced with the gene delivery polynucleotide and wherein the fifth sequence is optimized, a sixth sequence, wherein the sixth sequence comprises a first attachment site (attP) and a seventh sequence, wherein the seventh sequence comprises a second attachment site (attB) wherein each of the first sequence, second sequence, third sequence, fourth sequence, fifth sequence, sixth sequence, and seventh sequence have a 5' terminus and a 3 terminus, and wherein the 3' terminus of the first sequence comprising the first inverted terminal repeat gene sequence is adjacent to the 5' terminus of the third sequence, the 3' terminus of the third sequence is adjacent to the 5' terminus of the fourth sequence, the 3' terminus of the fourth sequence is adjacent to the 5' terminus of the fifth sequence and the 3' terminus of the fifth sequence is adjacent to the 5' terminus of the second sequence comprising a second inverted terminal repeat. In some alternatives, the gene encoding the double mutant of human dihydrofolate reductase comprises the DNA sequence:

```
                                               (SEQ ID NO: 2)
ATGGTTGGTTCGCTAAACTGCATCGTCGCTGTGTCCCAGAACATGGGCAT

CGGCAAGAACGGGGACTTCCCCTGGCCACCGCTCAGGAATGAATCCAGAT

ATTTCCAGAGAATGACCACAACCTCTTCAGTAGAAGGTAAACAGAATCTG

GTGATTATGGGTAAGAAGACCTGGTTCTCCATTCCTGAGAAGAATCGACC

TTTAAAGGGTAGAATTAATTTAGTTCTCAGCAGAGAACTCAAGGAACCTC

CACAAGGAGCTCATTTTCTTTCCAGAAGTCTAGATGATGCCTTAAAACTT

ACTGAACAACCAGAATTAGCAAATAAAGTAGACATGGTCTGGATAGTTGG

TGGCAGTTCTGTTTATAAGGAAGCCATGAATCACCCAGGCCATCTTAAAC

TATTTGTGACAAGGATCATGCAAGACTTTGAAAGTGACACGTTTTTTCCA

GAAATTGATTTGGAGAAATATAAACTTCTGCCAGAATACCCAGGTGTTCT

CTCTGATGTCCAGGAGGAGAAAGGCATTAAGTACAAATTTGAAGTATATG

AGAAGAATGATTAA.
```

In some alternatives, the double mutant of human dihydrofolate reductase comprises the protein sequence:

```
                                               (SEQ ID NO: 3)
MVGSLNCIVA VSQNMGIGKN GDFPWPPLRN ESRYFQRMTT

TSSVEGKQNL VIMGKKTWFS IPEKNRPLKG RINLVLSREL

KEPPQGAHFL SRSLDDALKL TEQPELANKV DMVWIVGGSS

VYKEAMNHPG HLKLFVTRIM QDFESDTFFP EIDLEKYKLL

PEYPGVLSDV QEEKGIKYKF EVYEKND.
```

In some alternatives, the gene delivery polynucleotide is circular. In some alternatives, the gene delivery polynucleotide is a minicircle. In some alternatives, the gene delivery polynucleotide is at least 1 kB to 5 kB. In some alternatives, the promoter region comprises an EF1 promoter sequence. In some alternatives, the fourth sequence comprises one, two, three, four, or five genes that encode proteins. In some alternatives, the fourth sequence is codon optimized to reduce the total GC/AT ratio of the fourth sequence. In some alternatives, the fourth sequence is optimized by codon optimization for expression in humans. In some alternatives, the fourth sequence is a consensus sequence generated from a plurality of nucleic acids that encode a plurality of related proteins. In some alternatives, the fourth sequence is a consensus sequence generated from a plurality of nucleic acids that encode a plurality of related proteins, such as a plurality of antibody binding domains, which are specific for the same epitope. In some alternatives, the plurality of related proteins comprise a plurality of antibody binding domains, wherein the plurality of antibody binding domains are specific for the same epitope. In some alternatives, the fifth sequence is codon optimized to reduce the total GC/AT ratio of the fifth sequence. In some alternatives, the fifth sequence is optimized by codon optimization for expression in humans. In some alternatives, the protein is a protein for therapy. In some alternatives, the codon optimization and/or consensus sequence is generated by comparing the variability of sequence and/or nucleobases utilized in a plurality of related sequences. In some alternatives, the protein comprises an antibody or a portion thereof, which may be humanized. In some alternatives, the double mutant of dihydrofolate reductase comprises amino acid mutations of L22F and F31S. In some alternatives, the double mutant of dihydrofolate reductase comprises amino acid mutations of L22F and F31S. In some alternatives, the T cells are precursor T cells. In some alternatives, the precursor T cells are hematopoietic stem cells. In some alternatives, the introducing is performed by electroporation. In some alternatives, the selecting is performed by increasing selective pressure through the selective marker cassette. In some alternatives, the selection reagent comprises an agent for selection. In some alternatives, the agent for selection is methotrexate. In some alternatives, the first concentration range is at least 50 nM-100 nM and the second concentration range is at least 75 to 150 nM. In some alternatives, the first concentration is 50 nM, 60 nM, 70 nM, 80 nM, 90 nM, or 100 nM or any concentration that is between a range of concentrations defined by any two of the aforementioned concentrations, and the second concentration range is 75 nM, 80 nM, 90 nM, 100 nM, 110 nM, 120 nM, 130 nM, 140 nM, or 150 nM or any concentration that is between a range of concentrations defined by any two of the aforementioned concentrations. In some alternatives, the first concentration range is at least 75 nM-150 nM and the second concentration range is at least 112.5 nM to 225 nM. In some alternatives, the first concentration is 75 nM, 85 nM, 95 nM, 105 nM, 115 nM, 125 nM, 135 nM, 145 nM, or 150 nM or any concentration that is between a range of concentrations defined by any two of the aforementioned concentrations, and the second concentration range is 112 nM, 122 nM, 132 nM, 142 nM, 152 nM, 162 nM, 172 nM, 182 nM, 192 nM, 202 nM, 212 nM, or 225 nM or any concentration that is between a range of concentrations defined by any two of the aforementioned concentrations. In some alternatives, the first concentration range is at least 300 nM-675 nM and the first concentration range is at least 450 nM to 1012 nM. In some alternatives, the first concentration is 300 nM, 350 nM, 400 nM, 450 nM, 500 nM, 550 nM, 600 nM, 650 nM, or 675 nM or any concentration that is between a range of concentrations defined by any two of the aforementioned concentrations, and the second concentration range is 450 nM, 500 nM, 550 nM, 600 nM, 650 nM, 700 nM, 750 nM, 800 nM, 850 nM, 900 nM, 1000 nM, or 1012 nM or any concentration that is between a range of concentrations defined by any two of the aforementioned concentrations. In some alternatives, the first round of selection comprises exposing the T-cells to the selection agent for 2, 3, 4, 5, 6 or 7 days before the second round of selection. In some alternatives, the second round of selection comprises exposing the T-cells to the selection agent for at least 2, 3, 4, 5, 6, 7, 8, 9, 10, 11, 12, 13, or 14 days or any time that is between a range of times defined by any two of the aforementioned time points before isolation. In some alternatives, the subject is human.

In some alternatives, a method of generating engineered multiplexed T-cells for adoptive T-cell immunotherapy is provided, wherein the method comprises providing a gene delivery polynucleotide, introducing the gene delivery polynucleotide into a T-cell, providing a vector encoding a Sleeping Beauty transposase, introducing the vector encoding the Sleeping Beauty transposase into the T-cell, selecting the cells comprising the gene delivery polynucleotide wherein selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range and isolating the T-cells expressing a phenotype under selective pressure. In some alternatives, the gene delivery polynucleotide comprises a first sequence, wherein the first sequence comprises a first inverted terminal repeat gene sequence, a second sequence, wherein the second sequence comprises a second inverted terminal repeat gene sequence, a third sequence, wherein the third sequence comprises a promoter region sequence, a fourth sequence, wherein the fourth sequence comprises at least one gene encoding a protein, and wherein the fourth sequence is optimized, a fifth sequence, wherein the fifth sequence comprises at least one selectable marker cassette encoding a double mutant of dihydrofolate reductase, wherein the double mutant of dihydrofolate reductase has a 15,000 fold or about 15,000 fold reduced affinity for methotrexate, wherein the methotrexate can be used as a selection mechanism to selectively amplify cells transduced with the gene delivery polynucleotide and wherein the fifth sequence is optimized, a sixth sequence, wherein the sixth sequence comprises a first attachment site (attP) and a seventh sequence, wherein the seventh sequence comprises a second attachment site (attB) wherein each of the first sequence, second sequence, third sequence, fourth sequence, fifth sequence, sixth sequence, and seventh sequence have a 5' terminus and a 3 ' terminus, and wherein the 3' terminus of the first sequence comprising the first inverted terminal repeat gene sequence is adjacent to the 5' terminus of the third sequence, the 3' terminus of the third sequence is adjacent to the 5' terminus of the fourth sequence, the 3' terminus of the fourth sequence is adjacent to the 5' terminus of the fifth sequence and the 3' terminus of the fifth sequence is adjacent to the 5' terminus of the second sequence comprising a second inverted terminal repeat. In some alternatives, the gene encoding the double mutant of human dihydrofolate reductase comprises the DNA sequence:

```
                                        (SEQ ID NO: 2)
ATGGTTGGTTCGCTAAACTGCATCGTCGCTGTGTCCCAGAACATGGGCAT

CGGCAAGAACGGGGACTTCCCCTGGCCACCGCTCAGGAATGAATCCAGAT

ATTTCCAGAGAATGACCACAACCTCTTCAGTAGAAGGTAAACAGAATCTG

GTGATTATGGGTAAGAAGACCTGGTTCTCCATTCCTGAGAAGAATCGACC

TTTAAAGGGTAGAATTAATTTAGTTCTCAGCAGAGAACTCAAGGAACCTC
```

```
CACAAGGAGCTCATTTTCTTTCCAGAAGTCTAGATGATGCCTTAAAACTT

ACTGAACAACCAGAATTAGCAAATAAAGTAGACATGGTCTGGATAGTTGG

TGGCAGTTCTGTTTATAAGGAAGCCATGAATCACCCAGGCCATCTTAAAC

TATTTGTGACAAGGATCATGCAAGACTTTGAAAGTGACACGTTTTTCCA

GAAATTGATTTGGAGAAATATAAACTTCTGCCAGAATACCCAGGTGTTCT

CTCTGATGTCCAGGAGGAGAAAGGCATTAAGTACAAATTTGAAGTATATG

AGAAGAATGATTAA.
```

In some alternatives, the double mutant of human dihydrofolate reductase comprises the protein sequence:

```
                                              (SEQ ID NO: 3)
MVGSLNCIVA VSQNMGIGKN GDFPWPPLRN ESRYFQRMTT

TSSVEGKQNL VIMGKKTWFS IPEKNRPLKG RINLVLSREL

KEPPQGAHFL SRSLDDALKL TEQPELANKV DMVWIVGGSS

VYKEAMNHPG HLKLFVTRIM QDFESDTFFP EIDLEKYKLL

PEYPGVLSDV QEEKGIKYKF EVYEKND.
```

In some alternatives, the gene delivery polynucleotide is circular. In some alternatives, the gene delivery polynucleotide is at least 1 kB to 5 kB. In some alternatives, the gene delivery polynucleotide is a minicircle. In some alternatives, the promoter region comprises an EF1 promoter sequence. In some alternatives, the fourth sequence comprises one, two, three, four, or five genes that encode proteins. In some alternatives, the fourth sequence is codon optimized to reduce the total GC/AT ratio of the fourth sequence. In some alternatives, the fourth sequence is optimized by codon optimization for expression in humans. In some alternatives, the fourth sequence is a consensus sequence generated from a plurality of nucleic acids that encode a plurality of related proteins. In some alternatives, the fourth sequence is a consensus sequence generated from a plurality of nucleic acids that encode a plurality of related proteins, such as a plurality of antibody binding domains, which are specific for the same epitope. In some alternatives, the plurality of related proteins comprise a plurality of antibody binding domains, wherein the plurality of antibody binding domains are specific for the same epitope. In some alternatives, the fifth sequence is codon optimized to reduce the total GC/AT ratio of the fifth sequence. In some alternatives, the fifth sequence is optimized by codon optimization for expression in humans. In some alternatives, the protein is a protein for therapy. In some alternatives, the codon optimization and/or consensus sequence is generated by comparing the variability of sequence and/or nucleobases utilized in a plurality of related sequences. In some alternatives, the protein comprises an antibody or a portion thereof, which may be humanized. In some alternatives, the double mutant of dihydrofolate reductase comprises amino acid mutations of L22F and F31S. In some alternatives, the double mutant of dihydrofolate reductase comprises amino acid mutations of L22F and F31S. In some alternatives, the introducing is performed by electroporation. In some alternatives, the selecting is performed by increasing selective pressure through the selective marker cassette. In some alternatives, the selection reagent comprises an agent for selection. In some alternatives, the agent for selection is methotrexate. In some alternatives, the first concentration range is at least 50 nM-100 nM and the second concentration range is at least 75 to 150 nM. In some alternatives, the first concentration is 50 nM, 60 nM, 70 nM, 80 nM, 90 nM, or 100 nM or any concentration that is between a range of concentrations defined by any two of the aforementioned concentrations, and the second concentration range is 75 nM, 80 nM, 90 nM, 100 nM, 110 nM, 120 nM, 130 nM, 140 nM, or 150 nM or any concentration that is between a range of concentrations defined by any two of the aforementioned concentrations. In some alternatives, the first concentration range is at least 75 nM-150 nM and the second concentration range is at least 112.5 nM to 225 nM. In some alternatives, the first concentration is 75 nM, 85 nM, 95 nM, 105 nM, 115 nM, 125 nM, 135 nM, 145 nM, or 150 nM or any concentration that is between a range of concentrations defined by any two of the aforementioned concentrations, and the second concentration range is 112 nM, 122 nM, 132 nM, 142 nM, 152 nM, 162 nM, 172 nM, 182 nM, 192 nM, 202 nM, 212 nM, or 225 nM or any concentration that is between a range of concentrations defined by any two of the aforementioned concentrations. In some alternatives, the first concentration range is at least 300 nM-675 nM and the first concentration range is at least 450 nM to 1012 nM. In some alternatives, the first concentration is 300 nM, 350 nM, 400 nM, 450 nM, 500 nM, 550 nM, 600 nM, 650 nM, or 675 nM or any concentration that is between a range of concentrations defined by any two of the aforementioned concentrations, and the second concentration range is 450 nM, 500 nM, 550 nM, 600 nM, 650 nM, 700 nM, 750 nM, 800 nM, 850 nM, 900 nM, 1000 nM, or 1012 nM or any concentration that is between a range of concentrations defined by any two of the aforementioned concentrations. In some alternatives, the first round of selection comprises exposing the T-cells to the selection agent for 2, 3, 4, 5, 6 or 7 days before the second round of selection. In some alternatives, the second round of selection comprises exposing the T-cells to the selection agent for at least 2, 3, 4, 5, 6, 7, 8, 9, 10, 11, 12, 13, or 14 days or any time that is between a range of times defined by any two of the aforementioned time points before isolation. In some alternatives, the T cells comprise precursor T cells. In some alternatives, the precursor T cells are hematopoietic stem cells.

In some alternatives, a method of generating engineered cells for adoptive T-cell immunotherapy comprising, providing a gene delivery polynucleotide, introducing the gene delivery polynucleotide into a precursor T cell, providing a vector encoding a Sleeping Beauty transposase, introducing the vector encoding the Sleeping Beauty transposase into the precursor T cell, selecting the precursor T cells comprising the gene delivery polynucleotide; wherein selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range and isolating the precursor T-cells expressing a phenotype under selective pressure. In some alternatives, the gene delivery polynucleotide is for stable insertion of a nucleic acid into an oligonucleotide wherein the nucleic acid for insertion is flanked by inverted terminal repeat gene sequences in the gene delivery polynucleotide and wherein the gene delivery polynucleotide is selectable, wherein the gene delivery polynucleotide comprises a first sequence, wherein the first sequence comprises a first inverted terminal repeat gene sequence, a second sequence, wherein the second sequence comprises a second inverted terminal repeat gene sequence, a third sequence, wherein the third sequence comprises a promoter region sequence, a fourth sequence, wherein the fourth sequence comprises at least one gene, wherein the at least one gene encodes a protein or encodes a sequence for mRNA transcription, and wherein the fourth sequence is optimized, a fifth sequence, wherein the fifth sequence comprises at least one selectable marker cassette encoding a double mutant of dihydrofolate reductase, wherein the double mutant of dihydrofolate reductase has a 15,000 fold or about 15,000 fold reduced affinity for methotrexate, wherein the methotrexate can be used to select for cells transduced with the gene delivery polynucleotide, to enhance the ratio of cells expressing the at least one gene and wherein the fifth sequence is optimized, a sixth sequence, wherein the sixth sequence comprises a first attachment site (attP) and a seventh sequence, wherein the seventh sequence comprises a second attachment site (attB); wherein each of the first sequence, second sequence, third sequence, fourth sequence, fifth sequence, sixth sequence, and seventh sequence have a 5' terminus and a 3 terminus, and wherein the 3' terminus of the first sequence comprising the first inverted terminal repeat gene sequence is adjacent to the 5' terminus of the third sequence, the 3' terminus of the third sequence is adjacent to the 5' terminus of the fourth sequence, the 3' terminus of the fourth sequence is adjacent to the 5' terminus of the fifth sequence and the 3' terminus of the fifth sequence is adjacent to the 5' terminus of the second sequence comprising a second inverted terminal repeat. In some alternatives, the gene delivery polynucleotide is circular. In some alternatives, the gene delivery polynucleotide is at least kB to 5 kB. In some alternatives, the promoter region comprises an EF1 promoter sequence. In some alternatives, the fourth sequence comprises one, two, three, four, or five genes that encode proteins. In some alternatives, the fourth sequence is codon optimized to reduce the total GC/AT ratio of the fourth sequence. In some alternatives, the fourth sequence is optimized by codon optimization for expression in humans. In some alternatives, the fourth sequence is a consensus sequence generated from a plurality of nucleic acids that encode a plurality of related proteins. In some alternatives, the fourth sequence is a consensus sequence generated from a plurality of nucleic acids that encode a plurality of related proteins, such as a plurality of antibody binding domains, which are specific for the same epitope. In some alternatives, the plurality of related proteins comprise a plurality of antibody binding domains, wherein the plurality of antibody binding domains are specific for the same epitope. In some alternatives, the fifth sequence is codon optimized to reduce the total GC/AT ratio of the fifth sequence. In some alternatives, the fifth sequence is optimized by codon optimization for expression in humans. In some alternatives, the codon optimization and/or consensus sequence is generated by comparing the variability of sequence and/or nucleobases utilized in a plurality of related sequences. In some alternatives, the protein is a protein for therapy. In some alternatives, the protein comprises an antibody or a portion thereof, which may be humanized. In some alternatives, the double mutant of dihydrofolate reductase comprises amino acid mutations of L22F and F31S. In some alternatives, the gene delivery polynucleotide is a minicircle. In some alternatives, the introducing is performed by electroporation. In some alternatives, the selecting is performed by increasing selective pressure through the selective marker cassette. In some alternatives, the selection reagent comprises an agent for selection. In some alternatives, the agent for selection is methotrexate. In some alternatives, the first concentration range is at least 50 nM-100 nM and the second concentration range is at least 75 to 150 nM. In some alternatives, the first concentration range is at least 75 nM-150 nM and the second concentration range is at least 112.5 nM to 225 nM. In some alternatives, the first concentration range is at least 300 nM-675 nM and the first concentration range is at least 450 nM to 1012 nM. In some alternatives, the first round of selection comprises exposing the T-cells to the selection agent for 2, 3, 4, 5, 6 or 7 days before the second round of selection. In some alternatives, the second round of selection comprises exposing the T-cells to the selection agent for at least 2, 3, 4, 5, 6, 7, 8, 9, 10, 11, 12, 13, or 14 days or any time that is between a range of times defined by any two of the aforementioned time points before isolation. In some alternatives, the T cell precursor is a hematopoietic stem cell.

In some alternatives, a method of increasing protein production in a precursor T-cell is provided wherein the method comprises providing a polynucleotide, introducing the polynucleotide into a cell, providing a vector encoding a Sleeping Beauty transposase; introducing the vector encoding the Sleeping Beauty transposase into the precursor T-cell, selecting the precursor T cells comprising the gene delivery polynucleotide, wherein selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range and isolating the precursor T cells expressing a phenotype under selective pressure. In some alternatives, the gene delivery polynucleotide is for stable insertion of a nucleic acid into an oligonucleotide wherein the nucleic acid for insertion is flanked by inverted terminal repeat gene sequences in the gene delivery polynucleotide and wherein the gene delivery polynucleotide is selectable, wherein the gene delivery polynucleotide comprises a first sequence, wherein the first sequence comprises a first inverted terminal repeat gene sequence, a second sequence, wherein the second sequence comprises a second inverted terminal repeat gene sequence, a third sequence, wherein the third sequence comprises a promoter region sequence, a fourth sequence, wherein the fourth sequence comprises at least one gene, wherein the at least one gene encodes a protein or encodes a sequence for mRNA transcription, and wherein the fourth sequence is optimized, a fifth sequence, wherein the fifth sequence comprises at least one selectable marker cassette encoding a double mutant of dihydrofolate reductase, wherein the double mutant of dihydrofolate reductase has a 15,000 fold or about 15,000 fold reduced affinity for methotrexate, wherein the methotrexate can be used to select for cells transduced with the gene delivery polynucleotide, to enhance the ratio of cells expressing the at least one gene and wherein the fifth sequence is optimized, a sixth sequence, wherein the sixth sequence comprises a first attachment site (attP) and a seventh sequence, wherein the seventh sequence comprises a second attachment site (attB); wherein each of the first sequence, second sequence, third sequence, fourth sequence, fifth sequence, sixth sequence, and seventh sequence have a 5' terminus and a 3 terminus, and wherein the 3' terminus of the first sequence comprising the first inverted terminal repeat gene sequence is adjacent to the 5' terminus of the third sequence, the 3' terminus of the third sequence is adjacent to the 5' terminus of the fourth sequence, the 3' terminus of the fourth sequence is adjacent to the 5' terminus of the fifth sequence and the 3' terminus of the fifth sequence is adjacent to the 5' terminus of the second sequence comprising a second inverted terminal repeat. In some alternatives, the gene delivery polynucleotide is circular. In some alternatives, the gene delivery polynucleotide is at least 1 kB to 5 kB. In some alternatives, the promoter region comprises an EF1 promoter sequence. In some alternatives, the fourth sequence comprises one, two, three, four, or five genes that encode proteins. In some alternatives, the fourth sequence is codon optimized to reduce the total GC/AT ratio of the fourth sequence. In some alternatives, the fourth sequence is optimized by codon optimization for expression in humans. In some alternatives, the fourth sequence is a consensus sequence generated from a plurality of nucleic acids that encode a plurality of related proteins. In some alternatives, the fourth sequence is a consensus sequence generated from a plurality of nucleic acids that encode a plurality of related proteins, such as a plurality of antibody binding domains, which are specific for the same epitope. In some alternatives, the plurality of related proteins comprise a plurality of antibody binding domains, wherein the plurality of antibody binding domains are specific for the same epitope. In some alternatives, the fifth sequence is codon optimized to reduce the total GC/AT ratio of the fifth sequence. In some alternatives, the fifth sequence is optimized by codon optimization for expression in humans. In some alternatives, the codon optimization and/or consensus sequence is generated by comparing the variability of sequence and/or nucleobases utilized in a plurality of related sequences. In some alternatives, the protein is a protein for therapy. In some alternatives, the protein comprises an antibody or a portion thereof, which may be humanized. In some alternatives, the double mutant of dihydrofolate reductase comprises amino acid mutations of L22F and F31S. In some alternatives, the gene delivery polynucleotide is a minicircle. In some alternatives, the introducing is performed by electroporation. In some alternatives, the selecting is performed by increasing selective pressure through the selective marker cassette. In some alternatives, the selection reagent comprises an agent for selection. In some alternatives, the agent for selection is methotrexate.

In some alternatives, wherein the first concentration range is at least 50 nM-100 nM and the second concentration range is at least 75 to 150 nM. In some alternatives, the first concentration range is at least 75 nM-150 nM and the second concentration range is at least 112.5 nM to 225 nM. In some alternatives, the first concentration range is at least 300 nM-675 nM and the second concentration range is at least 450 nM to 1012 nM. In some alternatives, the first round of selection comprises exposing the cells to the selection agent for 2, 3, 4, 5, 6 or 7 days before the second round of selection. In some alternatives, the second round of selection comprises exposing the cells to the selection agent for at least 2, 3, 4, 5, 6, or 7 days before isolation. In some alternatives, the precursor T cells are hematopoietic stem cells.

BRIEF DESCRIPTION OF THE DRAWINGS

FIG. 3A shows the percent GFP+/PI− and FIG. 3B shows the mean GFP relative fluorescence units (RFU).

FIG. 4A shows the percent GFP+/PI−; FIG. 4B shows the mean GFP relative fluorescence units (RFU).

As shown in FIGS. 6A-6C are the flow cytometric analysis of H9 cell populations nucleofected with 3 minicircles carrying transposons with different fluorescent proteins (FPs) (MC_T3/

GFP-T2A-DHFRdm, MC_T3/BFP-T2A-DHFRdm, MC_T3/mCherry-T2A-DHFRdm), 2 μg each and 6 μg of MC_SB100×DNA at different time points: FIG. 6A: 24 hours after transfection (transient expression), FIG. 6B: 1 week (stable integration), and FIG. 6C: 1 week of selection with 200 nM of MTX.

FIGS. 8A, 8B and 8C show the sequential selection for lymphocytes (FIG. 8A), single cells (FIG. 8B), and live cells (FIG. 8C). Shown in FIG. 8D are the high levels of GFP expression in both the CD8+ and CD8− populations. Note that for this donor, the majority of lymphocytes after stimulation are CD8+ T cells.

FIG. 10A shows the decreasing levels of GFP expression from day 2 to day 7. FIG. 10B shows the level of live cells from day 0 to day 7 of the transfected cell samples which had been treated with Miltenyi Transact beads on d0. FIG. 10C shows the level of live cells from day 0 to day 7 of the transfected cell samples in the absence of Transact beads. As shown, there is a slow growth of the cells transfected with mcGFP DNA in the presence of Miltenyi Transact beads.

FIGS. 11A-11I1 show the stable expression of transposon DNA with Sleeping Beauty in T-cells following 1 week of MTX selection. Shown are the flow cytometry scattergrams in which GFP production and proliferation of T-cells modified to express GFP after transfection with transposon DNA and Sleeping Beauty transposase DNA were investigated. FIGS. 11A, 11B, 11E and 11F show the scatter profiles to identify lymphocytes, while FIGS. 11A-11D show the flow cytometry analysis of cells treated with 100 nM MTX. FIGS. 11E-11H show the flow cytometry analysis of cells that were not treated with MTX. Shown in FIGS. 11A, 11C, 11E and 11G, are samples transfected with mcGFP alone. FIGS. 11B, 11D, 11F and 11H show the flow cytometry results of cells transfected with mcGFP and MC_SB100X (Sleeping Beauty transposase) DNA at 2:1. As demonstrated in FIG. 11D, in T-cells (both CD8+ and CD8−) co-transfected with mcGFP and SB100X such that the GFP gene is stably inserted into the cellular genome, about 95% of the cells stably express GFP in the presence of MTX at 100 nM while only about 23% express GFP in the absence of MTX.

FIGS. 12A-1-12D-1 show the proliferation and the GFP/CD8 expression in transposon-transfected lymphocytes after 14 days of MTX selection. Cell samples were transfected with no DNA (control), mcGFP alone, mcGFP and MC_SB100×DNA at a mcGFP:MC_SB100X ratio of 2:1 ratio, or mcGFP and MC_SB100×DNA at a mcGFP:MC_SB100X ratio of 1:1. After 1 week, the cells were selected using 0 nM MTX (control; FIGS. 12A-1 and 12A-2), 25 nM MTX (FIGS. 12D-1 and 12D-2), 50 nM MTX (FIGS. 12C-1 and 12C-2), or 100 nM MTX (FIGS. 12B-1 and 12B-2). The lymphocyte window, shown in the first and third panels of FIGS. 12A-1, 12A-2, 12B-1, 12B-2, 12C-1, 12C-2, 12D-1, 12-D2, demonstrates the survival of only stably transfected cells in the presence of higher concentrations of MTX. The live, single lymphocytes were gated for GFP and CD8 detection in the second and fourth panels of FIGS. 12A-1, 12A-2, 12B-1, 12B-2, 12C-1, 12C-2, 12D-1, 12-D2. For the cell samples transfected with mcGFP alone, GFP expression is lost over time (second panel of FIGS. 12A-1, 12B-1, 12C-1, 12D-1). However cells transfected with both mcGFP and MC_SB100X stably express GFP both with MTX selection (>90%) and without MTX selection (~20%) (fourth panels of FIGS. 12A-1, 12B-1, 12C-1, 12D-1, and second panels of FIGS. 12A-2, 12B-2, 12C-2, 12D-2). As shown in the samples transfected with mcGFP and MC_SB100×DNA, MTX was effective for selection at concentrations of 50 and 100 nM MTX and no significant difference was seen between the ratios 2:1 or 1:1. Note that the majority of lymphocytes are CD8+ T-cells.

FIGS. 13A-1-13D-2 show both the lymphocyte window and GFP/CD8 expression in transposon-transfected cells after 19 days of MTX selection. Cell samples were transfected with no DNA (control), mcGFP alone, mcGFP and MC_SB100×DNA at a mcGFP:MC_SB100X ratio of 2:1 ratio, or mcGFP and MC_SB100×DNA at a mcGFP:MC_SB100X ratio of 1:1. The cells were selected using 0 nM MTX (control; FIGS. 13A-1 and 13A-2), 25 nM MTX (FIGS. 13D-1 and 13D-2), 50 nM MTX (FIGS. 13C-1 and 13C-2), or 100 nM MTX (FIGS. 13B-1 and 13B-2). The lymphocyte window is shown in the first and third panels of FIGS. 13A-1, 13A-2, 13B-1, 13B-2, 13C-1, 13C-2, 13D-1, 13-D2, showing the survival of only stably transfected cells in the presence of MTX. The live, single lymphocytes were gated for GFP and CD8 detection in the second and fourth of panels of FIGS. 13A-1, 13A-2, 13B-1, 13B-2, 13C-1, 13C-2, 13D-1, 13-D2. For the cell samples transfected with mcGFP alone, GFP expression is lost over time (second panel of FIGS. 13A-1, 13B-1, 13C-1, 13D-1). However cells transfected with both mcGFP and MC_SB100X stably express GFP both with MTX selection (>90%) and without MTX selection (~20%) (fourth panels of FIGS. 13A-1, 13B-1, 13C-1, 13D-1, and second panels of FIGS. 13A-2, 13B-2, 13C-2, 13D-2). As shown in the samples transfected with mcGFP and MC_SB100×DNA, MTX was effective for selection at concentrations of 50 and 100 nM MTX, and slightly less for 25 nM. The mcGFP:SB ratios 2:1 or 1:1 were similarly effective.

FIG. 14A shows the level of live cells in the absence of MTX. FIG. 14B shows the levels of live cells after exposure to 100 nM MTX. FIG. 14C shows the levels of live cells after exposure to 50 nM. FIG. 14D shows the levels of live cells after exposure to 25 nM MTX. As MTX slows the growth of cells by inhibiting the metabolism of folic acid, only cells that were transfected with both the mcGFP transposon co-expressing the MTX-resistance gene (DHFRdm) and the MC_SB100X plasmid encoding the Sleeping Beauty Transposase were able to proliferate in the presence of high MTX, due to stable expression of the integrated transposon DNA.

FIG. 15A shows the level of GFP expression on days 2, 5, 7, 14, and 19 in the absence of MTX. FIG. 15B shows the level of GFP expression from days 7, 14, and 19 of lymphocytes transfected with mcGFP alone under MTX selection at MTX concentrations of 0 nM, 25 nM, 50 nM and 100 nM. FIG. 15C shows the GFP expression of T-cells transfected with mcGFP and MC_SB100X at a mcGFP:MC_SB100X ratio of 2:1 under MTX selection of 0 nM, 25 nM, 50 nM and 100 nM. FIG. 15D shows the GFP expression of T-cells transfected with mcGFP and MC_SB100X at a mcGFP: MC_SB100X ratio of 1:1 under control of MTX selection concentrations of 0 nM, 25 nM, 50 nM and 100 nM. As shown, the results from transfecting with mcGFP and MC_SB100X with a 2:1 and a 1:1 ratio were similar, with approximately 75% GFP expression at 25 nM and approximately 90% GFP expression at 50 and 100 nM after 1 week of MTX. Additionally, there was minimal difference in the GFP expression between the treatment with 50 nM MTX and 100 nM MTX.

FIGS. 17A-17D depict scattergrams of cells transfected with Sleeping Beauty transposons carrying a gene for expression of GFP. As shown are the cells fourteen days after transfection. Cells were electroporated with SB100X or transposons carrying genes for GFP. FIG. 17E depicts a time line.

FIG. 18A relates to 'GFP expression' and 'no methotrexate'; FIG. 18B relates to 'GFP expression' and 'mcGFP only'; FIG. 18C relates to 'GFP expression' and 'mcGFP:SB 2:1'; FIG. 18D relates to 'GFP expression' and 'mcGFP:SB 1:1'.

FIG. 20A relates to lymphocytes; FIG. 20B relates to single cells; FIG. 20C relates to live cells; FIG. 20D relates to GFP; FIG. 20E relates to a time-line.

FIG. 22A relates to DNA; FIG. 22B relates to RNA; FIG. 22C relates to controls.

FIG. 23B relates to controls; FIG. 23C relates to DNA; FIG. 23D relates to RNA.

As shown in FIG. 24A, cells were transfected with varying concentrations of GFP:SB (2.5 ug, 5 ug) and exposed to different concentrations of MTX (50 uM and 100 uM). As shown, cells were able to express GFP in the presence of MTX optimally at 50 uM MTX when they were transfected with 5 ug of GFP:SB. FIG. 24B relates to the experiment was performed using RNA, however, DNA has a higher efficiency for leading to expression of the protein.

FIG. 27A relates to percentage EGFRt expression and 0 methotrexate; FIG. 27B relates to percentage EGFRt expression and DNA; FIG. 27C relates to percentage EGFRt expression and RNA.

As shown in FIG. 28A, the CD8+ cells were able to grow when a lower concentration of DNA was transfected. However, with RNA, it was seen that a higher concentration led to better expression, but a lower concentration led to better initial growth of the cells (FIG. 28B). FIG. 28C depicts controls.

FIG. 31A relates to 'percent all' and '3FP:SB 4:1'; FIG. 31B relates to 'percent all' and '3FP:SB 2:1'; FIG. 31C relates to 'percent FB+' and '3FP:SB 4:1'; FIG. 31D relates to 'percent FP+' and '3FP:SB 2:1'.

FIG. 33A relates to lymphocytes; FIG. 33B relates to single cells; FIG. 33C relates to live cells; FIG. 33D relates to GFP; FIG. 33E relates to GFP−; FIG. 33F relates to GFP+; FIG. 33G relates to a time line.

FIG. 34A relates to 'percent all' and '2 colors'; FIG. 34B relates to 'percent FP+' and '2 colors'; FIG. 34C relates to 'percent all' and '3 colors'; FIG. 34D relates to 'percent FP+' and '3 colors'.

DETAILED DESCRIPTION

Figure 1:
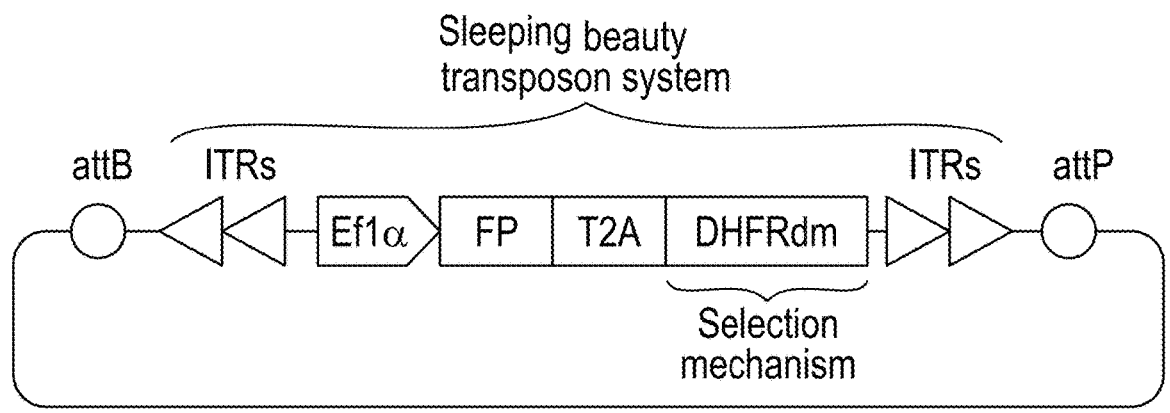
FIG. 1 shows an overall schematic of the gene delivery minicircle producer plasmid, MC_T3/FP-DHFRdm. The minicircle with T3 generation of Sleeping Beauty transposon comprises an EF1a promoter, a fusion of fluorescent protein (FP; maxGFP, mCherry, or Blue Fluorescent protein (BFP)), Thosea asigna virus 2A peptide (T2A), and double mutant of dihydrofolate reductase (DHFRdm) insensitive to methotrexate (MTX), positioned between inverted terminal repeats (ITRs, arrows). Recombination at attB/attP sites generates a minicircle while the remaining bacterial backbone is enzymatically degraded.

The following definitions are provided to facilitate understanding of the embodiments or alternatives of the invention.

As used herein, "a" or "an" can mean one or more than one.

As used herein, the term "about" indicates that a value includes the inherent variation of error for the method being employed to determine a value, or the variation that exists among experiments.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded. In some alternatives described herein, a gene delivery polynucleotide for stable insertion of a nucleic acid into a gene is provided. "Oligonucleotide" can be used interchangeable with nucleic acid and can refer to DNA or RNA, either double stranded or a single stranded piece or DNA or RNA.

A "gene" is the molecular unit of heredity of a living organism, describing some stretches of deoxyribonucleic acids (DNA) and ribonucleic acids (RNA) that code for a polypeptide or for an RNA chain that has a function in the organism, and can be a locatable region in the genome of an organism. In some alternatives described herein, a gene delivery polynucleotide for stable insertion of a nucleic acid into a gene, wherein the nucleic acid for insertion is flanked by inverted terminal repeat gene sequences in the gene delivery polynucleotide and wherein the gene delivery polynucleotide is selectable, is provided.

A "chromosome," is a packaged and organized chromatin, a complex of macromolecules found in cells, consisting of DNA, protein and RNA. In some alternatives, a gene delivery polynucleotide for stable insertion of a nucleic acid into a gene, wherein the nucleic acid for insertion is flanked by inverted terminal repeat gene sequences in the gene delivery polynucleotide and wherein the gene delivery polynucleotide is selectable, the gene delivery polynucleotide, is provided. In some alternatives, the nucleic acid is inserted into a gene of a chromosome.

A "promoter" is a nucleotide sequence that directs the transcription of a structural gene. In some alternatives, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., Mol. Endocrinol. 7:551 (1993); incorporated by reference in its entirety), cyclic AMP response elements (CREs), serum response elements (SREs; Treisman, Seminars in Cancer Biol. 1:47 (1990); incorporated by reference in its entirety), glucocorticoid response elements (GREs), and binding sites for other transcription factors, such as CRE/ATF (O'Reilly et al., J. Biol. Chem. 267:19938 (1992); incorporated by reference in its entirety), AP2 (Ye et al., J. Biol. Chem. 269:25728 (1994); incorporated by reference in its entirety), SP1, cAMP response element binding protein (CREB; Loeken, Gene Expr. 3:253 (1993); incorporated by reference in its entirety) and octamer factors (see, in general, Watson et al., eds., Molecular Biology of the Gene, 4th ed. (The Benjamin/Cummings Publishing Company, Inc. 1987; incorporated by reference in its entirety)), and Lemaigre and Rousseau, Biochem. J. 303:1 (1994); incorporated by reference in its entirety). As used herein, a promoter can be constitutively active, repressible or inducible. If a promoter is an inducible promoter, then the rate of transcription increases in response to an inducing agent. In contrast, the rate of transcription is not regulated by an inducing agent if the promoter is a constitutive promoter. Repressible promoters are also known. In some alternatives, a gene delivery polynucleotide is provided. In some alternatives, the gene delivery polynucleotide comprises a promoter sequence.

"Selectable marker cassette," is a gene introduced into a vector or a cell that confers a trait for artificial selection. A selectable marker cassette can be a screenable marker to allow a researcher to distinguish between wanted and unwanted cells, or to enrich for a specific cell type. In some alternatives, a gene delivery polynucleotide is provided. In some alternatives, the gene delivery polynucleotide comprises a selectable marker cassette.

"Dihydrofolate reductase", or DHFR, as described herein, is an enzyme that reduces dihydrofolic acid to tetrahydrofolic acid, using NADPH as electron donor, which can be converted to the kinds of tetrahydrofolate cofactors used in 1-carbon transfer chemistry. In some alternatives described herein, a gene delivery polynucleotide is provided. In some alternatives, the gene delivery polynucleotide comprises at least one selectable marker cassette encoding for a double mutant of dihydrofolate reductase.

"Methotrexate" (MTX), as described herein, is an antimetabolite and antifolate drug. It acts by inhibiting the metabolism of folic acid. In some alternatives, a method of generating engineered multiplexed T-cells for adoptive T-cell immunotherapy is provided. In the broadest sense, the method can comprise providing the gene delivery polynucleotide of any of the alternatives described herein, introducing the gene delivery polynucleotide into a T-cell, providing a vector encoding a Sleeping Beauty transposase, introducing the vector encoding the Sleeping Beauty transposase into the T-cell, selecting the cells comprising the gene delivery polynucleotide, wherein the selecting comprises a first round of selection and a second round of selection, wherein the first round of selection comprises adding a selection reagent at a first concentration range and the second round of selection comprises adding the same selection reagent at a second concentration range, wherein the second concentration range is greater than the first concentration range and, wherein the second concentration range is at least 1.5 fold higher than that of the first concentration range, and isolating the T-cells expressing a phenotype under this selective pressure. In some alternatives described herein, the selection reagent comprises an agent for selection. In some alternatives, the selection reagent is MTX.

An "inverted repeat" or IR is a sequence of nucleotides followed downstream by its reverse complement. Inverted repeats can have a number of important biological functions. They can define the boundaries in transposons and indicate regions capable of self-complementary base pairing (regions within a single sequence which can base pair with each other). These properties play an important role in genome instability and contribute to cellular evolution, genetic diversity and also to mutation and disease. In some alternatives, a gene delivery polynucleotide is provided. In some alternatives, the gene delivery polynucleotide comprises a first inverted terminal repeat gene sequence and a second inverted terminal repeat gene sequence. In some alternatives, the gene delivery polynucleotide comprises a sleeping beauty transposon positioned between two inverted repeat sequences.

Sleeping beauty transposase binds specific binding sites that are located on the IR of the Sleeping beauty transposon. The sequence of IR (Inverted repeat) is as follows:

```
                                          (SEQ ID NO: 1)
cagttgaagtcggaagtttacatacacttaagttggagtcattaaaactc gttttcaactacTccacaaatttcttgttaacaaacaatagttttggca agtcagttaggacatctactttgtgcatgacacaagtcattttccaaca attgtttacagacagattatttcacttataattcactgtatcacaattcc agtgggtcagaagtttacatacactaagttgactgtgcctttaaacagct tggaaaattccagaaaatgatgtcatggctttagaagcttctgatagact aattgacatcatttgagtcaattggaggtgtacctgtggatgtatttcaa gg
```

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein can also comprise non-peptide components, such as carbohydrate groups. Carbohydrates and other non-peptide substituents can be added to a protein by the cell in which the protein is produced, and will vary with the type of cell. Proteins are defined herein in terms of their amino acid backbone structures; substituents such as carbohydrate groups are generally not specified, but can be present nonetheless. In some alternatives, a gene delivery polynucleotide for stable insertion of a nucleic acid into a gene, wherein the nucleic acid for insertion is flanked by inverted terminal repeat gene sequences in the gene delivery polynucleotide and wherein the gene delivery polynucleotide is selectable, the gene delivery polynucleotide, is provided. In some alternatives, the gene delivery polynucleotide further comprises a sequence for at least one protein.

An "antibody" as described herein refers to a large Y-shape protein produced by plasma cells that is used by the immune system to identify and neutralize foreign objects such as bacteria and viruses. The antibody protein can comprise four polypeptide chains; two identical heavy chains and two identical light chains connected by disulfide bonds. Each chain is composed of structural domains called immunoglobulin domains. These domains can contain about 70-110 amino acids and are classified into different categories according to their size and function. In some alternatives, a gene delivery polynucleotide for stable insertion of a nucleic acid into a gene, wherein the nucleic acid for insertion is flanked by inverted terminal repeat gene sequences in the gene delivery polynucleotide and wherein the gene delivery polynucleotide is selectable, the gene delivery polynucleotide, is provided. In some alternatives, the gene delivery polynucleotide further comprises a sequence for at least one protein. In some alternatives, the gene delivery polynucleotide can comprise a sequence for an antibody or a portion thereof, which may be humanized.

A "chimeric antigen receptor" (CARs), also known as chimeric T-cell receptors, refers to artificial T-cell receptors that are engineered receptors, which graft an arbitrary specificity onto an immune effector cell. These receptors can be used to graft the specificity of a monoclonal antibody onto a T-cell, for example; with transfer of their coding sequence facilitated by retroviral vectors. The structure of the CAR can comprise single-chain variable fragments (scFv) derived from monoclonal antibodies, fused to CD3-zeta transmembrane and endodomain. Such molecules result in the transmission of a zeta signal in response to recognition by the scFv of its target. Some alternatives utilize a gene delivery polynucleotide for stable insertion of a nucleic acid into a gene, wherein the nucleic acid for insertion is flanked by inverted terminal repeat gene sequences in the gene delivery polynucleotide, and wherein the gene delivery polynucleotide is selectable. In some alternatives, the gene delivery polynucleotide further comprises a sequence for at least one protein. In some alternatives, the protein is a chimeric antigen receptor. Chimeric receptor can also be referred to as artificial T cell receptors, chimeric T cell receptors, chimeric immunoreceptors, and chimeric antigen receptors (CARs). These CARs are engineered receptors that can graft an arbitrary specificity onto an immune receptor cell. Chimeric antigen receptors or "CARs" are considered by some investigators in some contexts to include the antibody or antibody fragment, spacer, signaling domain, and transmembrane region. However, due to the surprising effects of modifying the different components or domains of the CAR, such as the epitope binding region (for example, antibody fragment, scFv, or portion thereof), spacer, transmembrane domain, and/or signaling domain), the components of the CAR are described herein in some contexts to include these features as independent elements. The variation of the different elements of the CAR can, for example, lead to stronger binding affinity for a specific epitope.

Artificial T-cell receptors, or CARs can be used as a therapy for cancer or viral infection using a technique called adoptive cell transfer. T-cells are removed from a patient and modified so that they express receptors specific for a molecule displayed on a cancer cell or virus, or virus-infected cell. The genetically engineered T-cells, which can then recognize and kill the cancer cells or the virus infected cells or promote clearance of the virus, are reintroduced into the patient. In some alternatives, the gene delivery polynucleotide can comprise a sequence for a chimeric antigen receptor. In some alternatives, a method of generating engineered multiplexed T-cells for adoptive T-cell immunotherapy is provided. In the broadest sense the method can comprise providing the gene delivery polynucleotide of any one of the alternatives described herein, introducing the gene delivery polynucleotide into a T-cell, providing a vector encoding a Sleeping Beauty transposase, introducing the vector encoding the Sleeping Beauty transposase into the T-cell, selecting the cells comprising the gene delivery polynucleotide, wherein selecting comprises a first round of selection and a second round of selection, wherein the first round of selection comprises adding a selection reagent at a first concentration range and the second round of selection comprises adding the selection reagent at a second concentration range, and wherein the second concentration range is at least 1.5 fold higher than that of the first concentration range and isolating the T-cells expressing a phenotype under selective pressure. In some alternatives, the selection reagent is MTX.

T-cell co-stimulation is desired for development of an effective immune response and this event occurs during the activation of lymphocytes. A co-stimulatory signal, is antigen non-specific and is provided by the interaction between co-stimulatory molecules expressed on the membrane of the antigen bearing cell and the T-cell. Co-stimulatory molecules can include but are not limited to CD28, CD80, and CD86. In some alternatives, a method for generating engineered multiplexed T-cell for adoptive T-cell immunotherapy is provided. In some alternatives, the T-cell is a chimeric antigen receptor bearing T-cell. In some alternatives, the chimeric antigen receptor bearing T-cell is engineered to express co-stimulatory ligands. In some alternatives, methods are provided for treating, inhibiting, or ameliorating cancer or a viral infection in a subject. In the broadest sense the method can comprise administering to the subject a T-cell of any of the alternatives described herein. Preferably, genetically engineered T cells are used to treat, inhibit, or ameliorate a cancer or a viral disease, wherein the genetically engineered T cells are obtained by preferential amplification of T cells that are transformed to express multiple transgenes encoding receptors or chimeric receptors specific for a molecule presented by a virus or a cancer cell and selection pressure on the transformed T cells is applied in a two-stage MTX selection, utilizing increasing concentrations of MTX. In some of these alternatives, the subject is an animal, such as domestic livestock or a companion animal and on other alternatives, the subject is a human. In some of these alternatives, the chimeric antigen bearing T-cell is engineered to express a co-stimulatory molecule. In some alternatives, the gene delivery polynucleotide comprises a sequence for at least one co-stimulatory molecule. In some alternatives, the gene delivery polynucleotide is circular. In some alternatives, the gene delivery polynucleotide is at least 1 kB to 6 kB. In some alternatives, the gene delivery polynucleotide is a minicircle.

"T cell precursors" as described herein refers to lymphoid precursor cells that can migrate to the thymus and become T cell precursors, which do not express a T cell receptor. All T cells originate from hematopoietic stem cells in the bone marrow. Hematopoietic progenitors (lymphoid progenitor cells) from hematopoietic stem cells populate the thymus and expand by cell division to generate a large population of immature thymocytes. The earliest thymocytes express neither CD4 nor CD8, and are therefore classed as double-negative ($CD4^-CD8^-$) cells. As they progress through their development, they become double-positive thymocytes ($CD4^+CD8^+$), and finally mature to single positive ($CD4^+CD8^-$ or $CD4^-CD8^+$) thymocytes that are then released from the thymus to peripheral tissues.

About 98% of thymocytes die during the development processes in the thymus by failing either positive selection or negative selection, whereas the other 2% survive and leave the thymus to become mature immunocompetent T cells.

The double negative (DN) stage of the precursor T cell is focused on producing a functional β-chain whereas the double positive (DP) stage is focused on producing a functional α-chain, ultimately producing a functional αβ T cell receptor. As the developing thymocyte progresses through the four DN stages (DN1, DN2, DN3, and DN4), the T cell expresses an invariant α-chain but rearranges the β-chain locus. If the rearranged β-chain successfully pairs with the invariant α-chain, signals are produced which cease rearrangement of the β-chain (and silence the alternate allele) and result in proliferation of the cell. Although these signals require this pre-TCR at the cell surface, they are dependent on ligand binding to the pre-TCR. These thymocytes will then express both CD4 and CD8 and progresses to the double positive (DP) stage where selection of the α-chain takes place. If a rearranged β-chain does not lead to any signaling (e.g. as a result of an inability to pair with the invariant α-chain), the cell may die by neglect (lack of signaling).

"Hematopoietic stem cells" or "HSC" as described herein, are precursor cells that can give rise to myeloid cells such as, for example, macrophages, monocytes, macrophages, neutrophils, basophils, eosinophils, erythrocytes, megakaryocytes/platelets, dendritic cells and lymphoid lineages (such as, for example, T-cells, B-cells, NK-cells). HSCs have a heterogeneous population in which three classes of stem cells exist, which are distinguished by their ratio of lymphoid to myeloid progeny in the blood (L/M).

In some alternatives, a method of generating engineered multiplexed T-cells for adoptive T-cell immunotherapy is provided, wherein the method comprises providing a gene delivery polynucleotide, introducing the gene delivery polynucleotide into a T-cell, providing a vector encoding a Sleeping Beauty transposase, introducing the vector encoding the Sleeping Beauty transposase into the T-cell, selecting the cells comprising the gene delivery polynucleotide wherein selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range and isolating the T-cells expressing a phenotype under selective pressure. In some alternatives, the gene delivery polynucleotide comprises a first sequence, wherein the first sequence comprises a first inverted terminal repeat gene sequence, a second sequence, wherein the second sequence comprises a second inverted terminal repeat gene sequence, a third sequence, wherein the third sequence comprises a promoter region sequence, a fourth sequence, wherein the fourth sequence comprises at least one gene encoding a protein, and wherein the fourth sequence is optimized, a fifth sequence, wherein the fifth sequence comprises at least one selectable marker cassette encoding a double mutant of dihydrofolate reductase, wherein the double mutant of dihydrofolate reductase has a 15,000 fold or about 15,000 fold reduced affinity for methotrexate, wherein the methotrexate can be used as a selection mechanism to selectively amplify cells transduced with the gene delivery polynucleotide and wherein the fifth sequence is optimized, a sixth sequence, wherein the sixth sequence comprises a first attachment site (attP) and a seventh sequence, wherein the seventh sequence comprises a second attachment site (attB) wherein each of the first sequence, second sequence, third sequence, fourth sequence, fifth sequence, sixth sequence, and seventh sequence have a 5' terminus and a 3' terminus, and wherein the 3' terminus of the first sequence comprising the first inverted terminal repeat gene sequence is adjacent to the 5' terminus of the third sequence, the 3' terminus of the third sequence is adjacent to the 5' terminus of the fourth sequence, the 3' terminus of the fourth sequence is adjacent to the 5' terminus of the fifth sequence and the 3' terminus of the fifth sequence is adjacent to the 5' terminus of the second sequence comprising a second inverted terminal repeat. In some alternatives, the gene encoding the double mutant of human dihydrofolate reductase comprises the DNA sequence:

(SEQ ID NO: 2)
ATGGTTGGTTCGCTAAACTGCATCGTCGCTGTGTCCCAGAACATGGGCAT

CGGCAAGAACGGGGACTTCCCCTGGCCACCGCTCAGGAATGAATCCAGAT

ATTTCCAGAGAATGACCACAACCTCTTCAGTAGAAGGTAAACAGAATCTG

GTGATTATGGGTAAGAAGACCTGGTTCTCCATTCCTGAGAAGAATCGACC

TTTAAAGGGTAGAATTAATTTAGTTCTCAGCAGAGAACTCAAGGAACCTC

CACAAGGAGCTCATTTTCTTTCCAGAAGTCTAGATGATGCCTTAAAACTT

ACTGAACAACCAGAATTAGCAAATAAAGTAGACATGGTCTGGATAGTTGG

TGGCAGTTCTGTTTATAAGGAAGCCATGAATCACCCAGGCCATCTTAAAC

TATTTGTGACAAGGATCATGCAAGACTTTGAAAGTGACACGTTTTTTCCA

GAAATTGATTTGGAGAAATATAAACTTCTGCCAGAATACCCAGGTGTTCT

CTCTGATGTCCAGGAGGAGAAAGGCATTAAGTACAAATTTGAAGTATATG

AGAAGAATGATTAA.

In some alternatives, the double mutant of human dihydrofolate reductase comprises the protein sequence:

(SEQ ID NO: 3)
MVGSLNCIVA VSQNMGIGKN GDFPWPPLRN ESRYFQRMTT

TSSVEGKQNL VIMGKKTWFS IPEKNRPLKG RINLVLSREL

KEPPQGAHFL SRSLDDALKL TEQPELANKV DMVWIVGGSS

VYKEAMNHPG HLKLFVTRIM QDFESDTFFP EIDLEKYKLL

PEYPGVLSDV QEEKGIKYKF EVYEKND.

In some alternatives, the gene delivery polynucleotide is circular. In some alternatives, the gene delivery polynucleotide is at least 1 kB to 5 kB. In some alternatives, the gene delivery polynucleotide is a minicircle. In some alternatives, the promoter region comprises an EF1 promoter sequence. In some alternatives, the fourth sequence comprises one, two, three, four, or five genes that encode proteins. In some alternatives, the fourth sequence is codon optimized to reduce the total GC/AT ratio of the fourth sequence. In some alternatives, the fourth sequence is optimized by codon optimization for expression in humans. In some alternatives, the fourth sequence is a consensus sequence generated from a plurality of nucleic acids that encode a plurality of related proteins. In some alternatives, the fourth sequence is a consensus sequence generated from a plurality of nucleic acids that encode a plurality of related proteins, such as a plurality of antibody binding domains, which are specific for the same epitope. In some alternatives, the plurality of related proteins comprise a plurality of antibody binding domains, wherein the plurality of antibody binding domains are specific for the same epitope. In some alternatives, the fifth sequence is codon optimized to reduce the total GC/AT ratio of the fifth sequence. In some alternatives, the fifth sequence is optimized by codon optimization for expression in humans. In some alternatives, the protein is a protein for therapy. In some alternatives, the codon optimization and/or consensus sequence is generated by comparing the variability of sequence and/or nucleobases utilized in a plurality of related sequences. In some alternatives, the protein comprises an antibody or a portion thereof, which may be humanized. In some alternatives, the double mutant of dihydrofolate reductase comprises amino acid mutations of L22F and F31S. In some alternatives, the double mutant of dihydrofolate reductase comprises amino acid mutations of L22F and F31S. In some alternatives, the introducing is performed by electroporation. In some alternatives, the selecting is performed by increasing selective pressure through the selective marker cassette. In some alternatives, the selection reagent comprises an agent for selection. In some alternatives, the agent for selection is methotrexate. In some alternatives, the first concentration range is at least 50 nM-100 nM and the second concentration range is at least 75 to 150 nM. In some alternatives, the first concentration is 50 nM, 60 nM, 70 nM, 80 nM, 90 nM, or 100 nM or any concentration that is between a range of concentrations defined by any two of the aforementioned concentrations, and the second concentration range is 75 nM, 80 nM, 90 nM, 100 nM, 110 nM, 120 nM, 130 nM, 140 nM, or 150 nM or any concentration that is between a range of concentrations defined by any two of the aforementioned concentrations. In some alternatives, the first concentration range is at least 75 nM-150 nM and the second concentration range is at least 112.5 nM to 225 nM. In some alternatives, the first concentration is 75 nM, 85 nM, 95 nM, 105 nM, 115 nM, 125 nM, 135 nM, 145 nM, or 150 nM or any concentration that is between a range of concentrations defined by any two of the aforementioned concentrations, and the second concentration range is 112 nM, 122 nM, 132 nM, 142 nM, 152 nM, 162 nM, 172 nM, 182 nM, 192 nM, 202 nM, 212 nM, or 225 nM or any concentration that is between a range of concentrations defined by any two of the aforementioned concentrations. In some alternatives, the first concentration range is at least 300 nM-675 nM and the first concentration range is at least 450 nM to 1012 nM. In some alternatives, the first concentration is 300 nM, 350 nM, 400 nM, 450 nM, 500 nM, 550 nM, 600 nM, 650 nM, or 675 nM or any concentration that is between a range of concentrations defined by any two of the aforementioned concentrations, and the second concentration range is 450 nM, 500 nM, 550 nM, 600 nM, 650 nM, 700 nM, 750 nM, 800 nM, 850 nM, 900 nM, 1000 nM, or 1012 nM or any concentration that is between a range of concentrations defined by any two of the aforementioned concentrations. In some alternatives, the first round of selection comprises exposing the T-cells to the selection agent for 2, 3, 4, 5, 6 or 7 days before the second round of selection. In some alternatives, the second round of selection comprises exposing the T-cells to the selection agent for at least 2, 3, 4, 5, 6, 7, 8, 9, 10, 11, 12, 13, or 14 days or any time that is between a range of times defined by any two of the aforementioned time points before isolation. In some alternatives, the T cells comprise precursor T cells. In some alternatives, the precursor T cells are hematopoietic stem cells.

In some alternatives, a method of generating engineered cells for adoptive T-cell immunotherapy comprising, providing a gene delivery polynucleotide, introducing the gene delivery polynucleotide into a precursor T cell, providing a vector encoding a Sleeping Beauty transposase, introducing the vector encoding the Sleeping Beauty transposase into the precursor T cell, selecting the precursor T cells comprising the gene delivery polynucleotide; wherein selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range and isolating the precursor T-cells expressing a phenotype under selective pressure. In some alternatives, the gene delivery polynucleotide is for stable insertion of a nucleic acid into an oligonucleotide wherein the nucleic acid for insertion is flanked by inverted terminal repeat gene sequences in the gene delivery polynucleotide and wherein the gene delivery polynucleotide is selectable, wherein the gene delivery polynucleotide comprises a first sequence, wherein the first sequence comprises a first inverted terminal repeat gene sequence, a second sequence, wherein the second sequence comprises a second inverted terminal repeat gene sequence, a third sequence, wherein the third sequence comprises a promoter region sequence, a fourth sequence, wherein the fourth sequence comprises at least one gene, wherein the at least one gene encodes a protein or encodes a sequence for mRNA transcription, and wherein the fourth sequence is optimized, a fifth sequence, wherein the fifth sequence comprises at least one selectable marker cassette encoding a double mutant of dihydrofolate reductase, wherein the double mutant of dihydrofolate reductase has a 15,000 fold or about 15,000 fold reduced affinity for methotrexate, wherein the methotrexate can be used to select for cells transduced with the gene delivery polynucleotide, to enhance the ratio of cells expressing the at least one gene and wherein the fifth sequence is optimized, a sixth sequence, wherein the sixth sequence comprises a first attachment site (attP) and a seventh sequence, wherein the seventh sequence comprises a second attachment site (attB); wherein each of the first sequence, second sequence, third sequence, fourth sequence, fifth sequence, sixth sequence, and seventh sequence have a 5' terminus and a 3 terminus, and wherein the 3' terminus of the first sequence comprising the first inverted terminal repeat gene sequence is adjacent to the 5' terminus of the third sequence, the 3' terminus of the third sequence is adjacent to the 5' terminus of the fourth sequence, the 3' terminus of the fourth sequence is adjacent to the 5' terminus of the fifth sequence and the 3' terminus of the fifth sequence is adjacent to the 5' terminus of the second sequence comprising a second inverted terminal repeat. In some alternatives, the gene delivery polynucleotide is circular. In some alternatives, the gene delivery polynucleotide is at least 1 kB to 5 kB. In some alternatives, the promoter region comprises an EF1 promoter sequence. In some alternatives, the fourth sequence comprises one, two, three, four, or five genes that encode proteins. In some alternatives, the fourth sequence is codon optimized to reduce the total GC/AT ratio of the fourth sequence. In some alternatives, the fourth sequence is optimized by codon optimization for expression in humans. In some alternatives, the fourth sequence is a consensus sequence generated from a plurality of nucleic acids that encode a plurality of related proteins. In some alternatives, the fourth sequence is a consensus sequence generated from a plurality of nucleic acids that encode a plurality of related proteins, such as a plurality of antibody binding domains, which are specific for the same epitope. In some alternatives, the plurality of related proteins comprise a plurality of antibody binding domains, wherein the plurality of antibody binding domains are specific for the same epitope. In some alternatives, the fifth sequence is codon optimized to reduce the total GC/AT ratio of the fifth sequence. In some alternatives, the fifth sequence is optimized by codon optimization for expression in humans. In some alternatives, the codon optimization and/or consensus sequence is generated by comparing the variability of sequence and/or nucleobases utilized in a plurality of related sequences. In some alternatives, the protein is a protein for therapy. In some alternatives, the protein comprises an antibody or a portion thereof, which may be humanized. In some alternatives, the double mutant of dihydrofolate reductase comprises amino acid mutations of L22F and F31S. In some alternatives, the gene delivery polynucleotide is a minicircle. In some alternatives, the introducing is performed by electroporation. In some alternatives, the selecting is performed by increasing selective pressure through the selective marker cassette. In some alternatives, the selection reagent comprises an agent for selection. In some alternatives, the agent for selection is methotrexate. In some alternatives, the first concentration range is at least 50 nM-100 nM and the second concentration range is at least 75 to 150 nM. In some alternatives, the first concentration range is at least 75 nM-150 nM and the second concentration range is at least 112.5 nM to 225 nM. In some alternatives, the first concentration range is at least 300 nM-675 nM and the first concentration range is at least 450 nM to 1012 nM. In some alternatives, the first round of selection comprises exposing the T-cells to the selection agent for 2, 3, 4, 5, 6 or 7 days before the second round of selection. In some alternatives, the second round of selection comprises exposing the T-cells to the selection agent for at least 2, 3, 4, 5, 6, 7, 8, 9, 10, 11, 12, 13, or 14 days or any time that is between a range of times defined by any two of the aforementioned time points before isolation. In some alternatives, the T cell precursor is a hematopoietic stem cell.

In some alternatives, a method of increasing protein production in a precursor T-cell is provided wherein the method comprises providing a polynucleotide, introducing the polynucleotide into a cell, providing a vector encoding a Sleeping Beauty transposase; introducing the vector encoding the Sleeping Beauty transposase into the precursor T-cell, selecting the precursor T cells comprising the gene delivery polynucleotide, wherein selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range and isolating the precursor T cells expressing a phenotype under selective pressure. In some alternatives, the gene delivery polynucleotide is for stable insertion of a nucleic acid into an oligonucleotide wherein the nucleic acid for insertion is flanked by inverted terminal repeat gene sequences in the gene delivery polynucleotide and wherein the gene delivery polynucleotide is selectable, wherein the gene delivery polynucleotide comprises a first sequence, wherein the first sequence comprises a first inverted terminal repeat gene sequence, a second sequence, wherein the second sequence comprises a second inverted terminal repeat gene sequence, a third sequence, wherein the third sequence comprises a promoter region sequence, a fourth sequence, wherein the fourth sequence comprises at least one gene, wherein the at least one gene encodes a protein or encodes a sequence for mRNA transcription, and wherein the fourth sequence is optimized, a fifth sequence, wherein the fifth sequence comprises at least one selectable marker cassette encoding a double mutant of dihydrofolate reductase, wherein the double mutant of dihydrofolate reductase has a 15,000 fold or about 15,000 fold reduced affinity for methotrexate, wherein the methotrexate can be used to select for cells transduced with the gene delivery polynucleotide, to enhance the ratio of cells expressing the at least one gene and wherein the fifth sequence is optimized, a sixth sequence, wherein the sixth sequence comprises a first attachment site (attP) and a seventh sequence, wherein the seventh sequence comprises a second attachment site (attB); wherein each of the first sequence, second sequence, third sequence, fourth sequence, fifth sequence, sixth sequence, and seventh sequence have a 5' terminus and a 3 terminus, and wherein the 3' terminus of the first sequence comprising the first inverted terminal repeat gene sequence is adjacent to the 5' terminus of the third sequence, the 3' terminus of the third sequence is adjacent to the 5' terminus of the fourth sequence, the 3' terminus of the fourth sequence is adjacent to the 5' terminus of the fifth sequence and the 3' terminus of the fifth sequence is adjacent to the 5' terminus of the second sequence comprising a second inverted terminal repeat. In some alternatives, the gene delivery polynucleotide is circular. In some alternatives, the gene delivery polynucleotide is at least 1 kB to 5 kB. In some alternatives, the promoter region comprises an EF1 promoter sequence. In some alternatives, the fourth sequence comprises one, two, three, four, or five genes that encode proteins. In some alternatives, the fourth sequence is codon optimized to reduce the total GC/AT ratio of the fourth sequence. In some alternatives, the fourth sequence is optimized by codon optimization for expression in humans. In some alternatives, the fourth sequence is a consensus sequence generated from a plurality of nucleic acids that encode a plurality of related proteins. In some alternatives, the fourth sequence is a consensus sequence generated from a plurality of nucleic acids that encode a plurality of related proteins, such as a plurality of antibody binding domains, which are specific for the same epitope. In some alternatives, the plurality of related proteins comprise a plurality of antibody binding domains, wherein the plurality of antibody binding domains are specific for the same epitope. In some alternatives, the fifth sequence is codon optimized to reduce the total GC/AT ratio of the fifth sequence. In some alternatives, the fifth sequence is optimized by codon optimization for expression in humans. In some alternatives, the codon optimization and/or consensus sequence is generated by comparing the variability of sequence and/or nucleobases utilized in a plurality of related sequences. In some alternatives, the protein is a protein for therapy. In some alternatives, the protein comprises an antibody or a portion thereof, which may be humanized. In some alternatives, the double mutant of dihydrofolate reductase comprises amino acid mutations of L22F and F31S. In some alternatives, the gene delivery polynucleotide is a minicircle. In some alternatives, the introducing is performed by electroporation. In some alternatives, the selecting is performed by increasing selective pressure through the selective marker cassette. In some alternatives, the selection reagent comprises an agent for selection. In some alternatives, the agent for selection is methotrexate.

In some alternatives, wherein the first concentration range is at least 50 nM-100 nM and the second concentration range is at least 75 to 150 nM. In some alternatives, the first concentration range is at least 75 nM-150 nM and the second concentration range is at least 112.5 nM to 225 nM. In some alternatives, the first concentration range is at least 300 nM-675 nM and the second concentration range is at least 450 nM to 1012 nM. In some alternatives, the first round of selection comprises exposing the cells to the selection agent for 2, 3, 4, 5, 6 or 7 days before the second round of selection. In some alternatives, the second round of selection comprises exposing the cells to the selection agent for at least 2, 3, 4, 5, 6, or 7 days before isolation. In some alternatives, the precursor T cells are hematopoietic stem cells.

A peptide or polypeptide encoded by a non-host DNA molecule is a "heterologous" peptide or polypeptide.

An "integrated genetic element" is a segment of DNA that has been incorporated into a chromosome of a host cell after that element is introduced into the cell through human manipulation. Within the present alternatives, integrated genetic elements can be derived from minicircles that are introduced into the cells by electroporation or other techniques. Integrated genetic elements are passed from the original host cell to its progeny. In some alternatives, an integrated genetic element is incorporated into a chromosome of a host cell by a gene delivery polynucleotide is circular. In some alternatives, the gene delivery polynucleotide is at least 1 kB to 6 kB. In some alternatives, the gene delivery polynucleotide is a minicircle.

A "cloning vector" or vector is a nucleic acid molecule, such as a minicircle, plasmid, cosmid, plastome, or bacteriophage that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transduced with the cloning vector. Marker genes typically include genes that provide tetracycline resistance or ampicillin resistance but in some alternatives can include a methotrexate resistance gene.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter. In some alternatives, an expression vector is provided. In some alternatives, the expression vector encodes a transposase. In some alternatives, the transposase is a Sleeping Beauty transposase. In some alternatives, expression vector is circular. In some alternatives, the expression vector is at least 1 kB to 6 kB. In some alternatives, the expression vector is a minicircle.

"Minicircles," as described herein, are small circular plasmid derivatives that have been freed from all prokaryotic vector parts. Minicircles can serve as an expression vector, where they have been applied as transgene carriers for the genetic modification of mammalian cells, with the advantage that, since they contain no bacterial DNA sequences, they are less likely to be perceived as foreign and destroyed. As such, typical transgene delivery methods involve plasmids, which contain foreign DNA. The smaller size of minicircles also extends their cloning capacity and facilitates their delivery into cells. Without being limiting, the preparation of minicircles can follow a two-step procedure, which can involve production of a parental plasmid (bacterial plasmid with eukaryotic inserts) in E. coli and induction of a site-specific recombinase at the end of this process but still in bacteria. These steps can be followed by the excision of prokaryotic vector parts via two recombinase-target sequences at both ends of the insert and recovery of the resulting minicircle (vehicle for the highly efficient modification of the recipient cell) and the miniplasmid by capillary gel electrophoresis (CGE).

The purified minicircle can be transferred into the recipient cell by transfection, by electroporation, or by other methods known to those skilled in the art. Conventional minicircles can lack an origin of replication, so they cannot replicate within the target cells and the encoded genes will disappear as the cell divides (which can be either an advantage or disadvantage depending on whether the application demands persistent or transient expression). Some alternatives utilize a gene delivery polynucleotide for stable insertion of a nucleic acid into a gene, wherein the nucleic acid for insertion is flanked by inverted terminal repeat gene sequences in the gene delivery polynucleotide, and wherein the gene delivery polynucleotide is selectable. In some alternatives, the gene delivery polynucleotide is a minicircle.

As used herein, "nucleofection", refers to a transfection method of exogenous nucleic acid(s) into a host cell and is performed by electroporation. In some alternatives, a method of generating engineered multiplexed T-cells for adoptive T-cell immunotherapy is provided. In the broadest sense the method can comprise providing the gene delivery polynucleotide of any of the alternatives described herein, introducing the gene delivery polynucleotide into a T-cell, selecting the cells comprising the gene delivery polynucleotide, wherein selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range and isolating the T-cells expressing a phenotype under selective pressure. In some alternatives, the selection reagent is MTX. In some alternatives, introducing the gene delivery polynucleotide into a T-cell can be performed by electroporation.

"Host cell" as described herein, is a cell that contains one or more nucleases, for example endonucleases, end-processing enzymes, and/or endonuclease/end-processing enzyme fusion proteins encompassed by the present alternatives or a vector encoding the same that supports the replication, and/or transcription or transcription and translation (expression) of one or more nucleases, for example endonucleases, end-processing enzymes, and/or endonuclease/end-processing enzyme fusion proteins. In some alternatives, host cells for use in the present alternatives can be eukaryotic cells. Host cells of the immune system can include T-cells. In some alternatives, a method of generating engineered multiplexed T-cells for adoptive T-cell immunotherapy is provided. In some alternatives, the method can comprise providing the gene delivery polynucleotide of any one of the alternatives described herein, introducing the gene delivery polynucleotide into a T-cell, providing a vector encoding a Sleeping Beauty transposase, introducing the vector encoding the Sleeping Beauty transposase into the T-cell, selecting the cells comprising the gene delivery polynucleotide, wherein the selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range and isolating the T-cells expressing a phenotype under selective pressure. In some alternatives, the selection reagent is MTX.

As described herein, "transposable element" (TE), transposon or retrotransposon, can be referred to as a DNA sequence that can change its position within the genome, sometimes creating or reversing mutations and altering the cell's genome size. Transposition often results in duplication of the TE. TEs can make up a large fraction of the C-value of eukaryotic cells. "C-values," as described herein, refers to amount, in picograms, of DNA contained within a haploid nucleus of one half the amount in a diploid somatic cells of a eukaryotic organism. In some cases, the terms C-value and genome size are used interchangeably, however in polyploids the C-value can represent two or more genomes contained within the same nucleus. In Oxytricha, which has a unique genetic system, they play a critical role in development. They are also very useful to researchers as a means to alter DNA inside a living organism. In some alternatives, a gene delivery polynucleotide for stable insertion of a nucleic acid into a gene, wherein the nucleic acid for insertion is flanked by inverted terminal repeat gene sequences in the gene delivery polynucleotide and wherein the gene delivery polynucleotide is selectable, the gene delivery polynucleotide, is provided. In some alternatives, the gene delivery polynucleotide comprises a transposon.

The "Sleeping Beauty transposon system" as described herein, is composed of a Sleeping Beauty (SB) transposase and a transposon that was designed in 1997 to insert specific sequences of DNA into genomes of vertebrate animals. DNA transposons can translocate from one DNA site to another in a simple, cut-and-paste manner. Transposition is a precise process in which a defined DNA segment is excised from one DNA molecule and moved to another site in the same or different DNA molecule or genome.

An SB transposase can insert a transposon into a TA dinucleotide base pair in a recipient DNA sequence. The insertion site can be elsewhere in the same DNA molecule, or in another DNA molecule (or chromosome). In mammalian genomes, including humans, there are approximately 200 million TA sites. The TA insertion site is duplicated in the process of transposon integration. This duplication of the TA sequence is a hallmark of transposition and used to ascertain the mechanism in some experiments. The transposase can be encoded either within the transposon or the transposase can be supplied by another source, in which case the transposon becomes a non-autonomous element.

In some alternatives, a gene delivery polynucleotide for stable insertion of a nucleic acid into a gene, wherein the nucleic acid for insertion is flanked by inverted terminal repeat gene sequences in the gene delivery polynucleotide and wherein the gene delivery polynucleotide is selectable, the gene delivery polynucleotide, is provided. In some alternatives, the gene delivery polynucleotide comprises a transposon. In some alternatives, the transposon is a Sleeping Beauty transposon. In some alternatives, the nucleic acid to be inserted is a Sleeping Beauty transposon flanked by inverted terminal repeat gene sequences.

In some alternatives, the gene delivery polynucleotide for stable insertion of nucleic acid is a minicircle. In some alternatives, the gene delivery polynucleotide for stable insertion of nucleic acid comprises a Sleeping Beauty transposon. In some alternatives, methods of generating engineered multiplexed T-cells are provided. In some alternatives, the method comprises delivering a Sleeping Beauty transposase to a cell. In some alternatives, methods of increasing protein production in a T-cell are provided. In some alternatives, the method comprises providing a vector encoding a Sleeping Beauty transposase. In some alternatives, the method comprises delivering a vector encoding a Sleeping Beauty transposase to a cell.

"Codon optimization" as described herein, refers to the design process of altering codons to codons known to increase maximum protein expression efficiency in a desired cell. In some alternatives, codon optimization is described, wherein codon optimization can be performed by using algorithms that are known to those skilled in the art to create synthetic genetic transcripts optimized for high protein yield. Programs containing algorithms for codon optimization are known to those skilled in the art. Programs can include, for example, OptimumGene™, GeneGPS® algorithms, etc. Additionally synthetic codon optimized sequences can be obtained commercially for example from Integrated DNA Technologies and other commercially available DNA sequencing services. In some alternatives, a gene delivery polynucleotide for stable insertion of a nucleic acid into a gene, wherein the nucleic acid for insertion is flanked by inverted terminal repeat gene sequences in the gene delivery polynucleotide and wherein the gene delivery polynucleotide is selectable, is provided. In some alternatives, the gene delivery polynucleotides are described, wherein the genes for the complete gene transcript are codon optimized for expression in humans. In some alternatives, the genes are optimized to have selected codons specifically for maximal protein expression in human cells, which can increase the concentration of proteins or CARs of a T-cell.

Codon optimization can be performed to reduce the occurrence of secondary structure in a polynucleotide, as well. In some alternatives, codon optimization can also be performed to reduce the total GC/AT ratio. Strict codon optimization can also lead to unwanted secondary structure or an undesirable GC content that leads to secondary structure. As such the secondary structures affect transcriptional efficiency. Programs such as GeneOptimizer can be used after codon usage optimization, for secondary structure avoidance and GC content optimization. These additional programs can be used for further optimization and troubleshooting after an initial codon optimization to limit secondary structures that may occur after the first round of optimization. Alternative programs for optimization are known to those skilled in the art. In some alternatives, a gene delivery polynucleotide for stable insertion of a nucleic acid into a gene, wherein the nucleic acid for insertion is flanked by inverted terminal repeat gene sequences in the gene delivery polynucleotide and wherein the gene delivery polynucleotide is selectable, provided. In some alternatives, the gene delivery polynucleotide comprises sequences that are codon optimized for expression in humans and/or to remove secondary structure and/or to reduce the total GC/AT ratio. In some alternatives, the sequences are optimized for secondary structure avoidance. In some alternatives, the sequences are optimized to reduce the total GC/AT ratio.

In some alternatives, a method of generating engineered multiplexed T-cells for adoptive T-cell immunotherapy is provided. In the broadest sense, the method can comprise providing the gene delivery polynucleotide of any one of the alternatives described herein, introducing the gene delivery polynucleotide into a T-cell, providing a vector encoding a Sleeping Beauty transposase, introducing the vector encoding the Sleeping Beauty transposase into the T-cell, selecting the cells comprising the gene delivery polynucleotide, wherein selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range, and isolating the T-cells expressing a phenotype under selective pressure. In some alternatives, the selection reagent is MTX.

Adoptive Immunotherapy for Cancer or a Viral Disease.

The premise of adoptive immunotherapy for cancer is transferring a patient's own tumor-specific T-cells into patients to facilitate the destruction of malignant cells. T-cells can be genetically-engineered to recognize tumor-specific antigens and exert cytotoxic activity against cancer cells. A method of adoptive immunotherapy for cancer is to isolate patient T-cells and introduce tumor recognition capability by expressing chimeric antigen receptors (CARs), membrane proteins that contain an extracellular tumor-binding domain linked to an intracellular signaling domain via a transmembrane segment. "Adoptive immunotherapy" or "T-cell adoptive transfer" refers to use of T-cell based cytotoxic response to attack cancer cells or specific cell targets. T-cells that have a natural or genetically engineered reactivity to a patient's cancer can be generated in vitro and then transferred back into the subject in need. Without being limiting, an example of adoptive transfer can be achieved by removing T-cells from a subject that has cancer or a viral disease and these T cells can be genetically engineered to express receptors specific for biomarkers found on a cancer cell or virus such that the genetically engineered T cells attack the cancer cells or virus or virus infected cells once the genetically engineered T-cells are transferred back into the subject. In some alternatives, a method of generating engineered multiplexed T-cells for adoptive T-cell immunotherapy is provided. In some alternatives, methods of targeting malignant cells for destruction are provided. In some alternatives a method of treating, inhibiting, or ameliorating a cancer or a viral disease in a subject is provided. In some alternatives the method of treating, inhibiting, or ameliorating a cancer or a viral disease in a subject comprises administering to the subject an engineered multiplexed T-cells for adoptive T-cell immunotherapy. In some alternatives, the subject is human.

The co-integration of additional genes can further increase the anti-tumor or antiviral activity of CAR-expressing T-cells. Comprehensive T-cell activation requires, in addition to initial tumor or viral recognition and signal initiation by CAR, engagement of costimulatory and cytokine receptors, which may not be present within the immunosuppressive environment of the tumor or the viral infected subject. To address this immunosuppressive environment of the tumor, for example, expression of co-stimulatory ligands such as CD80 and 4-1BBL in engineered, CAR-expressing T-cells can result in greater T-cell expansion due to auto-co-stimulation compared to expression of co-stimulatory ligands on tumor cells. Another challenge in T-cell immunotherapy is cell survival after infusion into patients. Induced expression of anti-apoptotic proteins has been shown to improve in vivo survival of T-cells. Tumor homing and infiltration can be increased by introduction of chemokine receptors in engineered T-cells and this approach can be especially useful for tumors that express chemokines that are not normally recognized by T-cells. Finally, T-cells can be engineered to better resist the immunosuppressive tumor microenvironment or the immunocompromised virally infected subject through, for example, induced cytokine expression. Thus, methods to rapidly generate engineered T-cells expressing multiple transgenes are important and advantageous for clinical translation of T-cell immunotherapy. In some alternatives, methods of generating engineered multiplexed T-cells for adoptive T-cell immunotherapy are provided. In some alternatives, the T-cells express chimeric antigen receptors. In some alternatives, T-cells expressing chimeric antigen receptors are engineered to express co-stimulatory ligands. In some alternatives, the T-cells expressing chimeric antigen receptors express co-stimulatory ligands. In some alternatives the co-stimulatory ligands are CD80. In some alternatives, the co-stimulatory ligands are 4-1BBL.

Adoptive cell transfer can refer to the transfer of cells, immune-derived cells, back into the same patient or into a different recipient host. For isolation of immune cells for adoptive transfer, blood can be drawn into tubes containing anticoagulant and the PBM (buffy coat) cells are isolated, typically by density barrier centrifugation. In T-cell based therapies, the cells can be expanded in vitro using cell culture methods relying heavily on the immunomodulatory action of interleukin-2 and returned to the patient in large numbers intravenously in an activated state. Anti-CD3 antibody can be used to promote the proliferation of T-cells in culture. Research into interleukin-21 indicates that it can also play an important role in enhancing the efficacy of T-cell based therapies prepared in vitro. Cells used in adoptive cell transfer can be used to deliver genetically modified lymphocytes, using recombinant DNA technology to achieve any number of goals. In alternatives described herein, adoptive cell transfer is used to transfer cells into a subject, wherein the cells are CAR expressing lymphocytes. In some alternatives, CAR expressing lymphocytes are host cells in methods for generating engineered multiplexed T-cells for adoptive T-cell immunotherapy. In some alternatives, the method comprises providing the gene delivery polynucleotide of the alternatives described herein, introducing the gene delivery polynucleotide into a T-cell, providing a vector encoding a Sleeping Beauty transposase, introducing the vector encoding the Sleeping Beauty transposase into the T-cell, selecting the cells comprising the gene delivery polynucleotide, wherein selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range, and isolating the T-cells expressing a phenotype under selective pressure. In some alternatives, the gene delivery polynucleotide comprises a sequence for a co-stimulatory ligand. In some alternatives, the gene delivery polynucleotide comprises a sequence for a chimeric antigen receptor. In some alternatives, the T-cell expresses a CAR. In alternatives described herein, the CAR expressing lymphocytes are genetically modified by minicircles wherein the minicircles comprise Sleeping Beauty transposons. In some alternatives, the selection reagent is MTX.

By way of example and not of limitation, genetically engineered T-cells can be created by infecting patient's cells with a transferring virus that contain a copy of a T-cell receptor (TCR) gene that is specialized to recognize, for example, tumor or viral antigens. It is important that the transferring virus is not able to reproduce within the cell however, but should integrate into the human genome. This is beneficial as new TCR gene remains stable in the T-cell. A patient's own T-cells are exposed to these transferring viruses and then are expanded non-specifically or stimulated using the genetically engineered TCR. The cells are then transferred back into the patient and are ready to mount an immune response against the tumor, virus, or viral infected cell. The use of adoptive cell transfer with genetically engineered T-cells is a promising new approach for the treatment of a variety of cancers or viral infections. In some alternatives, methods of adoptive immunotherapy for cancer are provided. In some alternatives, methods of adoptive immunotherapy for viral infections are provided.

The method of making genetically engineered T-cells by using a viral vector can have several drawbacks. Genetic modification of T-cells is typically accomplished using γ-retroviral or lentiviral vectors. While effective, drawbacks include cost of production, limited gene packaging capacity, and potential safety issues. Plasmids containing transposon systems such as Sleeping Beauty (SB) or piggyBac offer a non-viral approach for stably introducing genes into T-cells. Recently, the piggyBac system was used to produce stably-transfected mammalian cells expressing multiple transgenes of interest by delivery of multiple transposons. The SB system, first reactivated for mammalian cell use by Ivies and coworkers, has been used as the gene delivery modality in clinical trials of T-cell immunotherapy. Gene integration by SB has weaker preference for transcriptional units and their regulatory sequences compared to the γ-retroviral and lentiviral vectors and is therefore considered to be safer. In some alternatives described herein, genetic modification by minicircles comprising the Sleeping Beauty system are contemplated. In some alternatives described herein, genetic modification by minicircles comprising the piggyBac system are contemplated. In some alternatives described herein, genetic modification by minicircles comprising the Sleeping Beauty system are contemplated.

Minicircles are particularly attractive as transfection platforms for three reasons. First, the transfection efficiency of minicircles by electroporation is superior to that of their plasmid analogues. Second, transposition efficiency is higher in minicircles due to the shorter distance between the two transposon ends, which has been shown to affect transposase efficiency. Finally, as cell viability after nucleofection decreases with increasing construct size, minicircles are more advantageous given their smaller size compared to their analogous plasmids. To further improve transposition efficiency, the optimized SB100X hyperactive transposase developed by Izsvak et al. (*Nature Genet.* 2009, 41, 753-761; incorporated by reference in its entirety) can be used in combination with the T3 generation of SB previously by Yant et al (*Mol. Cell. Biol.* 2004, 24, 9239-9247; incorporated by reference in its entirety). In several alternatives described herein, methods for making a genetically modified T-cell for adoptive cell transfer are contemplated. In some alternatives, the methods comprise introducing a minicircle into a T-cell. In some alternatives, the introduction comprises electroporation delivery.

Another challenge in T-cell immunotherapy is cell survival after infusion into patients. Induced expression of anti-apoptotic proteins has been shown to improve in vivo survival of T-cells. Tumor homing and infiltration has been increased by introduction of chemokine receptors in engineered T-cells; this approach can be especially useful for tumors that express chemokines that are not normally recognized by T-cells. Finally, T-cells can be engineered to better resist the immunosuppressive tumor microenvironment through, for example, induced cytokine expression. Thus, methods to rapidly generate engineered T-cells expressing multiple transgenes are important and advantageous for clinical translation of T-cell immunotherapy. In some alternatives described herein, methods of introducing co-integration of additional genes for co-integration to further increase the anti-tumor activity of CAR-expressing T-cells are contemplated. In some alternatives, the additional genes encode co-stimulatory ligands. In some alternatives, the co-stimulatory ligand is CD80. In some alternatives, the co-stimulatory ligand is 4-1BBL. In some alternatives, the additional genes encode anti-apoptotic proteins. In some alternatives the additional genes encode chemokine receptors.

In some alternatives, methods of generating engineered multiplexed T-cells for adoptive T-cell immunotherapy are provided. In the broadest sense, the method can comprise providing the gene delivery polynucleotide of any of the alternatives described herein, introducing the gene delivery polynucleotide into a T-cell, providing a vector encoding a Sleeping Beauty transposase, introducing the vector encoding the Sleeping Beauty transposase into the T-cell, selecting the cells comprising the gene delivery polynucleotide, wherein selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range, and isolating the T-cells expressing a phenotype under selective pressure. In some alternatives, the T-cells are chimeric antigen receptor (CAR) expressing T-cells. In some alternatives, the selection reagent is MTX.

In some alternatives, methods of increasing protein production in a T-cell are provided. In the broadest sense, the method can comprise providing the gene delivery polynucleotide of any of the alternatives described herein, introducing the gene delivery polynucleotide into a T-cell, providing a vector encoding a Sleeping Beauty transposase, introducing the vector encoding the Sleeping Beauty transposase into the T-cell, selecting the cells comprising the gene delivery polynucleotide, wherein selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range, and isolating the T-cells expressing a phenotype under selective pressure. In some alternatives, the selection reagent is MTX. In some alternatives, the T-cells are chimeric antigen receptor (CAR) expressing T-cells.

As described herein, an alternative of the system comprises an engineered, non-viral gene delivery system comprising three key features: (1) Sleeping Beauty transposon system for stable gene expression, (2) minicircles for enhanced transfection, and (3) a double mutant of human dihydrofolate reductase (DHFRdm) as a selection mechanism (FIG. 1).

Minicircles are particularly attractive as transfection platforms for three reasons. First, the transfection efficiency of minicircles by electroporation is superior to that of their plasmid analogues. Second, transposition efficiency is higher in minicircles due to the shorter distance between the two transposon ends, which has been shown to affect transposase efficiency. Finally, as cell viability after nucleofection decreases with increasing construct size, minicircles are more desirable given their smaller size compared to their analogous plasmids. To further improve transposition efficiency, the optimized SB100X hyperactive transposase developed by Izsvak et al. (*Nature Genet.* 2009, 41, 753-761; incorporated herein by reference in its entirety) was used in combination with the T3 generation of SB transposon previously by Yant et al (*Mol. Cell. Biol.* 2004, 24, 9239-9247; incorporated herein by reference in its entirety). In some alternatives described herein, genetic modification of T-cells is performed using minicircles. In some alternatives, the minicircles comprise transposons. In some alternatives, the transposons comprise Sleeping Beauty transposons. In some alternatives, an optimized SB100X hyperactive transposase is used in combination with a T3 generation of SB transposon.

A selection mechanism for rapid selection of engineered T-cells can also be employed. The double mutant of human dihydrofolate reductase (DHFRdm, with amino acid mutations L22F and F31S) exhibits a 15,000-fold reduced affinity for methotrexate, a potent inhibitor of DHFR that results in blockade of thymidylate and purine synthesis. Expression of DHFRdm in T-cells imparts MTX resistance without compromising proliferative ability, expression of T-cell markers, or cytolytic ability. Additional advantages of this selection system include availability of clinical grade MTX, the use of a non-genotoxic drug, and the small gene size of DHFRdm (561 bp). Therefore, MTX can be used as a selection mechanism to selectively amplify SB-transduced cells. In some alternatives, the minicircles comprise a genetic sequence encoding a double mutant of human dihydrofolate reductase. In some alternatives, a selection method for rapid selection of engineered T-cells is provided. In some alternatives, the selection method comprises contacting engineered T-cells with clinical grade methotrexate. In some alternatives, the T-cells comprise a minicircle wherein the minicircle comprises a sequence for a double mutant of human dihydrofolate reductase. In some alternatives, the double mutant of human dihydrofolate reductase exhibits a 15,000 fold or about 15,000 fold reduced specificity for methotrexate. In some alternatives, methotrexate can be used to contact the T-cells for selectively amplifying cells transduced with minicircles, wherein the minicircles comprise a sequence for the double mutant of human dihydrofolate reductase. In some alternatives, the gene encoding the double mutant of human dihydrofolate reductase comprises the DNA sequence:

```
                                      (SEQ ID NO: 2)
ATGGTTGGTTCGCTAAACTGCATCGTCGCTGTGTCCCAGAACATGGGCAT

CGGCAAGAACGGGGACTTCCCCTGGCCACCGCTCAGGAATGAATCCAGAT

ATTTCCAGAGAATGACCACAACCTCTTCAGTAGAAGGTAAACAGAATCTG

GTGATTATGGGTAAGAAGACCTGGTTCTCCATTCCTGAGAAGAATCGACC

TTTAAAGGGTAGAATTAATTTAGTTCTCAGCAGAGAACTCAAGGAACCTC

CACAAGGAGCTCATTTTCTTTCCAGAAGTCTAGATGATGCCTTAAAACTT

ACTGAACAACCAGAATTAGCAAATAAAGTAGACATGGTCTGGATAGTTGG

TGGCAGTTCTGTTTATAAGGAAGCCATGAATCACCCAGGCCATCTTAAAC

TATTTGTGACAAGGATCATGCAAGACTTTGAAAGTGACACGTTTTTTCCA

GAAATTGATTTGGAGAAATATAAACTTCTGCCAGAATACCCAGGTGTTCT

CTCTGATGTCCAGGAGGAGAAAGGCATTAAGTACAAATTTGAAGTATATG

AGAAGAATGATTAA.
```

In some alternatives, the double mutant of human dihydrofolate reductase comprises the protein sequence:

```
                                      (SEQ ID NO: 3)
MVGSLNCIVA VSQNMGIGKN GDFPWPPLRN ESRYFQRMTT

TSSVEGKQNL VIMGKKTWFS IPEKNRPLKG RINLVLSREL

KEPPQGAHFL SRSLDDALKL TEQPELANKV DMVWIVGGSS

VYKEAMNHPG HLKLFVTRIM QDFESDTFFP EIDLEKYKLL

PEYPGVLSDV QEEKGIKYKF EVYEKND.
```

Stable transfer of up to three transgenes into the H9 T-cell line using multiplexed delivery of minicircles containing SB transposons followed by methotrexate (MTX) selection can be performed. Cells with higher number of gene integrations can be preferentially obtained by increasing selection pressure with MTX. Using a two-step selection method through two successive MTX selection rounds, 50% of cells expressing three transgene products can be obtained. In some alternatives, a method of stably transferring transgenes into a cell line is provided. In some alternatives, a method of introducing minicircles into a cell line is provided. In some alternatives, the minicircles comprise Sleeping Beauty transposons. In some alternatives, the method further comprises increasing selection pressure with methotrexate, wherein increasing the selection pressure comprises contacting the cell line with increasing concentrations of methotrexate. In some alternatives, the two rounds of methotrexate selection are performed.

Additional Alternatives

In some alternatives, a gene delivery polynucleotide for stable insertion of a nucleic acid into a gene, wherein the nucleic acid for insertion is flanked by inverted terminal repeat gene sequences in the gene delivery polynucleotide and wherein the gene delivery polynucleotide is selectable, the gene delivery polynucleotide, is provided. In the broadest sense, the gene delivery polynucleotide comprises a first sequence, wherein the first sequence comprises a first inverted terminal repeat gene sequence, a second sequence, wherein the second sequence comprises a second inverted terminal repeat gene sequence, a third sequence, wherein the third sequence comprises a promoter region sequence, a fourth sequence, wherein the fourth sequence comprises at least one gene encoding a protein, and wherein the fourth sequence is optimized, a fifth sequence, wherein the fifth sequence comprises at least one selectable marker cassette encoding a double mutant of dihydrofolate reductase, wherein the double mutant of dihydrofolate reductase has a 15,000 fold or about 15,000 fold reduced affinity for methotrexate, wherein the methotrexate can be used as a selection mechanism to selectively amplify cells transduced with the gene delivery polynucleotide and wherein the fifth sequence is optimized, a sixth sequence, wherein the sixth sequence comprises a first attachment site (attP), and a seventh sequence, wherein the seventh sequence comprises a second attachment site (attB); wherein each of the first sequence, second sequence, third sequence, fourth sequence, fifth sequence, sixth sequence, and seventh sequence have a 5' terminus and a 3 terminus, and wherein the 3' terminus of the first sequence comprising the first inverted terminal repeat gene sequence is adjacent to the 5' terminus of the third sequence, the 3' terminus of the third sequence is adjacent to the 5' terminus of the fourth sequence, the 3' terminus of the fourth sequence is adjacent to the 5' terminus of the fifth sequence and the 3' terminus of the fifth sequence is adjacent to the 5' terminus of the second sequence comprising a second inverted terminal repeat. In some alternatives, the gene encoding the double mutant of human dihydrofolate reductase comprises the DNA sequence:

(SEQ ID NO: 2)
ATGGTTGGTTCGCTAAACTGCATCGTCGCTGTGTCCCAGAACATGGGCAT

CGGCAAGAACGGGGACTTCCCCTGGCCACCGCTCAGGAATGAATCCAGAT

ATTTCCAGAGAATGACCACAACCTCTTCAGTAGAAGGTAAACAGAATCTG

GTGATTATGGGTAAGAAGACCTGGTTCTCCATTCCTGAGAAGAATCGACC

TTTAAAGGGTAGAATTAATTTAGTTCTCAGCAGAGAACTCAAGGAACCTC

CACAAGGAGCTCATTTTCTTTCCAGAAGTCTAGATGATGCCTTAAAACTT

ACTGAACAACCAGAATTAGCAAATAAAGTAGACATGGTCTGGATAGTTGG

TGGCAGTTCTGTTTATAAGGAAGCCATGAATCACCCAGGCCATCTTAAAC

TATTTGTGACAAGGATCATGCAAGACTTTGAAAGTGACACGTTTTTTCCA

GAAATTGATTTGGAGAAATATAAACTTCTGCCAGAATACCCAGGTGTTCT

CTCTGATGTCCAGGAGGAGAAAGGCATTAAGTACAAATTTGAAGTATATG

AGAAGAATGATTAA.

In some alternatives, the double mutant of human dihydrofolate reductase comprises the protein sequence:

(SEQ ID NO: 3)
MVGSLNCIVA VSQNMGIGKN GDFPWPPLRN ESRYFQRMTT

TSSVEGKQNL VIMGKKTWFS IPEKNRPLKG RINLVLSREL

KEPPQGAHFL SRSLDDALKL TEQPELANKV DMVWIVGGSS

VYKEAMNHPG HLKLFVTRIM QDFESDTFFP EIDLEKYKLL

PEYPGVLSDV QEEKGIKYKF EVYEKND.

In some alternatives, the gene delivery polynucleotide is circular. In some alternatives, the gene delivery polynucleotide is at least 1 kB to 6 kB. In some alternatives, the gene delivery polynucleotide is a minicircle. In some alternatives, the promoter region comprises an EF1 promoter sequence. In some alternatives, the fourth sequence comprises one, two, three, four, or five genes that encode proteins. In some alternatives, the fourth sequence is codon optimized to reduce the total GC/AT ratio of the fourth sequence. In some alternatives, the fourth sequence is a consensus sequence generated from a plurality of nucleic acids that encode a plurality of related proteins, such as a plurality of antibody binding domains, which are specific for the same epitope. In some alternatives, the fifth sequence is codon optimized to reduce the total GC/AT ratio of the fourth sequence. In some alternatives, the codon optimization and/or consensus sequence is generated by comparing the variability of sequence and/or nucleobases utilized in a plurality of related sequences. In some alternatives, the protein is a protein for therapy. In some alternatives, the protein comprises an antibody or a portion thereof. In some alternatives, the double mutant of dihydrofolate reductase comprises amino acid mutations of L22F and F31S. In some alternatives, the minicircle comprises a sequence for the double mutant of dihydrofolate reductase, the sequence comprising the DNA sequence (SEQ ID NO: 2)
ATGGTTGGTTCGCTAAACTGCATCGTCGCTGTGTCCCAGAACATGGGCAT

CGGCAAGAACGGGGACTTCCCCTGGCCACCGCTCAGGAATGAATCCAGAT

ATTTCCAGAGAATGACCACAACCTCTTCAGTAGAAGGTAAACAGAATCTG

GTGATTATGGGTAAGAAGACCTGGTTCTCCATTCCTGAGAAGAATCGACC

TTTAAAGGGTAGAATTAATTTAGTTCTCAGCAGAGAACTCAAGGAACCTC

CACAAGGAGCTCATTTTCTTTCCAGAAGTCTAGATGATGCCTTAAAACTT

ACTGAACAACCAGAATTAGCAAATAAAGTAGACATGGTCTGGATAGTTGG

TGGCAGTTCTGTTTATAAGGAAGCCATGAATCACCCAGGCCATCTTAAAC

TATTTGTGACAAGGATCATGCAAGACTTTGAAAGTGACACGTTTTTTCCA

GAAATTGATTTGGAGAAATATAAACTTCTGCCAGAATACCCAGGTGTTCT

CTCTGATGTCCAGGAGGAGAAAGGCATTAAGTACAAATTTGAAGTATATG

AGAAGAATGATTAA.

In some alternatives, the double mutant of dihydrofolate reductase comprises the protein sequence:

(SEQ ID NO: 3)
MVGSLNCIVA VSQNMGIGKN GDFPWPPLRN ESRYFQRMTT

TSSVEGKQNL VIMGKKTWFS IPEKNRPLKG RINLVLSREL

KEPPQGAHFL SRSLDDALKL TEQPELANKV DMVWIVGGSS

VYKEAMNHPG HLKLFVTRIM QDFESDTFFP EIDLEKYKLL

PEYPGVLSDV QEEKGIKYKF EVYEKND.

In some alternatives, a method of generating engineered multiplexed T-cells for adoptive T-cell immunotherapy is provided. In the broadest sense, the method can comprise providing the gene delivery polynucleotide of any of the alternatives described herein, introducing the gene delivery polynucleotide into a T-cell, providing a vector encoding a Sleeping Beauty transposase, introducing the vector encoding the Sleeping Beauty transposase into the T-cell, selecting the cells comprising the gene delivery polynucleotide, wherein selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range, and isolating the T-cells expressing a phenotype under selective pressure. In some alternatives, introducing is performed by electroporation. In some alternatives, the selecting is performed by increasing selective pressure through the selective marker cassette. In some alternatives, the selection reagent comprises an agent for selection. In some alternatives, the agent for selection is methotrexate. In some alternatives, the first concentration range is at least 50 nM-100 nM and the second concentration range is at least 75 to 150 nM. In some alternatives, the first concentration is 50 nM, 60 nM, 70 nM, 80 nM, 90 nM, or 100 nM or any concentration that is between a range of concentrations defined by any two of the aforementioned concentrations, and the second concentration range is 75 nM, 80 nM, 90 nM, 100 nM, 110 nM, 120 nM, 130 nM, 140 nM, or 150 nM or any concentration that is between a range of concentrations defined by any two of the aforementioned concentrations. In some alternatives, the first concentration range is at least 75 nM-150 nM and the second concentration range is at least 112.5 nM to 225 nM. In some alternatives, the first concentration is 75 nM, 85 nM, 95 nM, 105 nM, 115 nM, 125 nM, 135 nM, 145 nM, or 150 nM or any concentration that is between a range of concentrations defined by any two of the aforementioned concentrations, and the second concentration range is 112 nM, 122 nM, 132 nM, 142 nM, 152 nM, 162 nM, 172 nM, 182 nM, 192 nM, 202 nM, 212 nM, or 225 nM or any concentration that is between a range of concentrations defined by any two of the aforementioned concentrations. In some alternatives, the first concentration range is at least 300 nM-675 nM and the first concentration range is at least 450 nM to 1012 nM. In some alternatives, the first concentration is 300 nM, 350 nM, 400 nM, 450 nM, 500 nM, 550 nM, 600 nM, 650 nM, or 675 nM or any concentration that is between a range of concentrations defined by any two of the aforementioned concentrations, and the second concentration range is 450 nM, 500 nM, 550 nM, 600 nM, 650 nM, 700 nM, 750 nM, 800 nM, 850 nM, 900 nM, 1000 nM, or 1012 nM or any concentration that is between a range of concentrations defined by any two of the aforementioned concentrations. In some alternatives, the first round of selection comprises exposing the T-cells to the selection agent for 2, 3, 4, 5, 6 or 7 days before the second round of selection. In some alternatives, the second round of selection comprises exposing the T-cells to the selection agent for at least 2, 3, 4, 5, 6 or 7 days before isolation.

In some alternatives, a method of increasing protein production in a cell is provided. In the broadest sense, the method can comprise providing the gene delivery polynucleotide of any one of the alternatives described herein, introducing the gene delivery polynucleotide into a T-cell, providing a vector encoding a Sleeping Beauty transposase, introducing the vector encoding the Sleeping Beauty transposase into the T-cell, selecting the cells comprising the gene delivery polynucleotide, wherein selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range, and isolating the T-cells expressing a phenotype under selective pressure. In some alternatives, introducing is performed by electroporation. In some alternatives, selecting is performed by increasing selective pressure through the selective marker cassette. In some alternatives, the selection reagent comprises an agent for selection. In some alternatives, the agent for selection is methotrexate. In some alternatives, the low or first concentration range is at least 50 nM-100 nM and the higher or second concentration range is at least 75 to 150 nM. In some alternatives, the low or first concentration range is at least 75 nM-150 nM and the higher or second concentration range is at least 112.5 nM to 225 nM. In some alternatives, the low or first concentration range is at least 300 nM-675 nM and the higher or second concentration range is at least 450 nM to 1012 nM. In some alternatives, the first round of selection comprises exposing the T-cells to the selection agent for 2, 3, 4, 5, 6 or 7 days before the second round of selection. In some alternatives, the second round of selection comprises exposing the T-cells to the selection agent for at least 2, 3, 4, 5, 6 or 7 days before isolation.

In some alternatives, an engineered multiplexed T-cell for adoptive T-cell immunotherapy generated by any one of the methods of is provided. In some alternatives, the engineered multiplexed T-cells for adoptive T-cell immunotherapy is generated by a method, wherein the method comprises providing a gene delivery polynucleotide, introducing the gene delivery polynucleotide into a T-cell, providing a vector encoding a Sleeping Beauty transposase, introducing the vector encoding the Sleeping Beauty transposase into the T-cell, selecting the cells comprising the gene delivery polynucleotide wherein selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range and isolating the T-cells expressing a phenotype under selective pressure. In some alternatives, the gene delivery polynucleotide comprises a first sequence, wherein the first sequence comprises a first inverted terminal repeat gene sequence, a second sequence, wherein the second sequence comprises a second inverted terminal repeat gene sequence, a third sequence, wherein the third sequence comprises a promoter region sequence, a fourth sequence, wherein the fourth sequence comprises at least one gene encoding a protein, and wherein the fourth sequence is optimized, a fifth sequence, wherein the fifth sequence comprises at least one selectable marker cassette encoding a double mutant of dihydrofolate reductase, wherein the double mutant of dihydrofolate reductase has a 15,000 fold or about 15,000 fold reduced affinity for methotrexate, wherein the methotrexate can be used as a selection mechanism to selectively amplify cells transduced with the gene delivery polynucleotide and wherein the fifth sequence is optimized, a sixth sequence, wherein the sixth sequence comprises a first attachment site (attP) and a seventh sequence, wherein the seventh sequence comprises a second attachment site (attB) wherein each of the first sequence, second sequence, third sequence, fourth sequence, fifth sequence, sixth sequence, and seventh sequence have a 5' terminus and a 3 terminus, and wherein the 3' terminus of the first sequence comprising the first inverted terminal repeat gene sequence is adjacent to the 5' terminus of the third sequence, the 3' terminus of the third sequence is adjacent to the 5' terminus of the fourth sequence, the 3' terminus of the fourth sequence is adjacent to the 5' terminus of the fifth sequence and the 3' terminus of the fifth sequence is adjacent to the 5' terminus of the second sequence comprising a second inverted terminal repeat. In some alternatives, the gene encoding the double mutant of human dihydrofolate reductase comprises the DNA sequence:

(SEQ ID NO: 2)
ATGGTTGGTTCGCTAAACTGCATCGTCGCTGTGTCCCAGAACATGGG

CATCGGCAAGAACGGGGACTTCCCCTGGCCACCGCTCAGGAATGAAT

CCAGATATTTCCAGAGAATGACCACAACCTCTTCAGTAGAAGGTAAA

CAGAATCTGGTGATTATGGGTAAGAAGACCTGGTTCTCCATTCCTGA

GAAGAATCGACCTTTAAAGGGTAGAATTAATTTAGTTCTCAGCAGAG

AACTCAAGGAACCTCCACAAGGAGCTCATTTTCTTTCCAGAAGTCTA

GATGATGCCTTAAAACTTACTGAACAACCAGAATTAGCAAATAAAGT

AGACATGGTCTGGATAGTTGGTGGCAGTTCTGTTTATAAGGAAGCCA

TGAATCACCCAGGCCATCTTAAACTATTTGTGACAAGGATCATGCAA

GACTTTGAAAGTGACACGTTTTTTCCAGAAATTGATTTGGAGAAATA

TAAACTTCTGCCAGAATACCCAGGTGTTCTCTCTGATGTCCAGGAGG

AGAAAGGCATTAAGTACAAATTTGAAGTATATGAGAAGAATGATTAA.

In some alternatives, the double mutant of human dihydrofolate reductase comprises the protein sequence:

(SEQ ID NO: 3)
MVGSLNCIVA VSQNMGIGKN GDFPWPPLRN ESRYFQRMTT

TSSVEGKQNL VIMGKKTWFS IPEKNRPLKG RINLVLSREL

KEPPQGAHFL SRSLDDALKL TEQPELANKV DMVWIVGGSS

VYKEAMNHPG HLKLFVTRIM QDFESDTFFP EIDLEKYKLL

PEYPGVLSDV QEEKGIKYKF EVYEKND.

In some alternatives, the gene delivery polynucleotide is circular. In some alternatives, the gene delivery polynucleotide is at least 1 kB to 5 kB. In some alternatives, the gene delivery polynucleotide is a minicircle. In some alternatives, the promoter region comprises an EF1 promoter sequence. In some alternatives, the fourth sequence comprises one, two, three, four, or five genes that encode proteins. In some alternatives, the fourth sequence is codon optimized to reduce the total GC/AT ratio of the fourth sequence. In some alternatives, the fourth sequence is optimized by codon optimization for expression in humans. In some alternatives, the fourth sequence is a consensus sequence generated from a plurality of nucleic acids that encode a plurality of related proteins. In some alternatives, the fourth sequence is a consensus sequence generated from a plurality of nucleic acids that encode a plurality of related proteins, such as a plurality of antibody binding domains, which are specific for the same epitope. In some alternatives, the plurality of related proteins comprise a plurality of antibody binding domains, wherein the plurality of antibody binding domains are specific for the same epitope. In some alternatives, the fifth sequence is codon optimized to reduce the total GC/AT ratio of the fifth sequence. In some alternatives, the fifth sequence is optimized by codon optimization for expression in humans. In some alternatives, the protein is a protein for therapy. In some alternatives, the codon optimization and/or consensus sequence is generated by comparing the variability of sequence and/or nucleobases utilized in a plurality of related sequences. In some alternatives, the protein comprises an antibody or a portion thereof, which may be humanized. In some alternatives, the double mutant of dihydrofolate reductase comprises amino acid mutations of L22F and F31S. In some alternatives, the double mutant of dihydrofolate reductase comprises amino acid mutations of L22F and F31S. In some alternatives, the introducing is performed by electroporation. In some alternatives, the selecting is performed by increasing selective pressure through the selective marker cassette. In some alternatives, the selection reagent comprises an agent for selection. In some alternatives, the agent for selection is methotrexate. In some alternatives, the first concentration range is at least 50 nM-100 nM and the second concentration range is at least 75 to 150 nM. In some alternatives, the first concentration is 50 nM, 60 nM, 70 nM, 80 nM, 90 nM, or 100 nM or any concentration that is between a range of concentrations defined by any two of the aforementioned concentrations, and the second concentration range is 75 nM, 80 nM, 90 nM, 100 nM, 110 nM, 120 nM, 130 nM, 140 nM, or 150 nM or any concentration that is between a range of concentrations defined by any two of the aforementioned concentrations. In some alternatives, the first concentration range is at least 75 nM-150 nM and the second concentration range is at least 112.5 nM to 225 nM. In some alternatives, the first concentration is 75 nM, 85 nM, 95 nM, 105 nM, 115 nM, 125 nM, 135 nM, 145 nM, or 150 nM or any concentration that is between a range of concentrations defined by any two of the aforementioned concentrations, and the second concentration range is 112 nM, 122 nM, 132 nM, 142 nM, 152 nM, 162 nM, 172 nM, 182 nM, 192 nM, 202 nM, 212 nM, or 225 nM or any concentration that is between a range of concentrations defined by any two of the aforementioned concentrations. In some alternatives, the first concentration range is at least 300 nM-675 nM and the first concentration range is at least 450 nM to 1012 nM. In some alternatives, the first concentration is 300 nM, 350 nM, 400 nM, 450 nM, 500 nM, 550 nM, 600 nM, 650 nM, or 675 nM or any concentration that is between a range of concentrations defined by any two of the aforementioned concentrations, and the second concentration range is 450 nM, 500 nM, 550 nM, 600 nM, 650 nM, 700 nM, 750 nM, 800 nM, 850 nM, 900 nM, 1000 nM, or 1012 nM or any concentration that is between a range of concentrations defined by any two of the aforementioned concentrations. In some alternatives, the first round of selection comprises exposing the T-cells to the selection agent for 2, 3, 4, 5, 6 or 7 days before the second round of selection. In some alternatives, the second round of selection comprises exposing the T-cells to the selection agent for at least 2, 3, 4, 5, 6, 7, 8, 9, 10, 11, 12, 13, or 14 days or any time that is between a range of times defined by any two of the aforementioned time points before isolation. In some alternatives, the gene delivery polynucleotide comprises a first sequence, wherein the first sequence comprises a first inverted terminal repeat gene sequence, a second sequence, wherein the second sequence comprises a second inverted terminal repeat gene sequence, a third sequence, wherein the third sequence comprises a promoter region sequence, a fourth sequence, wherein the fourth sequence comprises at least one gene encoding a protein, and wherein the fourth sequence is optimized, a fifth sequence, wherein the fifth sequence comprises at least one selectable marker cassette encoding a double mutant of dihydrofolate reductase, wherein the double mutant of dihydrofolate reductase has a 15,000 fold or about 15,000 fold reduced affinity for methotrexate, wherein the methotrexate can be used as a selection mechanism to selectively amplify cells transduced with the gene delivery polynucleotide and wherein the fifth sequence is optimized, a sixth sequence, wherein the sixth sequence comprises a first attachment site (attP) and a seventh sequence, wherein the seventh sequence comprises a second attachment site (attB) wherein each of the first sequence, second sequence, third sequence, fourth sequence, fifth sequence, sixth sequence, and seventh sequence have a 5' terminus and a 3 ' terminus, and wherein the 3' terminus of the first sequence comprising the first inverted terminal repeat gene sequence is adjacent to the 5' terminus of the third sequence, the 3' terminus of the third sequence is adjacent to the 5' terminus of the fourth sequence, the 3' terminus of the fourth sequence is adjacent to the 5' terminus of the fifth sequence and the 3' terminus of the fifth sequence is adjacent to the 5' terminus of the second sequence comprising a second inverted terminal repeat. In some alternatives, the gene encoding the double mutant of human dihydrofolate reductase comprises the DNA sequence:

```
                                            (SEQ ID NO: 2)
ATGGTTGGTTCGCTAAACTGCATCGTCGCTGTGTCCCAGAACATGGGCAT

CGGCAAGAACGGGGACTTCCCCTGGCCACCGCTCAGGAATGAATCCAGAT

ATTTCCAGAGAATGACCACAACCTCTTCAGTAGAAGGTAAACAGAATCTG

GTGATTATGGGTAAGAAGACCTGGTTCTCCATTCCTGAGAAGAATCGACC

TTTAAAGGGTAGAATTAATTTAGTTCTCAGCAGAGAACTCAAGGAACCTC

CACAAGGAGCTCATTTTCTTTCCAGAAGTCTAGATGATGCCTTAAAACTT

ACTGAACAACCAGAATTAGCAAATAAAGTAGACATGGTCTGGATAGTTGG

TGGCAGTTCTGTTTATAAGGAAGCCATGAATCACCCAGGCCATCTTAAAC

TATTTGTGACAAGGATCATGCAAGACTTTGAAAGTGACACGTTTTTTCCA

GAAATTGATTTGGAGAAATATAAACTTCTGCCAGAATACCCAGGTGTTCT

CTCTGATGTCCAGGAGGAGAAAGGCATTAAGTACAAATTTGAAGTATATG

AGAAGAATGATTAA.
```

In some alternatives, the double mutant of human dihydrofolate reductase comprises the protein sequence:

```
                                    (SEQ ID NO: 3)
  MVGSLNCIVA VSQNMGIGKN GDFPWPPLRN ESRYFQRMTT

TSSVEGKQNL VIMGKKTWFS IPEKNRPLKG RINLVLSREL

KEPPQGAHFL SRSLDDALKL TEQPELANKV DMVWIVGSS

VYKEAMNHPG HLKLFVTRIM QDFESDTFFP EIDLEKYKLL

PEYPGVLSDV QEEKGIKYKF EVYEKND.
```

In some alternatives, the gene delivery polynucleotide is circular. In some alternatives, the gene delivery polynucleotide is at least 1 kB to 5 kB. In some alternatives, the gene delivery polynucleotide is a minicircle. In some alternatives, the promoter region comprises an EF1 promoter sequence. In some alternatives, the fourth sequence comprises one, two, three, four, or five genes that encode proteins. In some alternatives, the fourth sequence is codon optimized to reduce the total GC/AT ratio of the fourth sequence. In some alternatives, the fourth sequence is optimized by codon optimization for expression in humans. In some alternatives, the fourth sequence is a consensus sequence generated from a plurality of nucleic acids that encode a plurality of related proteins. In some alternatives, the fourth sequence is a consensus sequence generated from a plurality of nucleic acids that encode a plurality of related proteins, such as a plurality of antibody binding domains, which are specific for the same epitope. In some alternatives, the plurality of related proteins comprise a plurality of antibody binding domains, wherein the plurality of antibody binding domains are specific for the same epitope. In some alternatives, the fifth sequence is codon optimized to reduce the total GC/AT ratio of the fifth sequence. In some alternatives, the fifth sequence is optimized by codon optimization for expression in humans. In some alternatives, the protein is a protein for therapy. In some alternatives, the codon optimization and/or consensus sequence is generated by comparing the variability of sequence and/or nucleobases utilized in a plurality of related sequences. In some alternatives, the protein comprises an antibody or a portion thereof, which may be humanized. In some alternatives, the double mutant of dihydrofolate reductase comprises amino acid mutations of L22F and F31S. In some alternatives, the introducing is performed by electroporation. In some alternatives, the selecting is performed by increasing selective pressure through the selective marker cassette. In some alternatives, the selection reagent comprises an agent for selection. In some alternatives, the agent for selection is methotrexate. In some alternatives, the first concentration range is at least 50 nM-100 nM and the second concentration range is at least 75 to 150 nM. In some alternatives, the first concentration is 50 nM, 60 nM, 70 nM, 80 nM, 90 nM, or 100 nM or any concentration that is between a range of concentrations defined by any two of the aforementioned concentrations, and the second concentration range is 75 nM, 80 nM, 90 nM, 100 nM, 110 nM, 120 nM, 130 nM, 140 nM, or 150 nM or any concentration that is between a range of concentrations defined by any two of the aforementioned concentrations. In some alternatives, the first concentration range is at least 75 nM-150 nM and the second concentration range is at least 112.5 nM to 225 nM. In some alternatives, the first concentration is 75 nM, 85 nM, 95 nM, 105 nM, 115 nM, 125 nM, 135 nM, 145 nM, or 150 nM or any concentration that is between a range of concentrations defined by any two of the aforementioned concentrations, and the second concentration range is 112 nM, 122 nM, 132 nM, 142 nM, 152 nM, 162 nM, 172 nM, 182 nM, 192 nM, 202 nM, 212 nM, or 225 nM or any concentration that is between a range of concentrations defined by any two of the aforementioned concentrations. In some alternatives, the first concentration range is at least 300 nM-675 nM and the first concentration range is at least 450 nM to 1012 nM. In some alternatives, the first concentration is 300 nM, 350 nM, 400 nM, 450 nM, 500 nM, 550 nM, 600 nM, 650 nM, or 675 nM or any concentration that is between a range of concentrations defined by any two of the aforementioned concentrations, and the second concentration range is 450 nM, 500 nM, 550 nM, 600 nM, 650 nM, 700 nM, 750 nM, 800 nM, 850 nM, 900 nM, 1000 nM, or 1012 nM or any concentration that is between a range of concentrations defined by any two of the aforementioned concentrations. In some alternatives, the first round of selection comprises exposing the T-cells to the selection agent for 2, 3, 4, 5, 6 or 7 days before the second round of selection. In some alternatives, the second round of selection comprises exposing the T-cells to the selection agent for at least 2, 3, 4, 5, 6, 7, 8, 9, 10, 11, 12, 13, or 14 days or any time that is between a range of times defined by any two of the aforementioned time points before isolation.

In some alternatives, a method of treating, inhibiting, or ameliorating cancer or a disease in a subject is provided, wherein the method comprises administering to the subject the modified or engineered multiplexed T-cell as described below. In some alternatives, the engineered multiplexed T-cells for adoptive T-cell immunotherapy is generated by a method, wherein the method comprises providing a gene delivery polynucleotide, introducing the gene delivery polynucleotide into a T-cell, providing a vector encoding a Sleeping Beauty transposase, introducing the vector encoding the Sleeping Beauty transposase into the T-cell, selecting the cells comprising the gene delivery polynucleotide wherein selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range and isolating the T-cells expressing a phenotype under selective pressure. In some alternatives, the gene delivery polynucleotide comprises a first sequence, wherein the first sequence comprises a first inverted terminal repeat gene sequence, a second sequence, wherein the second sequence comprises a second inverted terminal repeat gene sequence, a third sequence, wherein the third sequence comprises a promoter region sequence, a fourth sequence, wherein the fourth sequence comprises at least one gene encoding a protein, and wherein the fourth sequence is codon optimized for expression in humans, a fifth sequence, wherein the fifth sequence comprises at least one selectable marker cassette encoding a double mutant of dihydrofolate reductase, wherein the double mutant of dihydrofolate reductase has a 15,000 fold or about 15,000 fold reduced affinity for methotrexate, wherein the methotrexate can be used as a selection mechanism to selectively amplify cells transduced with the gene delivery polynucleotide and wherein the fifth sequence is codon optimized for expression in humans, a sixth sequence, wherein the sixth sequence comprises a first attachment site (attP) and a seventh sequence, wherein the seventh sequence comprises a second attachment site (attB) wherein each of the first sequence, second sequence, third sequence, fourth sequence, fifth sequence, sixth sequence, and seventh sequence have a 5' terminus and a 3' terminus, and wherein the 3' terminus of the first sequence comprising the first inverted terminal repeat gene sequence is adjacent to the 5' terminus of the third sequence, the 3' terminus of the third sequence is adjacent to the 5' terminus of the fourth sequence, the 3' terminus of the fourth sequence is adjacent to the 5' terminus of the fifth sequence and the 3' terminus of the fifth sequence is adjacent to the 5' terminus of the second sequence comprising a second inverted terminal repeat. In some alternatives, the gene encoding the double mutant of human dihydrofolate reductase comprises the DNA sequence:

```
                                          (SEQ ID NO: 2)
ATGGTTGGTTCGCTAAACTGCATCGTCGCTGTGTCCCAGAACATGGGCAT

CGGCAAGAACGGGGACTTCCCCTGGCCACCGCTCAGGAATGAATCCAGAT

ATTTCCAGAGAATGACCACAACCTCTTCAGTAGAAGGTAAACAGAATCTG

GTGATTATGGGTAAGAAGACCTGGTTCTCCATTCCTGAGAAGAATCGACC

TTTAAAGGGTAGAATTAATTTAGTTCTCAGCAGAGAACTCAAGGAACCTC
```

```
-continued
CACAAGGAGCTCATTTTCTTTCCAGAAGTCTAGATGATGCCTTAAAACTT

ACTGAACAACCAGAATTAGCAAATAAAGTAGACATGGTCTGGATAGTTGG

TGGCAGTTCTGTTTATAAGGAAGCCATGAATCACCCAGGCCATCTTAAAC

TATTTGTGACAAGGATCATGCAAGACTTTGAAAGTGACACGTTTTTTCCA

GAAATTGATTTGGAGAAATATAAACTTCTGCCAGAATACCCAGGTGTTCT

CTCTGATGTCCAGGAGGAGAAAGGCATTAAGTACAAATTTGAAGTATATG

AGAAGAATGATTAA.
```

In some alternatives, the double mutant of human dihydrofolate reductase comprises the protein sequence:

```
                                          (SEQ ID NO: 3)
MVGSLNCIVA VSQNMGIGKN GDFPWPPLRN ESRYFQRMTT

TSSVEGKQNL VIMGKKTWFS IPEKNRPLKG RINLVLSREL

KEPPQGAHFL SRSLDDALKL TEQPELANKV DMVWIVGGSS

VYKEAMNHPG HLKLFVTRIM QDFESDTFFP EIDLEKYKLL

PEYPGVLSDV QEEKGIKYKF EVYEKND.
```

In some alternatives, the gene delivery polynucleotide is circular. In some alternatives, the gene delivery polynucleotide is a minicircle. In some alternatives, the gene delivery polynucleotide is at least 1 kB to 5 kB. In some alternatives, the promoter region comprises an EF1 promoter sequence. In some alternatives, the fourth sequence comprises one, two, three, four, or five genes that encode proteins. In some alternatives, the fourth sequence is codon optimized to reduce the total GC/AT ratio of the fourth sequence. In some alternatives, the fourth sequence is optimized by codon optimization for expression in humans. In some alternatives, the fourth sequence is a consensus sequence generated from a plurality of nucleic acids that encode a plurality of related proteins. In some alternatives, the fourth sequence is a consensus sequence generated from a plurality of nucleic acids that encode a plurality of related proteins, such as a plurality of antibody binding domains, which are specific for the same epitope. In some alternatives, the plurality of related proteins comprise a plurality of antibody binding domains, wherein the plurality of antibody binding domains are specific for the same epitope. In some alternatives, the fifth sequence is codon optimized to reduce the total GC/AT ratio of the fifth sequence. In some alternatives, the fifth sequence is optimized by codon optimization for expression in humans. In some alternatives, the protein is a protein for therapy. In some alternatives, the codon optimization and/or consensus sequence is generated by comparing the variability of sequence and/or nucleobases utilized in a plurality of related sequences. In some alternatives, the protein comprises an antibody or a portion thereof, which may be humanized. In some alternatives, the double mutant of dihydrofolate reductase comprises amino acid mutations of L22F and F31S. In some alternatives, the double mutant of dihydrofolate reductase comprises amino acid mutations of L22F and F31S. In some alternatives, the introducing is performed by electroporation. In some alternatives, the selecting is performed by increasing selective pressure through the selective marker cassette. In some alternatives, the selection reagent comprises an agent for selection. In some alternatives, the agent for selection is methotrexate. In some alternatives, the first concentration range is at least 50 nM-100 nM and the second concentration range is at least 75 to 150 nM. In some alternatives, the first concentration is 50 nM, 60 nM, 70 nM, 80 nM, 90 nM, or 100 nM or any concentration that is between a range of concentrations defined by any two of the aforementioned concentrations, and the second concentration range is 75 nM, 80 nM, 90 nM, 100 nM, 110 nM, 120 nM, 130 nM, 140 nM, or 150 nM or any concentration that is between a range of concentrations defined by any two of the aforementioned concentrations. In some alternatives, the first concentration range is at least 75 nM-150 nM and the second concentration range is at least 112.5 nM to 225 nM. In some alternatives, the first concentration is 75 nM, 85 nM, 95 nM, 105 nM, 115 nM, 125 nM, 135 nM, 145 nM, or 150 nM or any concentration that is between a range of concentrations defined by any two of the aforementioned concentrations, and the second concentration range is 112 nM, 122 nM, 132 nM, 142 nM, 152 nM, 162 nM, 172 nM, 182 nM, 192 nM, 202 nM, 212 nM, or 225 nM or any concentration that is between a range of concentrations defined by any two of the aforementioned concentrations. In some alternatives, the first concentration range is at least 300 nM-675 nM and the first concentration range is at least 450 nM to 1012 nM. In some alternatives, the first concentration is 300 nM, 350 nM, 400 nM, 450 nM, 500 nM, 550 nM, 600 nM, 650 nM, or 675 nM or any concentration that is between a range of concentrations defined by any two of the aforementioned concentrations, and the second concentration range is 450 nM, 500 nM, 550 nM, 600 nM, 650 nM, 700 nM, 750 nM, 800 nM, 850 nM, 900 nM, 1000 nM, or 1012 nM or any concentration that is between a range of concentrations defined by any two of the aforementioned concentrations. In some alternatives, the first round of selection comprises exposing the T-cells to the selection agent for 2, 3, 4, 5, 6 or 7 days before the second round of selection. In some alternatives, the second round of selection comprises exposing the T-cells to the selection agent for at least 2, 3, 4, 5, 6, 7, 8, 9, 10, 11, 12, 13, or 14 days or any time that is between a range of times defined by any two of the aforementioned time points before isolation. In some alternatives, the subject is human.

Several of the material and methods are described in greater detail below.

Plasmids.

The pMC_T3/GFP-T2A-DHFRdm mini-circle (MC) plasmid that carries the T3 SB transposon cassette containing an EF1a promoter, maxGFP gene, Thoseaasigna virus 2A peptide (T2A) and a double mutant of dihydrofolate reductase (DHFRdm) insensitive to methotrexate (MTX) was constructed using pMC_T3/eGFP_IRES_FGFR (Nucleic Acids Research, 2012, 1-10 doi:10.1093/nar/gks213, incorporated in its entirety herein) as a backbone, implementing the cloning strategy described previously (Cold Spring Harbor Protoc; 2012; doi:10.1101/pdb.ip067876) to create the GFP-T2A-DHFRdm cassette. MaxGFP (Lonza) and pEGFRt-T2A-IMPDHdm-T2A-DHFRdm (generously provided by Michael Jensen) plasmids were used as templates for PCR. BmtI and BamHI sites were introduced for swapping genes for fluorescent proteins. Plasmid MC_SB100X was described previously (Nucleic Acids Research, 2012, 1-10 doi:10.1093/nar/gks213, incorporated in its entirety herein). Minicircles were produced and purified according to the System Biosciences user manual for minicircle DNA vector technology. All plasmids were amplified under endotoxin free conditions using an Endofree Plasmid Kit (Qiagen).

H9 Culture and Transfection.

H9 cells were cultured in DMEM with 10% FBS. The optimized nucleofection protocol for H9 cells (Lonza) was followed (program X-001, Nucleofector Kit V). Per nucleofection, $1 \times 10^6$ cells were used with varying amounts of MC DNA. Cells were grown for a week after nucleofection to achieve stable transfection. For MTX selection, cells were cultured in DMEM with 10% FBS supplemented with different concentrations of MTX.

Flow Cytometry Analysis.

Live cells were selected based on propidium iodide exclusion by adding propidium iodide in the flow cytometry buffer to 2 µg/ml. Flow cytometry analysis was carried out on a MACSQuant Analyzer (Miltenyi Biotec) and LSRII (BD Biosciences). Collected data was analyzed with FlowJo software. Appropriate negative controls (untransfected H9 cells with and without propidium iodide staining, as well as cells transfected with single genes for GFP, BFP, and mCherry) were used for compensation and gating. A Becton Dickinson FACSAria II was used for cell sorting. Part of flow cytometry work was conducted at the UW Immunology Flow Cytometry Facility.

Determination of transposon copy number.

Genomic DNA was extracted with Puregene Kit A according to the manufacturer's instructions (Qiagen), and qPCR was performed using a 7300 Real-Time PCR System (Applied Biosystems) using Universal SYBR Green Supermix (BioRad). Primers for qPCR were designed using Primer3 software:

```
maxGFP forward primer:
                              (SEQ ID NO: 4)
5'-ACAAGATCATCCGCAGCAAC-3';

reverse primer:
                              (SEQ ID NO: 5)
5'-TTGAAGTGCATGTGGCTGTC-3';

GAPDH forward primer:
                              (SEQ ID NO: 6)
5'-ACAACTTTGGTATCGTGGAAGG-3';

GAPDH reverse primer:
                              (SEQ ID NO: 7)
5'-GCCATCACGCCACAGTTTC-3'.
```

MaxGFP primers are specific for the maxGFP gene in the transposon. Standard curves were generated using genomic DNA of a H9 clone with a single insertion of transposon ("gold standard") obtained by limiting dilution method. Copy number was calculated using the AACT method (Schmittgen, T. D. and Livak, K. J. (2008), incorporated in its entirety herein).

Characterization of SBTS Integration Distribution.

A population of T3/GFP-T2A-DHFRdm transfected-H9 cells selected with 200 nM MTX was plated in 96 well plates at a concentration of 0.5 cells/well in DMEM 10% FBS along with irradiated (5000 R) H9 feeder cells at 5,000 cells/well. Plates were incubated for 2-3 weeks, after which clonal populations were moved to larger plates and expanded. GFP expression was confirmed by flow cytometry. Relative RT-qPCR analysis was performed using DNA of 60 individual clones in order to determine transposon copy number.

Optimization of Stable Gene Transfer to H9 Cells.

Minicircle constructs, which have bacterial plasmid sequences removed, were used for all gene transfer studies. Minicircles can be generated as described previously by Kay et al. and colleagues (Chen, Z. Y.; He, C. Y.; Ehrhardt, A.; Kay, M. A. Molecular Therapy 2003, 8, 495-500 and Kay, M. A.; He, C. Y.; Chen, Z. Y. Nat. Biotechnol. 2010, 28, 1287-U96; incorporated herein by reference in their entirety). Three reporter minicircles containing transposons expressing different fluorescent proteins (maxGFP, mCherry, or BFP) under the EF1 alpha promoter were constructed. The selection gene, a double mutant of dihydrofolate reductase (DHFRdm) that confers metabolic resistance to MTX, was cloned in frame after the T2A sequence. The SB100X transposase gene was also prepared in a separate minicircle construct for co-delivery with transposon minicircles.

There are four transposase binding sites in a transposon (two per inverted terminal repeat). Bound transposase were proposed to interact with each other to promote juxtaposition of the two transposon ends. Overexpression of transposase has been hypothesized to lead to inhibition of transposition due to interaction of free transposase with bound transposase, thus preventing the juxtaposition step. Therefore, the optimal transposon/transposase ratio needed to be determined whether these genes are delivered on separate constructs. Reports of the inhibition phenomenon have been varied.

Figure 2:
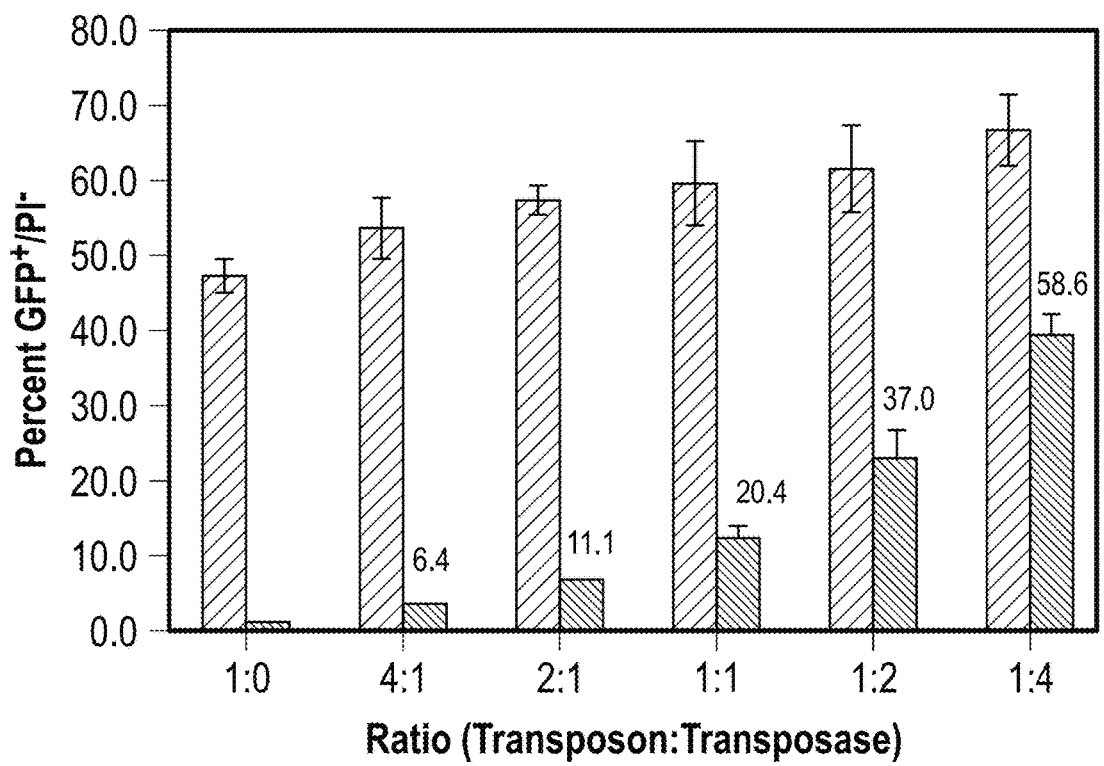
FIG. 2 shows a series of bar graphs that demonstrate the optimization of the transposon:transposase DNA ratio. H9 cells were nucleofected with 2 μg of MC_T3/eGFP-T2A-DHFRdm DNA (transposon) and increasing amounts of MC_SB100X (transposase) DNA (0.5, 1, 2, 4, 8 ug). Flow cytometry was performed at 24 hours (striped bars) and at 7 days (black bars) after nucleofection to assess transient and stable transfection efficiency. Numbers above the bars indicate integration efficiency, which is calculated as percent of stable over transient GFP expression.

The efficiency of transient transfection were evaluated at 24 hours post-nucleofection and at stable transposition (7 days post-nucleofection) at various transposon/transposase ratios using the reporter minicircle expressing maxGFP by flow cytometry. Attention is drawn to FIG. 2, which shows the optimization of transposon:transposase ratio. The H9 T-cell line was used as the transfection test-bed. Initial transfection efficiency ranged from 47.5%±2.2% to 66.9%±4.5%, increasing with increased amount of transposase minicircle. In the absence of transposase, minimal stable transfection (<1%) was detected 7 days post-nucleofection. The percentage of GFP$^+$ cells increased with the transposon/transposase ratio, reaching 39.2%±3.0% at 1:4 ratio, which reflects 58.6% integration efficiency of the initial transiently-integrated population. Higher ratios were not tested due to reduced cell viability. The overexpression inhibition effect was not observed in this tested range of transposon/transposase ratios. Therefore, from the results, the transduction experiments were carried out using this optimized transposon/transposase ratio of 1:4.

Selection of Engineered Cells with Methotrexate.

Figure 3A:
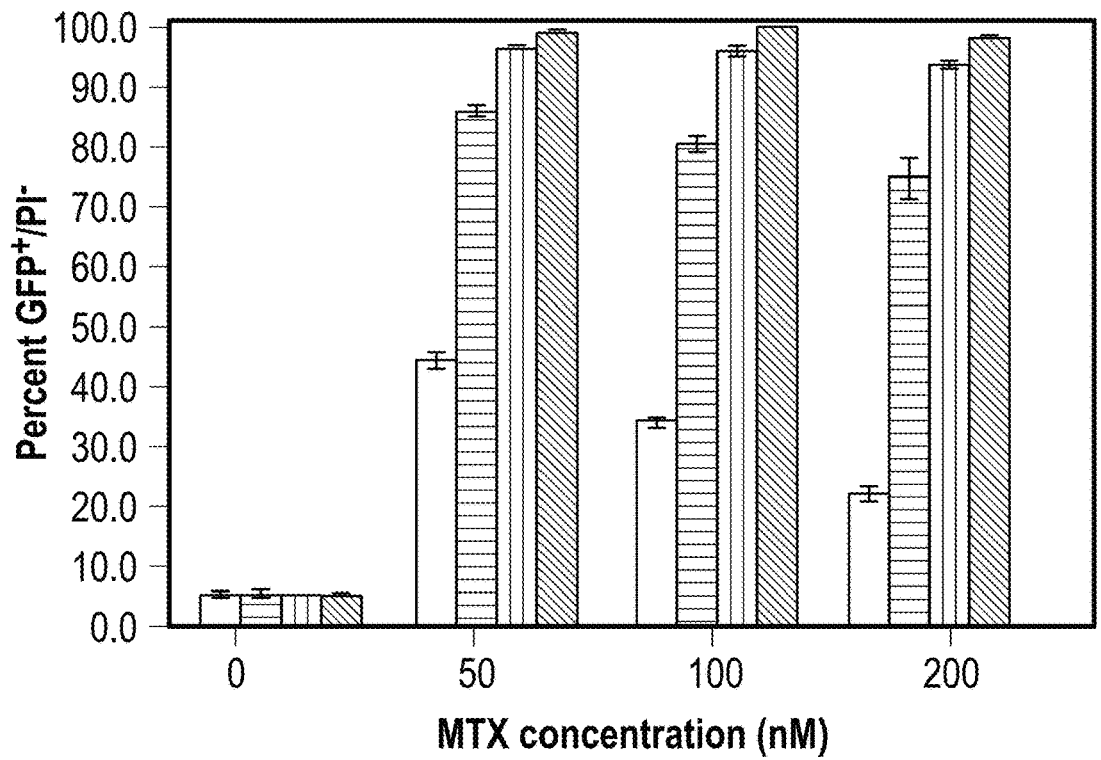
FIGS. 3A and 3B show a series of bar graphs, which demonstrate the effect of MTX concentration during the selection process. Flow cytometric analysis of H9 cell populations stably transfected with T3/GFP-T2A-DHFRdm transposon DNA grown in the presence of increasing concentrations of MTX (0, 50, 100, and 200 nM) at 3 days (white bars), 5 days (horizontal stripes), 7 days (vertical stripes), and 10 days (black bars) was performed.
Figure 3B:
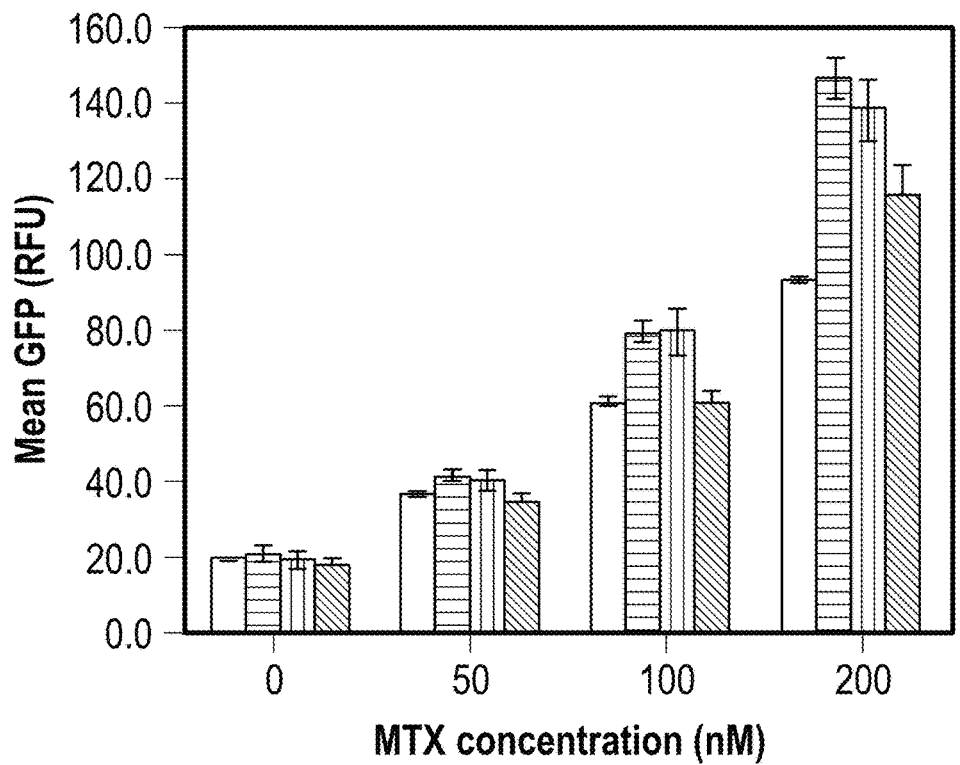

It was hypothesized that cells can be selected with multiple integration events using higher MTX concentrations due to increased selection pressure for DHFRdm expression. Cells stably transduced with the T3/maxGFP-T2A-DHRFdm transposon were therefore grown in the presence of increasing MTX concentrations (ranging from 50 to 200 nM) and GFP expression was evaluated by flow cytometry over 10 days. Attention is drawn to FIGS. 3A and 3B, which shows the effect of methotrexate (MTX) concentration during selection. The initial selection efficiency, assessed with 3 days of MTX selection, was decreased with increasing MTX concentration (FIG. 3A). However, populations with >94% GFP+ cells were obtained by 7 days post-selection under all conditions. The mean GFP fluorescence in GFP$^+$ cells increased with selection pressure (FIG. 3B); the mean fluorescence in cells selected with 200 nM MTX was 6.4-fold higher than unselected cells and 3.3-fold higher than cells selected with 50 nM MTX. As shown, the positive correlation between mean GFP expression in GFP+ cells and MTX concentration suggests that increasing MTX concentration selects for cells with increased DHFRdm expression and therefore, multiple integration events.

Figure 4A:
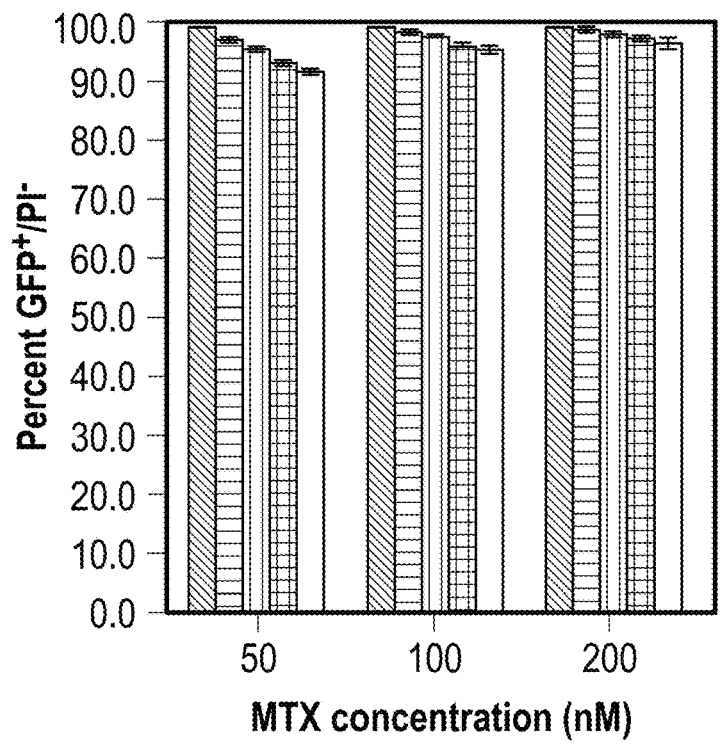
FIGS. 4A and 4B show a series of bar graphs that demonstrate the transgene persistence after MTX withdrawal. As shown is the flow cytometric analysis of H9 cell populations that were stably transfected with T3/GFP-T2A-DHFRdm transposon grown in media supplemented with different concentrations of MTX (50, 100, and 200 nM) for 2 weeks (black bars), after which MTX selection was withdrawn and data collected at different time points afterwards: 1 week (horizontal stripes), 2 weeks (vertical stripes), 3 weeks (checked bars), and 4 weeks (white bars).
Figure 4B:
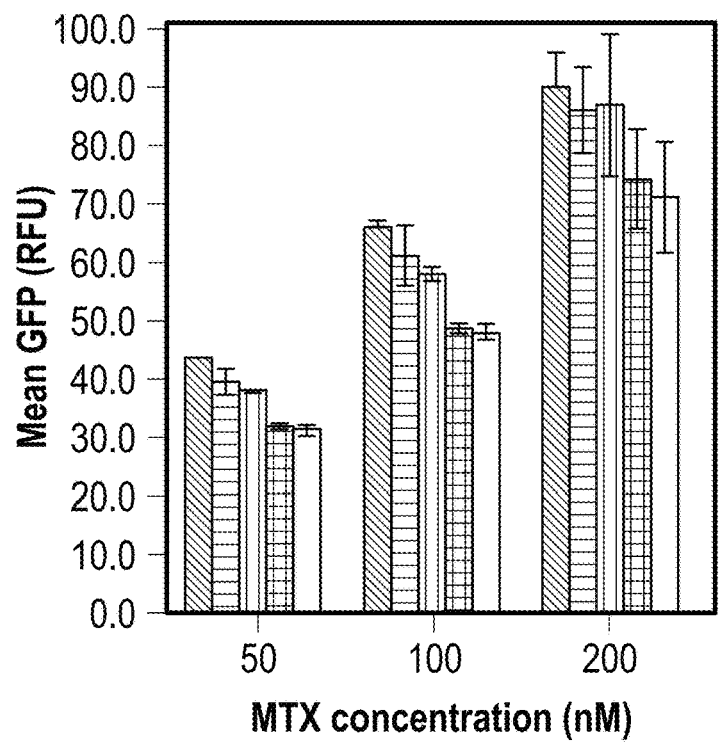

The amplified cell populations selected with 2 weeks of MTX treatment maintained most of their transgene expression even upon MTX withdrawal up to 4 weeks. Attention is drawn to FIGS. 4A and 4B, which shows the transgene persistence after methotrexate (MTX) withdrawal. Four weeks post-MTX withdrawal, the GFP$^+$ population remained >90% in all populations (FIG. 4A), although cells selected with 200 nM MTX had the highest GFP$^+$ population (97%), likely due to selection of cells with multiple integration events. The mean GFP expression in all populations decreased by 21%, 27%, and 28% for 200 nM, 100 nM, and 50 nM MTX selection, respectively by 4 weeks post-MTX withdrawal (FIG. 4B). As such, the decrease in mean GFP expression might be due to promoter silencing or preferential expansion of cells with lower GFP expression at the absence of selective pressure.

Analysis of Distribution of Integration.

To test the hypothesis that increased MTX selection pressure would select for cells with multiple integration events, the average number of transposon copy numbers in MTX-selected cell populations was determined using RT-qPCR with GFP primers. First, a "gold standard" clone with a single copy of integrated transposon was generated by limiting dilution method. The average number of integrations in the original stably-transduced population before MTX selection was determined by RT-qPCR analysis of the GFP$^+$ cells obtained by cell sorting. A trend of increasing average transposon copy number with increasing selection pressure was observed. Attention is drawn to FIG. 5A, which shows the transposon copy number per human haploid genome. The average integration events in cells selected with 200 nM MTX was 2.1±0.45 compared to an average of 1.1±0.02 integration events in GFP+ cells before MTX selection. RT-qPCR was performed in triplicates and data represents a single biological replica for the sorted population and 3 biological replicas for MTX selection. Statistical difference was assessed by Student's t-test.

Figure 5A:
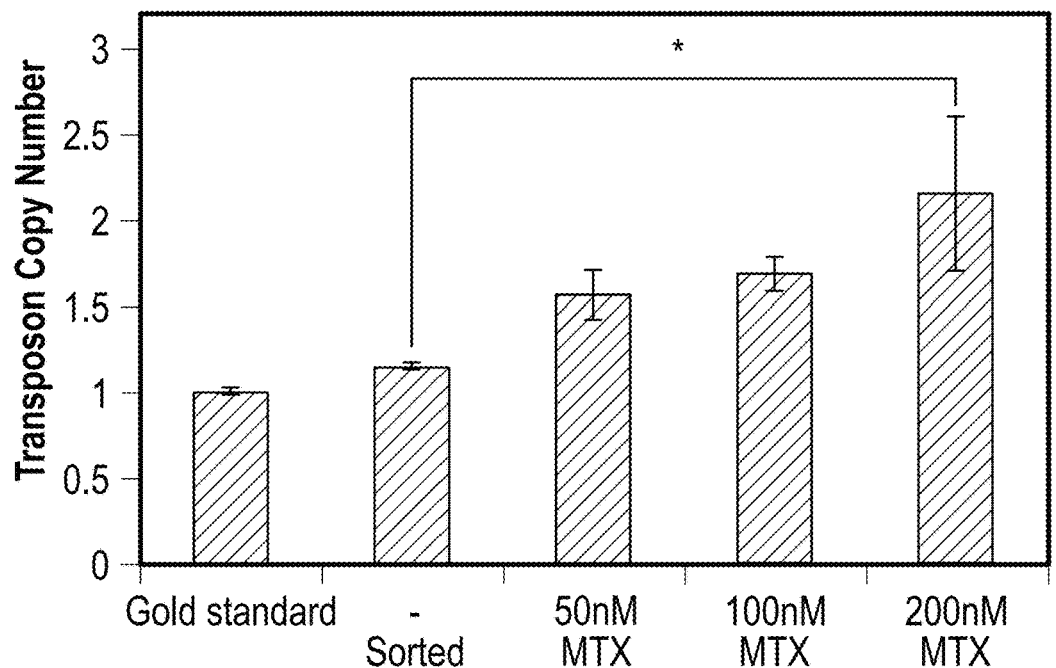
FIG. 5A shows the transposon copy number per human haploid genome. Genomic DNA was isolated from populations of H9 cells stably transfected with T3/GFP-T2A-DHFRdm transposon DNA before and after selection with different concentrations of MTX (50, 100, and 200 nM). The average transposon copy number was determined by quantitative PCR. The "Gold standard" was generated by the limiting dilution method. The "Sorted" population was created by sorting the original H9 population (8% of integrated transposon) to 100% GFP positive cells. The asterisk (*) above the bracketed bar graphs indicates the difference between 200 nM MTX and sorted population was significantly different according to a Student's T-test (P=0.04).
Figure 5B:
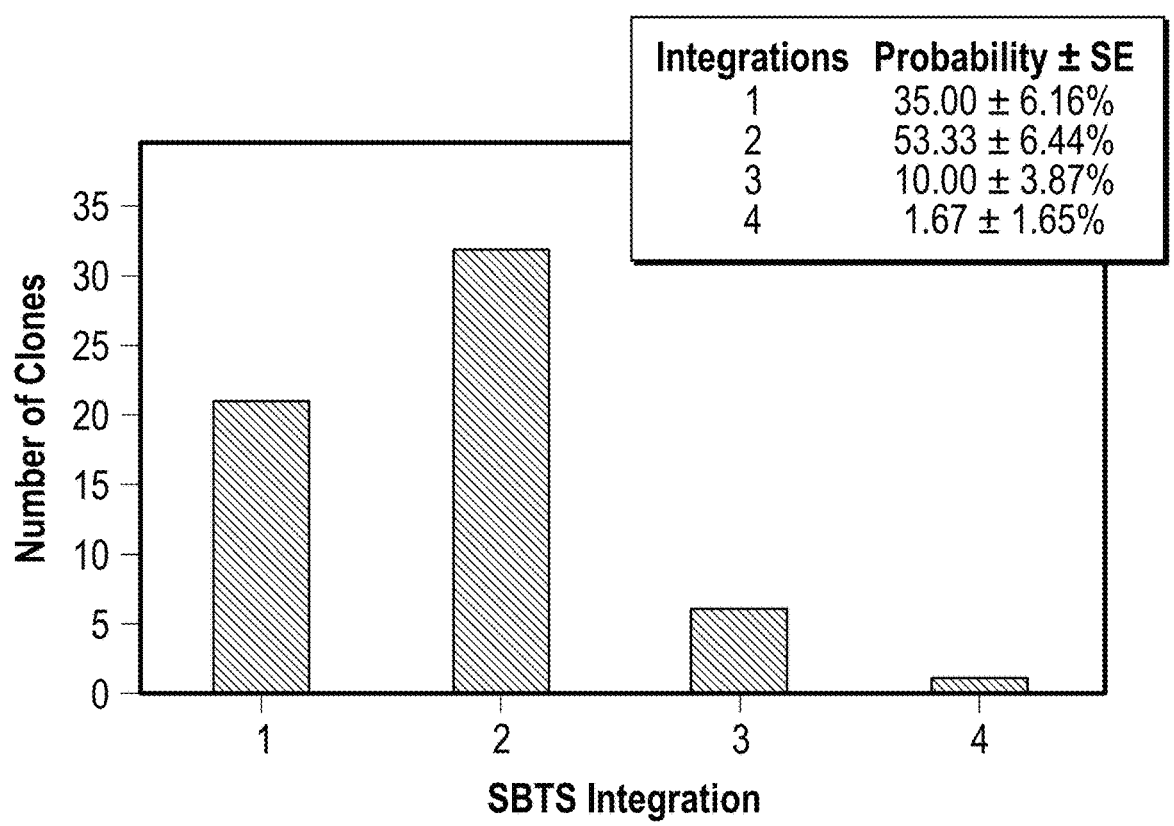
FIG. 5B shows the distribution of transposon integration events. Sixty clones were isolated by limited dilution method from an H9 population that was previously selected with 200 nM MTX to 100% cells with integrated T3/GFP-T2A-DHFRdm transposon. Genomic DNA was isolated and transposon copy number determined by relative RT-qPCR. Numbers were rounded to the nearest integer value (e.g., 0.5-1.5 was rounded to 1). N=60; mean±standard deviation=1.78±0.69. Probabilities of integration events and standard error were calculated from these data (inset table).

The distribution of integration events in cells selected with 200 nM MTX was then analyzed. Sixty clones were generated by limiting dilution method, GFP expression confirmed by flow cytometry, genomic DNA isolated, and the number of GFP genes per haploid genome analyzed by RT-PCR. The distribution of integration events is shown in FIG. 5B. Most clones (~65%) contained multiple copies of GFP. The average number of integration events was 1.8 which correlates well with the average transposon copy number in the cell population selected with 200 nM MTX (FIG. 5A).

Demonstration of Multiplexed Gene Integration.

Figure 6A:
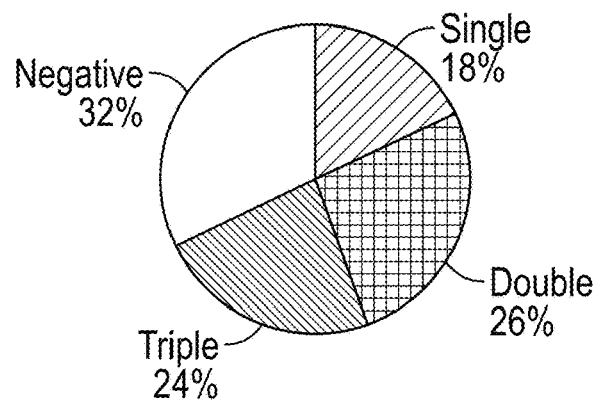
FIGS. 6A-6C show a series of pie graphs representing the analysis of the multiplexing of transposons.
Figure 6B:
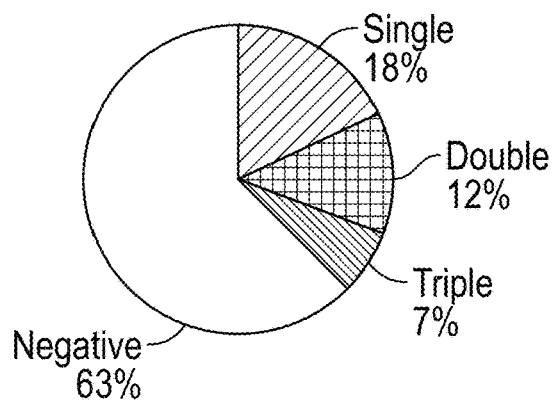
Figure 6C:
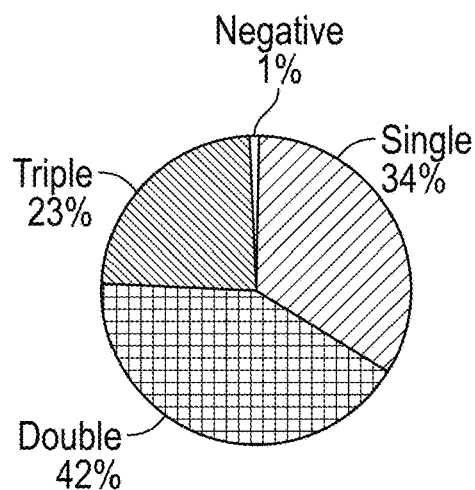
Figure 7:
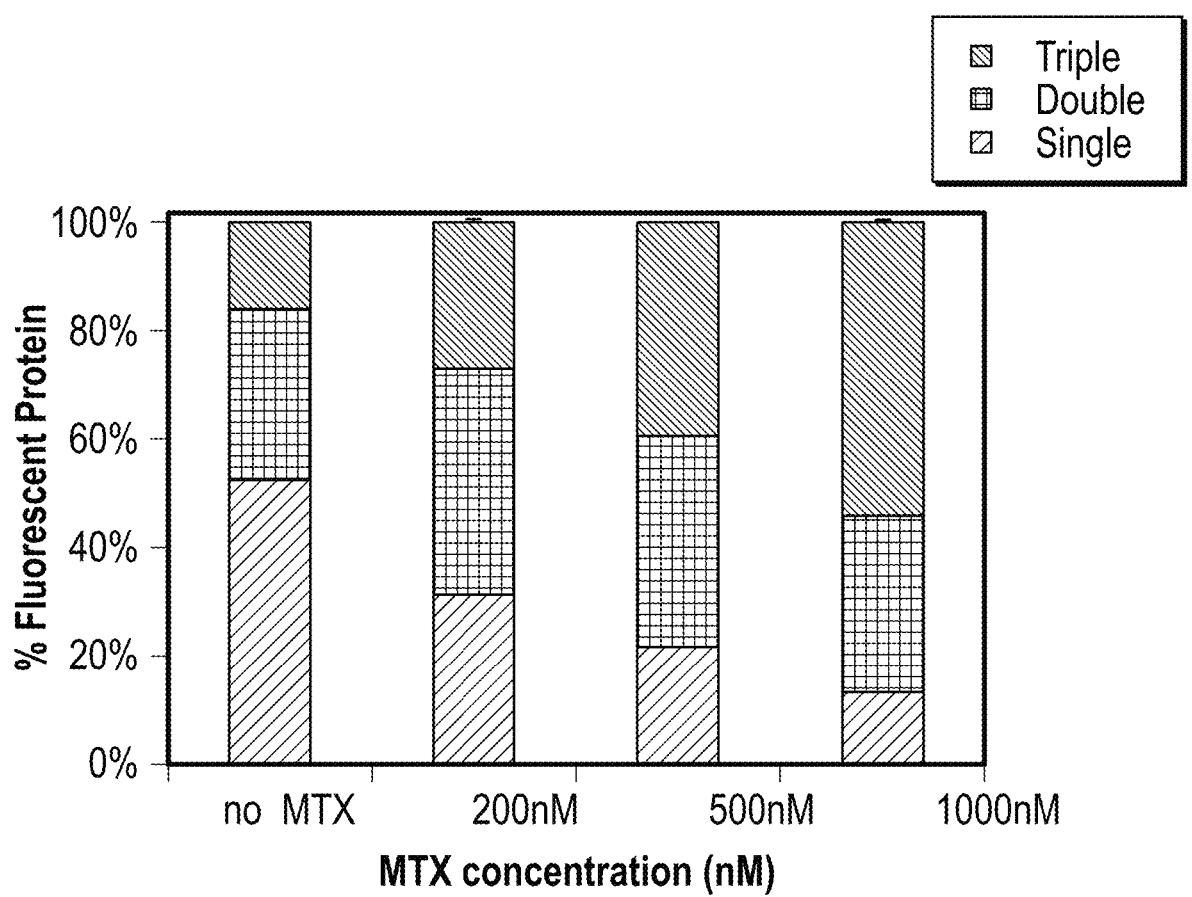
FIG. 7 shows the bar graph analysis of step selection of the distribution of expression of single, double, and triple FPs. H9 cell population stably transfected with three transposons was selected with 200 nM MTX for a week and then was exposed to higher MTX concentrations of 500 and 1000 nM.

Since it was previously demonstrated that a majority of the population of transduced cells amplified under 200 nM MTX selection pressure contained multiple transposon copies, multiplexed gene integration was then assessed under these conditions. H9 cells were nucleofected with three minicircles containing three different reporter genes (maxGFP, mCherry, and BFP) in transposon cassettes and the SB100X transposase minicircle. Stably-transduced cells were then selected for 7 days with 200 nM and cell population assessed by flow cytometry analysis. Attention is drawn to FIGS. 6A-6C, which shows the flow cytometric analysis of H9 cell populations nucleofected with 3 minicircles carrying transposons with different fluorescent proteins (MC_T3/GFP-T2A-DHFRdm, MC_T3/BFP-T2A-DHFRdm, MC_T3/mCherry-T2A-DHFRdm), 2 µg each and 6 µg of MC_SB100xDNA at different time points after transfection. Initial transfection efficiency assessed 24 hours after nucleofection, was 68% (FIG. 6A). The stably-transduced population was 37±1.4%, reflecting 54% integration efficiency. Of this population, 19±0.6% expressed two or three different fluorescent proteins. Stably-transduced cells grown for 1 week in the presence of 200 nM MTX were then analyzed; 23±1.0% of this selected population expressed all three reporter proteins (FIG. 6A). In order to further increase the population of cells expressing triple transgenes, cells selected by 200 nM MTX were subjected to a second selection step with increased MTX concentrations. Attention is drawn to FIG. 7, which shows a bar graph demonstrating the results of an H9 cell population stably transfected with three transposons selected with 200 nM MTX for a week and then exposed to higher MTX concentrations of 500 and 1000 nM. As shown, cells that were cultured in 500 nM or 1000 nM MTX for an additional week resulting in an increased population (38.5±1.0% and 53.1±0.3%, respectively) of cells expressing triple transgenes. Cell viability rebounded to ~70% during the second round of selection due to further selection for overexpression of the DHFRdm gene.

Stable Expression of Transposon DNA with Sleeping Beauty in T-Cells with Methotrexate Selection.

Freshly thawed peripheral blood mononuclear cells (PBMCs) were electroporated using Amaxa™ Nucleofector™ Technology. The cells were transfected with 10 μg of minicircle GFP (MC_T3/GFP-T2A-DHFRdm) and different amounts of SB100X hyperactive transposase (0, 5, or 10 μg). Control cells were transfected with either the non-minicircle pMAXGFP vector (10 ug) or with no DNA. The cells were then stimulated with Miltenyi Transact beads 4 to 6 hours after transfection in the presence of IL-2 and IL-15. The cells were then aliquoted so that there were 400,000 cells per well of a 96-well U-bottomed plate. The cells were treated with methotrexate at 7 days after transfection with 0, 25, 50, or 100 nM of methotrexate. At days 2, 5, 7, 14, and 19, the cells were counted by trypan blue, stained, and analyzed.

Figure 8A:
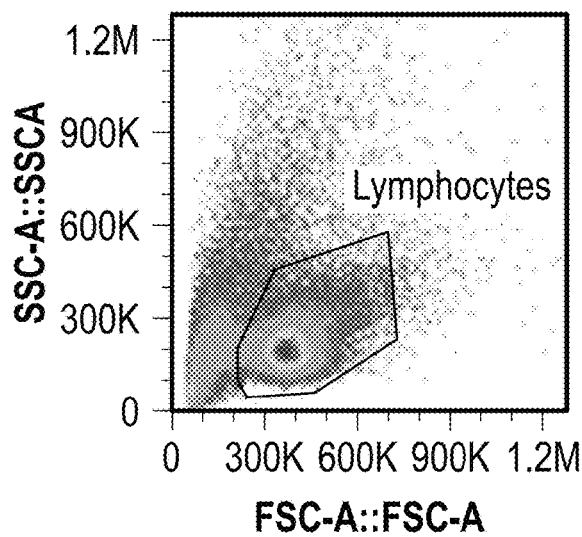
FIGS. 8A-8D show an example of the flow analysis for the stable expression of transposon DNA with Sleeping Beauty in lymphocytes after MTX selection. Freshly thawed PBMC cells were electroporated with minicircle GFP (mcGFP) DNA (MC_T3/GFP-T2A-DHFRdm) and Sleeping Beauty transposase DNA (MC_SB100X), then stimulated with Miltenyi Transact beads which selectively activate T-cells by binding to CD3 and CD28. 1 week after electroporation, samples of the PBMC cells were selected using 25, 50 and 100 nM MTX for 12 days (50 nM shown here).
Figure 8B:
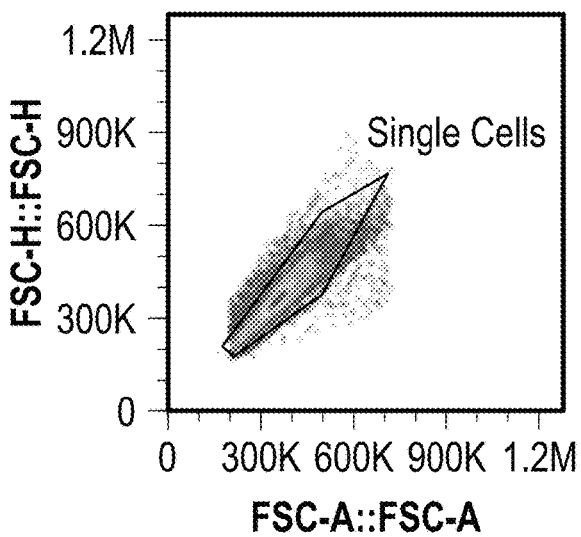
Figure 8C:
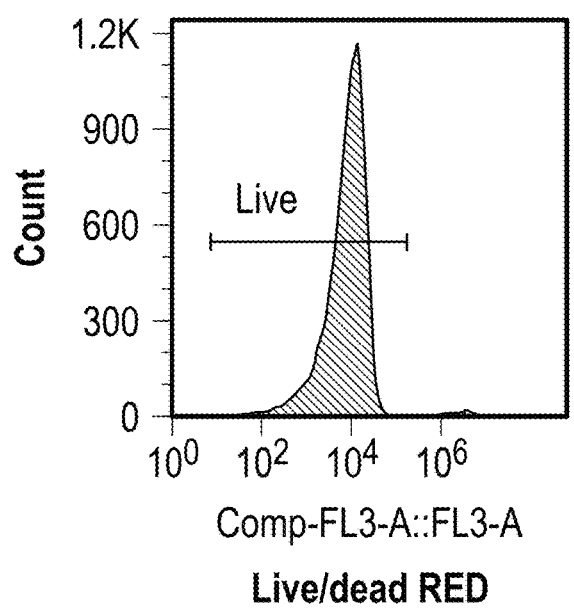
Figure 8D:
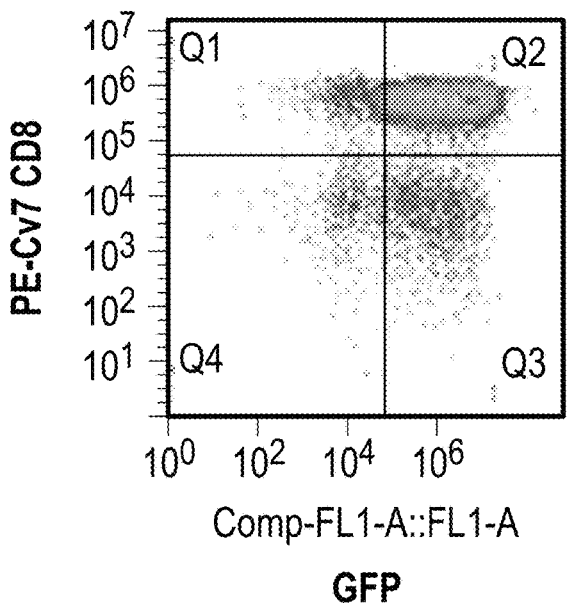

Attention is drawn to FIGS. 8A-8D which show an example of the flow analysis of the lymphocytes expressing GFP after minicircle transfection. Single cells (FIG. 8B) from the lymphocyte window (FIG. 8A) were analyzed for viability with the Invitrogen LIVE/DEAD red stain (FIG. 8C). Live lymphocytes were then analyzed for CD8 and GFP expression (FIG. 8D). As shown in FIG. 8D, after selecting with 50 nM methotrexate, the majority of lymphocytes were CD8+ and expressed GFP.

Stable Expression of Transposon DNA with Sleeping Beauty in T-Cells after One Week.

Figure 9A:
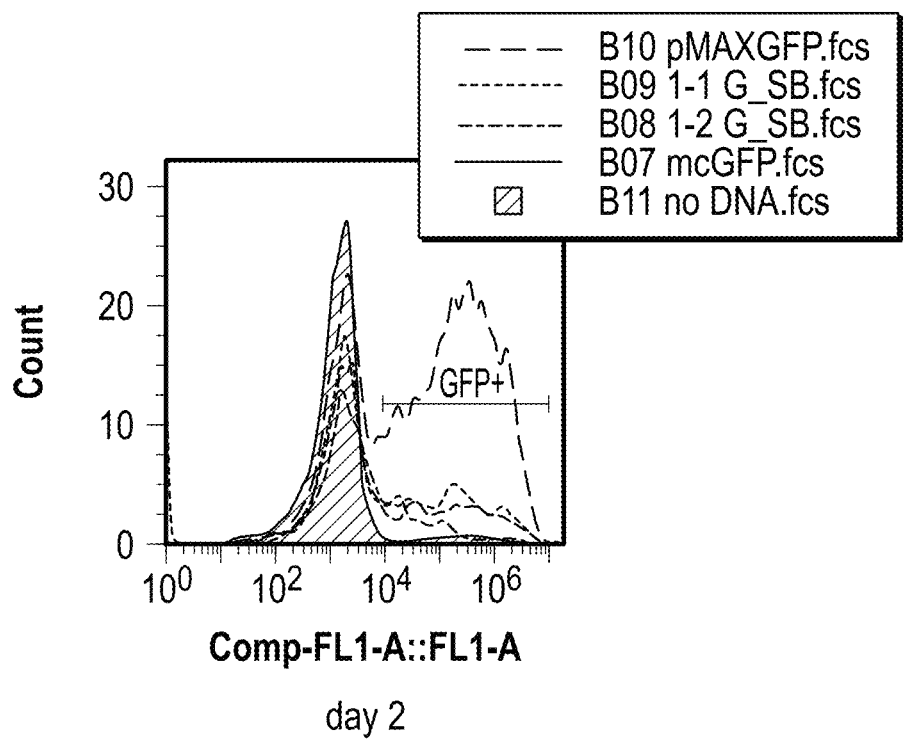
FIGS. 9A-9B show histograms of the initial expression of transposon DNA with Sleeping Beauty in lymphocytes. PBMC were transfected with either mcGFP DNA alone (10 ug), mcGFP (10 ug) and MC_SB100×DNA (5 ug) at a mcGFP:MC_SB100X ratio of 2:1, mcGFP (10 ug) and MC_SB100×DNA (10 ug) at a mcGFP:MC_SB100X ratio of 1:1, a pMAXGFP (10 ug) control, or a no DNA control. Shown in FIG. 9A are the results for cells in which Transact beads were not added, two days after transfection as an example of the initial electroporation efficiency. Shown in FIG. 9B are the results in cells exposed to transact beads after five days. While by day 5 the levels of mcGFP DNA decline to near control levels, the expression of mcGFP in cells co-transfected with transposase remain elevated.
Figure 9B:
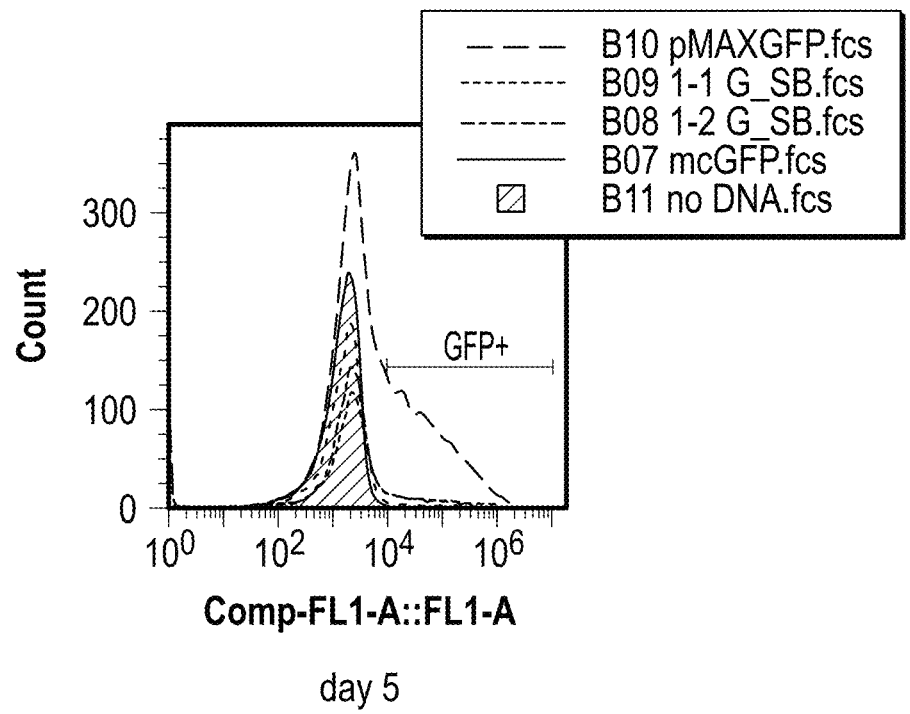

In order to assess the expression of the minicircle DNA in the week before MTX selection, flow analysis was performed and then compared for cells transfected with pMAXGFP, 1:1 ratio of GFP transposon:SB100X, 1:2 ratio of transposon:SB100X, mcGFP alone, or no DNA control. Attention is drawn to FIGS. 9A and 9B, which shows the results of a FACS assay on cells at two days (in the absence of Transact beads) and five days (in the presence of Transact beads) after electroporation. As shown, there is a loss of GFP expression over time without MTX. However, GFP expression persists in cells transfected with GFP transposon DNA only if there were co-transfected with SB100X transposase.

Figure 10A:
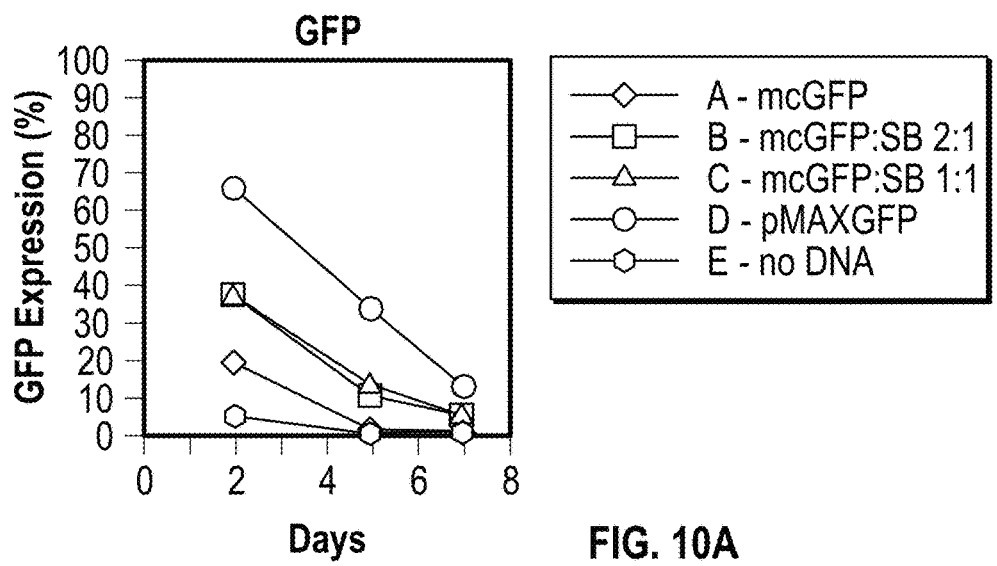
FIGS. 10A-10C show the expression of GFP transposon DNA and the levels of cell growth in transfected lymphocytes in the week before MTX addition. PBMC were transfected with either mcGFP DNA alone, mcGFP and MC_SB100×DNA at a mcGFP:MC_SB100X ratio of 2:1, mcGFP and MC_SB100×DNA at a mcGFP:MC_SB100X ratio of 1:1, a pMAXGFP control (10 ug), or a no DNA control.
Figure 10B:
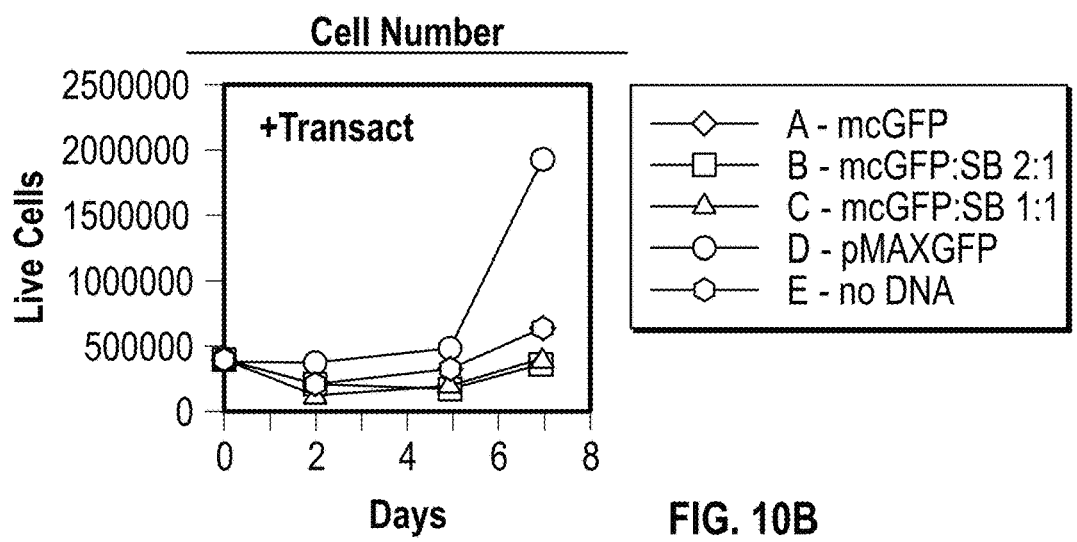
Figure 10C:
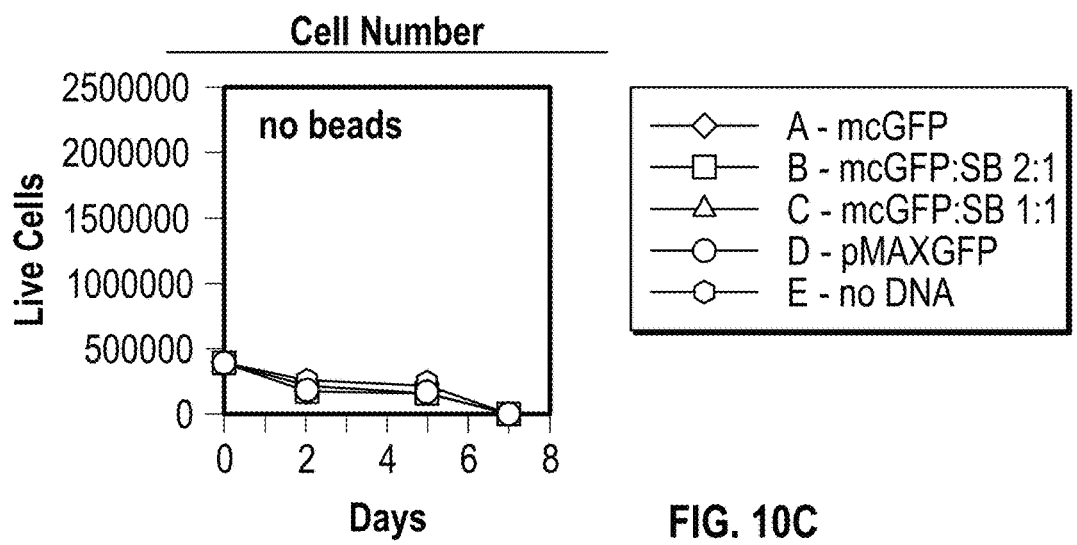

Attention is drawn to FIGS. 10A-10C, which show graphs of the levels of GFP expression and cell growth from days 2 to 7. As shown in FIG. 10A, the amounts of percent GFP expression decreases over time (pMAXGFP (10 ug), mcGFP:MC_SB100X 1:1, and mcGFP:MC_SB100X 2:1). There was a slow increase of live cells in the presence of Transact beads (FIG. 10B), but not without the beads (FIG. 10C), indicating the importance of the beads for cell growth.

Cell Selection with MTX for 7 Days and 12 Days.

Figure 11A:
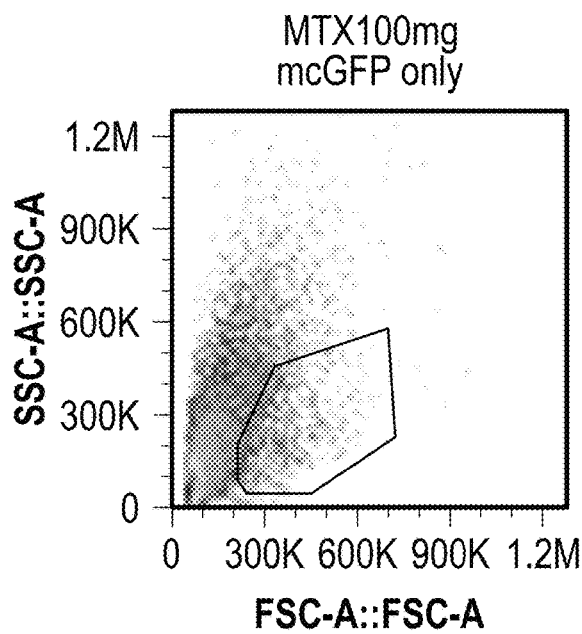
Figure 11B:
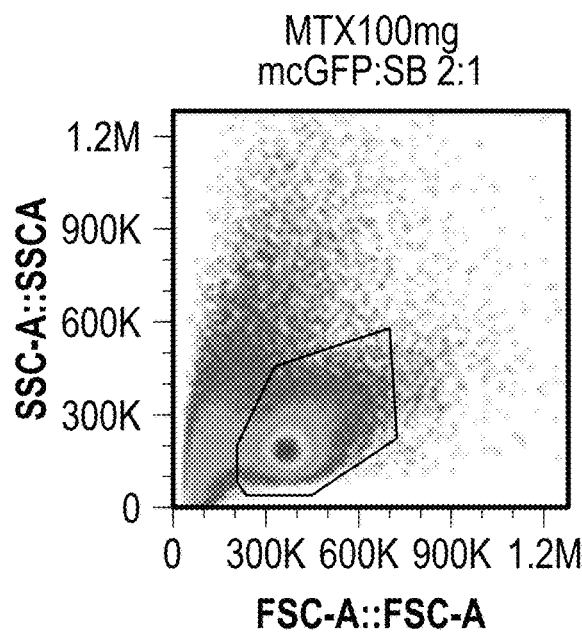
Figure 11C:
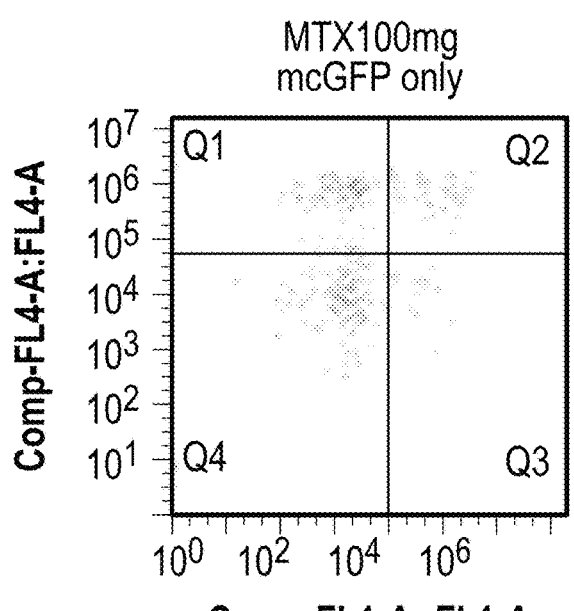
FIGS. 11C, 11D, 11G and 11H show CD8 and GFP expression.
Figure 11D:
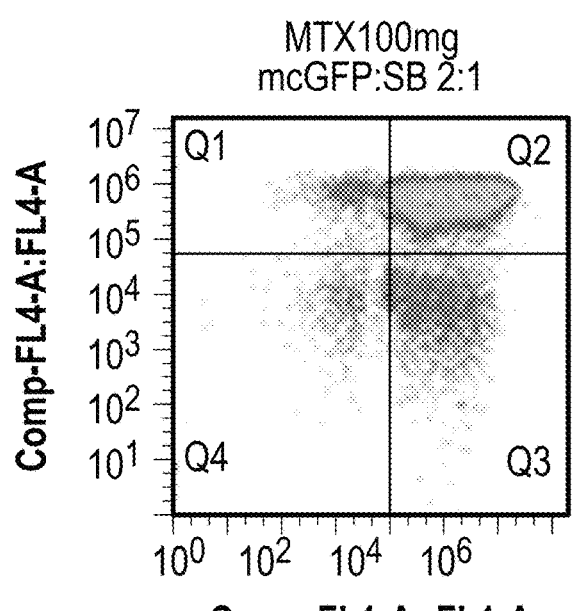
Figure 11E:
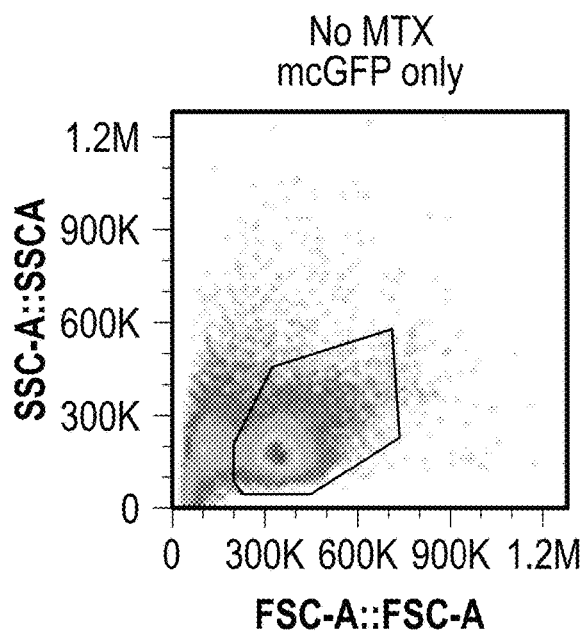
Figure 11F:
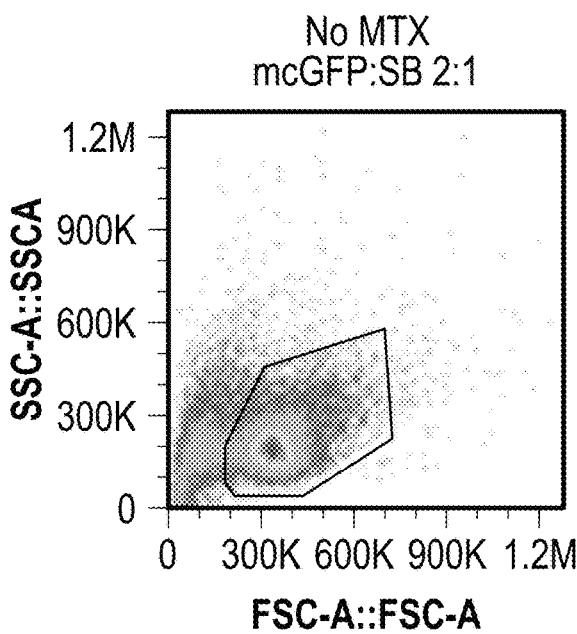
Figure 11G:
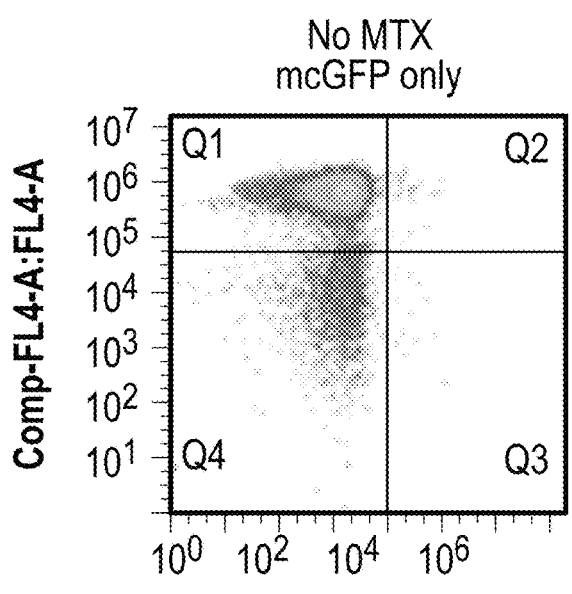
Figure 11H:
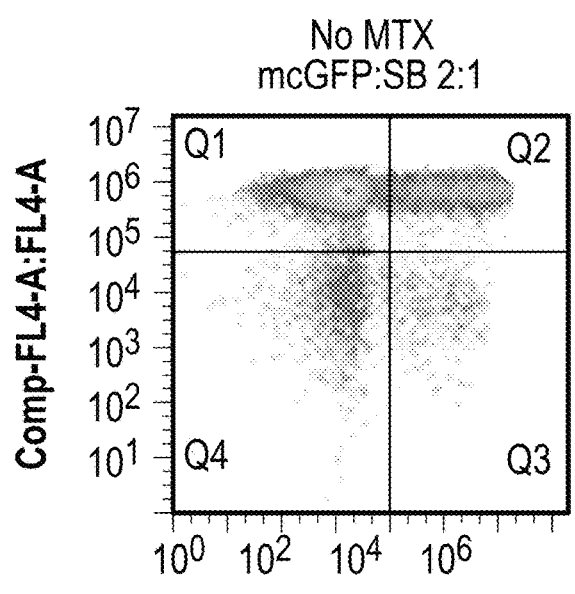

After 1 week, samples of the transfected cells were exposed to different levels of MTX (25, 50, or 100 nM) to enrich for cells expressing the minicircle transposon. Cells that stably express the DHFRdm MTX-resistance gene as well as GFP due to transposase integration should survive higher MTX concentrations. Attention is drawn to FIGS. 11A-11I1, which show the results of a FACS assay of the transfected cells after treatment with 100 nM methotrexate for 7 days. In cells treated with 100 nM MTX, only cells transfected with both transposon and transposase DNA express GFP. As shown, 100 nM MTX selection was effective with GFP expression at both ratios of mcGFP to SB at a 2:1 mcGFP:MC_SB100X ratio and at a 1:1 mcGFP:MC_SB100X ratio after cell selection with MTX for seven days.

Figures 1, 12A:
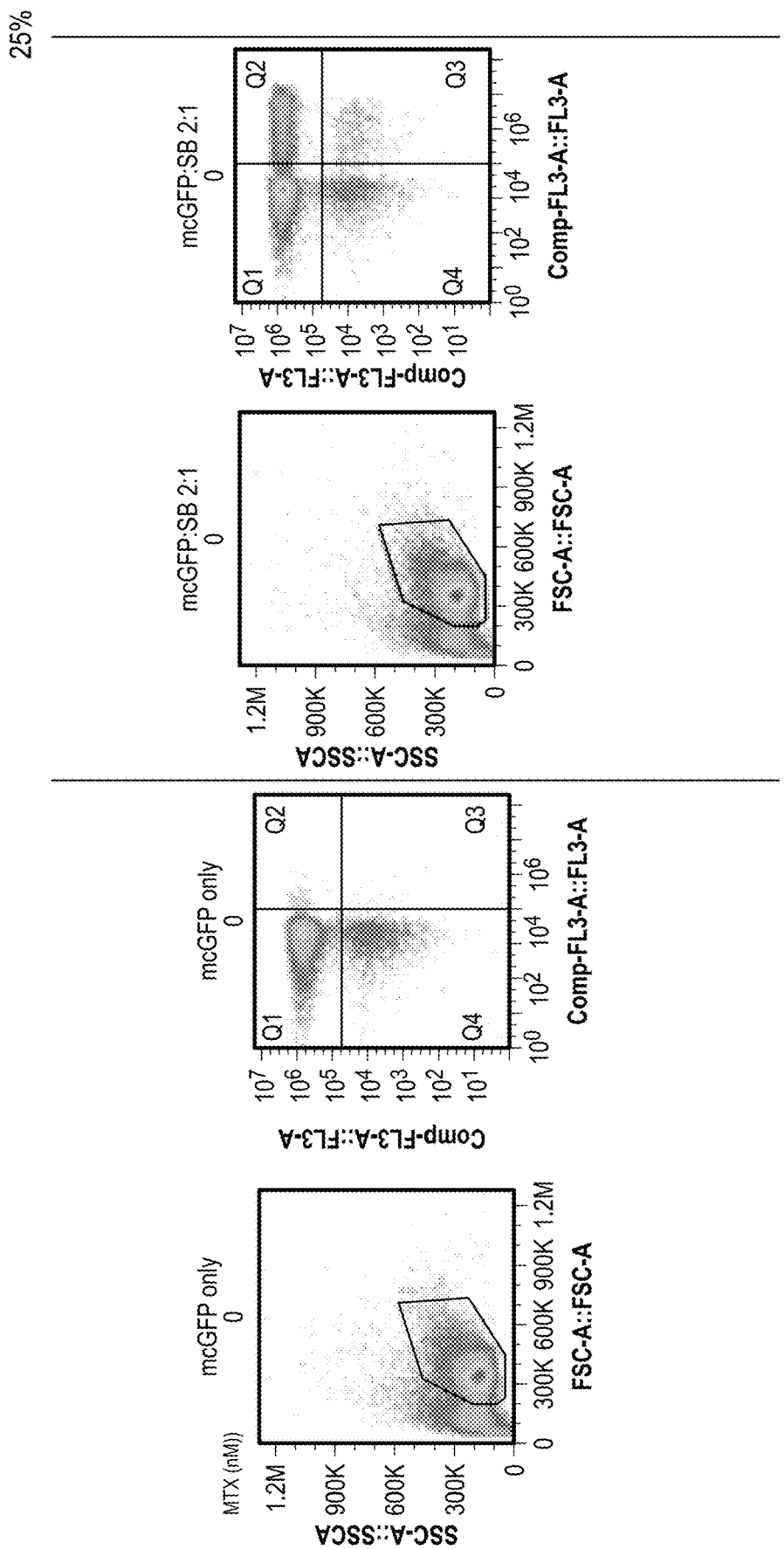
Figures 2, 12A:
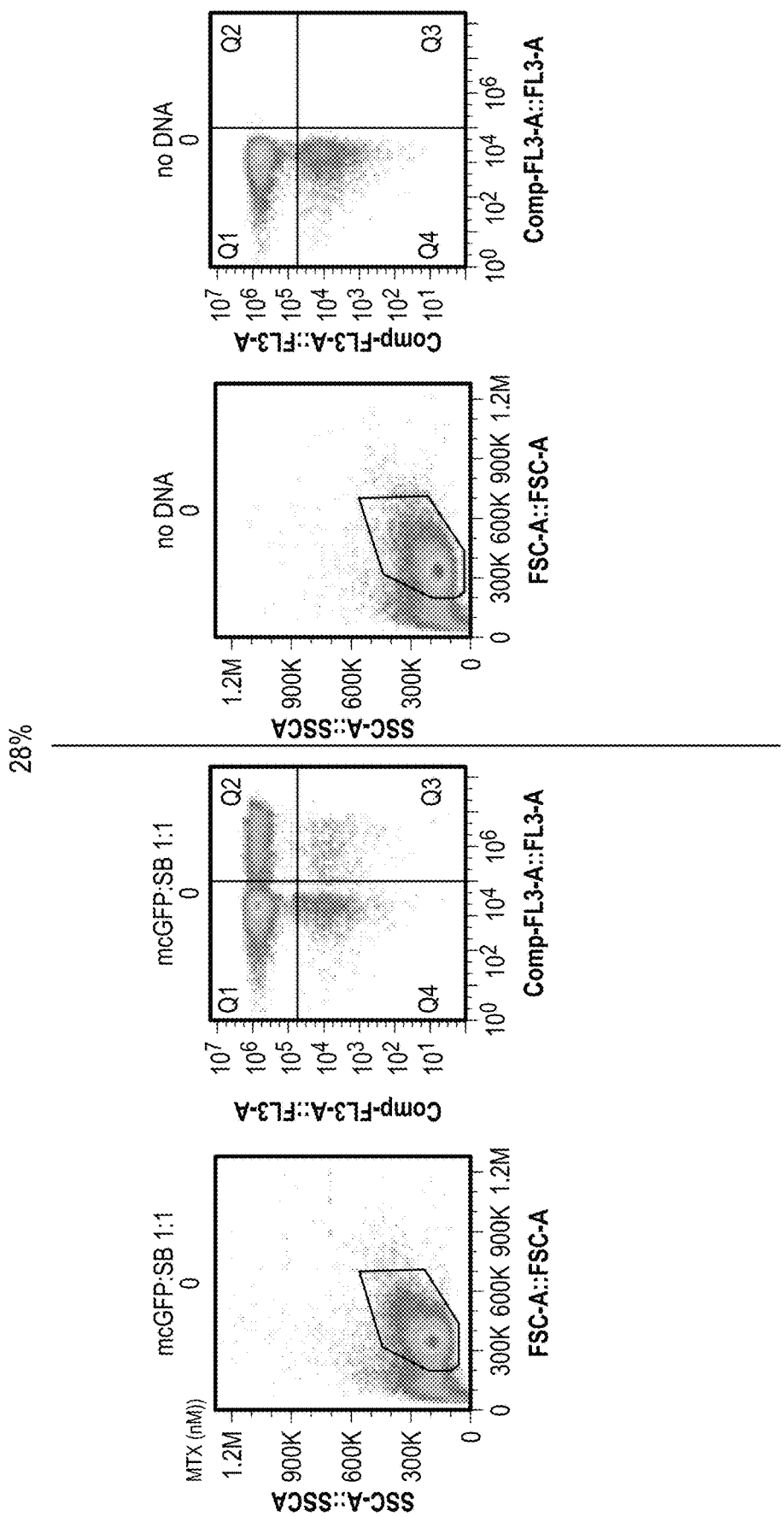
Figures 1, 12B:
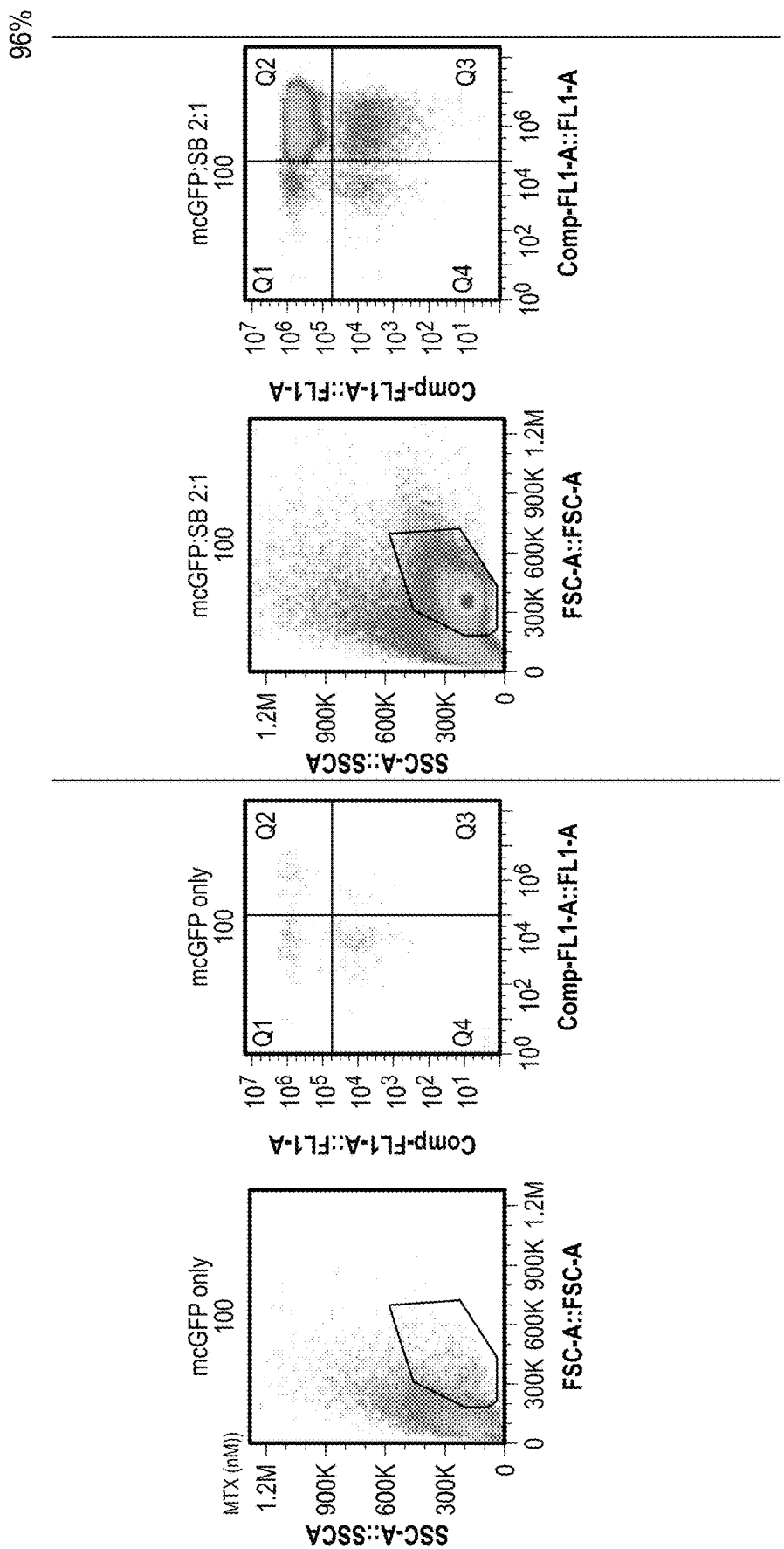
Figures 2, 12B:
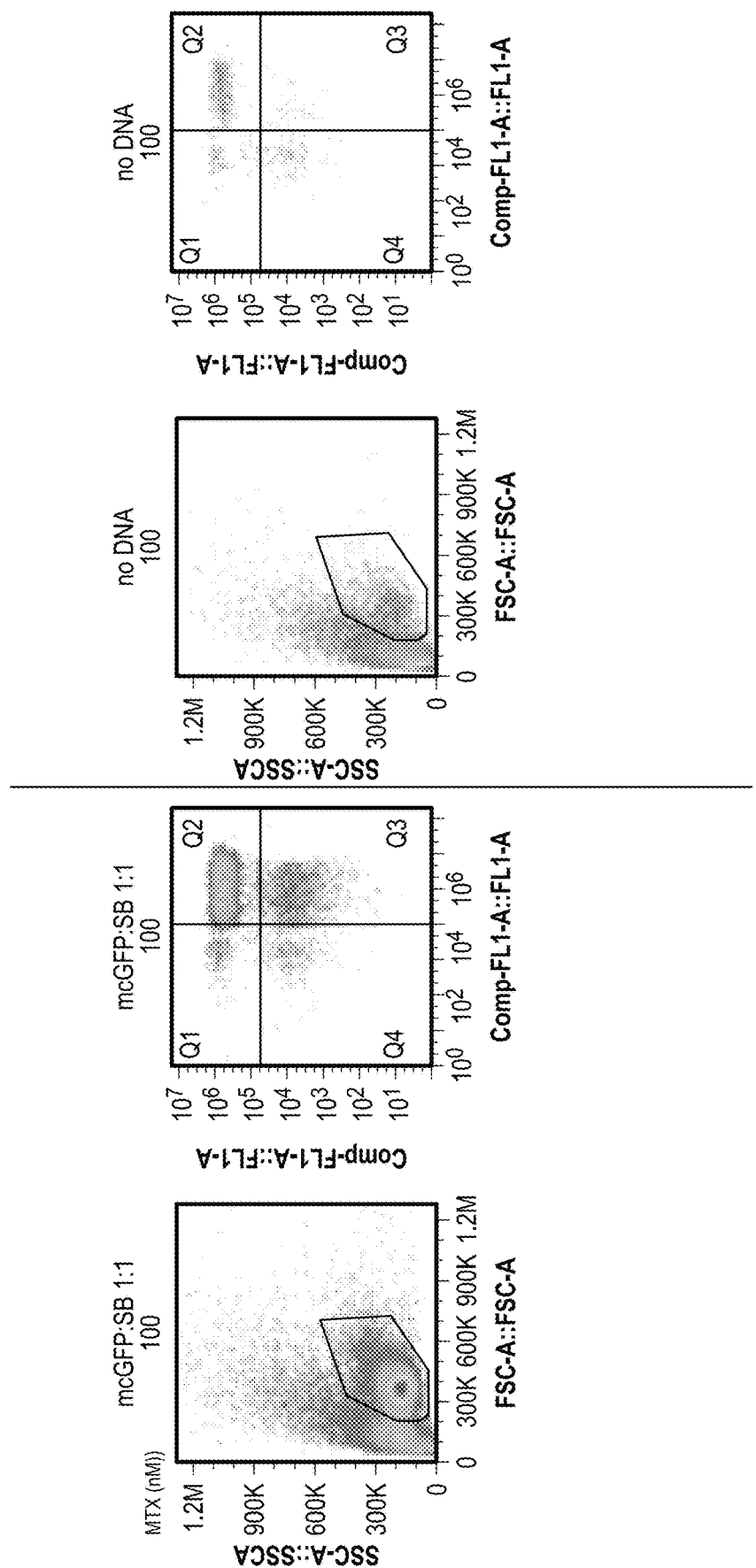
Figures 1, 12C:
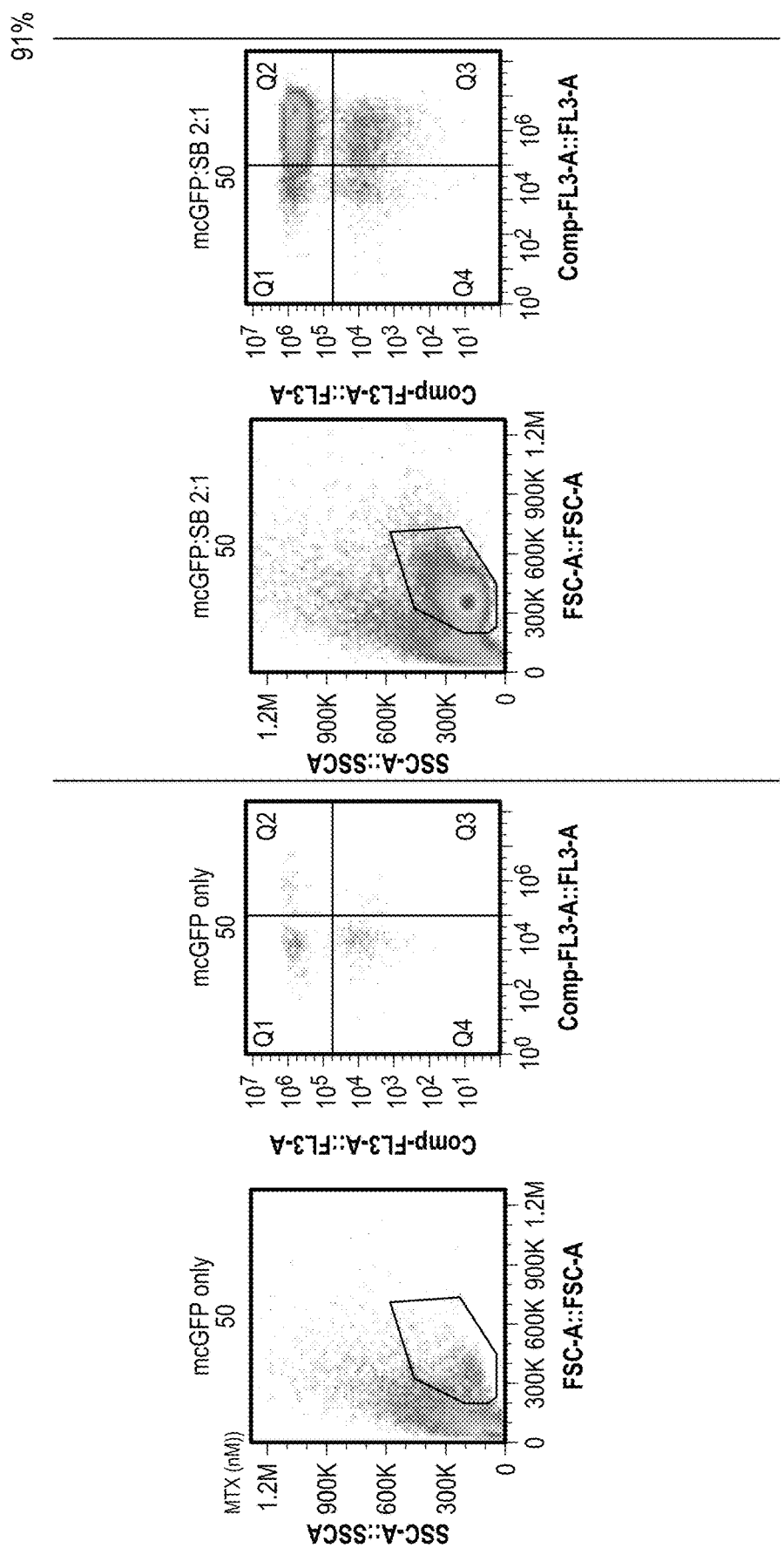
Figures 2, 12C:
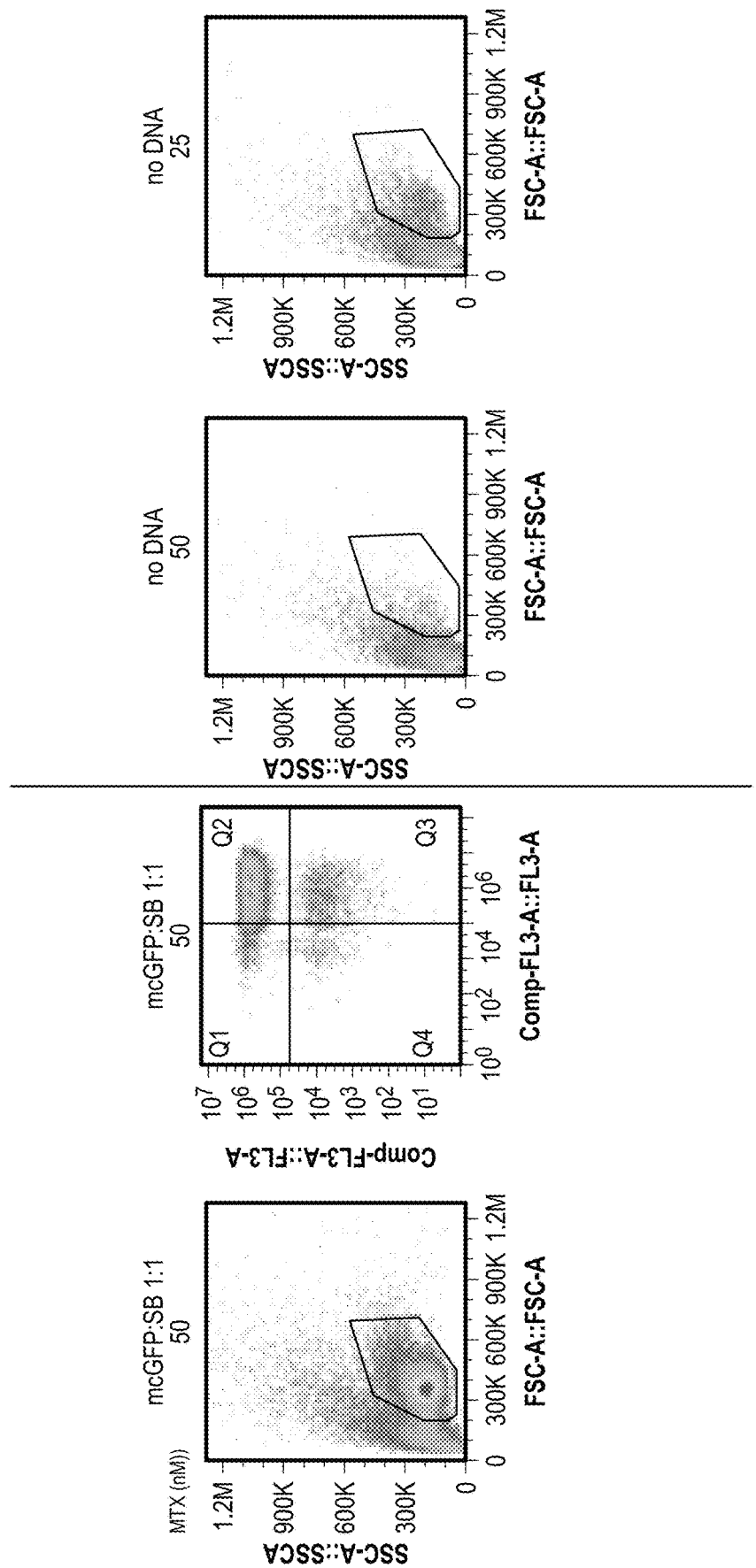
Figures 1, 12D:
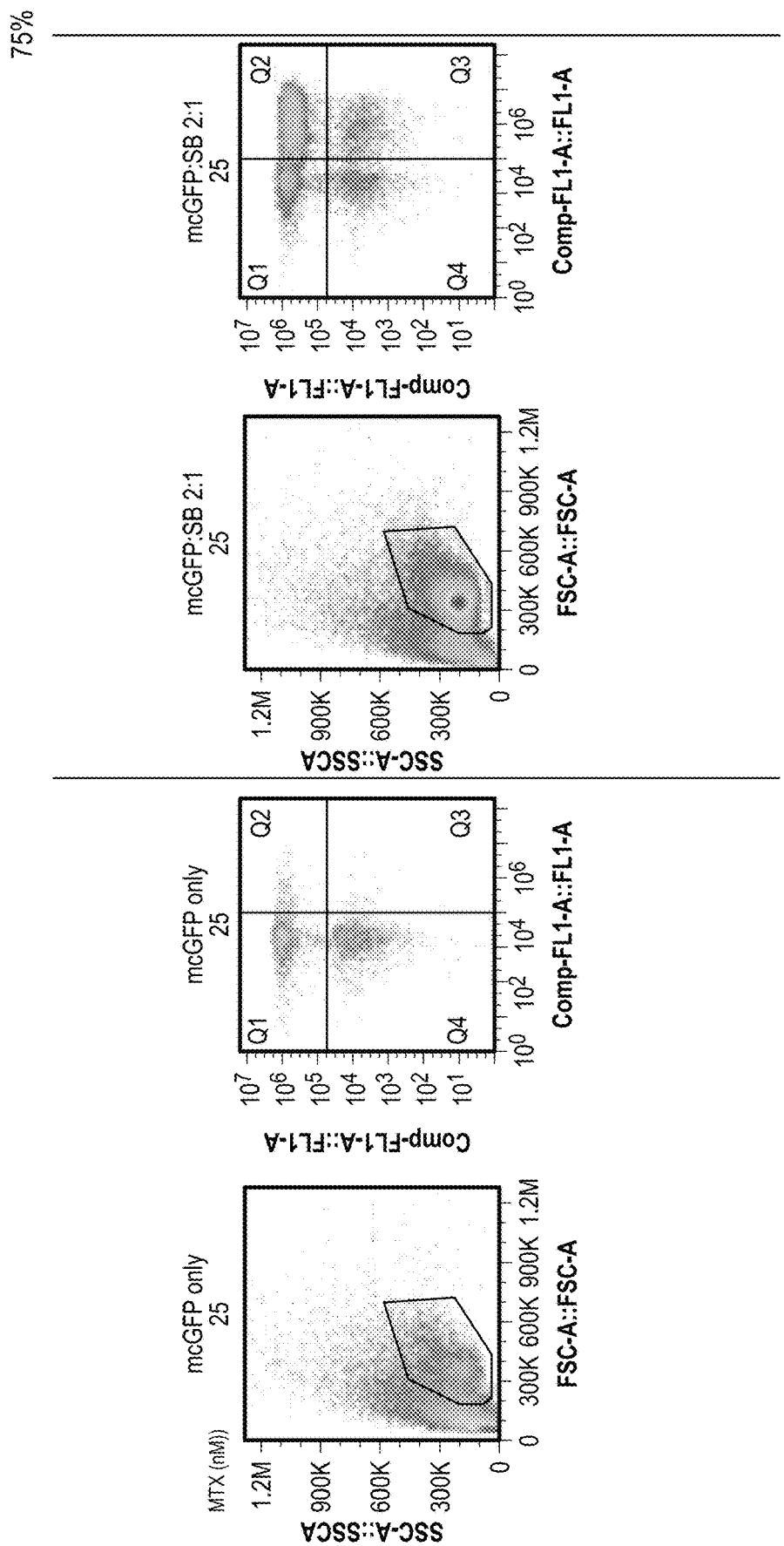
Figures 2, 12D:
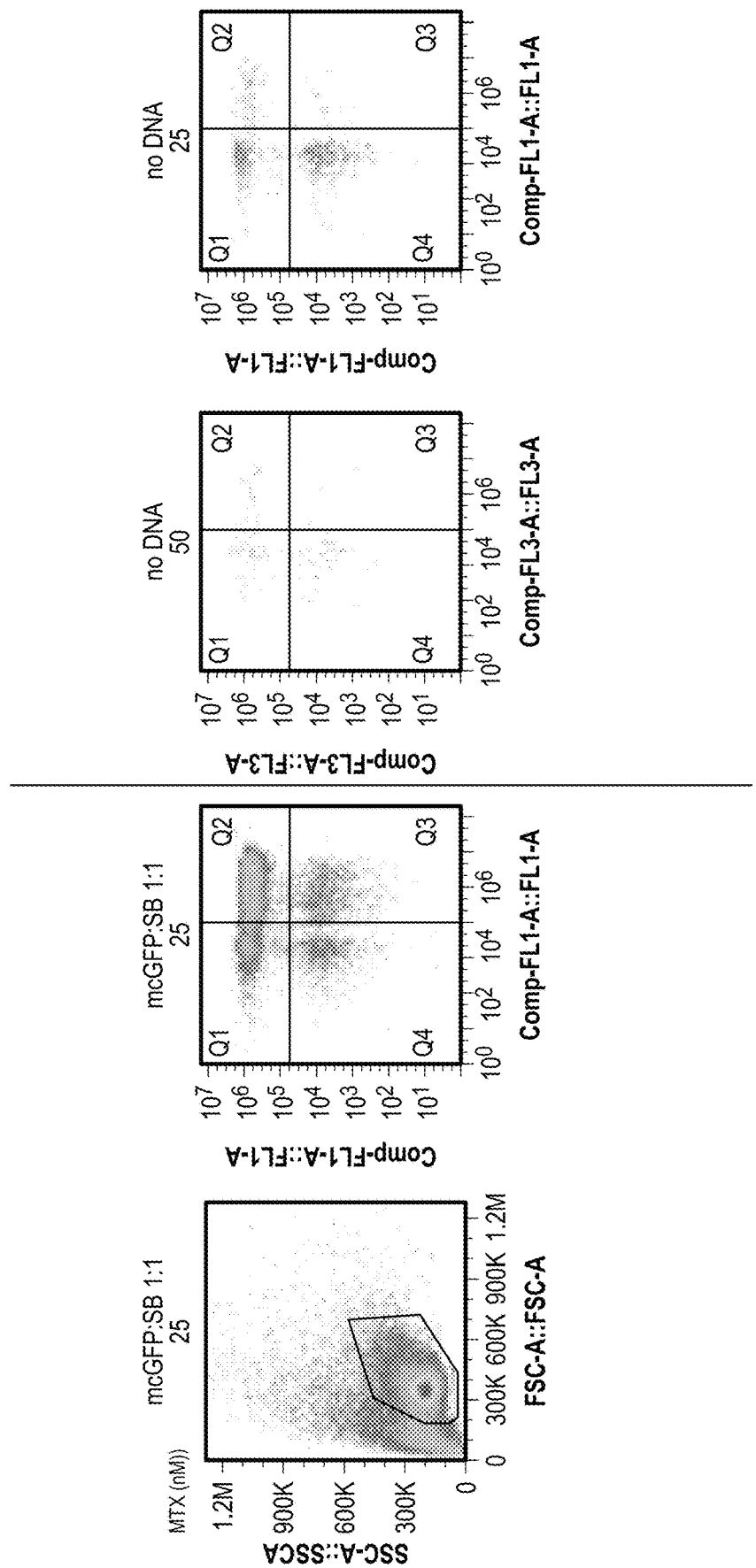
Figures 1, 13A:
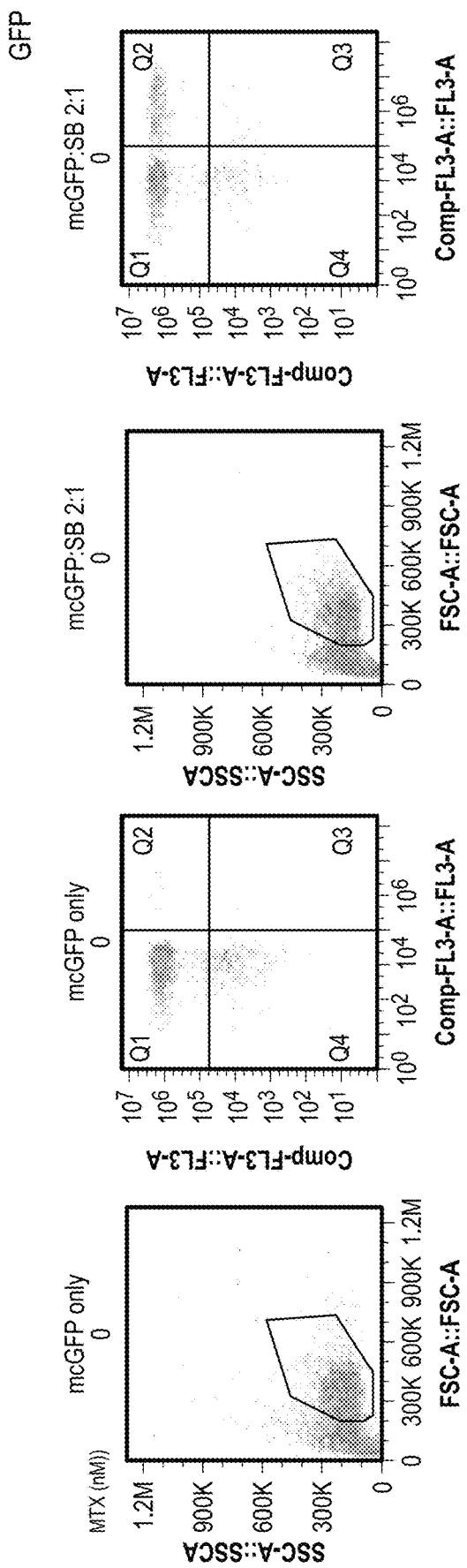
Figures 2, 13A:
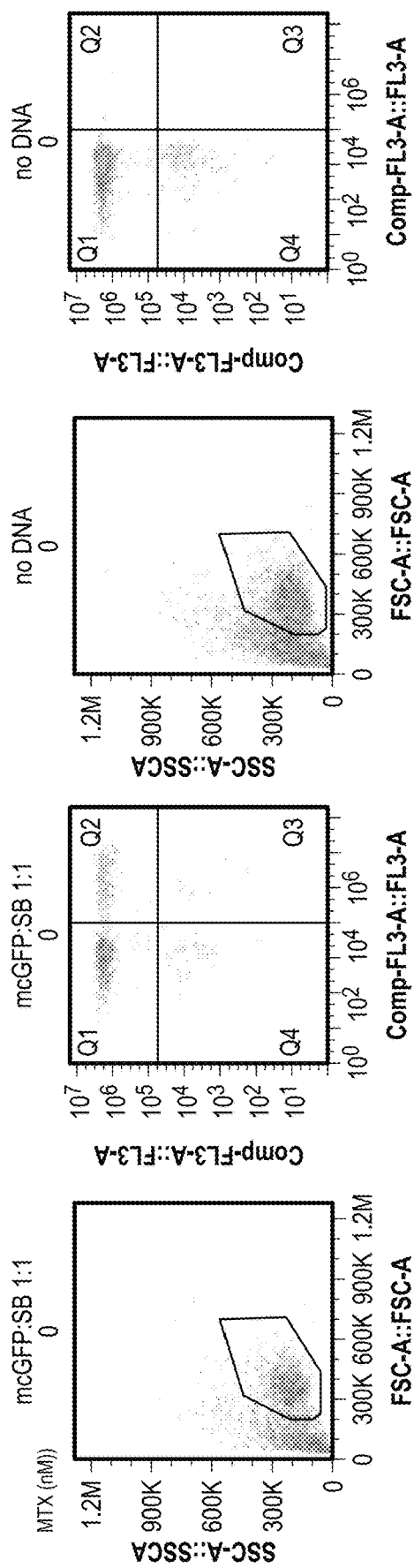
Figures 1, 13B:
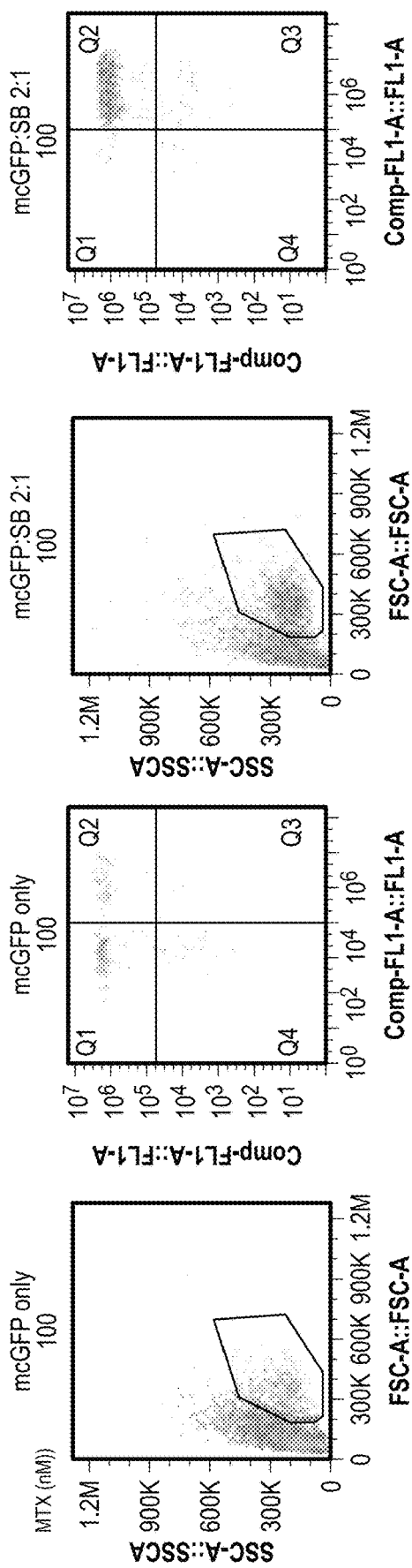
Figures 2, 13B:
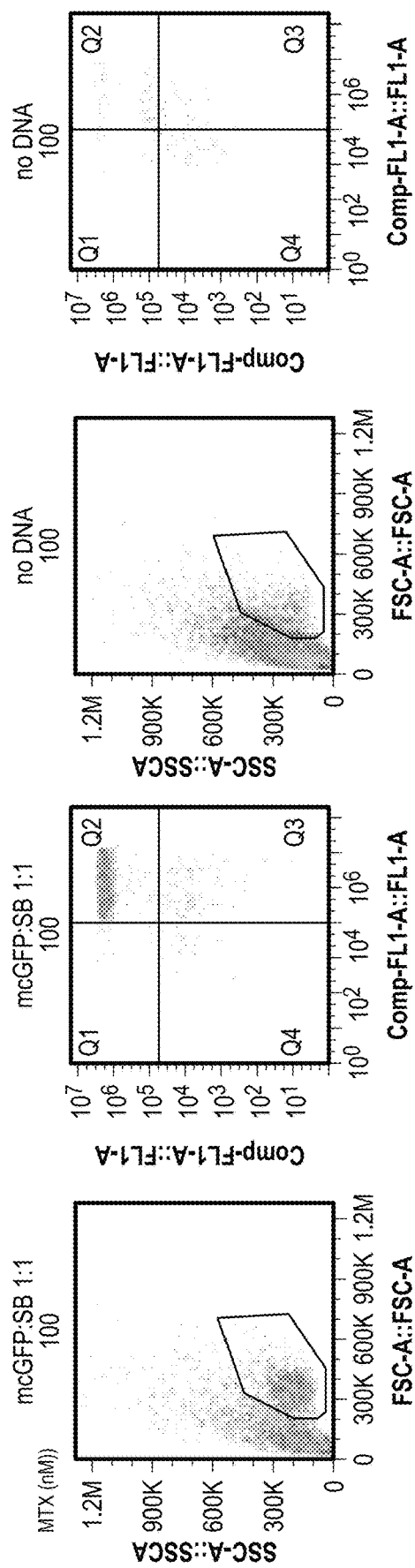
Figures 1, 13C:
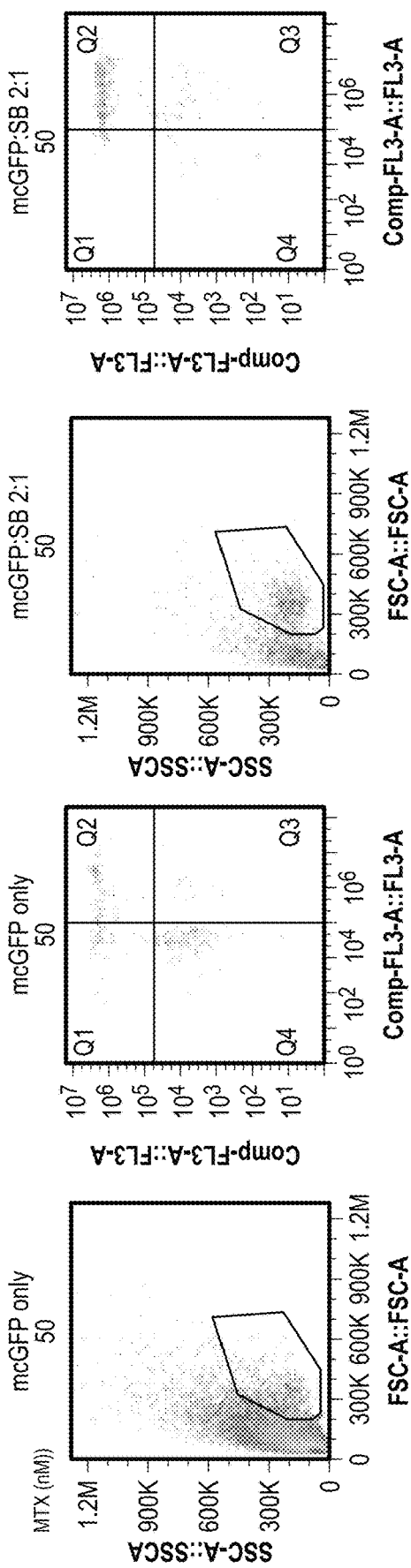
Figures 2, 13C:
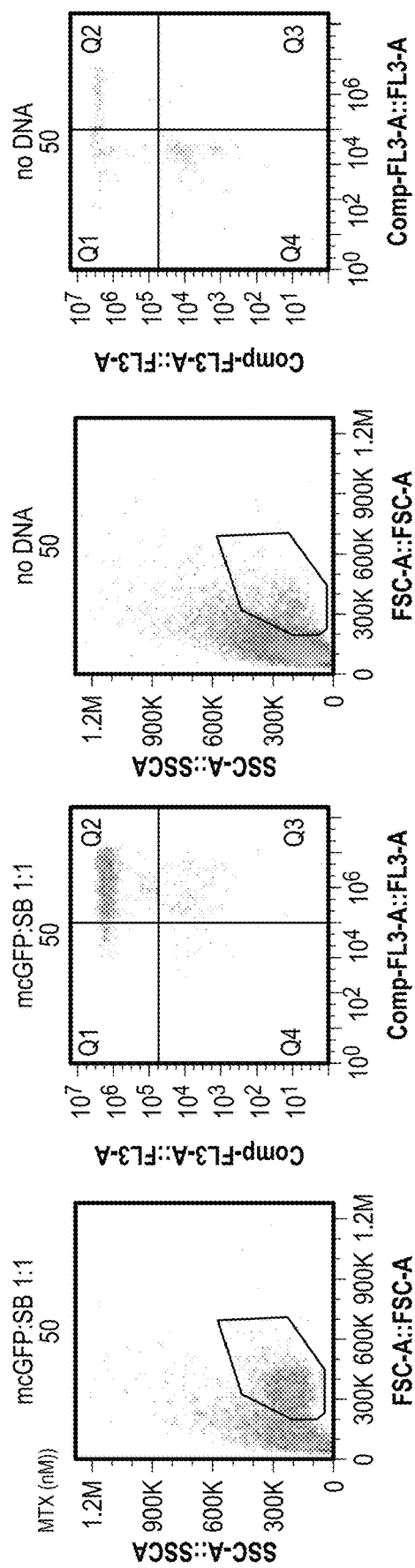
Figures 1, 13D:
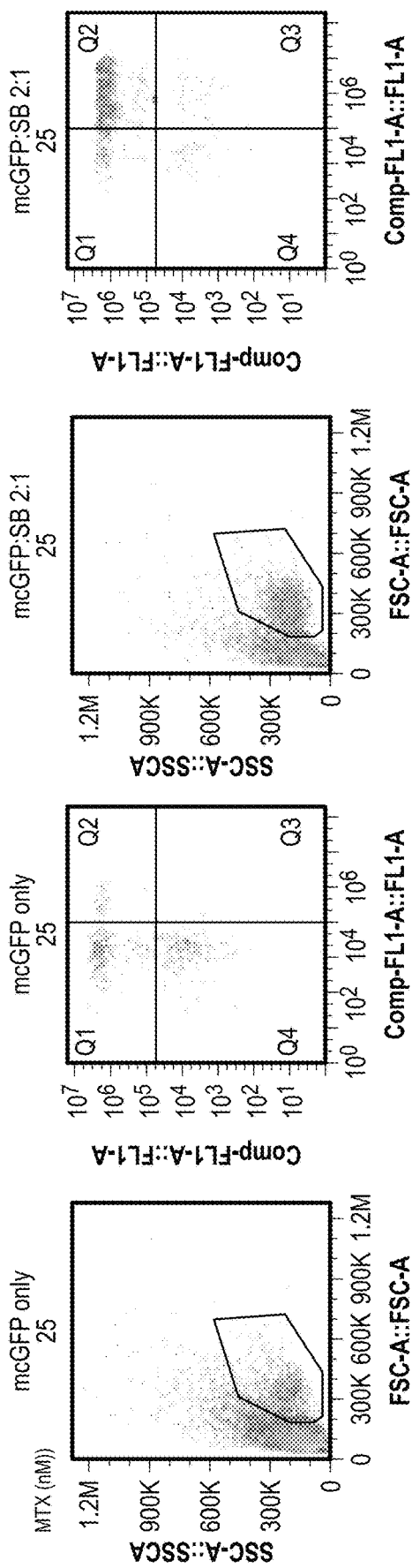
Figures 2, 13D:
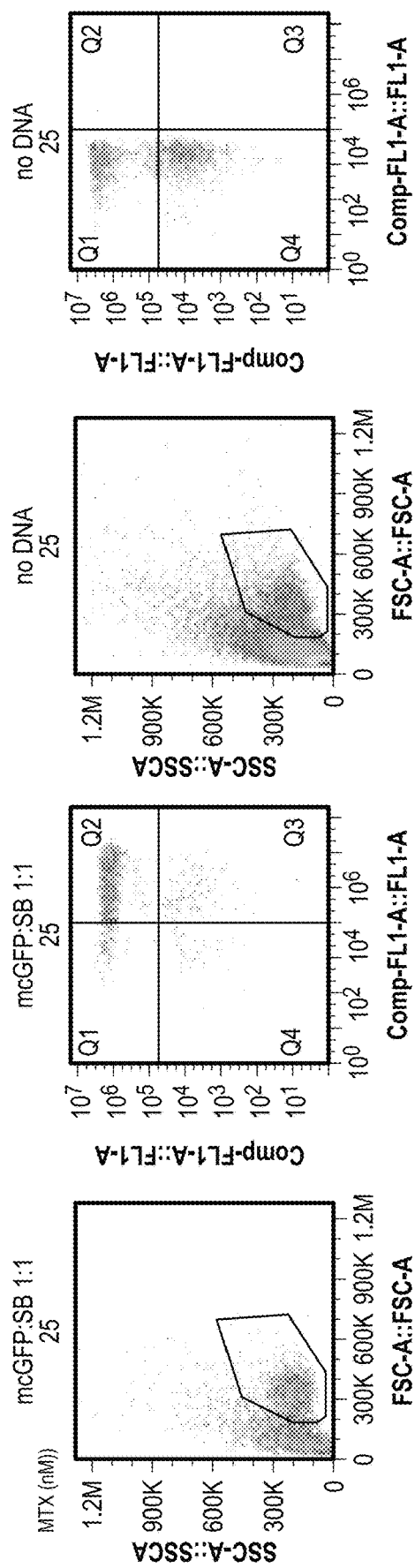
Figure 14A:
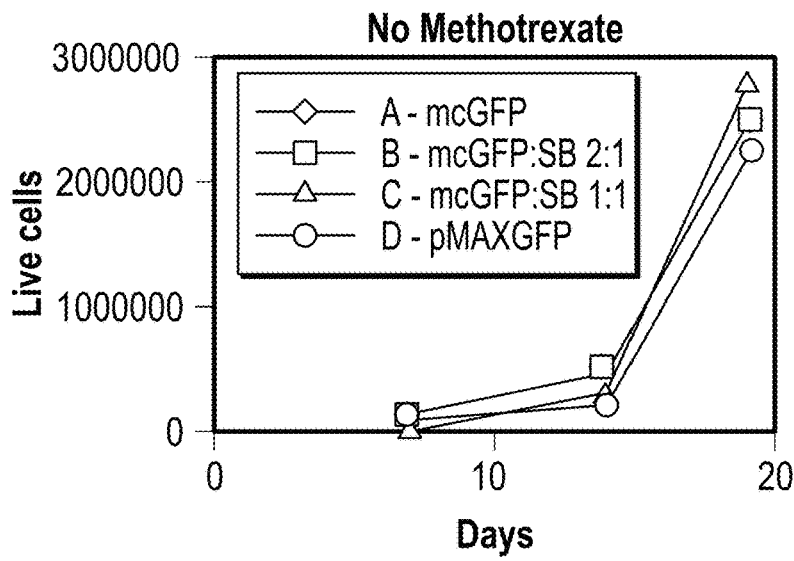
FIGS. 14A-14D show the live cell counts of cells that stably express transposon DNA and undergoes MTX selection. Trypan blue cell counts were taken at 7, 14, and 19 days post transfection. PBMC samples were transfected with no DNA (control), mcGFP alone, mcGFP and MC_SB100× DNA at a mcGFP:MC_SB100X ratio of 2:1 ratio, or mcGFP and MC_SB100×DNA at a mcGFP:MC_SB100X ratio of 1:1. The cells were selected on day 7 using 0 nM MTX (control), 25 nM MTX, 50 nM MTX, or 100 nM MTX.
Figure 14B:
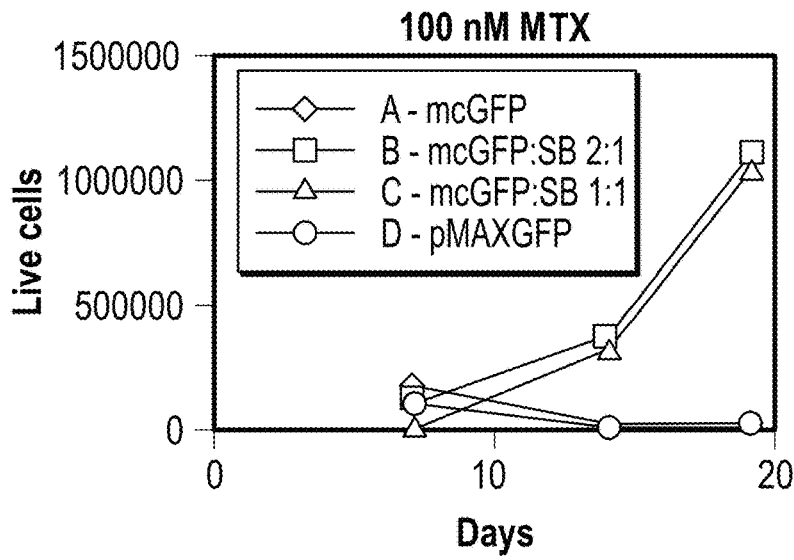
Figure 14C:
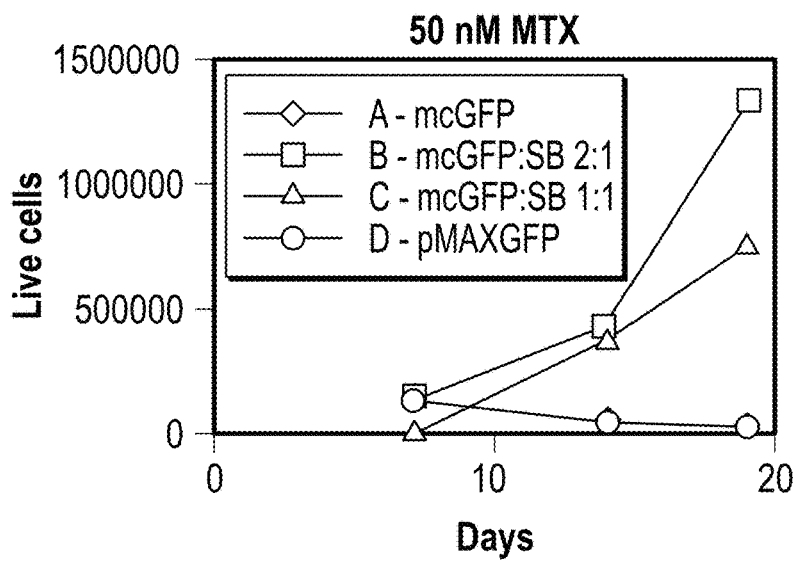
Figure 14D:
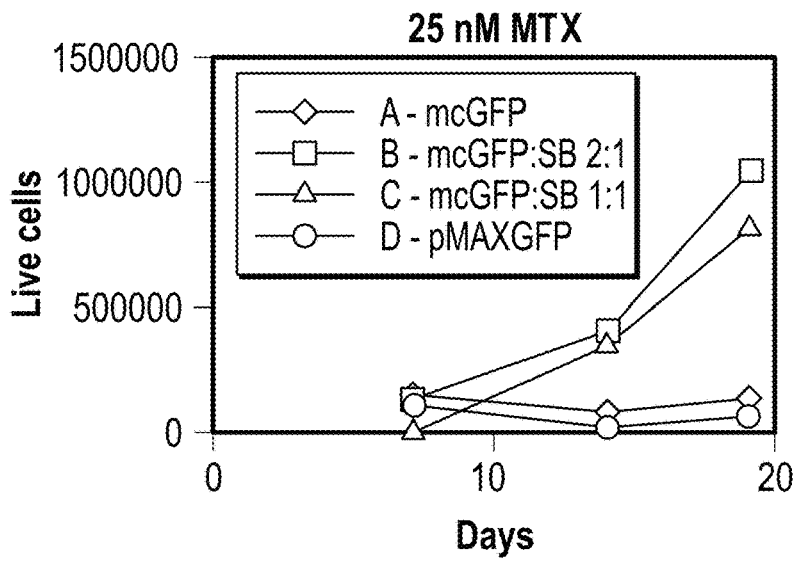
Figure 15A:
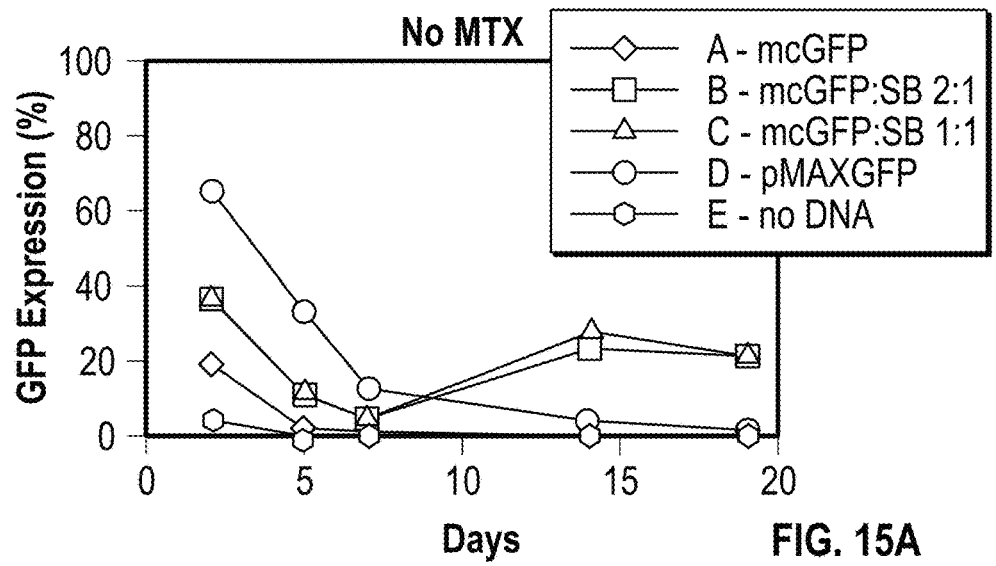
FIGS. 15A-15D show an analysis of GFP expression by lymphocytes stably expressing GFP transposon DNA with Sleeping Beauty transposase under MTX selection. PBMC samples were transfected with mcGFP alone, mcGFP and MC_SB100X at a mcGFP:MC_SB100X ratio of 2:1, mcGFP and MC_SB100X at a mcGFP:MC_SB100X ratio of 1:1, pMAXGFP (10 ug), and no DNA (control). Cells were exposed to MTX on day 7 after transfection, and GFP expression was measured for live, single lymphocytes.
Figure 15B:
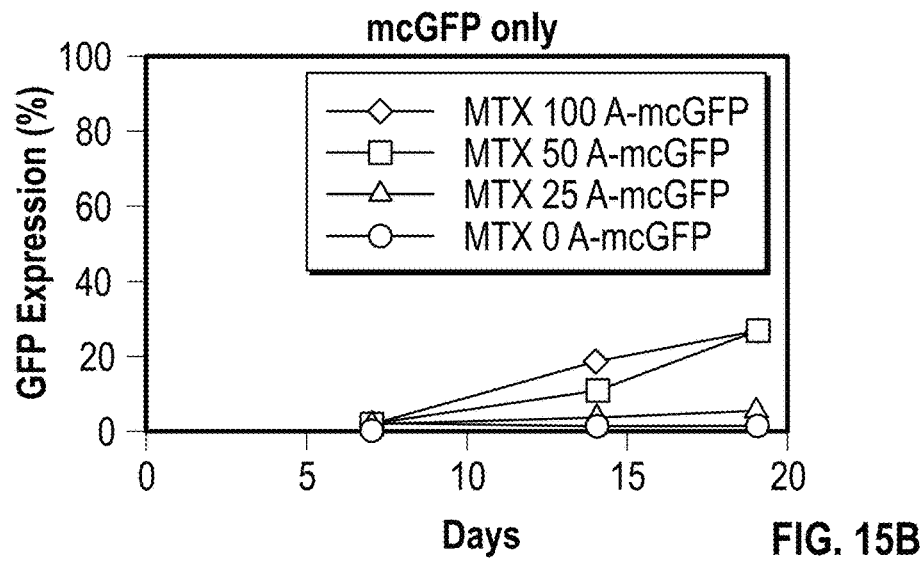
Figure 15C:
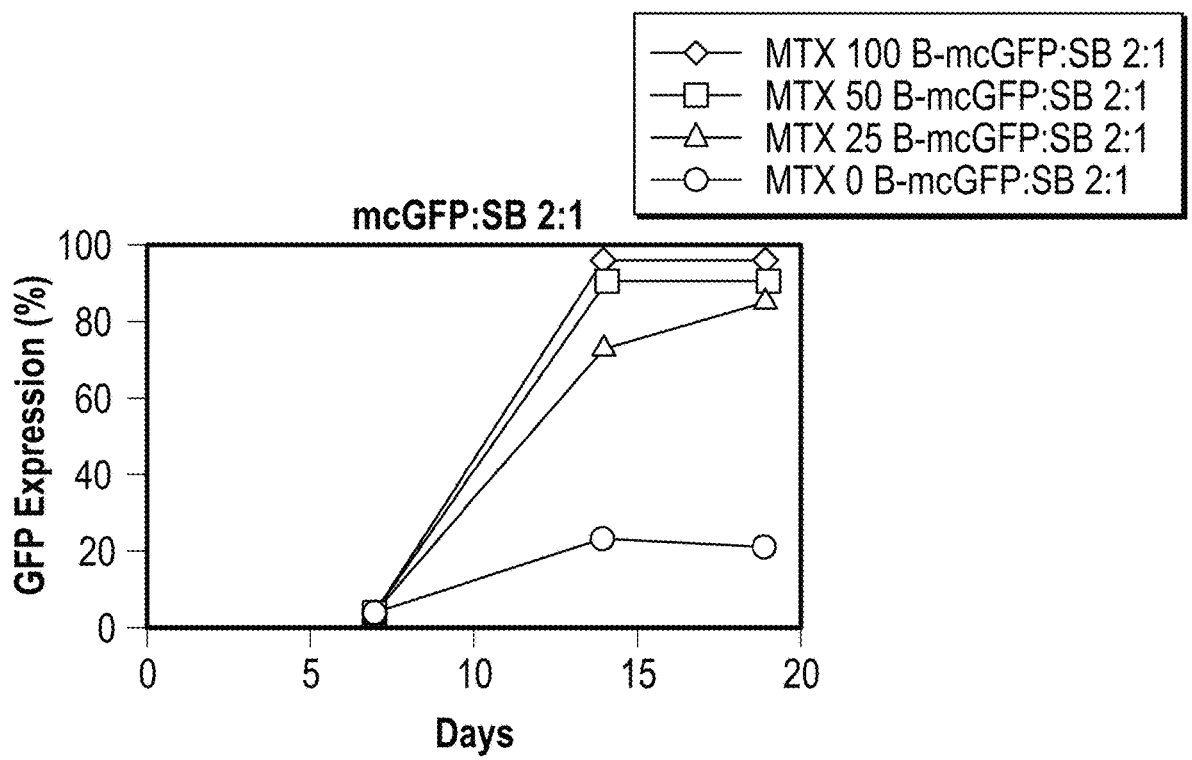
Figure 15D:
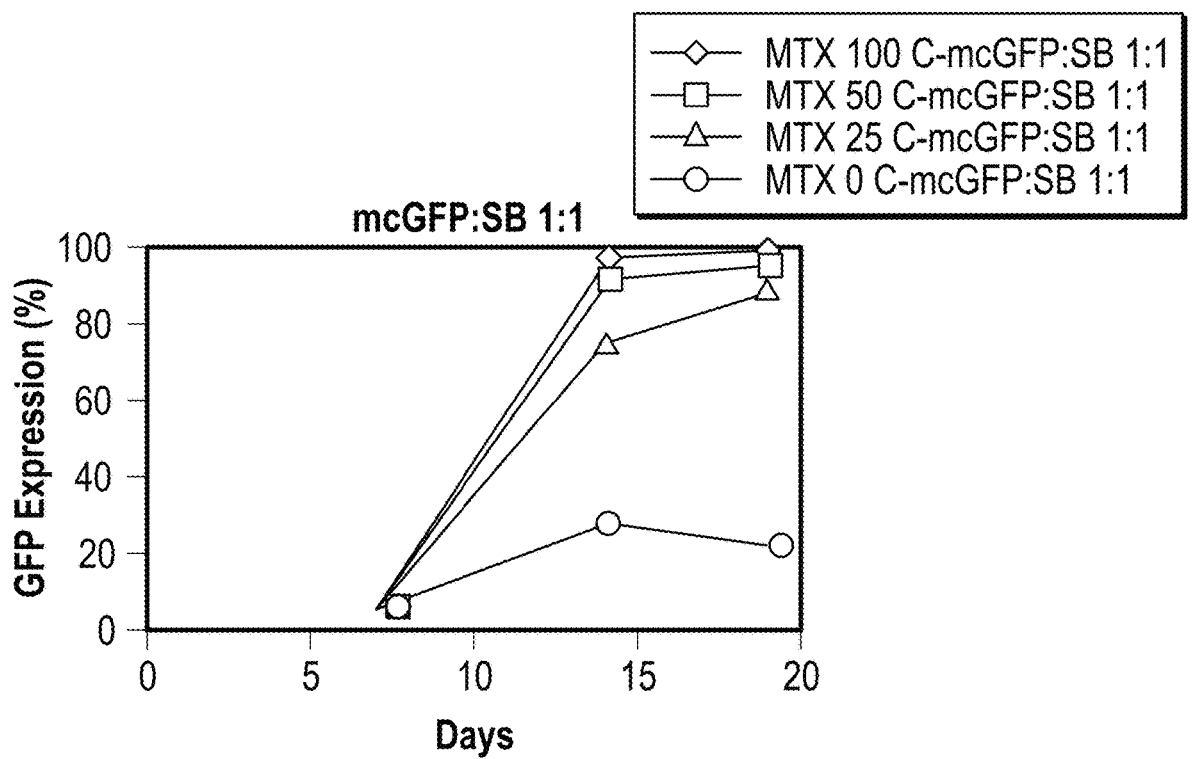
Figure 16:
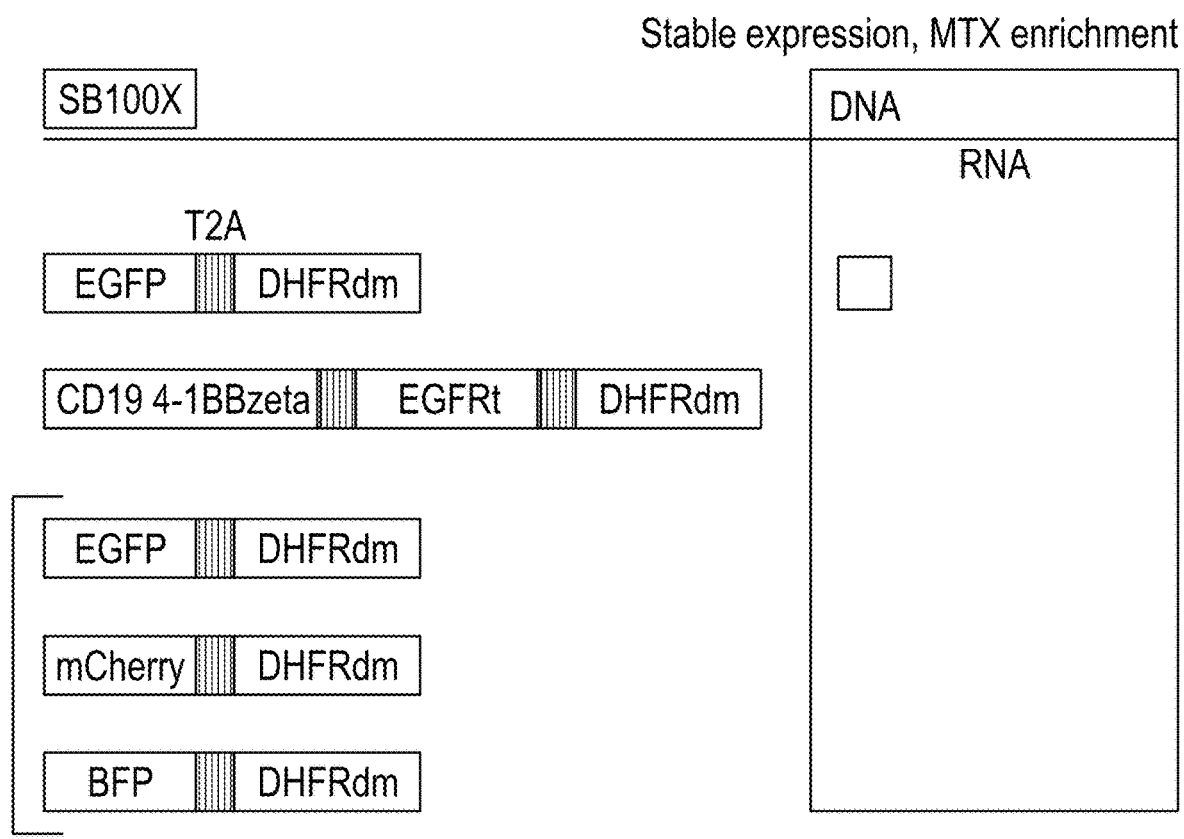
FIG. 16: Sleeping Beauty Transposons: minicircle constructs. As shown in the figure are the schematics of several sleeping beauty constructs designed for several alternatives described herein.
Figure 17A:
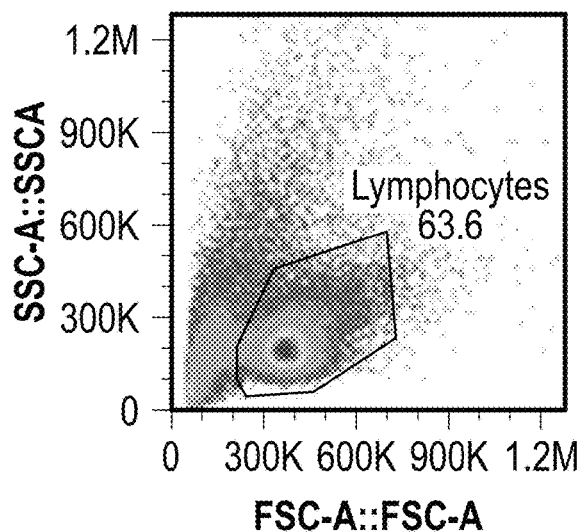
FIGS. 17A-17E relate to cells transfected with Sleeping Beauty transposons carrying a gene for expression of GFP.
Figure 17B:
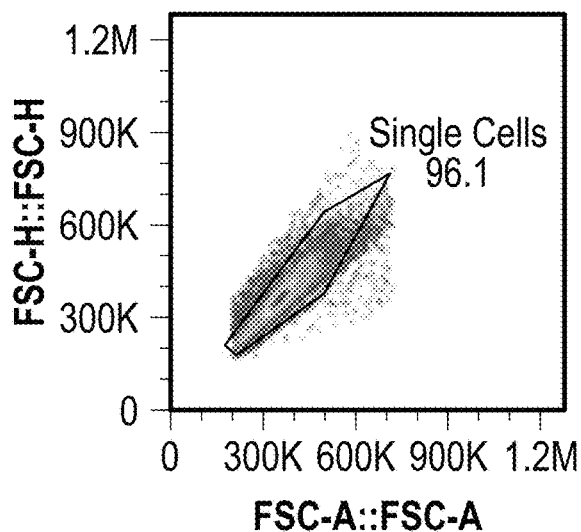
Figure 17C:
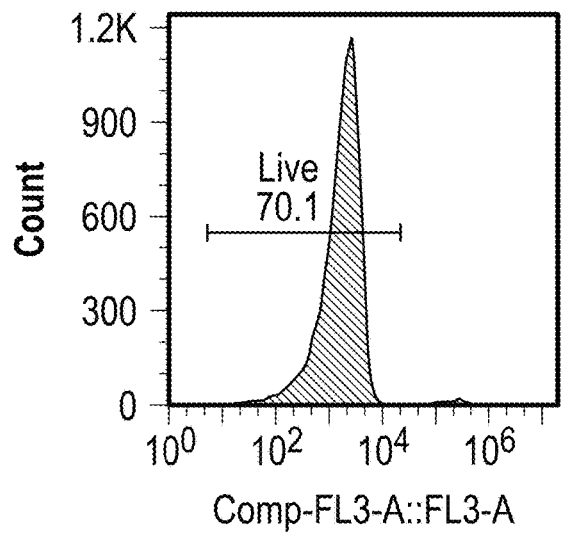
Figure 17D:
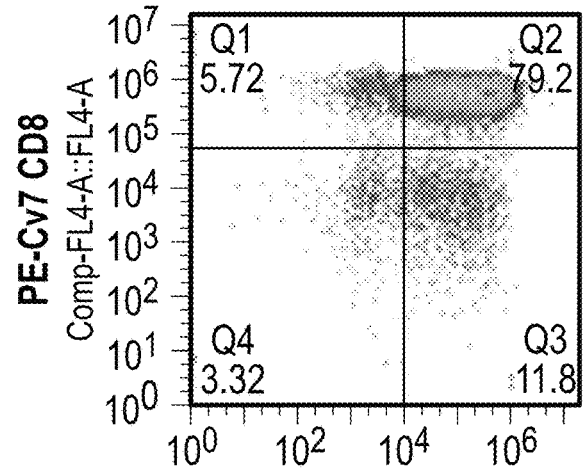
Figure 17E:
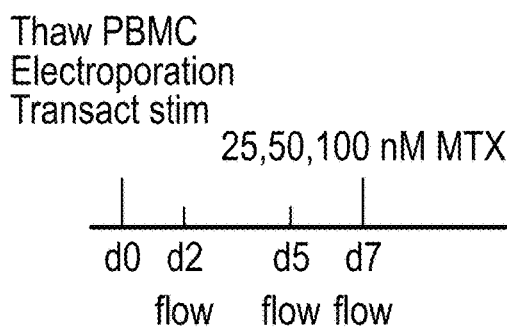
Figure 18A:
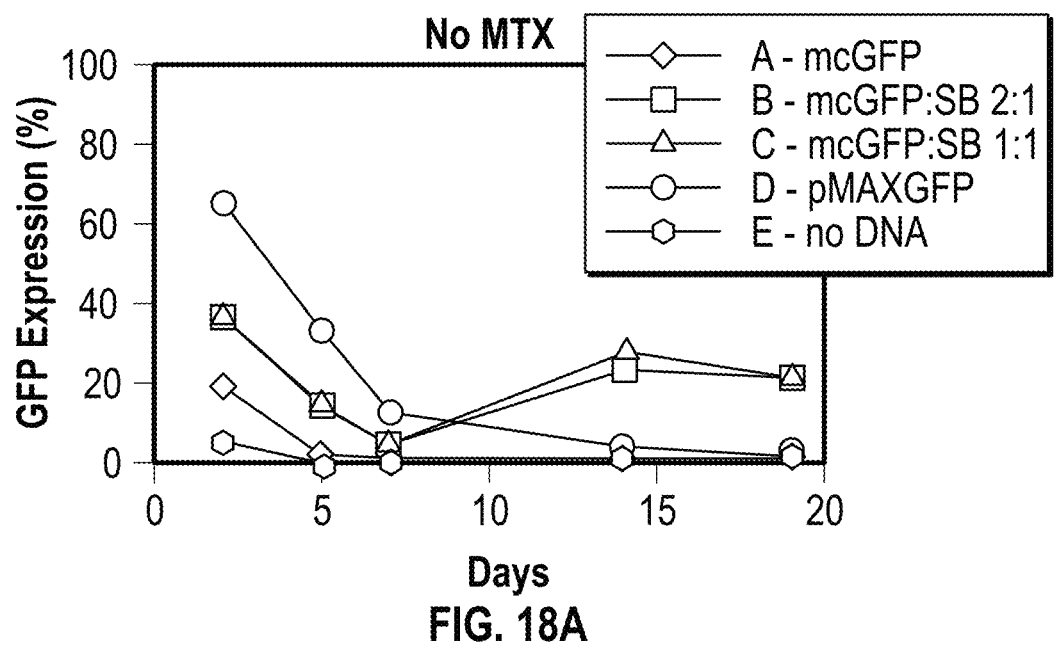
FIGS. 18A-18D are graphs relating to GFP expression Sleeping Beauty Transposons and MTX:GFP transposon. As shown, cells were transfected with different ratios of mcGFP plasmids and the Sleeping Beauty transposon carrying a gene for expression of GFP (McGFP:SB at a 1:1 and 2:1 ratio). As shown, GFP expression was low with no MTX was added after 18 days. With the Sleeping Beauty transposon, it is shown that there is an increase in GFP expression in the presence of MTX.
Figure 18B:
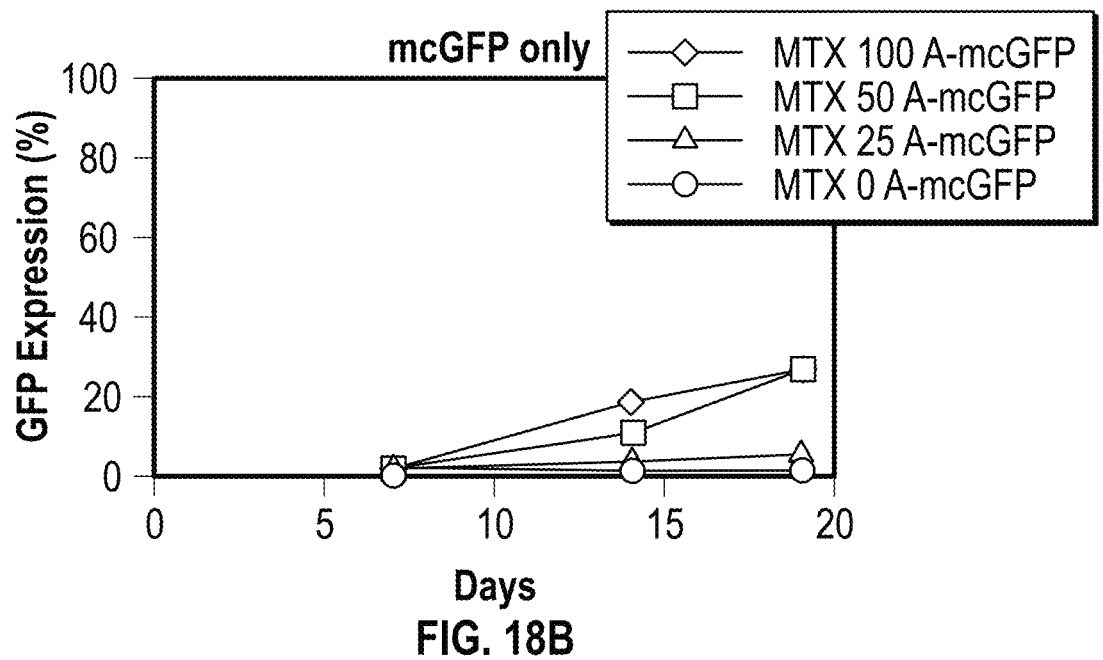
Figure 18C:
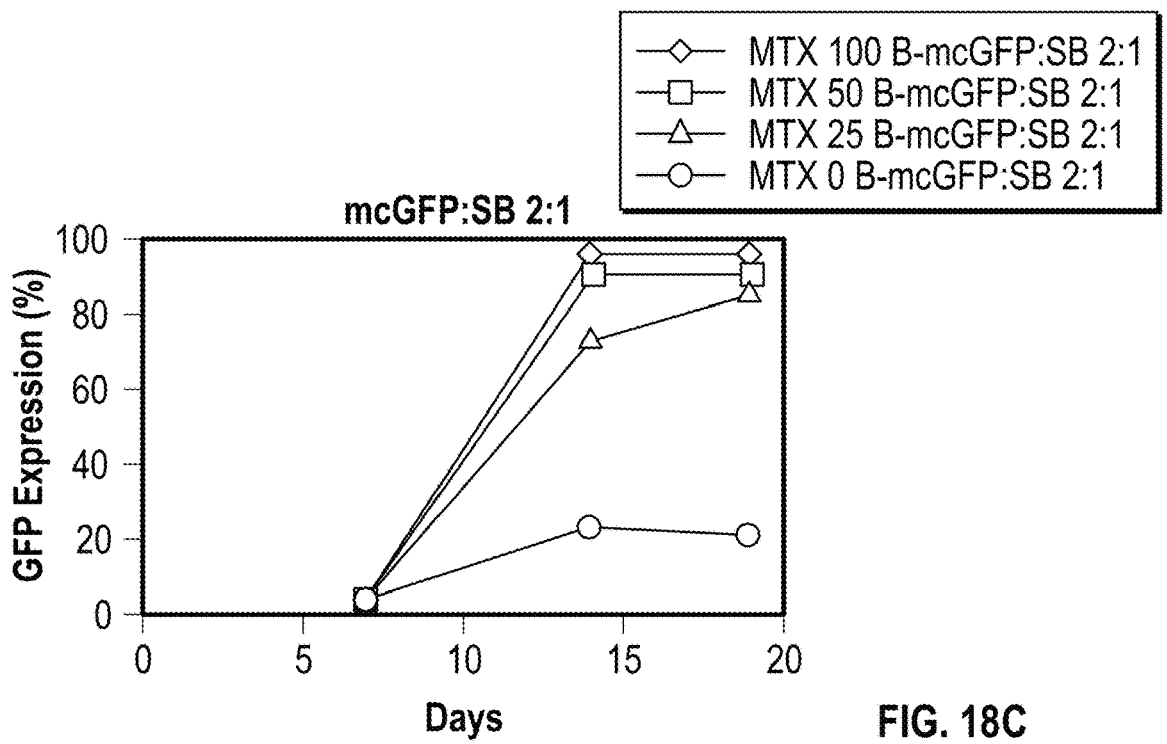
Figure 18D:
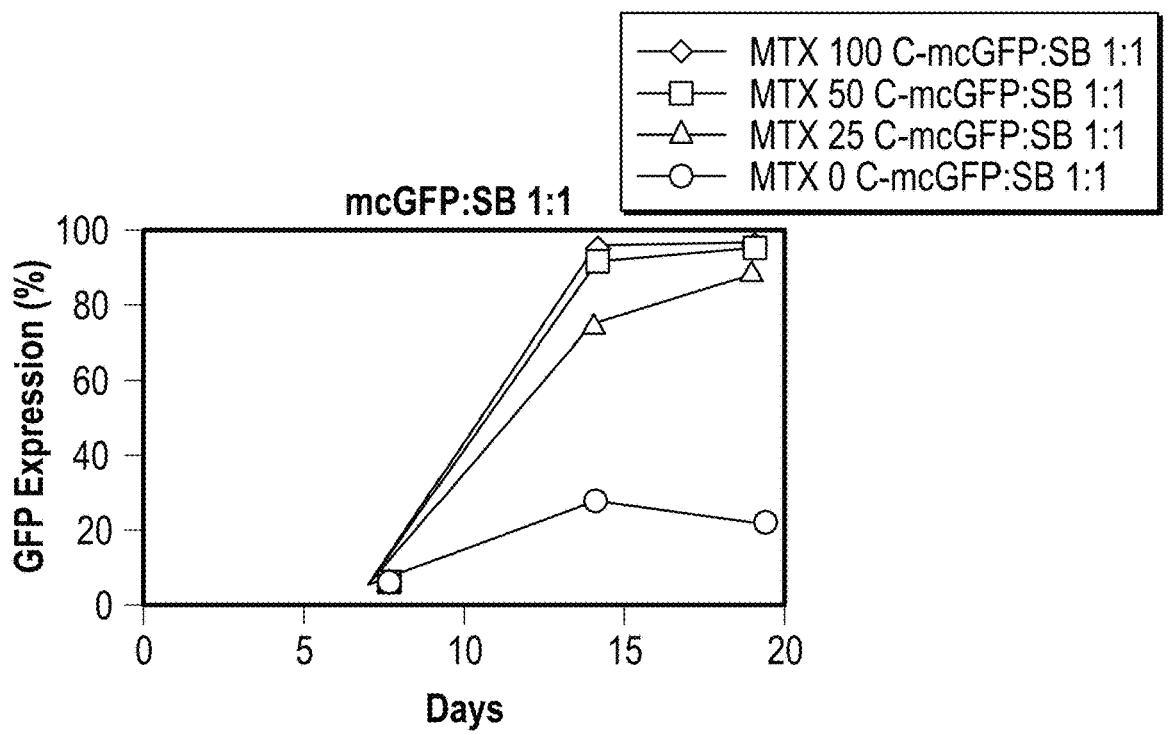
Figure 19:
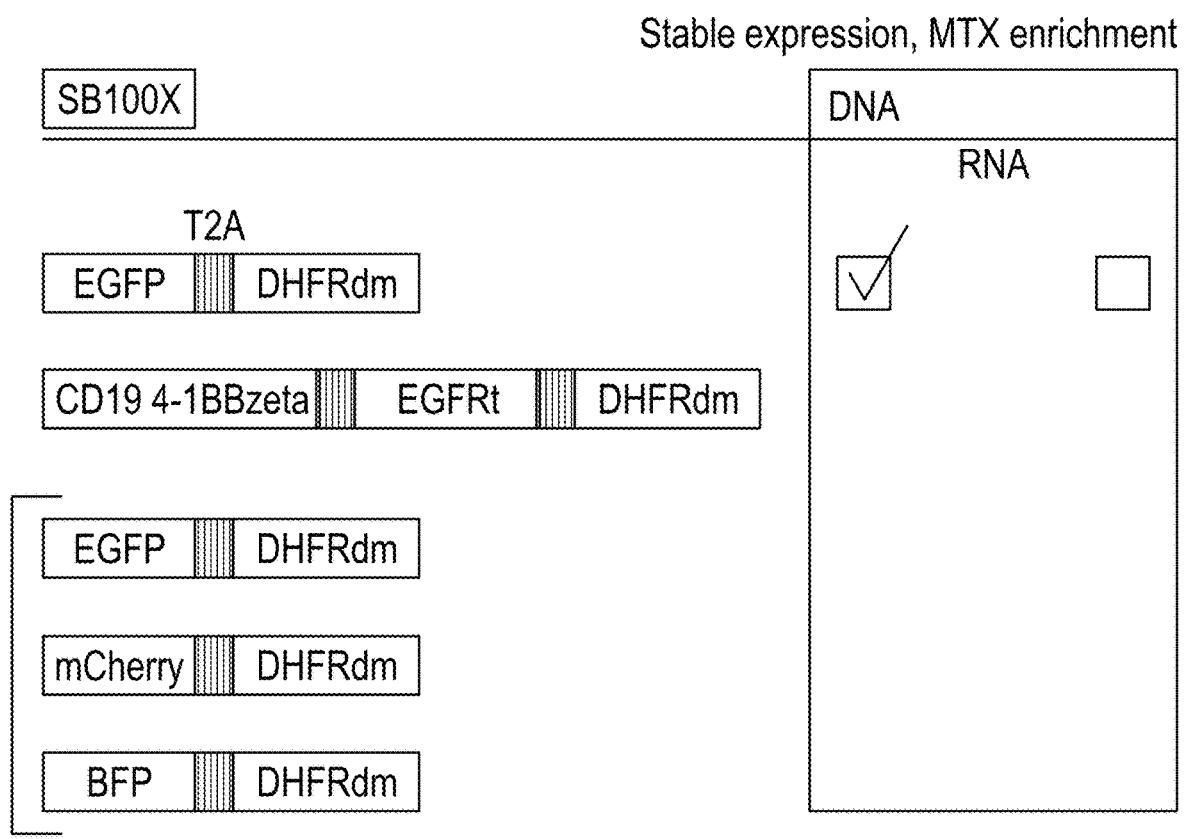
FIG. 19. Sleeping Beauty Transposons: minicircle constructs. As shown in the figure are the schematics of several sleeping beauty constructs designed for several alternatives described herein.
Figure 20A:
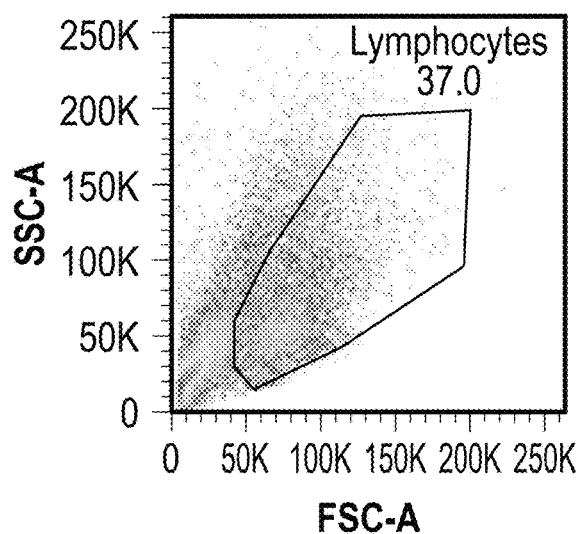
FIGS. 20A-20E relate to Sleeping Beauty Transposons and MTX:GFP transposon—SB100×DNA and RNA. Cells were electroporated with SB100X (DNA or RNA) or transposons carrying genes for GFP, CARS, or GFP/mCherry/ BFP.
Figure 20B:
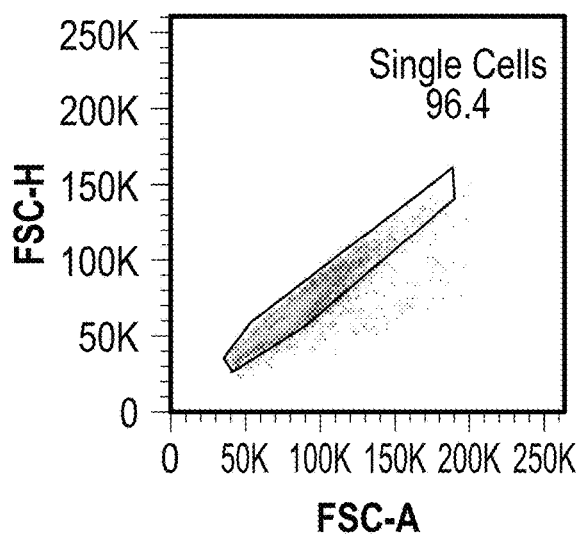
Figure 20C:
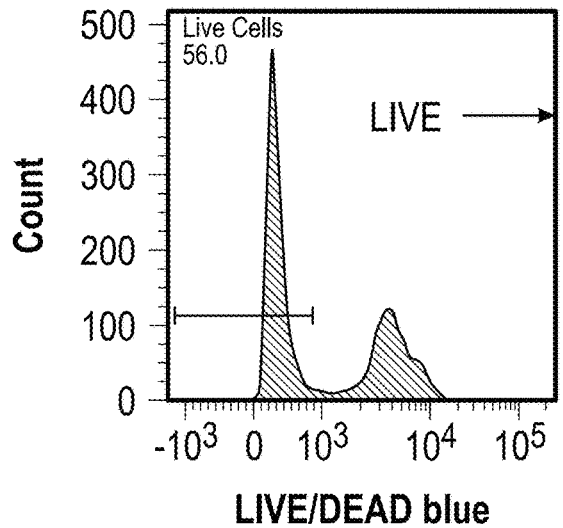
Figure 20D:
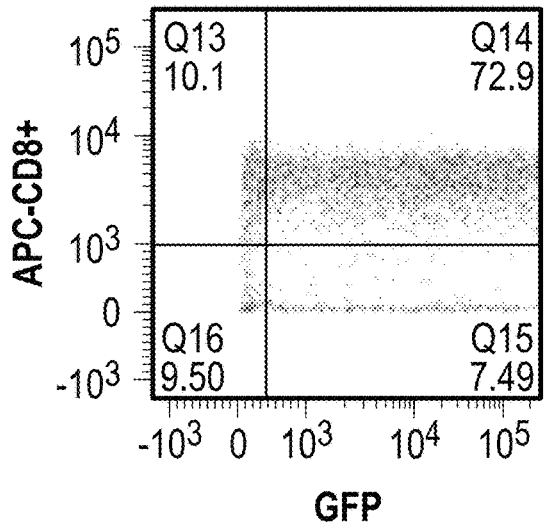
Figure 20E:
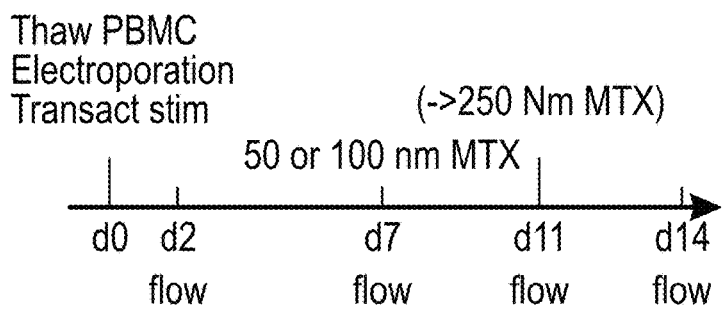
Figure 21A:
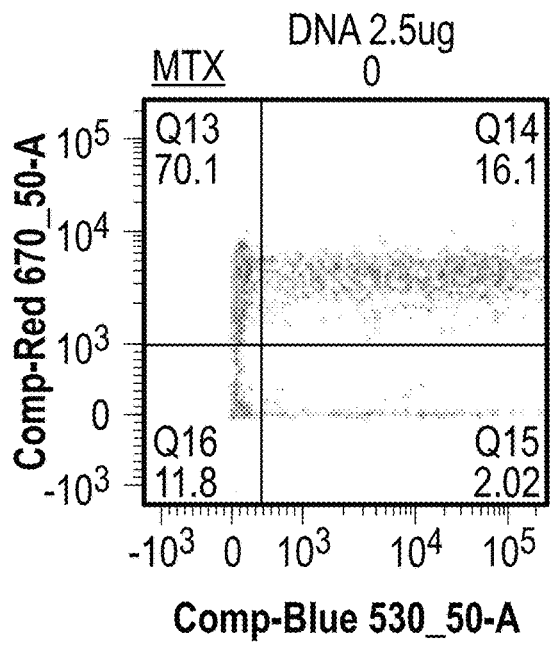
FIGS. 21A-21L are scattergrams relating to Sleeping Beauty Transposons and MTX:GFP transposon—SB100× DNA and RNA. As shown in the figure are several scattergrams of the cells that are transfected with GFP gene carrying transposons. Several samples of cells are transfected with DNA comprising a gene for GFP expression (2.5 ug and 5 ug), mcGFP only, and RNA (1 ug and 3 ug). The samples are split and grown under the influence of varying concentrations of MTX at 0 uM, 50 uM and 100 uM.
Figure 21B:
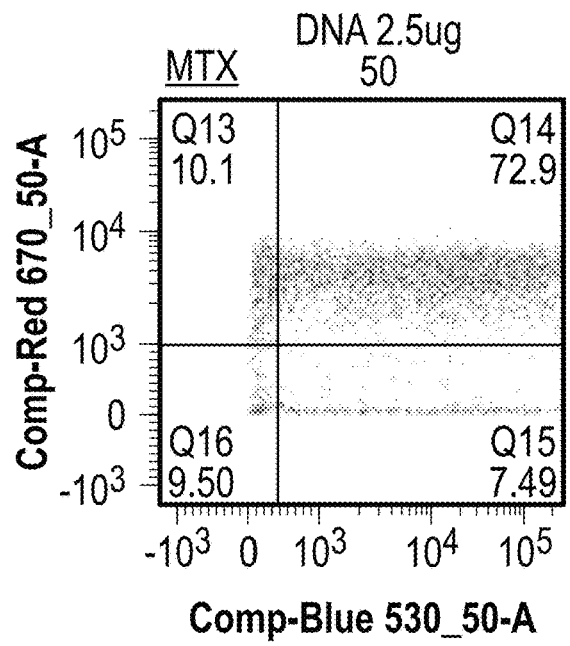
Figure 21C:
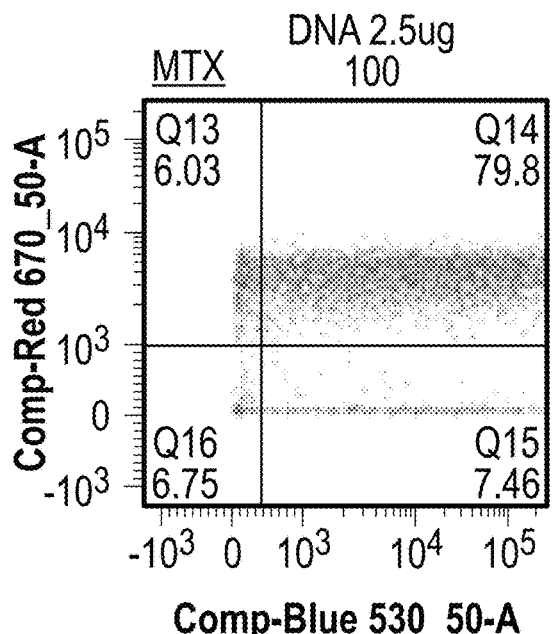
Figure 21D:
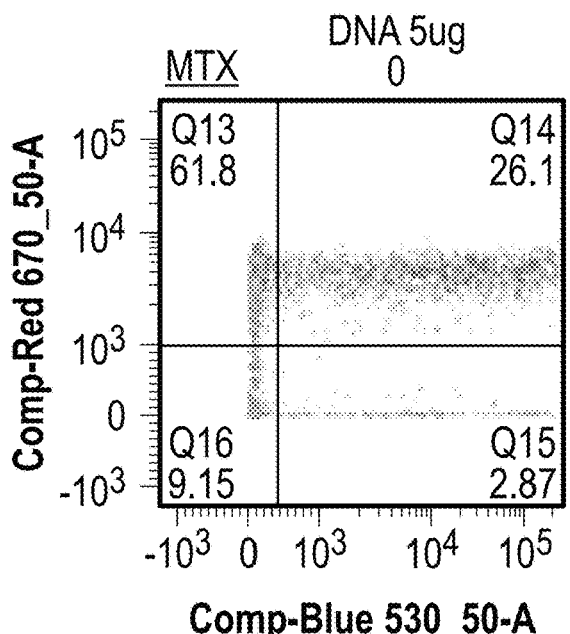
Figure 21E:
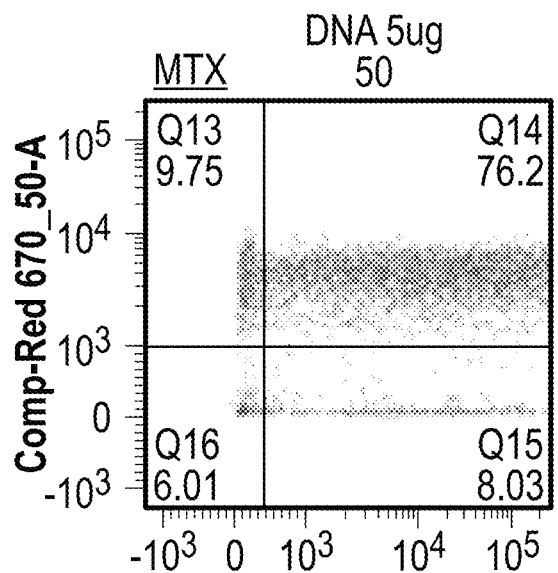
Figure 21F:
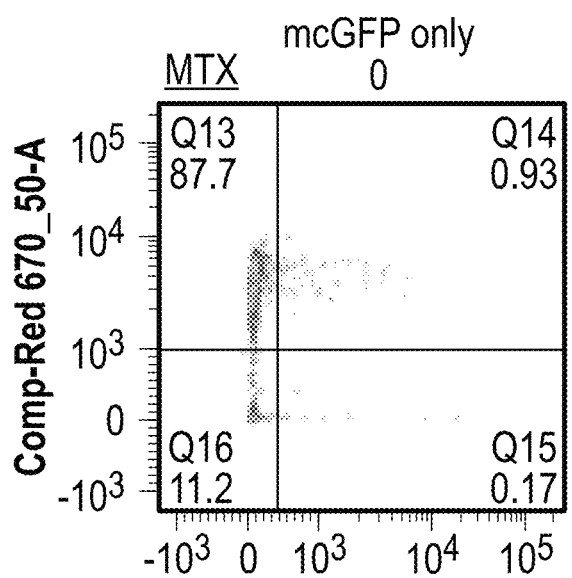
Figure 21G:
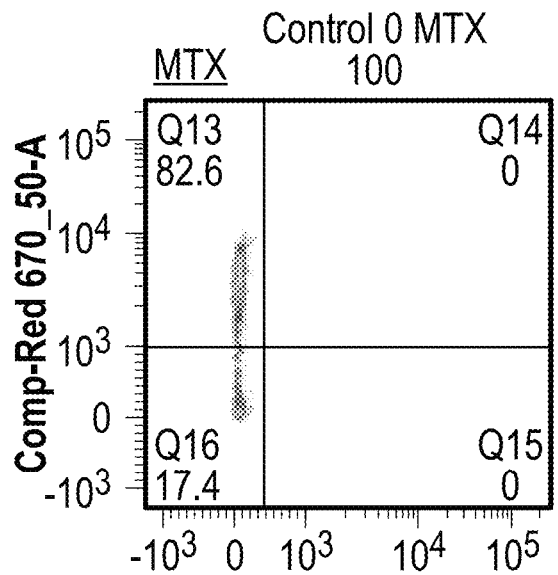
Figure 21H:
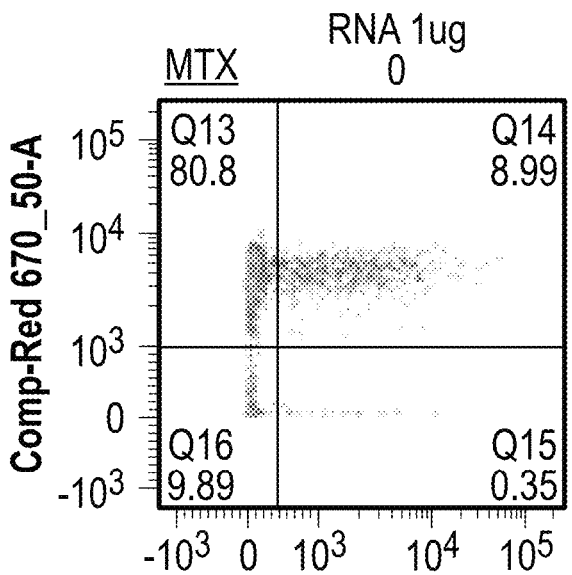
Figure 21I:
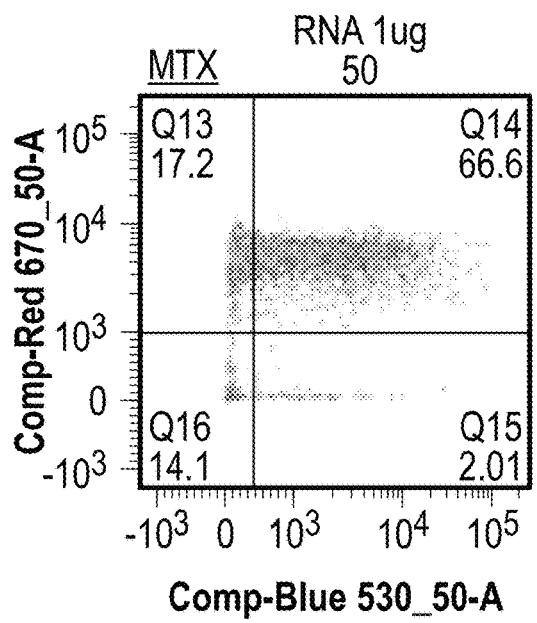
Figure 21J:
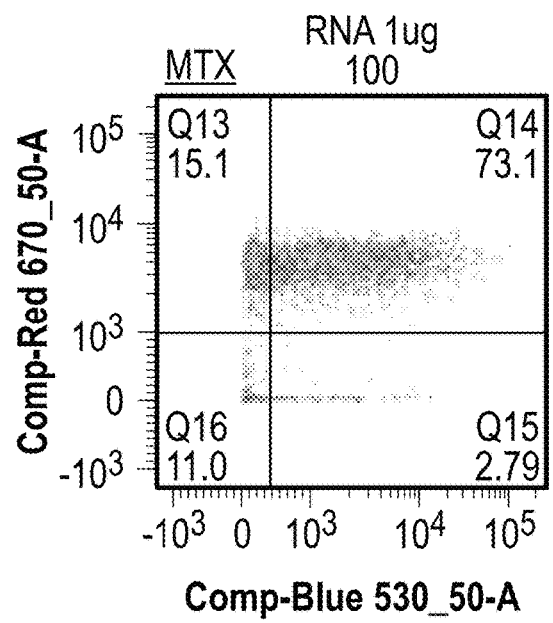
Figure 21K:
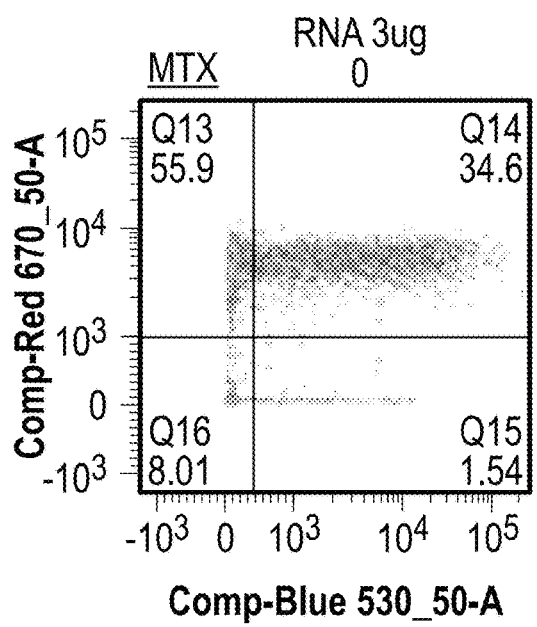
Figure 21L:
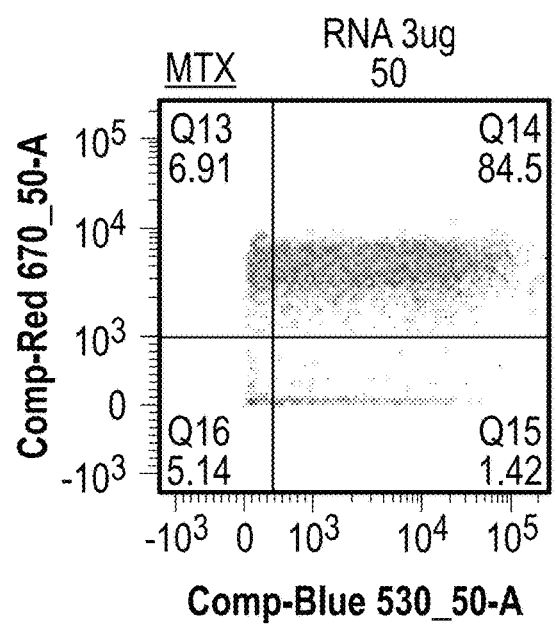
Figure 22A:
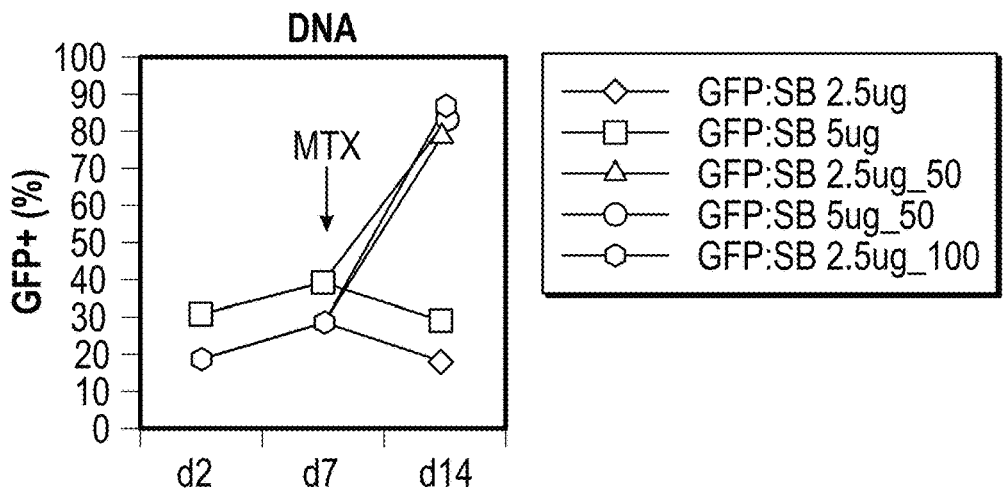
FIGS. 22A-22C relate to Sleeping Beauty Transposons and MTX:GFP transposon—SB100×DNA and RNA. Cells were transfected with Sleeping Beauty transposons carrying a gene for GFP expression at different concentrations as seen in the top left panel. MTX was then added at day 7 after transfection. As shown, cells transfected with 50 ug to 100 ug can express GFP after day 7 to day 14.
Figure 22B:
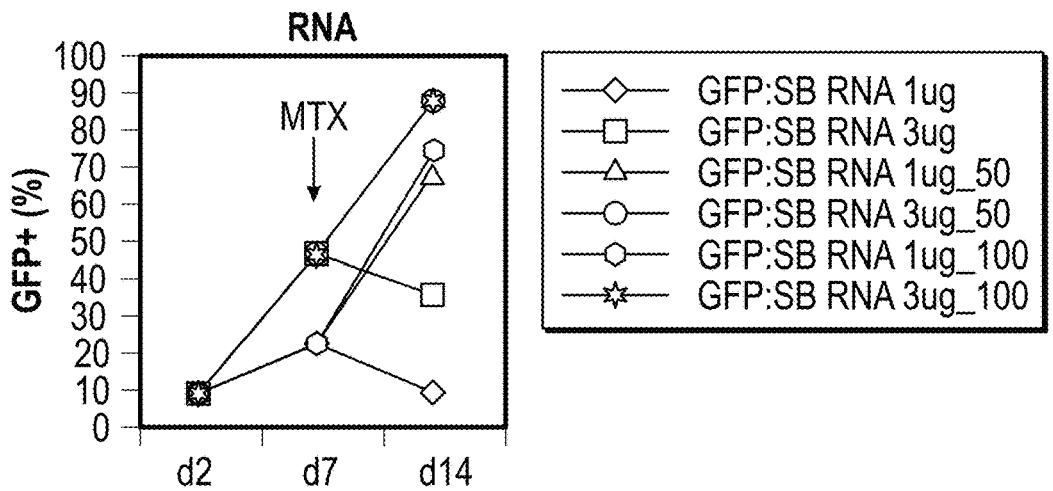
Figure 22C:
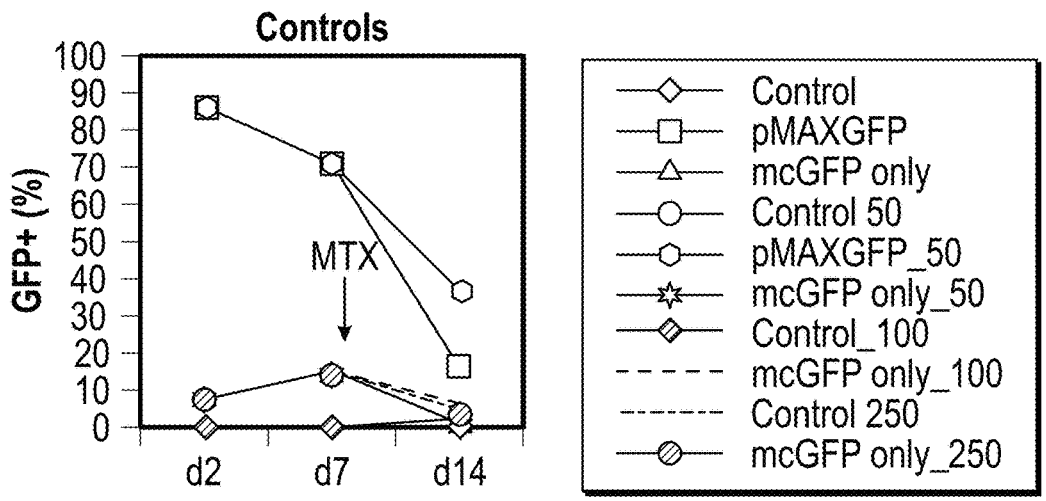
Figure 23A:
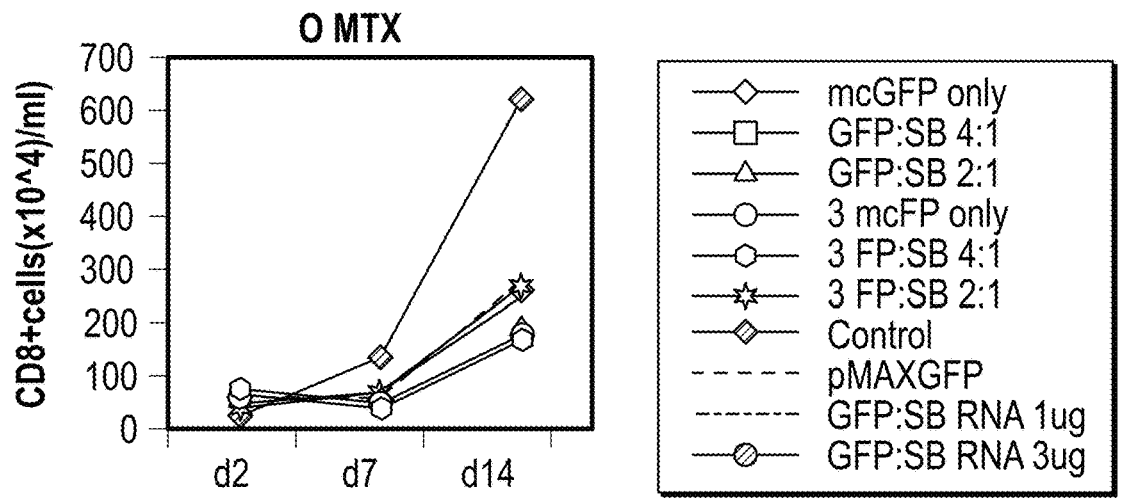
FIGS. 23A-23D relates to GFP expressing DNA and RNA in the presence of MTX. As shown cells transfected with mcGFP, GFP:SB, and GFP:SB RNA were grown and exposed to MTX seven days after transfection. As a control, cells were grown to fourteen days without exposure to MTX (FIG. 23A).
Figure 23B:
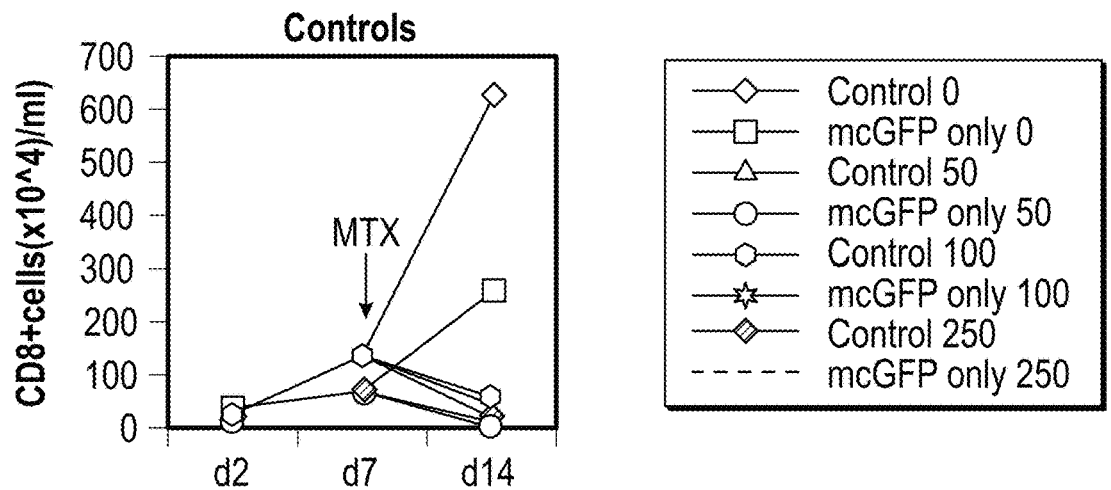
Figure 23C:
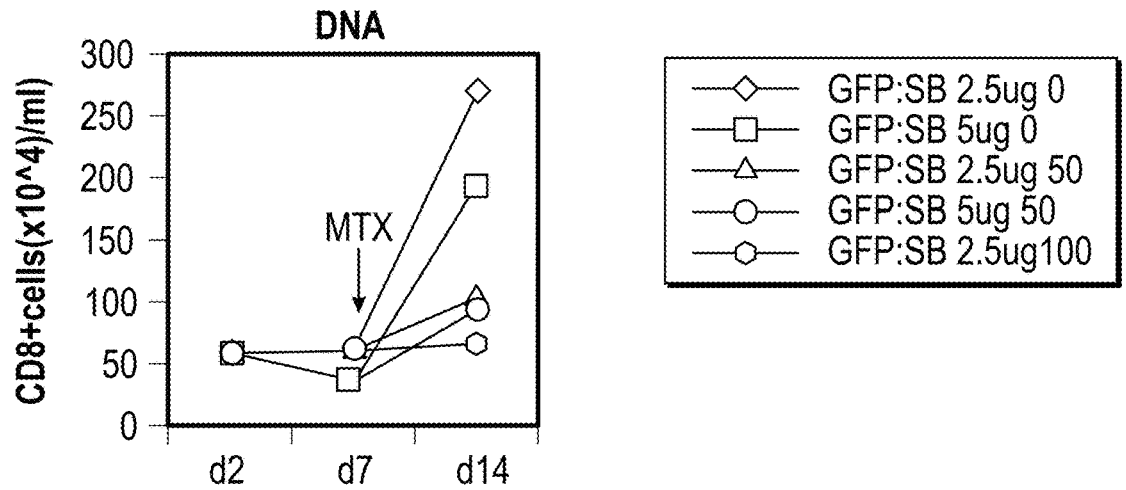
Figure 23D:
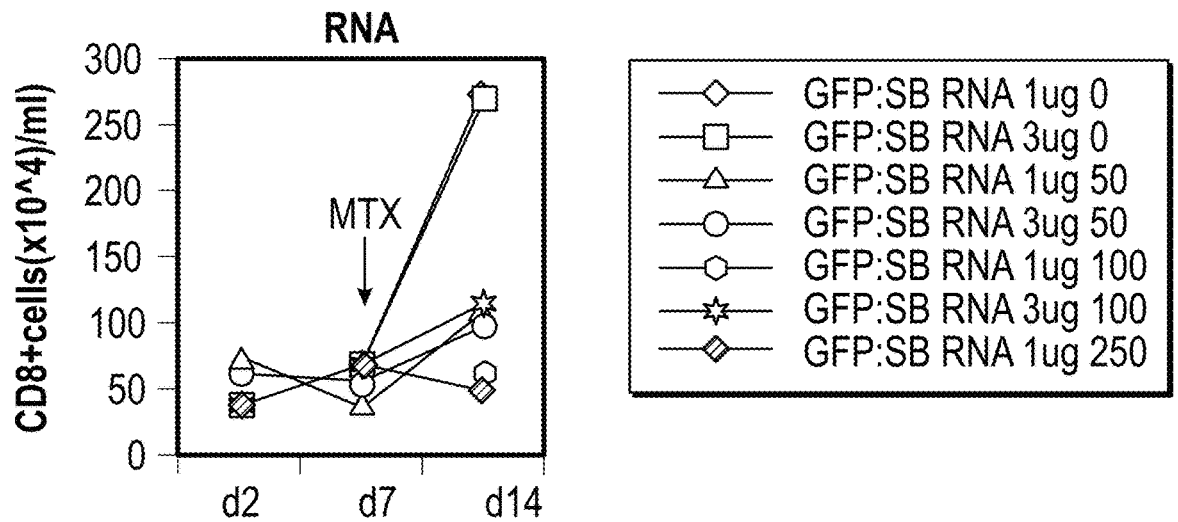
Figure 24A:
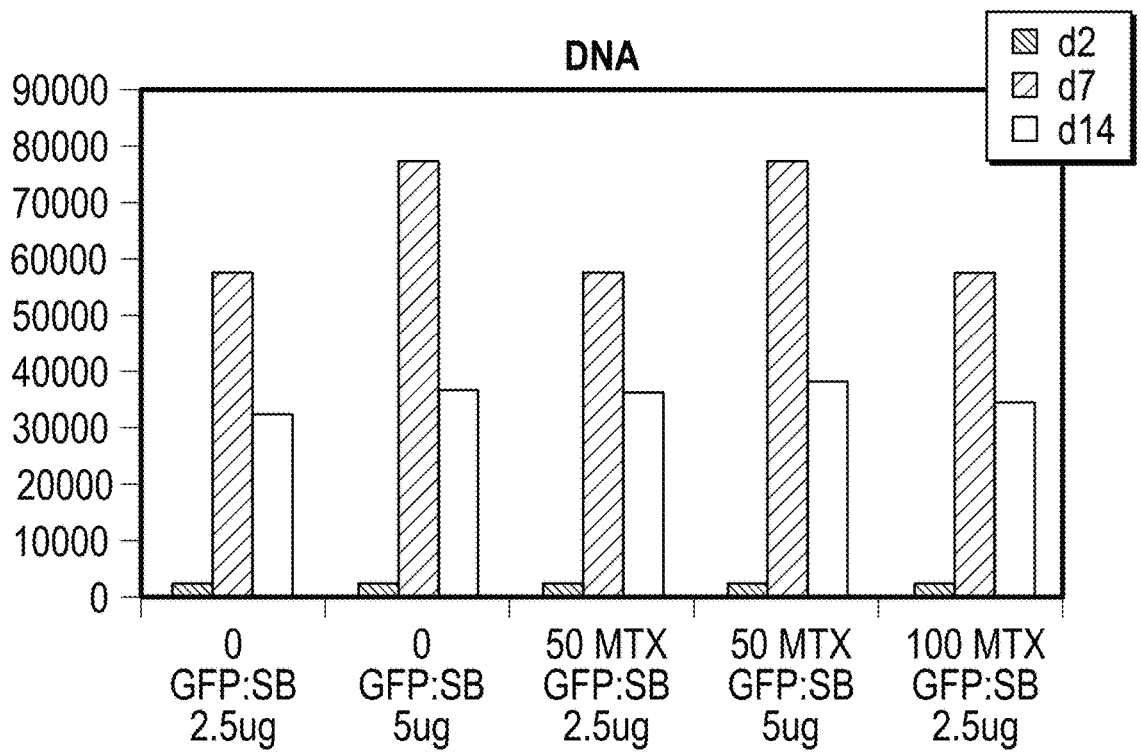
FIGS. 24A-24B relate to expression of GFP in cells transfected with GFP:SB.
Figure 24B:
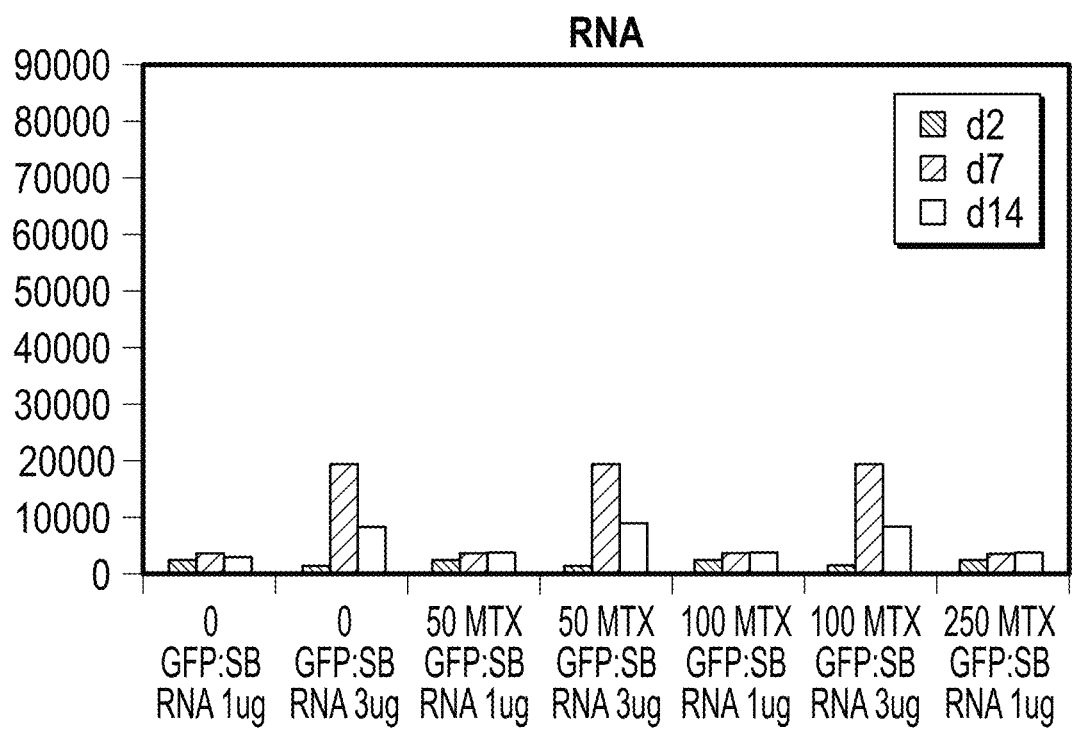
Figure 25:
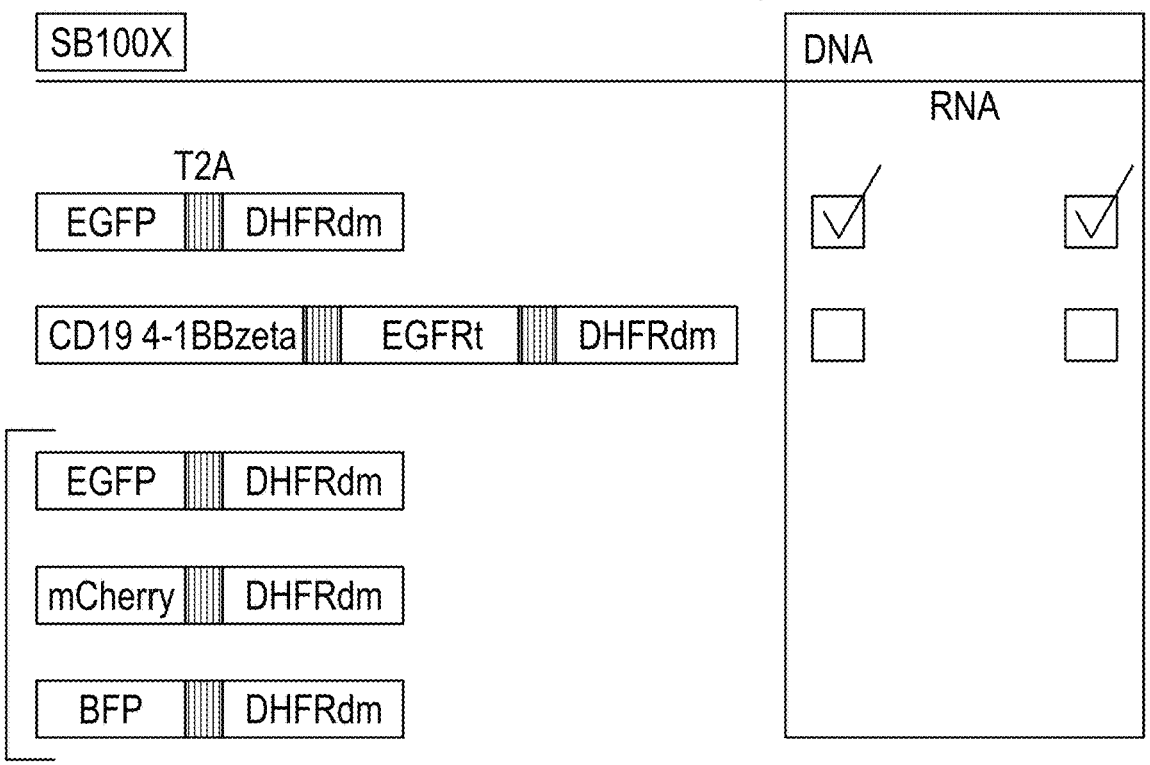
FIG. 25. Sleeping Beauty Transposons: minicircle constructs. As shown in the figure are the schematics of several sleeping beauty constructs designed for several alternatives described herein.
Figure 26A:
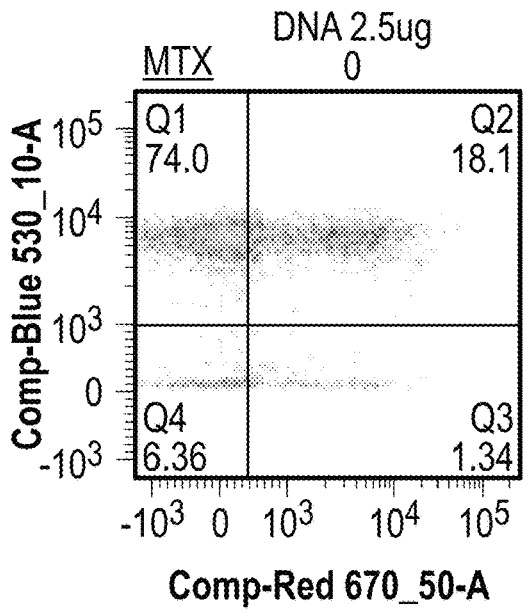
FIGS. 26A-26J relate to expression of CD19CAR. A Sleeping Beauty construct carrying a gene for CD19CAR was constructed (SB:CD19CAR). Cells were transfected with either DNA (2.5 ug or 5 ug), or RNA (1 ug or 3 ug). As shown, cells that were transfected with DNA or RNA at both concentrations were able to express the CD19CAR in the presence of 50 uM MTX. This was also shown for cells that were transfected with the RNA at 1 ug in the presence of 100 uM MTX.
Figure 26B:
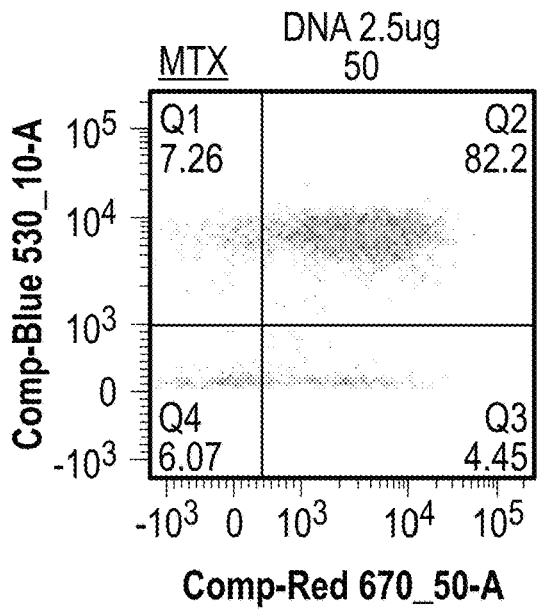
Figure 26C:
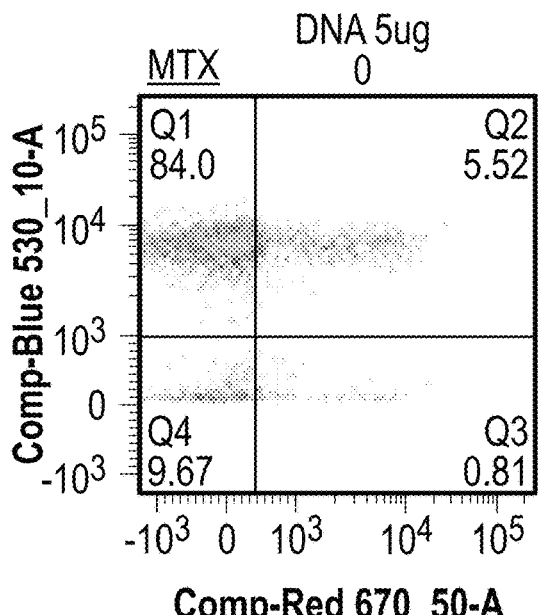
Figure 26D:
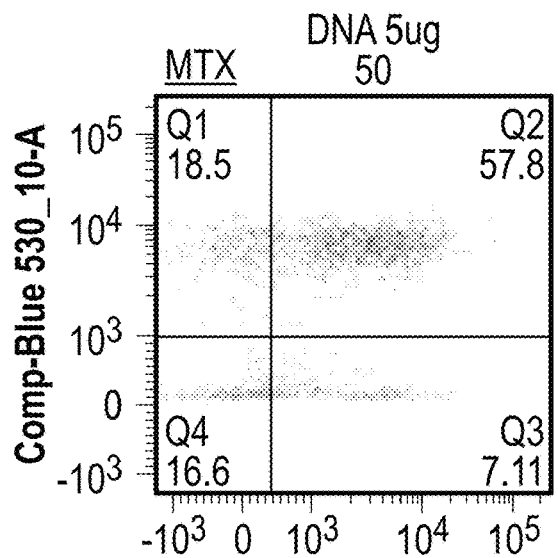
Figure 26E:
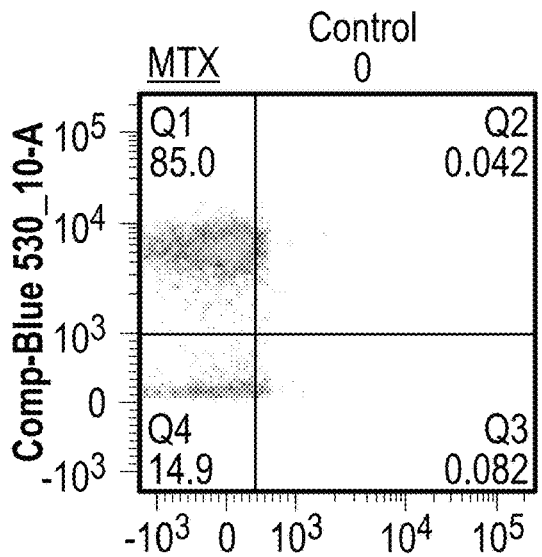
Figure 26F:
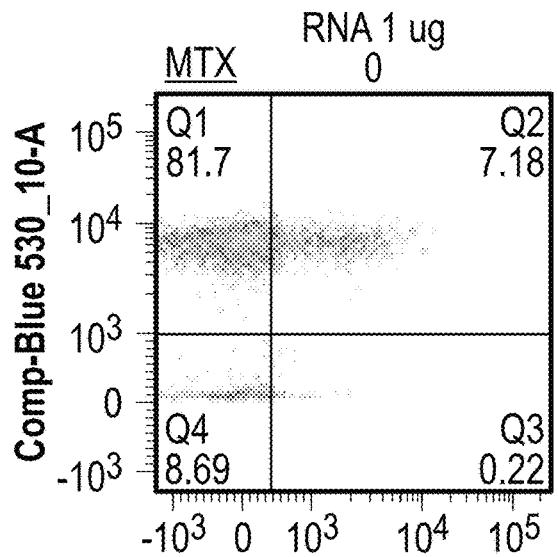
Figure 26G:
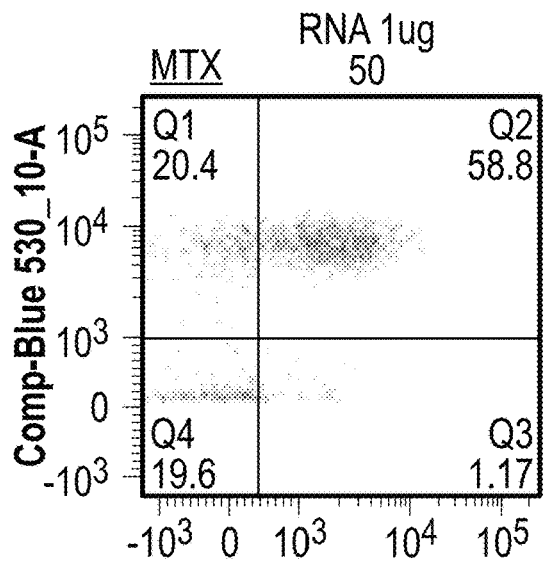
Figure 26H:
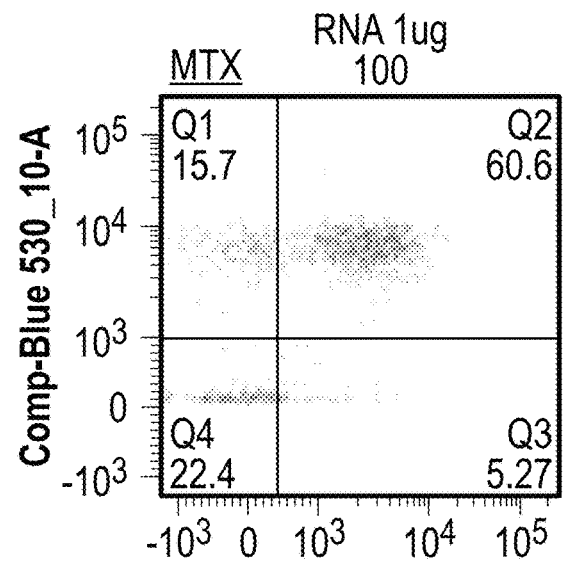
Figure 26I:
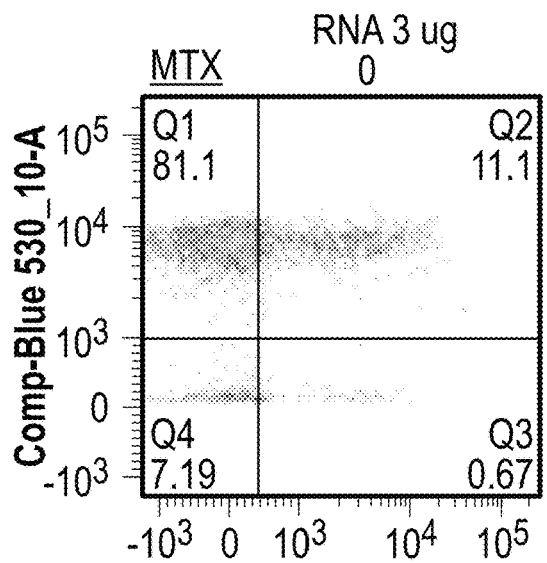
Figure 26J:
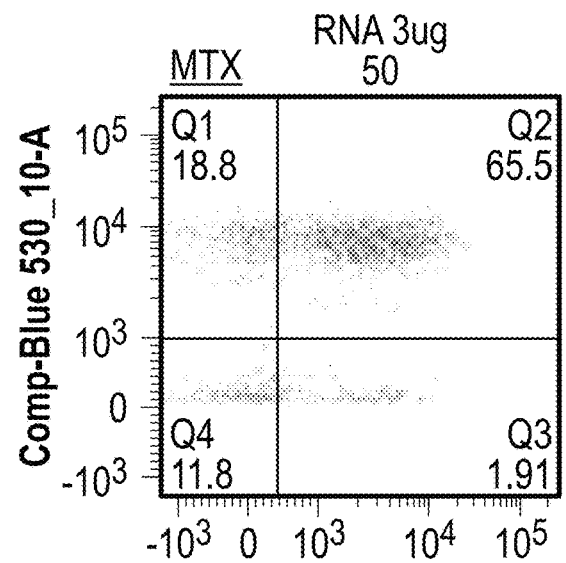
Figure 27A:
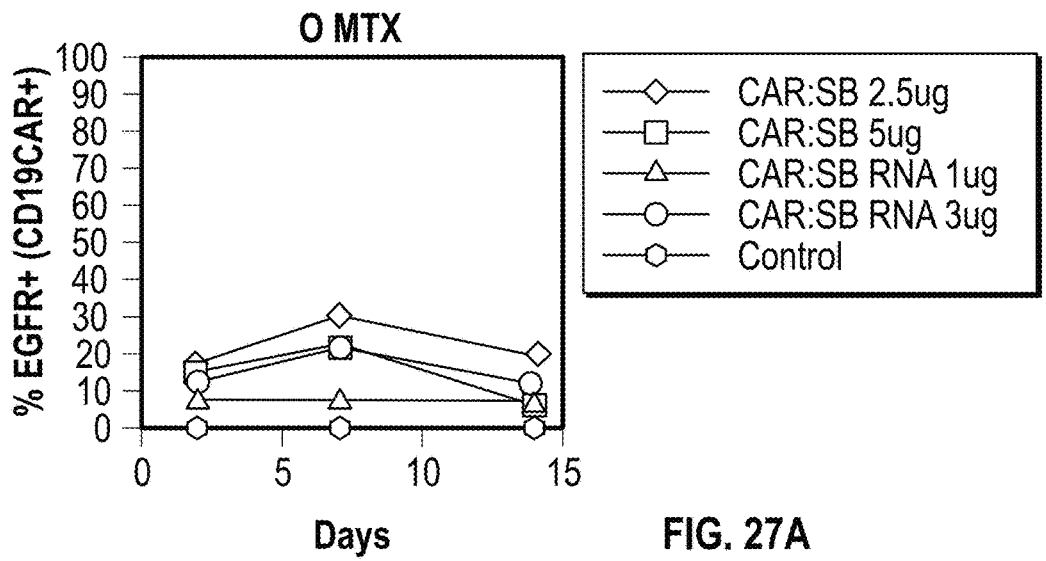
FIGS. 27A-27C are graphs relating to expression of CD19CAR. A Sleeping Beauty construct carrying a gene for CD19CAR was constructed (SB:CD19CAR). Cells were transfected with either DNA (2.5 ug or 5 ug), or RNA (1 ug or 3 ug). Cells were grown and at day seven after transfection, were exposed to MTX. The CD19CAR also included an EGFRt tag. As shown, detection of the tag correlates to the expression of the CD19CAR. After exposure to MTX, detection of the tag was seen in cells that were transfected with the DNA carrying the Sleeping Beauty construct carrying a gene for CAR19 as well as the cells transfected with the RNA carrying the Sleeping Beauty construct carrying a gene for CAR19.
Figure 27B:
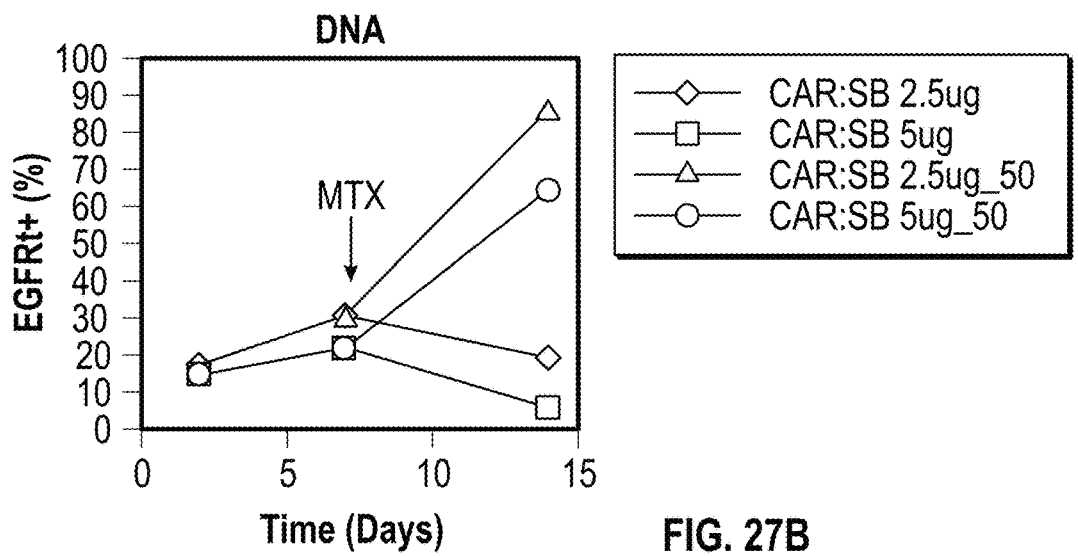
Figure 27C:
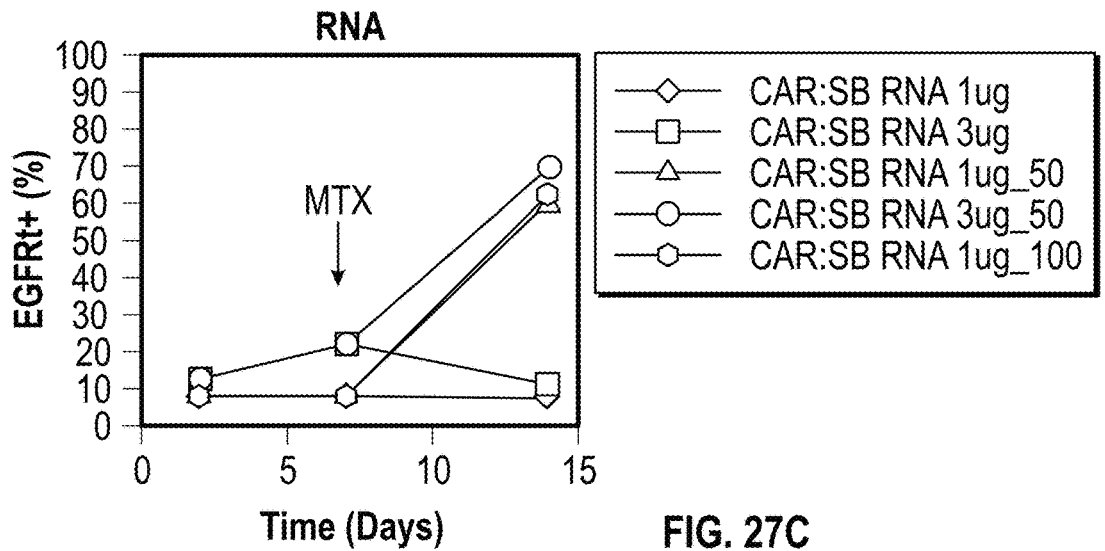
Figure 28A:
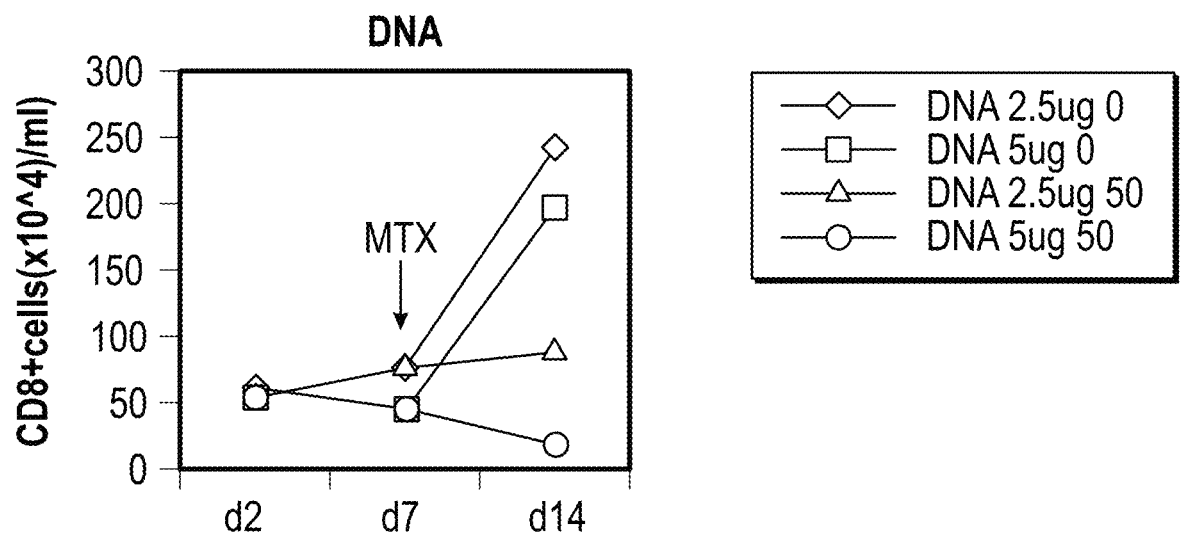
FIGS. 28A-28C show graphs relating to Sleeping Beauty Transposons and MTX:CD19 CAR:CD8+ cell growth. Expression of CD19CAR. A Sleeping Beauty construct carrying a gene for CD19CAR was constructed (SB: CD19CAR). Cells were transfected with either DNA (2.5 ug or 5 ug), or RNA (1 ug or 3 ug). Cells were grown and at day seven after transfection, were exposed to MTX.
Figure 28B:
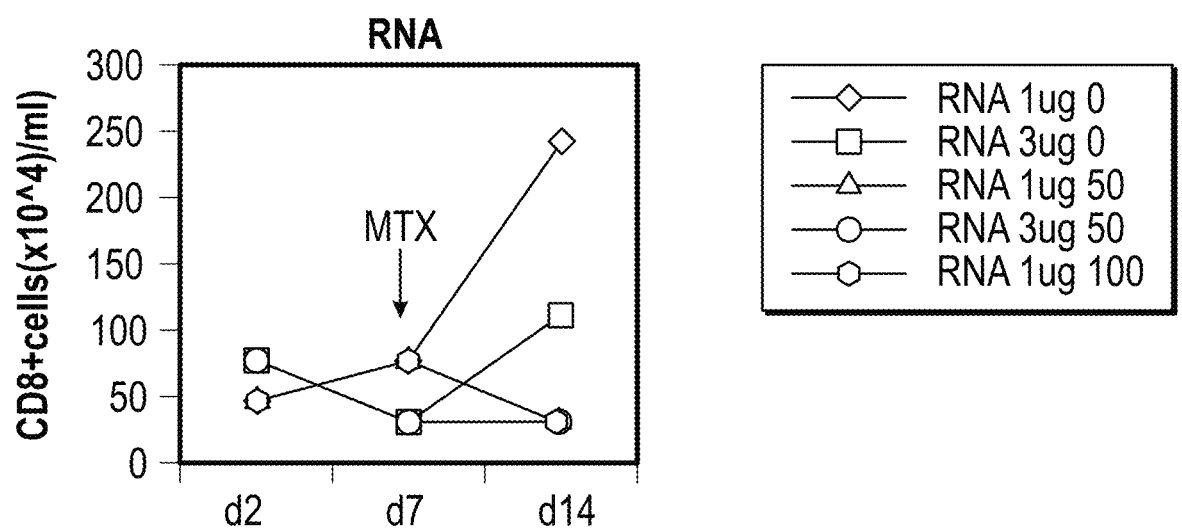
Figure 28C:
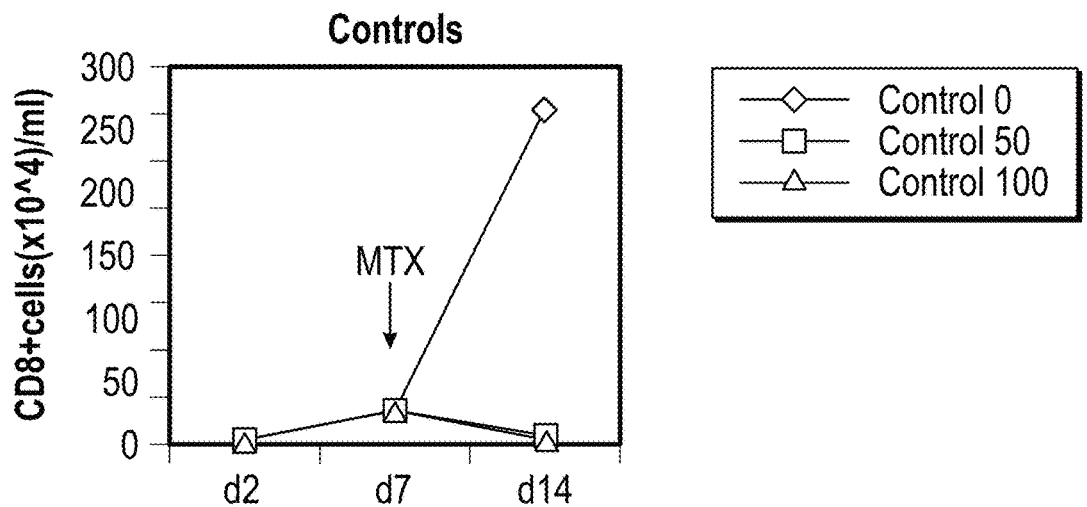
Figure 29:
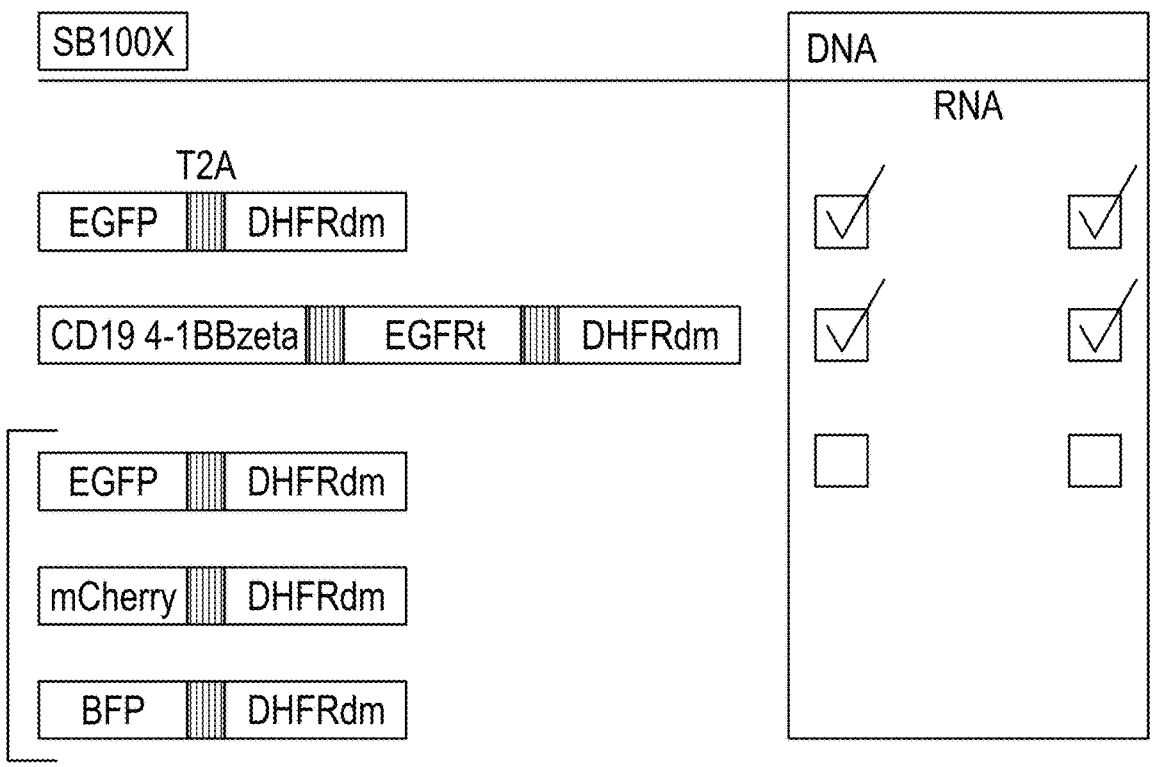
FIG. 29. Sleeping Beauty Transposons: minicircle constructs. As shown in the figure are the schematics of several sleeping beauty constructs designed for several alternatives described herein.
Figure 30A:
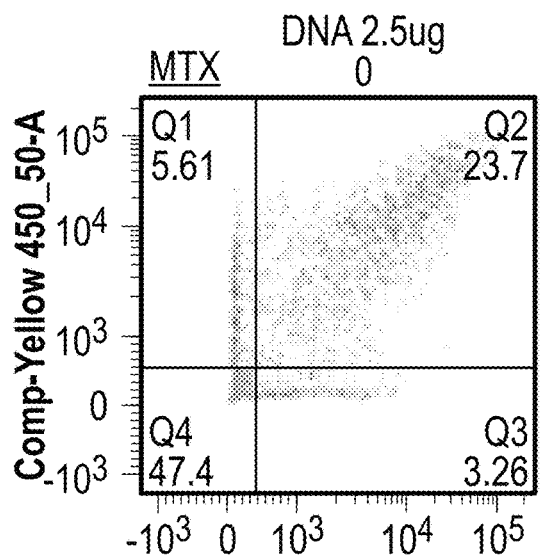
FIGS. 30A-30J are scattergrams relating to Sleeping Beauty Transposons and MTX: Multiplex 3 FP's. Cells were electroporated with DNA or mcFP and grown in the presence of MTX. Afterwards, cells were analyzed for expression of mCherry, BFP, and/or GFP as indicated by the scattergrams.
Figure 30B:
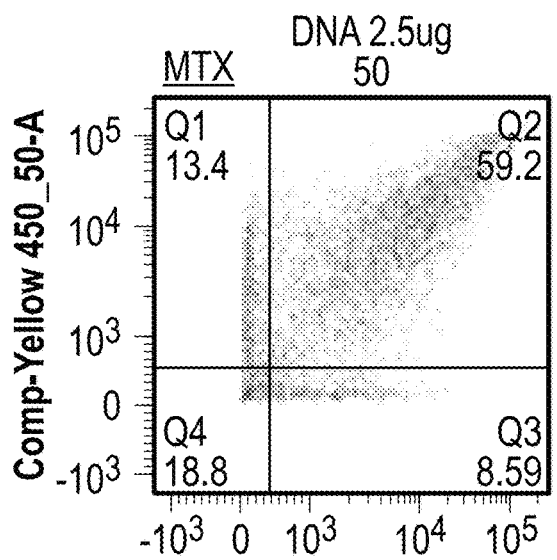
Figure 30C:
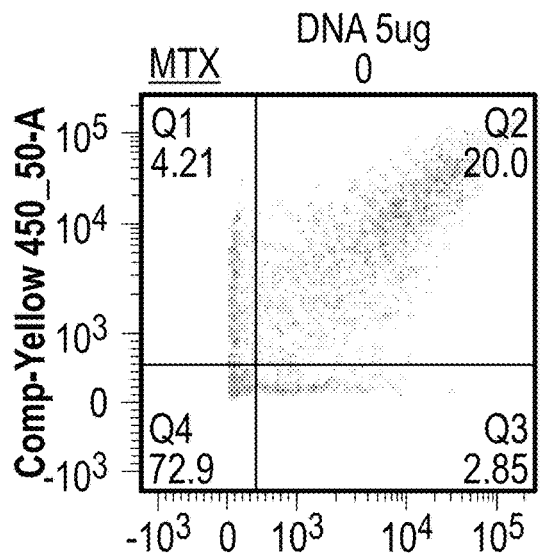
Figure 30D:
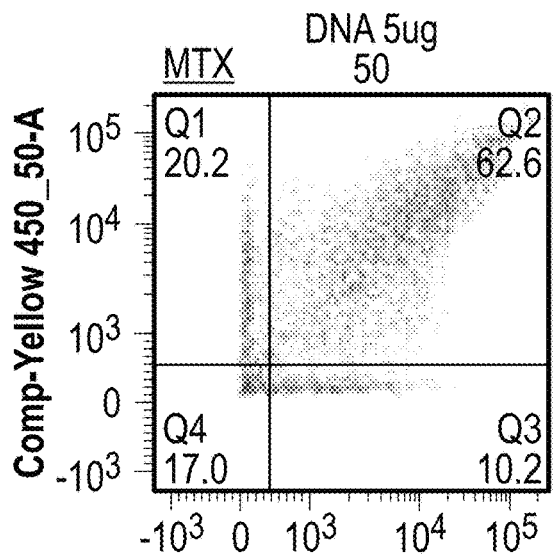
Figure 30E:
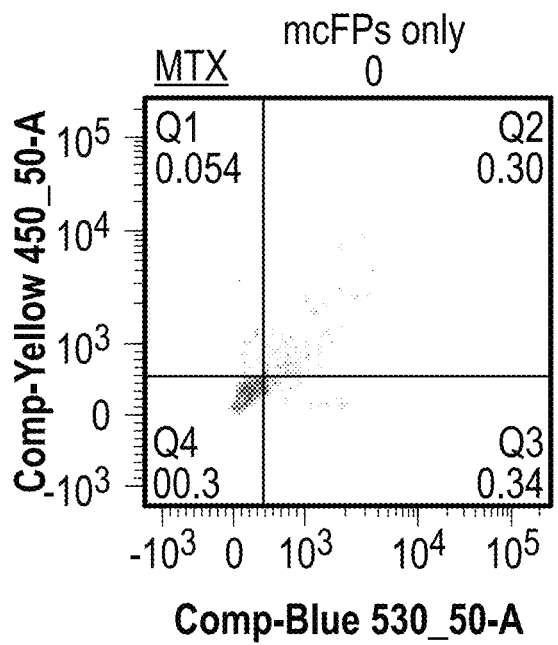
Figure 30F:
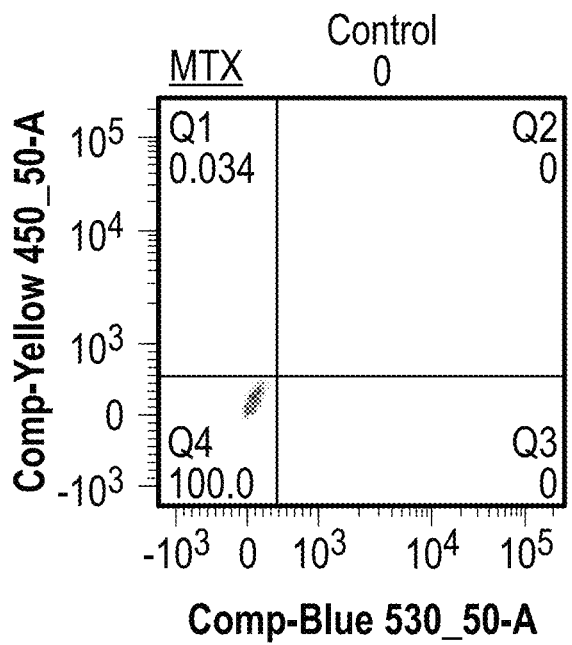
Figure 30G:
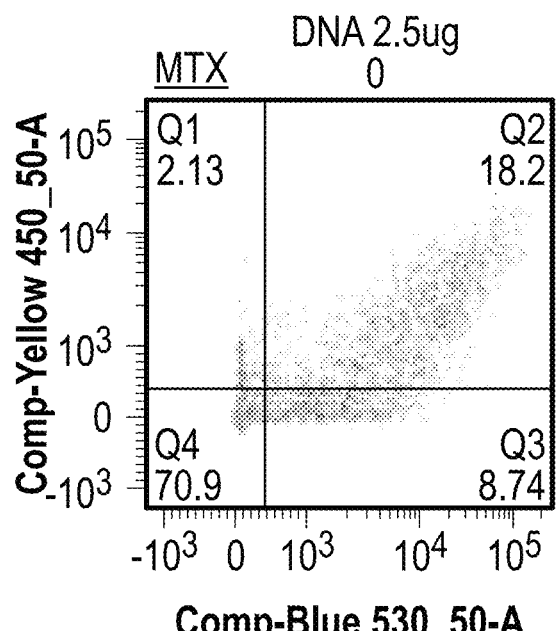
Figure 30H:
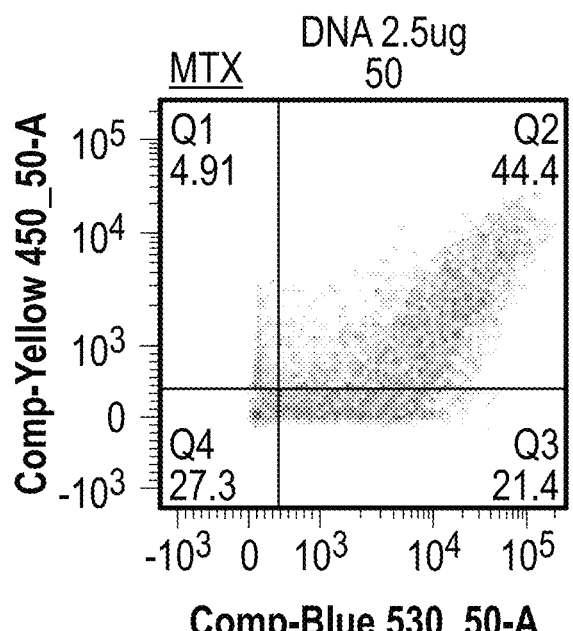
Figure 30:
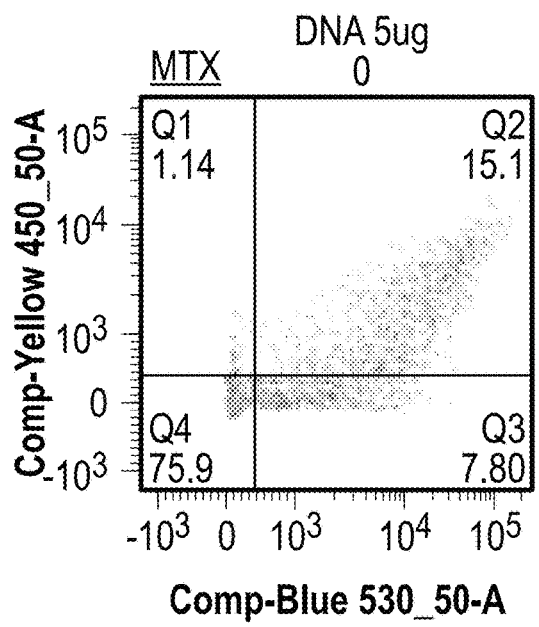
Figure 30:
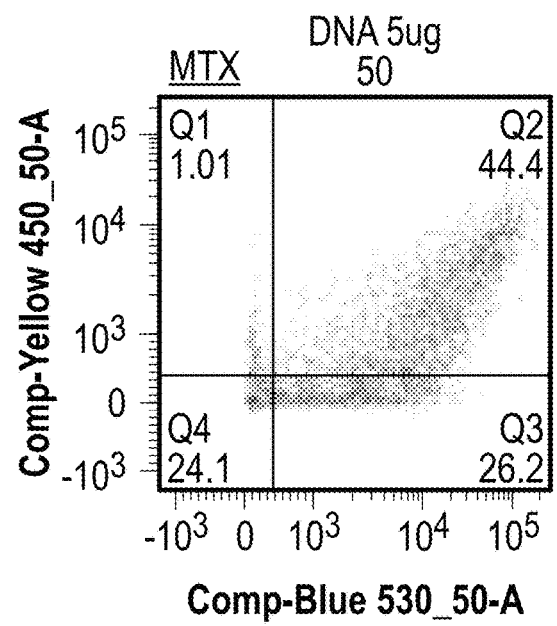
Figure 31A:
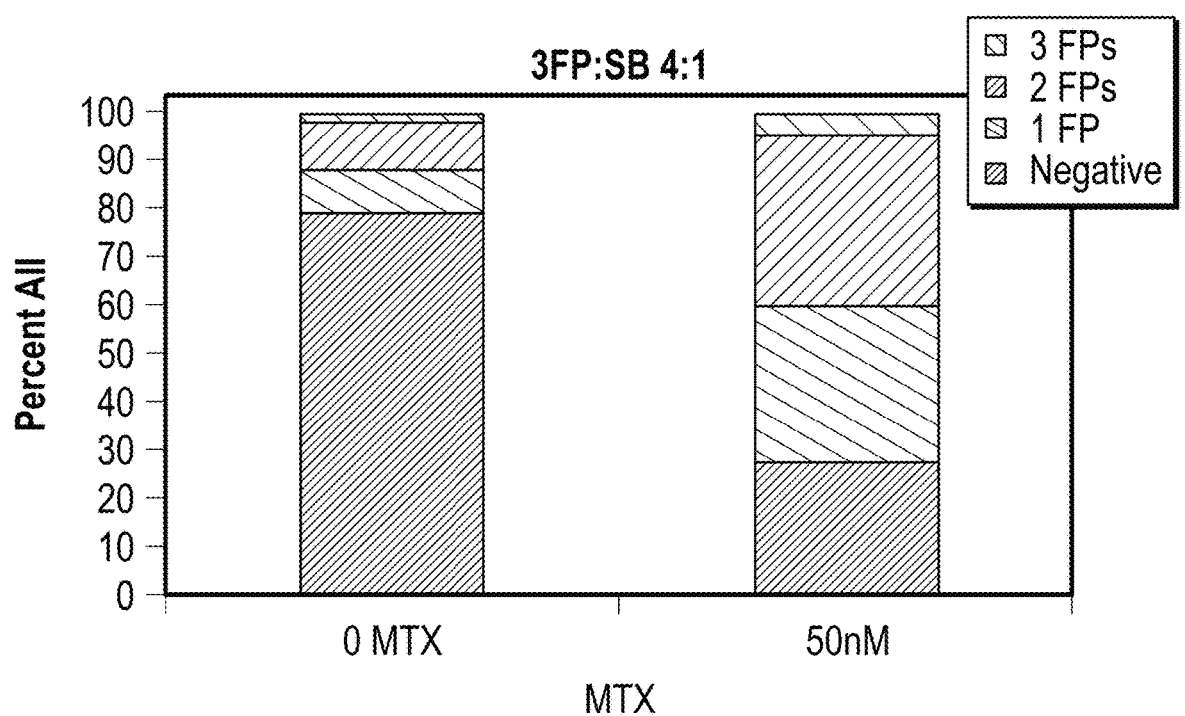
FIGS. 31A-31D are graphs relating to Sleeping Beauty Transposons and MTX: Multiplex 3 FP's.
Figure 31B:
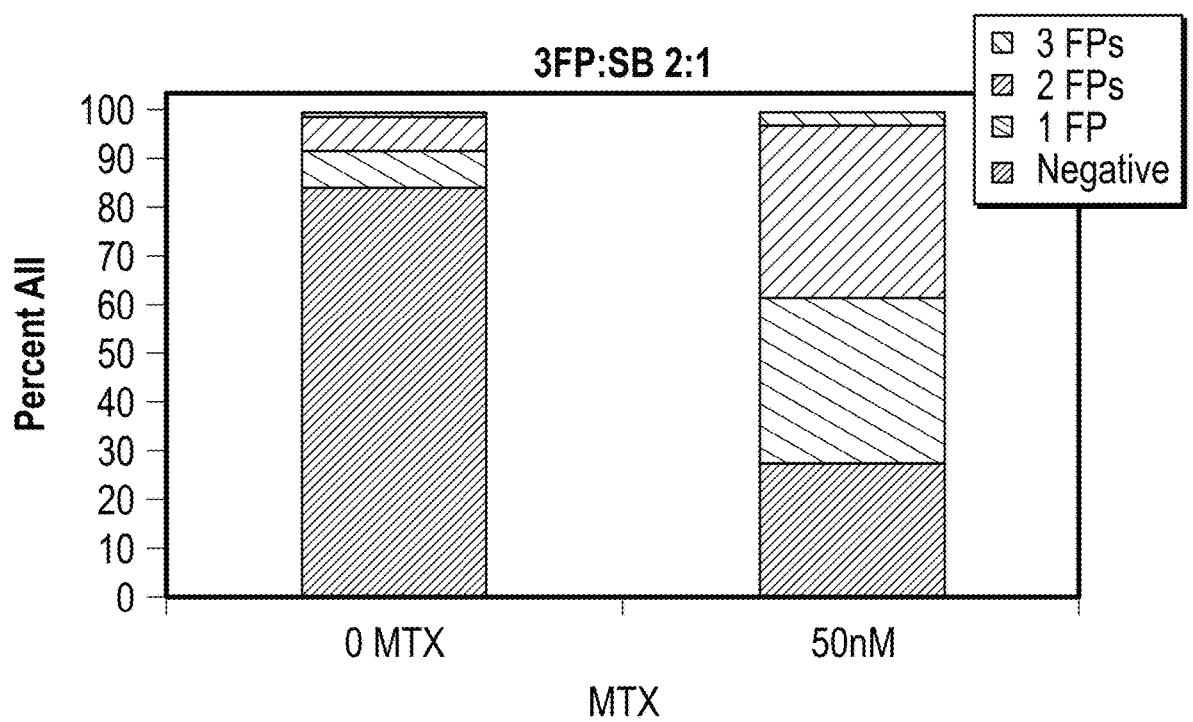
Figure 31C:
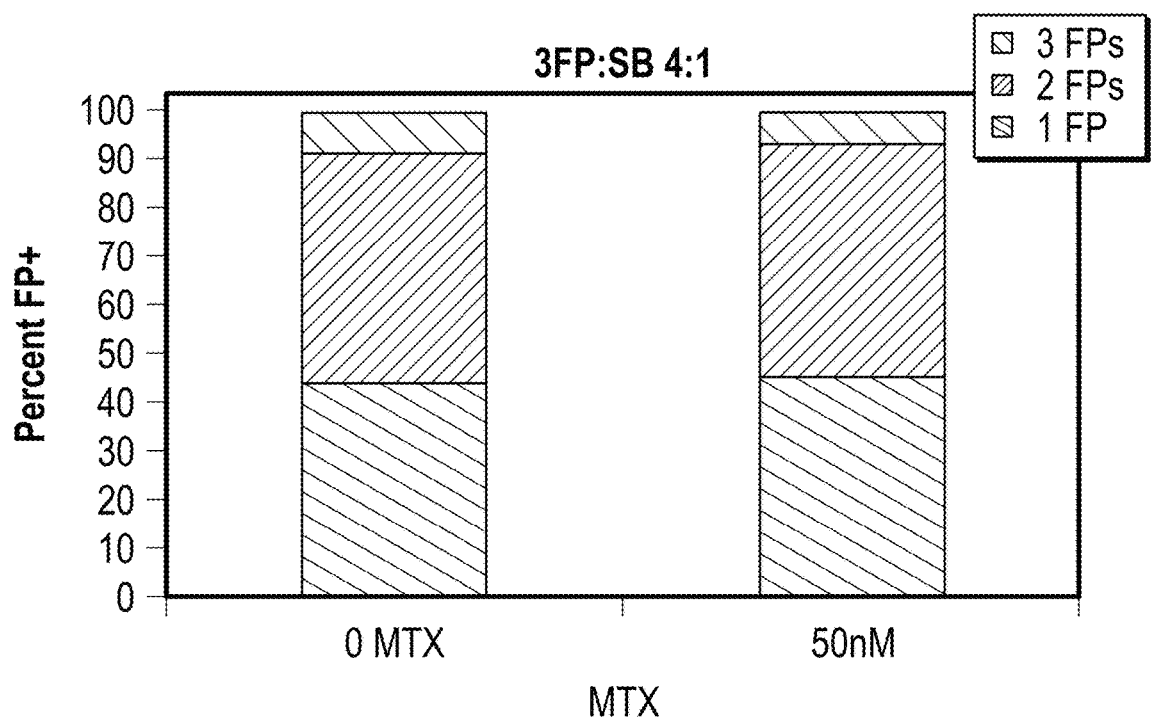
Figure 31D:
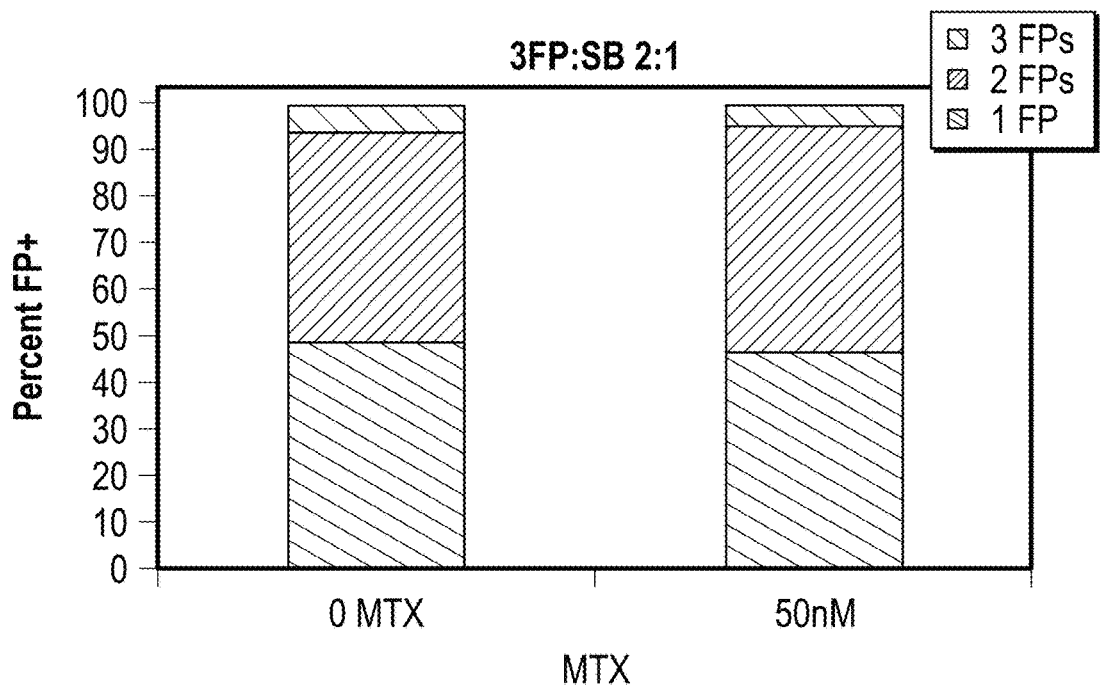
Figure 32:
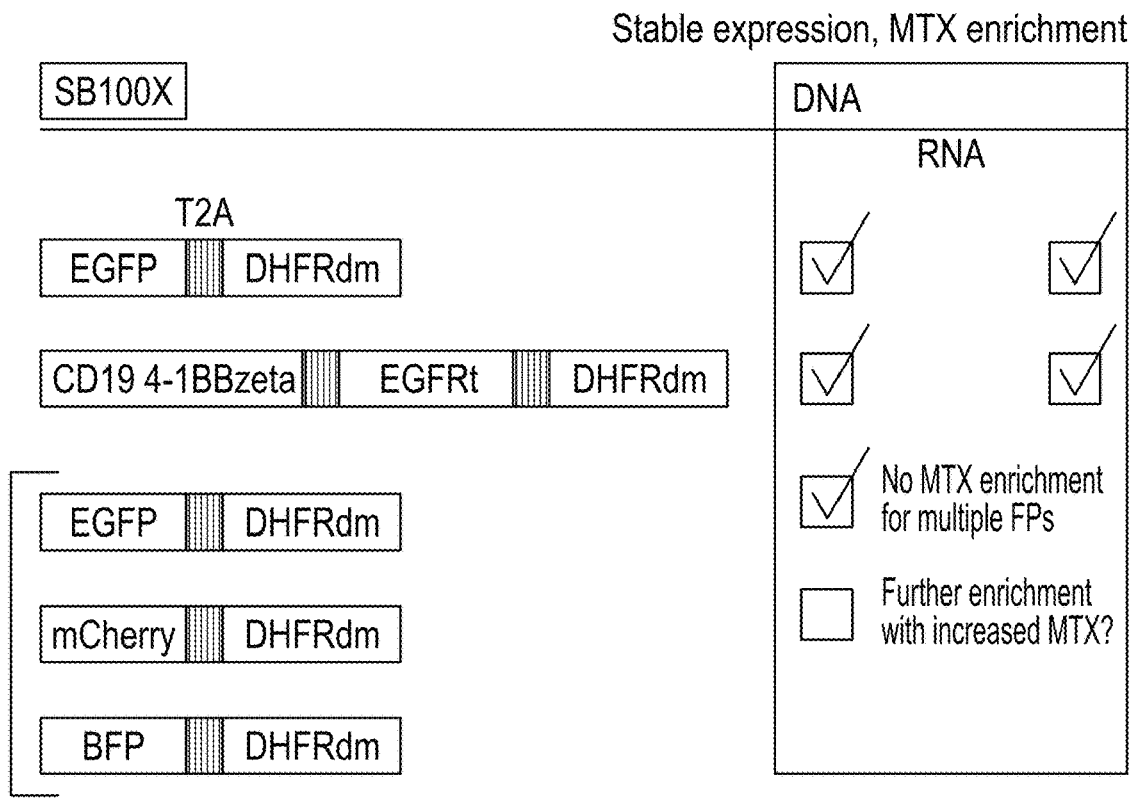
FIG. 32. Sleeping Beauty Transposons: minicircle constructs. As shown in the figure are the schematics of several sleeping beauty constructs designed for several alternatives described herein.
Figures 33A, 33B:
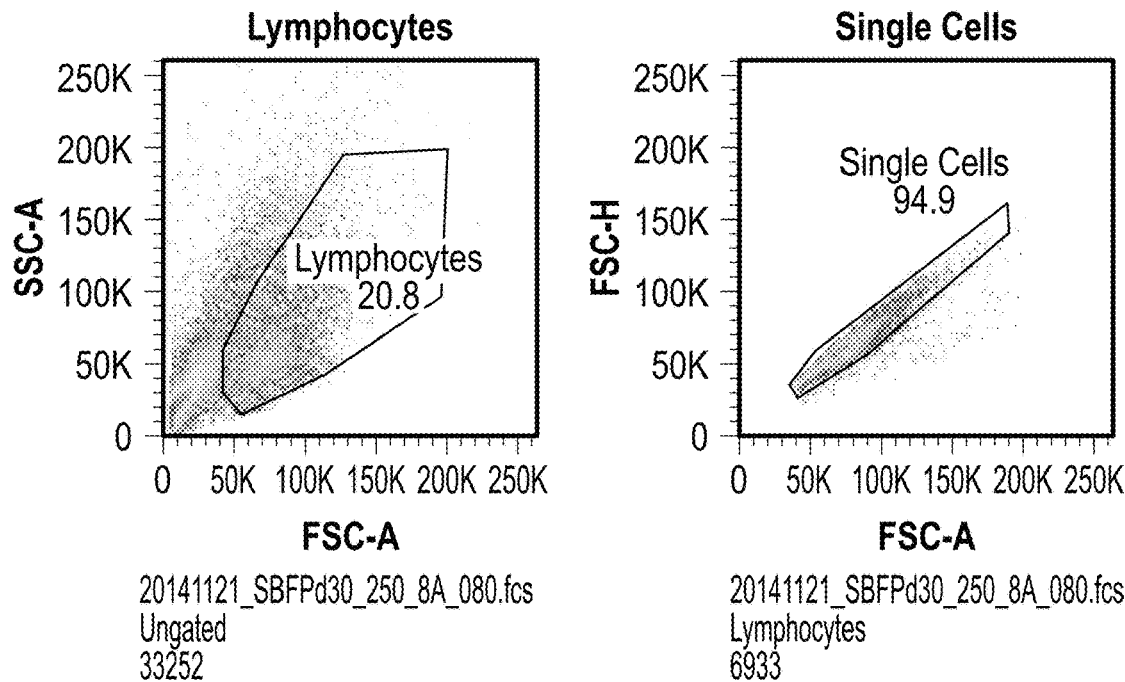
FIGS. 33A-33G relate to cells electroporated with DNA comprising Sleeping Beauty transposons were subjected to different concentrations of MTX at the second round of selection.
Figure 33C:
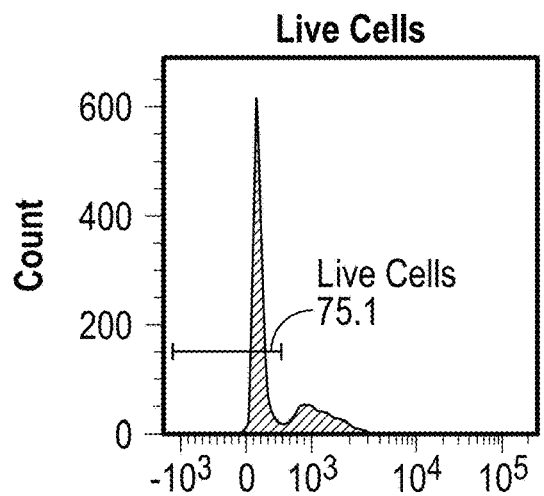
Figures 33D, 33E, 33F:
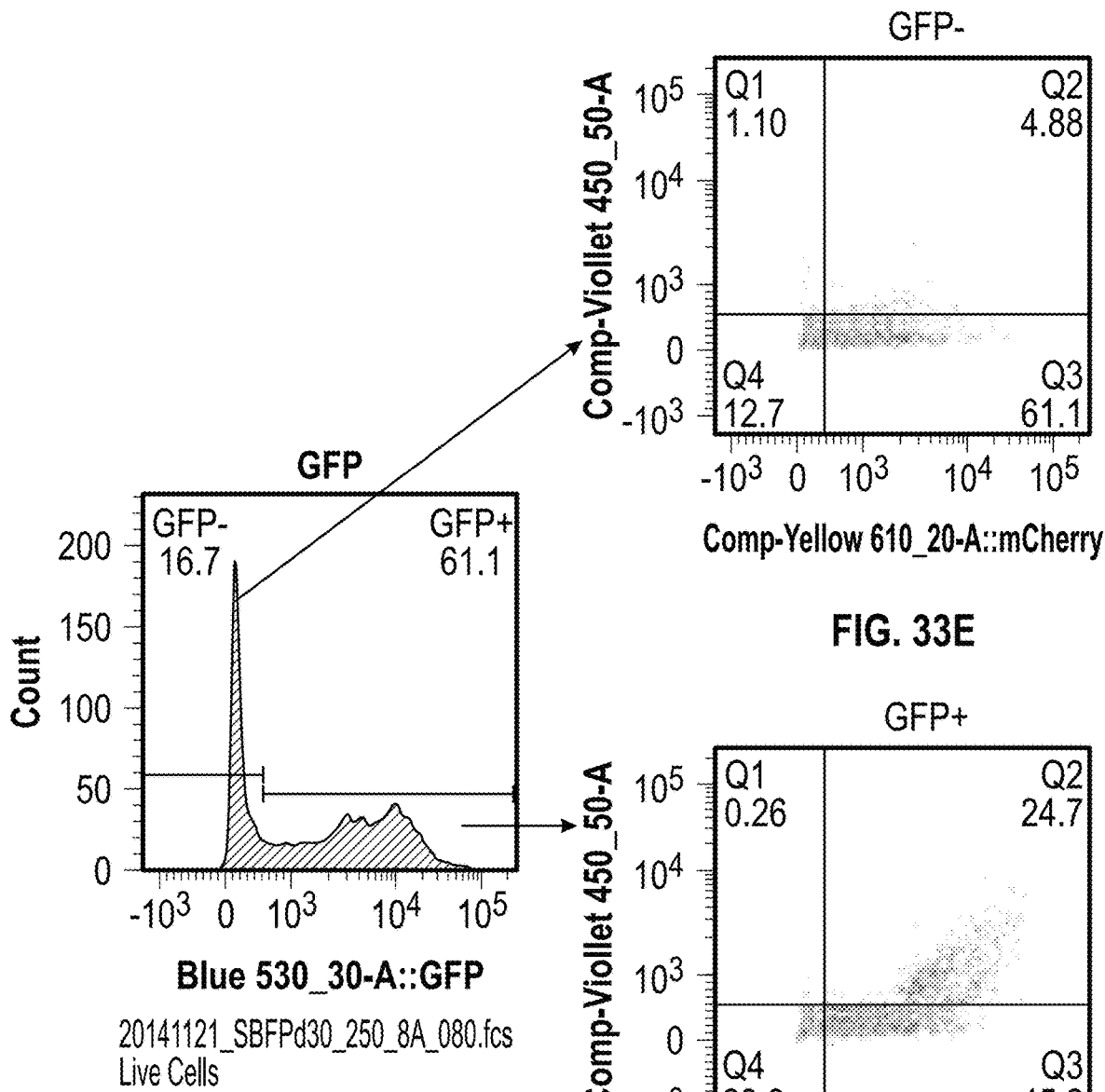
Figure 33G:
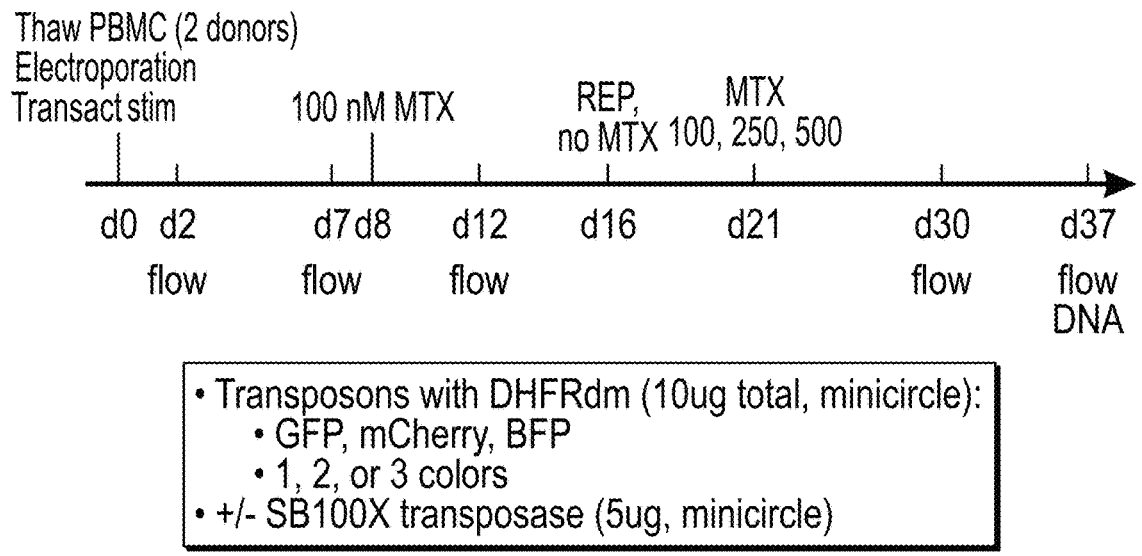
Figure 34A:
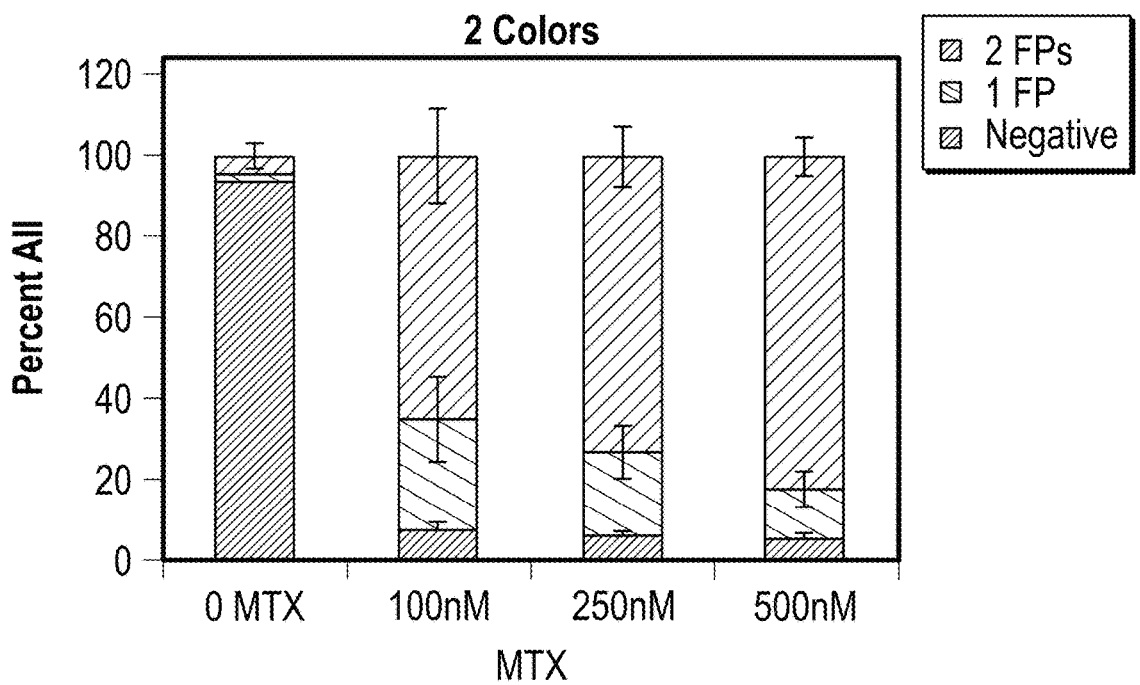
FIGS. 34A-34D are graphs relating to expression of marker proteins in cells electroporated with DNA comprising Sleeping Beauty transposons in the presence of different concentrations of MTX (0, 100 nM, 250 nM, and 500 nM).
Figure 34B:
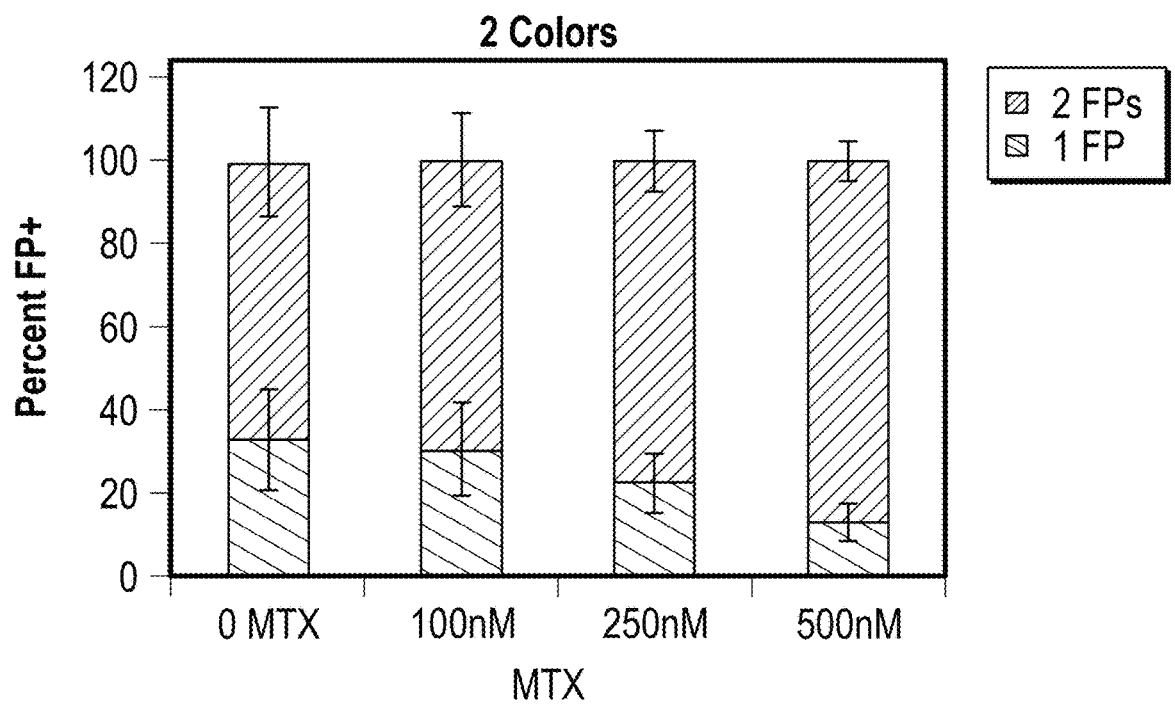
Figure 34C:
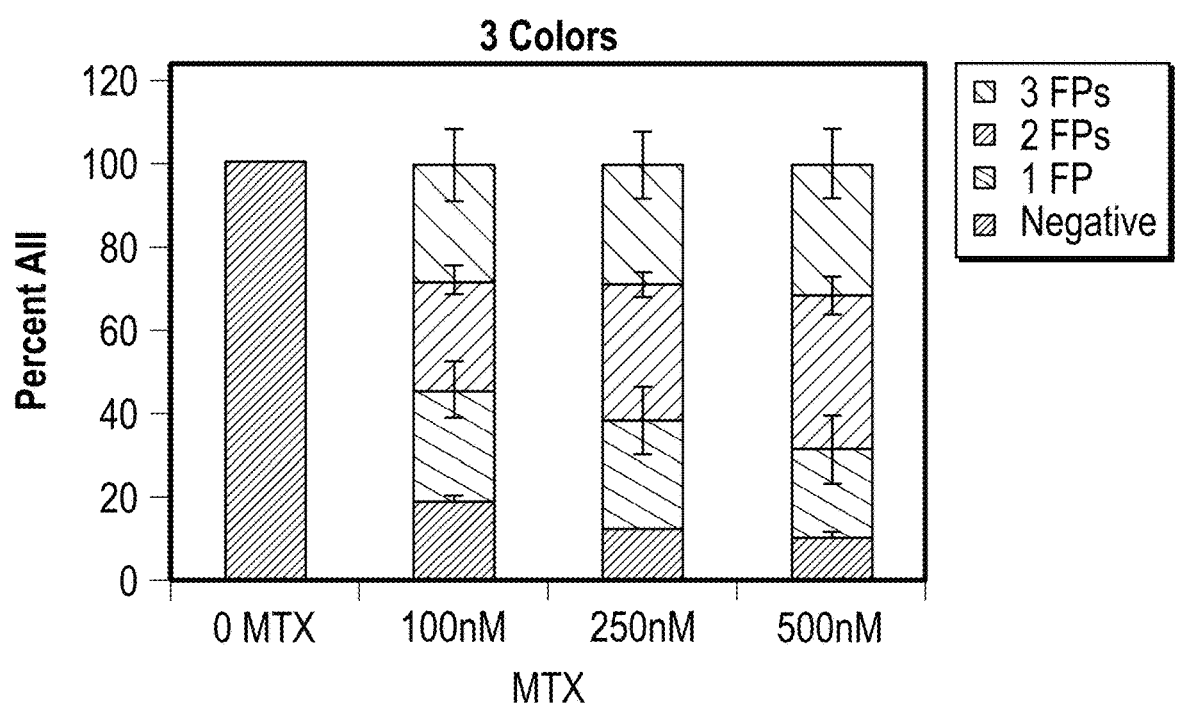
Figure 34D:
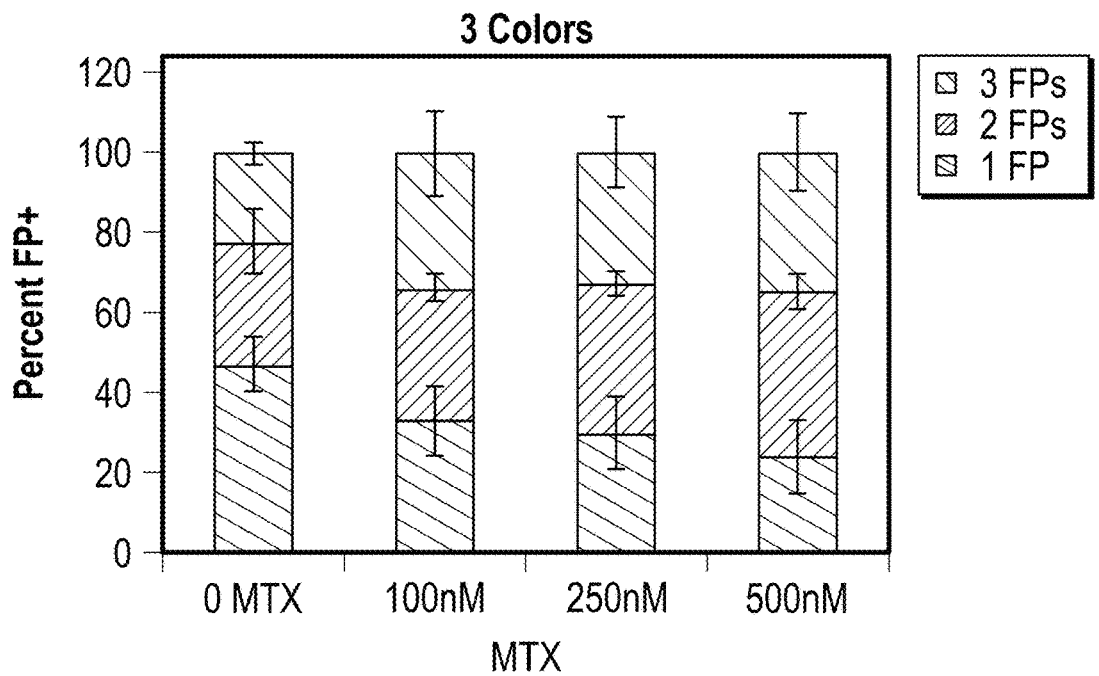
Figure 35:
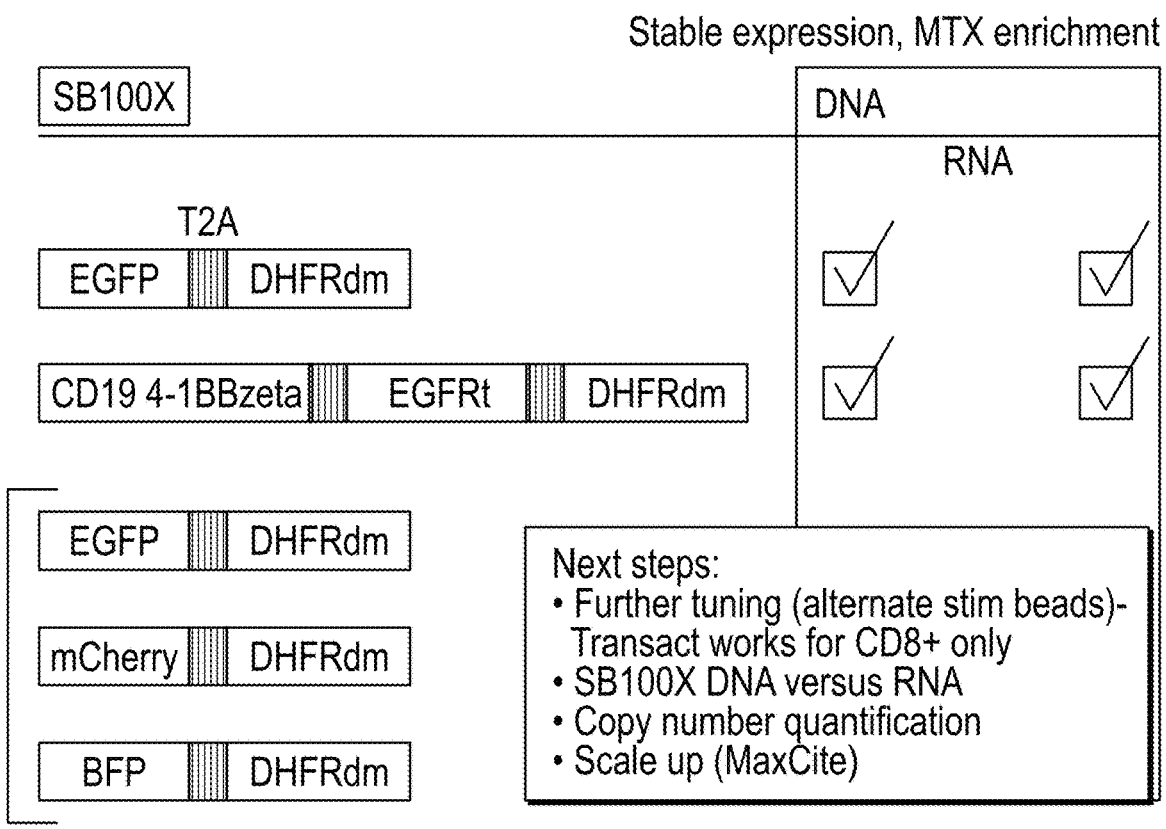
FIG. 35. Sleeping Beauty Transposons: minicircle constructs. As shown in the figure are the schematics of several sleeping beauty constructs designed for several alternatives described herein.

Attention is drawn to FIGS. 12A-1-D-2 and FIGS. 13A-1-D-2 which show the results of a FACS assay of the transfected cells after treatment with methotrexate for 7 and 12 days, respectively. Scatter plots and CD8+/GFP expression for live lymphocytes are shown for each condition. Percent GFP expression in lymphocytes is given in boxes in FIG. 12A-1-12D-2.

As shown in FIG. 12A-1-12D-2 at 7 days, cells treated with 0 or 25 nM MTX show about 25% or 75% of the cells expressing GFP, respectively. In contrast, at least 90% of the cells express GFP at 50 and 100 nM MTX. As shown, MTX selection was equally effective for enrichment of GFP expression at 50 nM and 100 nM, and at both ratios of mcGFP to SB at a 2:1 mcGFP:MC_SB100X ratio and a 1:1 mcGFP:MC_SB100X ratio. As expected, in the absence of SB transposase and in the no DNA controls there is no appreciable GFP expression. Note that the expression of GFP is similar in CD8+ and CD8− lymphocytes.

Stable Expression of Transposon DNA with Sleeping Beauty in T-Cells with Methotrexate Selection—Cell Counts.

The cell growth of PBMC that stably expressing the transposon DNA under MTX selection, was later assessed. Note that due to stimulation with Transact beads and growth in the presence of IL2 and IL-15, the majority of the surviving cells are T cells by 1 week. As shown in FIGS. 14A-14D, the amounts of live cells following treatment with MTX at 0 nM, 25 nM, 50 nM, and 100 nM methotrexate was determined with trypan blue cell counts at days 7, 14, and 19 days (days 0, 7, and 12 of MTX). In the control (0 nM MTX), the number of live cells increased over time for all DNA conditions. However, in the presence of MTX, only the cells that were transfected with both the SB transposase and the minicircle transposon that coexpresses GFP and the DHFRdm resistance gene were able to divide, indicating that SB is required for stable expression of the transposon.

Stable Expression of Transposon DNA with Sleeping Beauty in T-Cells with Methotrexate Selection—GFP Expression.

The stable expression of transposon DNA with Sleeping Beauty in T-cells during MTX selection was assessed by determining the GFP expression of the transfected cells over 19 days. Attention is drawn to FIGS. 14A-14D which shows increasing GFP expression over time in cells transfected with transposon DNA and Sleeping Beauty in T-cells following methotrexate selection starting at day 7 (0, 25, 50, and 100 nM). As shown in the control with no methotrexate selection from days 2, 5, 7, 14, and 19, the expression of GFP in the cells transfected with mcGFP and SB is maintained at ~20%, while the expression steadily decreases in the mcGFP alone and pMAXGFP controls. In the presence of MTX selection, GFP expression increases over time, with highest levels seen with 50 and 100 nM MTX. As shown, the ratios of mcGFP:MC_SB100X had no difference between a ratio of 1:1 and 2:1. Additionally there was minimal difference in the mean fluorescence intensity in cells that were exposed to either 50 nM or 100 nM MTX. The low levels of GFP expression (~20%) with mcGFP alone in the presence of MTX is likely due to transposon-independent stable integration, and the absolute number of cells in these conditions is very low as shown in FIGS. 14A-14D.

In one alternative, a gene delivery polynucleotide for stable insertion of a nucleic acid into a gene, wherein the nucleic acid for insertion is flanked by inverted terminal repeat gene sequences in the gene delivery polynucleotide and wherein the gene delivery polynucleotide is selectable is provided, wherein the gene delivery polynucleotide comprises a first sequence, wherein the first sequence comprises a first inverted terminal repeat gene sequence, a second sequence, wherein the second sequence comprises a second inverted terminal repeat gene sequence, a third sequence, wherein the third sequence comprises a promoter region sequence, a fourth sequence, wherein the fourth sequence comprises at least one gene encoding a protein, and wherein the fourth sequence is optimized, a fifth sequence, wherein the fifth sequence comprises at least one selectable marker cassette encoding a double mutant of dihydrofolate reductase, wherein the double mutant of dihydrofolate reductase has a 15,000 fold or about 15,000 fold reduced affinity for methotrexate, wherein the methotrexate can be used as a selection mechanism to selectively amplify cells transduced with the gene delivery polynucleotide and wherein the fifth sequence is optimized, a sixth sequence, wherein the sixth sequence comprises a first attachment site (attP) and a seventh sequence, wherein the seventh sequence comprises a second attachment site (attB) wherein each of the first sequence, second sequence, third sequence, fourth sequence, fifth sequence, sixth sequence, and seventh sequence have a 5' terminus and a 3 terminus, and wherein the 3' terminus of the first sequence comprising the first inverted terminal repeat gene sequence is adjacent to the 5' terminus of the third sequence, the 3' terminus of the third sequence is adjacent to the 5' terminus of the fourth sequence, the 3' terminus of the fourth sequence is adjacent to the 5' terminus of the fifth sequence and the 3' terminus of the fifth sequence is adjacent to the 5' terminus of the second sequence comprising a second inverted terminal repeat. In some alternatives, the gene encoding the double mutant of human dihydrofolate reductase comprises the DNA sequence:

```
                                          (SEQ ID NO: 2)
ATGGTTGGTTCGCTAAACTGCATCGTCGCTGTGTCCCAGAACATGGGCAT

CGGCAAGAACGGGGACTTCCCCTGGCCACCGCTCAGGAATGAATCCAGAT

ATTTCCAGAGAATGACCACAACCTCTTCAGTAGAAGGTAAACAGAATCTG

GTGATTATGGGTAAGAAGACCTGGTTCTCCATTCCTGAGAAGAATCGACC

TTTAAAGGGTAGAATTAATTTAGTTCTCAGCAGAGAACTCAAGGAACCTC

CACAAGGAGCTCATTTTCTTTCCAGAAGTCTAGATGATGCCTTAAAACTT

ACTGAACAACCAGAATTAGCAAATAAAGTAGACATGGTCTGGATAGTTGG

TGGCAGTTCTGTTTATAAGGAAGCCATGAATCACCCAGGCCATCTTAAAC

TATTTGTGACAAGGATCATGCAAGACTTTGAAAGTGACACGTTTTTTCCA
```

-continued
```
GAAATTGATTTGGAGAAATATAAACTTCTGCCAGAATACCCAGGTGTTCT

CTCTGATGTCCAGGAGGAGAAAGGCATTAAGTACAAATTTGAAGTATATG

AGAAGAATGATTAA.
```

In some alternatives, the double mutant of human dihydrofolate reductase comprises the protein sequence:

```
                                          (SEQ ID NO: 3)
MVGSLNCIVA VSQNMGIGKN GDFPWPPLRN ESRYFQRMTT

TSSVEGKQNL VIMGKKTWFS IPEKNRPLKG RINLVLSREL

KEPPQGAHFL SRSLDDALKL TEQPELANKV DMVWIVGGSS

VYKEAMNHPG HLKLFVTRIM QDFESDTFFP EIDLEKYKLL

PEYPGVLSDV QEEKGIKYKF EVYEKND.
```

In some alternatives, the gene delivery polynucleotide is circular. In some alternatives, the gene delivery polynucleotide is at least 1 kB to 5 kB. In some alternatives, the gene delivery polynucleotide is a minicircle. In some alternatives, the gene delivery polynucleotide is a minicircle. In some alternatives, the promoter region comprises an EF1 promoter sequence. In some alternatives, the fourth sequence comprises one, two, three, four, or five genes that encode proteins. In some alternatives, the fourth sequence is codon optimized to reduce the total GC/AT ratio of the fourth sequence. In some alternatives, the fourth sequence is optimized by codon optimization for expression in humans. In some alternatives, the fourth sequence is a consensus sequence generated from a plurality of nucleic acids that encode a plurality of related proteins. In some alternatives, the fourth sequence is a consensus sequence generated from a plurality of nucleic acids that encode a plurality of related proteins, such as a plurality of antibody binding domains, which are specific for the same epitope. In some alternatives, the plurality of related proteins comprise a plurality of antibody binding domains, wherein the plurality of antibody binding domains are specific for the same epitope. In some alternatives, the fifth sequence is codon optimized to reduce the total GC/AT ratio of the fifth sequence. In some alternatives, the fifth sequence is optimized by codon optimization for expression in humans. In some alternatives, the protein is a protein for therapy. In some alternatives, the codon optimization and/or consensus sequence is generated by comparing the variability of sequence and/or nucleobases utilized in a plurality of related sequences. In some alternatives, the protein comprises an antibody or a portion thereof, which may be humanized. In some alternatives, the double mutant of dihydrofolate reductase comprises amino acid mutations of L22F and F31S.

In some alternatives, a method of generating engineered multiplexed T-cells for adoptive T-cell immunotherapy is provided, wherein the method comprises providing a gene delivery polynucleotide as described herein, introducing the gene delivery polynucleotide into a T-cell, providing a vector encoding a Sleeping Beauty transposase, introducing the vector encoding the Sleeping Beauty transposase into the T-cell, selecting the cells comprising the gene delivery polynucleotide wherein selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range and isolating the T-cells expressing a phenotype under selective pressure. In some alternatives, the gene delivery polynucleotide comprises a first sequence, wherein the first sequence comprises a first inverted terminal repeat gene sequence, a second sequence, wherein the second sequence comprises a second inverted terminal repeat gene sequence, a third sequence, wherein the third sequence comprises a promoter region sequence, a fourth sequence, wherein the fourth sequence comprises at least one gene encoding a protein, and wherein the fourth sequence is optimized, a fifth sequence, wherein the fifth sequence comprises at least one selectable marker cassette encoding a double mutant of dihydrofolate reductase, wherein the double mutant of dihydrofolate reductase has a 15,000 fold or about 15,000 fold reduced affinity for methotrexate, wherein the methotrexate can be used as a selection mechanism to selectively amplify cells transduced with the gene delivery polynucleotide and wherein the fifth sequence is optimized, a sixth sequence, wherein the sixth sequence comprises a first attachment site (attP) and a seventh sequence, wherein the seventh sequence comprises a second attachment site (attB) wherein each of the first sequence, second sequence, third sequence, fourth sequence, fifth sequence, sixth sequence, and seventh sequence have a 5' terminus and a 3 terminus, and wherein the 3' terminus of the first sequence comprising the first inverted terminal repeat gene sequence is adjacent to the 5' terminus of the third sequence, the 3' terminus of the third sequence is adjacent to the 5' terminus of the fourth sequence, the 3' terminus of the fourth sequence is adjacent to the 5' terminus of the fifth sequence and the 3' terminus of the fifth sequence is adjacent to the 5' terminus of the second sequence comprising a second inverted terminal repeat. In some alternatives, the gene encoding the double mutant of human dihydrofolate reductase comprises the DNA sequence:

(SEQ ID NO: 2)
ATGGTTGGTTCGCTAAACTGCATCGTCGCTGTGTCCCAGAACATGGGCAT

CGGCAAGAACGGGGACTTCCCCTGGCCACCGCTCAGGAATGAATCCAGAT

ATTTCCAGAGAATGACCACAACCTCTTCAGTAGAAGGTAAACAGAATCTG

GTGATTATGGGTAAGAAGACCTGGTTCTCCATTCCTGAGAAGAATCGACC

TTTAAAGGGTAGAATTAATTTAGTTCTCAGCAGAGAACTCAAGGAACCTC

CACAAGGAGCTCATTTTCTTTCCAGAAGTCTAGATGATGCCTTAAAACTT

ACTGAACAACCAGAATTAGCAAATAAAGTAGACATGGTCTGGATAGTTGG

TGGCAGTTCTGTTTATAAGGAAGCCATGAATCACCCAGGCCATCTTAAAC

TATTTGTGACAAGGATCATGCAAGACTTTGAAAGTGACACGTTTTTTCCA

GAAATTGATTTGGAGAAATATAAACTTCTGCCAGAATACCCAGGTGTTCT

CTCTGATGTCCAGGAGGAGAAAGGCATTAAGTACAAATTTGAAGTATATG

AGAAGAATGATTAA.

In some alternatives, the double mutant of human dihydrofolate reductase comprises the protein sequence:

(SEQ ID NO: 3)
MVGSLNCIVA VSQNMGIGKN GDFPWPPLRN ESRYFQRMTT

TSSVEGKQNL VIMGKKTWFS IPEKNRPLKG RINLVLSREL

KEPPQGAHFL SRSLDDALKL TEQPELANKV DMVWIVGGSS

VYKEAMNHPG HLKLFVTRIM QDFESDTFFP EIDLEKYKLL

PEYPGVLSDV QEEKGIKYKF EVYEKND.

In some alternatives, the gene delivery polynucleotide is circular. In some alternatives, the gene delivery polynucleotide is at least 1 kB to 5 kB. In some alternatives, the gene delivery polynucleotide is a minicircle. In some alternatives, the promoter region comprises an EF1 promoter sequence. In some alternatives, the fourth sequence comprises one, two, three, four, or five genes that encode proteins. In some alternatives, the fourth sequence is codon optimized to reduce the total GC/AT ratio of the fourth sequence. In some alternatives, the fourth sequence is optimized by codon optimization for expression in humans. In some alternatives, the fourth sequence is a consensus sequence generated from a plurality of nucleic acids that encode a plurality of related proteins. In some alternatives, the fourth sequence is a consensus sequence generated from a plurality of nucleic acids that encode a plurality of related proteins, such as a plurality of antibody binding domains, which are specific for the same epitope. In some alternatives, the plurality of related proteins comprise a plurality of antibody binding domains, wherein the plurality of antibody binding domains are specific for the same epitope. In some alternatives, the fifth sequence is codon optimized to reduce the total GC/AT ratio of the fifth sequence. In some alternatives, the fifth sequence is optimized by codon optimization for expression in humans. In some alternatives, the protein is a protein for therapy. In some alternatives, the codon optimization and/or consensus sequence is generated by comparing the variability of sequence and/or nucleobases utilized in a plurality of related sequences. In some alternatives, the protein comprises an antibody or a portion thereof, which may be humanized. In some alternatives, the double mutant of dihydrofolate reductase comprises amino acid mutations of L22F and F31S. In some alternatives, the introducing is performed by electroporation. In some alternatives, the selecting is performed by increasing selective pressure through the selective marker cassette. In some alternatives, the selection reagent comprises an agent for selection. In some alternatives, the agent for selection is methotrexate. In some alternatives, the first concentration range is at least 50 nM-100 nM and the second concentration range is at least 75 to 150 nM. In some alternatives, the first concentration is 50 nM, 60 nM, 70 nM, 80 nM, 90 nM, or 100 nM or any concentration that is between a range of concentrations defined by any two of the aforementioned concentrations, and the second concentration range is 75 nM, 80 nM, 90 nM, 100 nM, 110 nM, 120 nM, 130 nM, 140 nM, or 150 nM or any concentration that is between a range of concentrations defined by any two of the aforementioned concentrations. In some alternatives, the first concentration range is at least 75 nM-150 nM and the second concentration range is at least 112.5 nM to 225 nM. In some alternatives, the first concentration is 75 nM, 85 nM, 95 nM, 105 nM, 115 nM, 125 nM, 135 nM, 145 nM, or 150 nM or any concentration that is between a range of concentrations defined by any two of the aforementioned concentrations, and the second concentration range is 112 nM, 122 nM, 132 nM, 142 nM, 152 nM, 162 nM, 172 nM, 182 nM, 192 nM, 202 nM, 212 nM, or 225 nM or any concentration that is between a range of concentrations defined by any two of the aforementioned concentrations. In some alternatives, the first concentration range is at least 300 nM-675 nM and the first concentration range is at least 450 nM to 1012 nM. In some alternatives, the first concentration is 300 nM, 350 nM, 400 nM, 450 nM, 500 nM, 550 nM, 600 nM, 650 nM, or 675 nM or any concentration that is between a range of concentrations defined by any two of the aforementioned concentrations, and the second concentration range is 450 nM, 500 nM, 550 nM, 600 nM, 650 nM, 700 nM, 750 nM, 800 nM, 850 nM, 900 nM, 1000 nM, or 1012 nM or any concentration that is between a range of concentrations defined by any two of the aforementioned concentrations. In some alternatives, the first round of selection comprises exposing the T-cells to the selection agent for 2, 3, 4, 5, 6 or 7 days before the second round of selection. In some alternatives, the second round of selection comprises exposing the T-cells to the selection agent for at least 2, 3, 4, 5, 6, 7, 8, 9, 10, 11, 12, 13, or 14 days or any time that is between a range of times defined by any two of the aforementioned time points before isolation.

In some alternatives, a method of increasing protein production in a T-cell is provided, wherein the method comprises providing a polynucleotide described herein, introducing the polynucleotide into a cell, providing a vector encoding a Sleeping Beauty transposase, introducing the vector encoding the Sleeping Beauty transposase into the T-cell, selecting the cells comprising the gene delivery polynucleotide wherein selecting comprises a first round of selection and a second round of selection, wherein the first round of selection comprises adding a selection reagent at a first concentration range and the second round of selection comprises adding the selection reagent at a second concentration range, wherein the second concentration range is higher than the first concentration range and, wherein the second concentration range is at least 1.5 fold higher than that of the first concentration range and isolating the cells expressing a phenotype under selective pressure. In some alternatives, the introducing is performed by electroporation. In some alternatives, the selecting is performed by increasing selective pressure through the selective marker cassette. In some alternatives, the selection reagent comprises an agent for selection. In some alternatives, the agent for selection is methotrexate. In some alternatives, the first concentration range is at least 50 nM-100 nM and the second concentration range is at least 75 to 150 nM. In some alternatives, the first concentration is 50 nM, 60 nM, 70 nM, 80 nM, 90 nM, or 100 nM or any concentration that is between a range of concentrations defined by any two of the aforementioned concentrations, and the second concentration range is 75 nM, 80 nM, 90 nM, 100 nM, 110 nM, 120 nM, 130 nM, 140 nM, or 150 nM or any concentration that is between a range of concentrations defined by any two of the aforementioned concentrations. In some alternatives, the first concentration range is at least 75 nM-150 nM and the second concentration range is at least 112.5 nM to 225 nM. In some alternatives, the first concentration is 75 nM, 85 nM, 95 nM, 105 nM, 115 nM, 125 nM, 135 nM, 145 nM, or 150 nM or any concentration that is between a range of concentrations defined by any two of the aforementioned concentrations, and the second concentration range is 112 nM, 122 nM, 132 nM, 142 nM, 152 nM, 162 nM, 172 nM, 182 nM, 192 nM, 202 nM, 212 nM, or 225 nM or any concentration that is between a range of concentrations defined by any two of the aforementioned concentrations. In some alternatives, the first concentration range is at least 300 nM-675 nM and the first concentration range is at least 450 nM to 1012 nM. In some alternatives, the first concentration is 300 nM, 350 nM, 400 nM, 450 nM, 500 nM, 550 nM, 600 nM, 650 nM, or 675 nM or any concentration that is between a range of concentrations defined by any two of the aforementioned concentrations, and the second concentration range is 450 nM, 500 nM, 550 nM, 600 nM, 650 nM, 700 nM, 750 nM, 800 nM, 850 nM, 900 nM, 1000 nM, or 1012 nM or any concentration that is between a range of concentrations defined by any two of the aforementioned concentrations. In some alternatives, the first round of selection comprises exposing the T-cells to the selection agent for 2, 3, 4, 5, 6 or 7 days before the second round of selection. In some alternatives, the second round of selection comprises exposing the T-cells to the selection agent for at least 2, 3, 4, 5, 6, 7, 8, 9, 10, 11, 12, 13, or 14 days or any time that is between a range of times defined by any two of the aforementioned time points before isolation.

In some alternatives, the gene delivery polynucleotide comprises a first sequence, wherein the first sequence comprises a first inverted terminal repeat gene sequence, a second sequence, wherein the second sequence comprises a second inverted terminal repeat gene sequence, a third sequence, wherein the third sequence comprises a promoter region sequence, a fourth sequence, wherein the fourth sequence comprises at least one gene encoding a protein, and wherein the fourth sequence is optimized, a fifth sequence, wherein the fifth sequence comprises at least one selectable marker cassette encoding a double mutant of dihydrofolate reductase, wherein the double mutant of dihydrofolate reductase has a 15,000 fold or about 15,000 fold reduced affinity for methotrexate, wherein the methotrexate can be used as a selection mechanism to selectively amplify cells transduced with the gene delivery polynucleotide and wherein the fifth sequence is optimized, a sixth sequence, wherein the sixth sequence comprises a first attachment site (attP) and a seventh sequence, wherein the seventh sequence comprises a second attachment site (attB) wherein each of the first sequence, second sequence, third sequence, fourth sequence, fifth sequence, sixth sequence, and seventh sequence have a 5' terminus and a 3 terminus, and wherein the 3' terminus of the first sequence comprising the first inverted terminal repeat gene sequence is adjacent to the 5' terminus of the third sequence, the 3' terminus of the third sequence is adjacent to the 5' terminus of the fourth sequence, the 3' terminus of the fourth sequence is adjacent to the 5' terminus of the fifth sequence and the 3' terminus of the fifth sequence is adjacent to the 5' terminus of the second sequence comprising a second inverted terminal repeat. In some alternatives, the gene encoding the double mutant of human dihydrofolate reductase comprises the DNA sequence:

```
                                    (SEQ ID NO: 2)
ATGGTTGGTTCGCTAAACTGCATCGTCGCTGTGTCCCAGAACATGGGCAT

CGGCAAGAACGGGGACTTCCCCTGGCCACCGCTCAGGAATGAATCCAGAT

ATTTCCAGAGAATGACCACAACCTCTTCAGTAGAAGGTAAACAGAATCTG

GTGATTATGGGTAAGAAGACCTGGTTCTCCATTCCTGAGAAGAATCGACC

TTTAAAGGGTAGAATTAATTTAGTTCTCAGCAGAGAACTCAAGGAACCTC

CACAAGGAGCTCATTTTCTTTCCAGAAGTCTAGATGATGCCTTAAAACTT

ACTGAACAACCAGAATTAGCAAATAAAGTAGACATGGTCTGGATAGTTGG

TGGCAGTTCTGTTTATAAGGAAGCCATGAATCACCCAGGCCATCTTAAAC

TATTTGTGACAAGGATCATGCAAGACTTTGAAAGTGACACGTTTTTTCCA

GAAATTGATTTGGAGAAATATAAACTTCTGCCAGAATACCCAGGTGTTCT
```

-continued

```
CTCTGATGTCCAGGAGGAGAAAGGCATTAAGTACAAATTTGAAGTATATG

AGAAGAATGATTAA.
```

In some alternatives, the double mutant of human dihydrofolate reductase comprises the protein sequence:

```
                                          (SEQ ID NO: 3)
MVGSLNCIVA VSQNMGIGKN GDFPWPPLRN ESRYFQRMTT

TSSVEGKQNL VIMGKKTWFS IPEKNRPLKG RINLVLSREL

KEPPQGAHFL SRSLDDALKL TEQPELANKV DMVWIVGGSS

VYKEAMNHPG HLKLFVTRIM QDFESDTFFP EIDLEKYKLL

PEYPGVLSDV QEEKGIKYKF EVYEKND.
```

In some alternatives, the gene delivery polynucleotide is circular. In some alternatives, the gene delivery polynucleotide is at least 1 kB to 5 kB. In some alternatives, the gene delivery polynucleotide is a minicircle. In some alternatives, the gene delivery polynucleotide is a minicircle. In some alternatives, the promoter region comprises an EF1 promoter sequence. In some alternatives, the fourth sequence comprises one, two, three, four, or five genes that encode proteins. In some alternatives, the fourth sequence is codon optimized to reduce the total GC/AT ratio of the fourth sequence. In some alternatives, the fourth sequence is optimized by codon optimization for expression in humans. In some alternatives, the fourth sequence is a consensus sequence generated from a plurality of nucleic acids that encode a plurality of related proteins. In some alternatives, the fourth sequence is a consensus sequence generated from a plurality of nucleic acids that encode a plurality of related proteins, such as a plurality of antibody binding domains, which are specific for the same epitope. In some alternatives, the plurality of related proteins comprise a plurality of antibody binding domains, wherein the plurality of antibody binding domains are specific for the same epitope. In some alternatives, the fifth sequence is codon optimized to reduce the total GC/AT ratio of the fifth sequence. In some alternatives, the fifth sequence is optimized by codon optimization for expression in humans. In some alternatives, the codon optimization and/or consensus sequence is generated by comparing the variability of sequence and/or nucleobases utilized in a plurality of related sequences. In some alternatives, the protein comprises an antibody or a portion thereof, which may be humanized. In some alternatives, the double mutant of dihydrofolate reductase comprises amino acid mutations of L22F and F31S. In some alternatives, the introducing is performed by electroporation. In some alternatives, the selecting is performed by increasing selective pressure through the selective marker cassette. In some alternatives, the selection reagent comprises an agent for selection. In some alternatives, the agent for selection is methotrexate. In some alternatives, the first concentration range is at least 50 nM-100 nM and the second concentration range is at least 75 to 150 nM. In some alternatives, the first concentration is 50 nM, 60 nM, 70 nM, 80 nM, 90 nM, or 100 nM or any concentration that is between a range of concentrations defined by any two of the aforementioned concentrations, and the second concentration range is 75 nM, 80 nM, 90 nM, 100 nM, 110 nM, 120 nM, 130 nM, 140 nM, or 150 nM or any concentration that is between a range of concentrations defined by any two of the aforementioned concentrations. In some alternatives, the first concentration range is at least 75 nM-150 nM and the second concentration range is at least 112.5 nM to 225 nM. In some alternatives, the first concentration is 75 nM, 85 nM, 95 nM, 105 nM, 115 nM, 125 nM, 135 nM, 145 nM, or 150 nM or any concentration that is between a range of concentrations defined by any two of the aforementioned concentrations, and the second concentration range is 112 nM, 122 nM, 132 nM, 142 nM, 152 nM, 162 nM, 172 nM, 182 nM, 192 nM, 202 nM, 212 nM, or 225 nM or any concentration that is between a range of concentrations defined by any two of the aforementioned concentrations. In some alternatives, the first concentration range is at least 300 nM-675 nM and the first concentration range is at least 450 nM to 1012 nM. In some alternatives, the first concentration is 300 nM, 350 nM, 400 nM, 450 nM, 500 nM, 550 nM, 600 nM, 650 nM, or 675 nM or any concentration that is between a range of concentrations defined by any two of the aforementioned concentrations, and the second concentration range is 450 nM, 500 nM, 550 nM, 600 nM, 650 nM, 700 nM, 750 nM, 800 nM, 850 nM, 900 nM, 1000 nM, or 1012 nM or any concentration that is between a range of concentrations defined by any two of the aforementioned concentrations. In some alternatives, the first round of selection comprises exposing the T-cells to the selection agent for 2, 3, 4, 5, 6 or 7 days before the second round of selection. In some alternatives, the second round of selection comprises exposing the T-cells to the selection agent for at least 2, 3, 4, 5, 6, 7, 8, 9, 10, 11, 12, 13, or 14 days or any time that is between a range of times defined by any two of the aforementioned time points before isolation.

In some alternatives, a method of treating, inhibiting, or ameliorating cancer or a disease in a subject, the method comprising administering to the subject a modified T-cell as described herein. In some alternatives, the subject is human.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group

What is claimed is:

1. A method of generating engineered multiplexed T-cells for adoptive T-cell immunotherapy comprising:
    (a) introducing into a population of T-cells a first minicircle and a second minicircle to obtain a first population of transfected T-cells, wherein each minicircle comprises a gene delivery polynucleotide, wherein the gene delivery polynucleotide comprises:
        (i) a first inverted terminal repeat (ITR),
        (ii) a promoter,
        (iii) a nucleic acid encoding a polypeptide, wherein the polypeptide of the first minicircle is different from the polypeptide of the second minicircle,
        (iv) a nucleic acid encoding a double mutant of dihydrofolate reductase (DHFR) comprising the nucleotide sequence as set forth in SEQ ID NO:2,
        (v) a second ITR,
        wherein (i) to (v) have a 5' to 3' order in the gene delivery polynucleotide;
    (b) introducing a vector encoding a Sleeping Beauty transposase into the first population of transfected T-cells to obtain a second population of transfected T-cells;
    (c) selecting for T-cells comprising the first minicircle and the second minicircle in the second population of transfected T-cells, wherein the selecting comprises a first round of selection comprising contacting the second population of transfected T-cells with methotrexate at a first concentration range, and a second round of selection comprising contacting the second population of transfected T-cells with methotrexate at a second concentration range, wherein the second concentration range is at least 1.5 fold higher than that of the first concentration range; and
    (d) isolating the selected T-cells, wherein at least 75% of the selected T-cells express both (a) the polypeptide of the first minicircle, and (b) the polypeptide of the second minicircle.

2. The method of claim 1, further comprising obtaining each minicircle by:
    (i) providing a plasmid comprising an attP attachment site (attP), an attB attachment site (attB), and the gene delivery polynucleotide, wherein the gene delivery polynucleotide is located between the attP and the attB, and
    (ii) inducing site-specific recombination in the plasmid, thereby obtaining the first minicircle or the second minicircle.

3. The method of claim 1, wherein expression of the of the polypeptide of the first minicircle and the polypeptide of the second minicircle gene delivery polynucleotide in the isolated T-cells persists after withdrawal of the methotrexate for at least 2 weeks.

4. The method of claim 3, further comprising measuring expression in the isolated T-cells of the polypeptide of the first minicircle and the polypeptide of the second minicircle at least 2 weeks after withdrawal of the methotrexate.

5. The method of claim 1, wherein the first concentration range is 50 nM-100 nM and the second concentration range is 75 nM to 150 nM.

6. The method of claim 1, wherein the first concentration range is 75 nM-150 nM and the second concentration range is 112.5 nM to 225 nM.

7. The method of claim 1, wherein the first concentration range is 300 nM-675 nM and the second concentration range is 450 nM to 1012 nM.

8. The method of claim 1, wherein the first round of selection comprises contacting the second population of transfected T-cells to the methotrexate at the first concentration range for at least 2 days before the second round of selection.

9. The method of claim 1, wherein the second round of selection comprises contacting the second population of transfected T-cells to the methotrexate at the second concentration range for at least 2 days.

10. The method of claim 1, wherein the promoter is an EF1 promoter.

11. The method of claim 1, wherein the first ITR and the second ITR are each derived from a Sleeping Beauty transposon.

12. The method of claim 1, wherein the nucleic acid encoding a polypeptide is codon optimized for expression in a human.

13. The method of claim 1, wherein the polypeptide comprises a chimeric antigen receptor (CAR).

14. The method of claim 13, wherein the CAR comprises an anti-CD19 CAR.

15. The method of claim 1, wherein the population of T-cells comprises a cell selected from the group consisting of a CD4+ T-cell, a CD8+ T-cell, a precursor T-cell, and a hematopoietic stem cell.

16. The method of claim 1, further comprising administering the isolated T-cells to a subject.

17. The method of claim 16, wherein the subject is human.

* * * * *